(12) United States Patent
Spencer et al.

(10) Patent No.: US 10,888,608 B2
(45) Date of Patent: *Jan. 12, 2021

(54) COSTIMULATION OF CHIMERIC ANTIGEN RECEPTORS BY MYD88 AND CD40 POLYPEPTIDES

(71) Applicant: BELLICUM PHARMACEUTICALS, INC., Houston, TX (US)

(72) Inventors: David Spencer, Houston, TX (US); Aaron Edward Foster, Houston, TX (US); Kevin Slawin, Houston, TX (US)

(73) Assignee: Bellicum Pharmaceuticals, Inc., Houston, TX (US)

( * ) Notice: Subject to any disclaimer, the term of this patent is extended or adjusted under 35 U.S.C. 154(b) by 446 days.

This patent is subject to a terminal disclaimer.

(21) Appl. No.: 14/842,710

(22) Filed: Sep. 1, 2015

(65) Prior Publication Data

US 2016/0058857 A1 Mar. 3, 2016

Related U.S. Application Data

(60) Provisional application No. 62/044,885, filed on Sep. 2, 2014, provisional application No. 62/115,735, filed on Feb. 13, 2015, provisional application No. 62/143,503, filed on Apr. 6, 2015.

(51) Int. Cl.
| | |
|---|---|
| *C12N 15/09* | (2006.01) |
| *A61K 39/00* | (2006.01) |
| *C07K 14/705* | (2006.01) |
| *C12N 9/64* | (2006.01) |
| *C12N 9/90* | (2006.01) |
| *C07K 14/47* | (2006.01) |

(52) U.S. Cl.
CPC .... *A61K 39/0011* (2013.01); *A61K 39/00117* (2018.08); *A61K 39/001104* (2018.08); *A61K 39/001106* (2018.08); *A61K 39/001112* (2018.08); *A61K 39/001124* (2018.08); *A61K 39/001168* (2018.08); *A61K 39/001171* (2018.08); *A61K 39/001188* (2018.08); *A61K 39/001189* (2018.08); *A61K 39/001193* (2018.08); *A61K 39/001195* (2018.08); *C07K 14/4702* (2013.01); *C07K 14/70578* (2013.01); *C12N 9/6472* (2013.01); *C12N 9/90* (2013.01); *A61K 2039/5156* (2013.01); *A61K 2039/5158* (2013.01); *C07K 2319/03* (2013.01); *C07K 2319/70* (2013.01); *C12Y 304/22062* (2013.01); *C12Y 502/01008* (2013.01)

(58) Field of Classification Search
None
See application file for complete search history.

(56) References Cited

U.S. PATENT DOCUMENTS

| | | |
|---|---|---|
| 4,514,506 A | 4/1985 | Braatz et al. |
| 5,384,253 A | 1/1995 | Krzyek et al. |
| 5,538,880 A | 7/1996 | Lundquist et al. |
| 5,550,214 A | 8/1996 | Eberlein et al. |
| 5,550,318 A | 8/1996 | Eberlein et al. |
| 5,589,343 A | 12/1996 | Marchand et al. |
| 5,610,042 A | 3/1997 | Chang et al. |
| 5,645,992 A | 7/1997 | Lott et al. |
| 5,648,226 A | 7/1997 | Van Den Eynde et al. |
| 5,709,995 A | 1/1998 | Chisari et al. |
| 5,719,054 A | 2/1998 | Bouursnell et al. |
| 5,741,899 A | 4/1998 | Capon et al. |
| 5,750,395 A | 5/1998 | Fikes et al. |
| 5,780,036 A | 7/1998 | Chisari |
| 5,830,462 A | 11/1998 | Crabtree et al. |
| 5,834,266 A | 11/1998 | Crabtree et al. |
| 5,840,839 A | 11/1998 | Wang et al. |
| 5,869,337 A | 2/1999 | Crabtree et al. |
| 5,869,608 A | 2/1999 | Cadlwell et al. |
| 5,871,753 A | 2/1999 | Crabtree et al. |
| 5,925,565 A | 7/1999 | Berlioz et al. |
| 5,935,819 A | 8/1999 | Eichner et al. |
| 5,955,596 A | 9/1999 | Zagursky et al. |
| 5,965,242 A | 10/1999 | Patton et al. |
| 5,994,313 A | 11/1999 | Crabtree et al. |

(Continued)

FOREIGN PATENT DOCUMENTS

| | | |
|---|---|---|
| EP | 0 273 085 | 7/1988 |
| EP | 0 510 691 | 10/1992 |

(Continued)

OTHER PUBLICATIONS

Lerich et al., Cleavable Linkers in Chemical Biology, Bioorganic & Medicinal Chemistry 20: 571-582 (20012) (Year: 2012).*
Office Action dated Feb. 7, 2017 in U.S. Appl. No. 14/210,034, filed Mar. 13, 2014 and published as US 2014-0286987 on Sep. 25, 2014.
Chang et al., "Transgene-enforced co-stimulation of CD4+ T cells leads to enhanced and sustained anti-tumor effector functioning" Cytotherapy (2007) 9:771-784.
Warner et al., "MyD88: a critical adaptor protein in innate immunity signal transduction" J. Immunol. (2013) 190:3-4.

(Continued)

*Primary Examiner* — Phillip Gambel
(74) *Attorney, Agent, or Firm* — Jones Day

(57) ABSTRACT

The technology relates generally to the field of immunology and relates in part to methods for activating T cells and other cells resulting in an immune response against a target antigen. The technology also relates to costimulation of therapeutic cells that express chimeric antigen receptors that recognize target antigens using chimeric MyD88- and CD40-derived polypeptides. The technology further relates in part to therapeutic cells that express chimeric antigen receptors, wherein the chimeric antigen receptors have an endodomain that includes MyD88- and CD40-derived polypeptides, and methods for treating patients using the modified therapeutic cells.

16 Claims, 52 Drawing Sheets

Specification includes a Sequence Listing.

(56) References Cited

U.S. PATENT DOCUMENTS

| | | |
|---|---|---|
| 6,011,018 A | 1/2000 | Crabtree et al. |
| 6,043,082 A | 3/2000 | Crabtree et al. |
| 6,046,047 A | 4/2000 | Crabtree et al. |
| 6,046,158 A | 4/2000 | Ariizumi et al. |
| 6,054,436 A | 4/2000 | Crabtree et al. |
| 6,497,876 B1 | 12/2002 | Maraskovsky et al. |
| 6,558,951 B1 | 5/2003 | Tomai et al. |
| 6,670,186 B1 | 12/2003 | Nair et al. |
| 6,943,245 B2 | 9/2005 | Killary et al. |
| 7,404,950 B2 | 7/2008 | Spencer et al. |
| 8,404,817 B2 | 3/2013 | Sherman et al. |
| 8,691,210 B2 | 4/2014 | Spencer et al. |
| 8,771,671 B2 | 7/2014 | Spencer et al. |
| 8,822,647 B2 | 9/2014 | Jensen |
| 8,999,949 B2 | 4/2015 | Spencer et al. |
| 9,315,559 B2 | 4/2016 | Spencer et al. |
| 9,428,569 B2 | 8/2016 | Spencer |
| 9,572,835 B2 | 2/2017 | Spencer et al. |
| 9,944,690 B2 | 4/2018 | Spencer et al. |
| 9,976,122 B2 | 5/2018 | Spencer et al. |
| 2003/0082163 A1 | 5/2003 | Shu |
| 2003/0091593 A1 | 5/2003 | Bachmann et al. |
| 2003/0092132 A1 | 5/2003 | Williams |
| 2003/0108527 A1 | 6/2003 | Seya et al. |
| 2003/0147881 A1 | 8/2003 | Cheung |
| 2003/0153518 A1 | 8/2003 | Foxwell et al. |
| 2003/0206917 A1 | 11/2003 | Tykocinski et al. |
| 2003/0232055 A1 | 12/2003 | Medzhitov |
| 2004/0019195 A1 | 1/2004 | Scholm et al. |
| 2004/0116333 A1 | 6/2004 | Lin et al. |
| 2004/0209836 A1 | 10/2004 | Spencer |
| 2005/0113564 A1 | 5/2005 | Campana |
| 2005/0215472 A1 | 9/2005 | Schulke et al. |
| 2006/0247191 A1 | 11/2006 | Finney et al. |
| 2007/0081963 A1 | 4/2007 | Oh et al. |
| 2008/0269160 A1 | 10/2008 | Spencer et al. |
| 2008/0274140 A1 | 11/2008 | Weiner et al. |
| 2009/0175880 A1 | 7/2009 | Keler et al. |
| 2009/0311183 A1 | 12/2009 | Devy et al. |
| 2010/0105136 A1 | 4/2010 | Carter |
| 2010/0196336 A1 | 8/2010 | Park et al. |
| 2010/0203067 A1 | 8/2010 | Spencer et al. |
| 2011/0033383 A1 | 2/2011 | Spencer et al. |
| 2011/0201780 A1 | 8/2011 | Reed et al. |
| 2011/0286980 A1 | 11/2011 | Brenner et al. |
| 2011/0287038 A1 | 11/2011 | Slawin et al. |
| 2013/0071414 A1 | 3/2013 | Dotti |
| 2013/0131315 A1 | 5/2013 | Su |
| 2013/0183333 A1 | 7/2013 | Spencer et al. |
| 2013/0280220 A1* | 10/2013 | Ahmed ............... C12N 15/85 424/93.21 |
| 2013/0287748 A1 | 10/2013 | June |
| 2013/0287752 A1 | 10/2013 | Davila |
| 2013/0295110 A1 | 11/2013 | Binder |
| 2013/0315884 A1 | 11/2013 | Galetto |
| 2013/0323834 A1 | 12/2013 | Brenner |
| 2014/0023647 A1 | 1/2014 | Slawin et al. |
| 2014/0087468 A1 | 3/2014 | Spencer et al. |
| 2014/0120622 A1* | 5/2014 | Gregory ............... A61K 35/26 435/462 |
| 2014/0134142 A1 | 5/2014 | Cellectis |
| 2014/0255360 A1 | 9/2014 | Spencer et al. |
| 2014/0255363 A1 | 9/2014 | Metelitsa |
| 2014/0286987 A1 | 9/2014 | Spencer et al. |
| 2014/0287490 A1 | 9/2014 | Spencer et al. |
| 2014/0308259 A1 | 10/2014 | Scholler |
| 2014/0322275 A1 | 10/2014 | Brogdon |
| 2015/0093401 A1* | 4/2015 | Pule ............... C07K 16/2887 424/185.1 |
| 2015/0111294 A1 | 4/2015 | Spencer et al. |
| 2015/0139943 A1 | 5/2015 | Campana et al. |
| 2015/0306140 A1 | 10/2015 | Spencer et al. |
| 2015/0328292 A1 | 11/2015 | Spencer et al. |
| 2016/0046700 A1 | 2/2016 | Foster et al. |
| 2016/0058857 A1 | 3/2016 | Spencer et al. |
| 2016/0166613 A1 | 6/2016 | Spencer et al. |
| 2016/0175359 A1 | 6/2016 | Spencer et al. |
| 2017/0002321 A1 | 1/2017 | Spencer et al. |
| 2017/0166877 A1 | 6/2017 | Bayle et al. |
| 2017/0182140 A1 | 6/2017 | Spencer et al. |
| 2018/0201663 A1 | 7/2018 | Spencer et al. |
| 2018/0265566 A1 | 9/2018 | Spencer et al. |
| 2018/0305667 A1 | 10/2018 | Spencer et al. |

FOREIGN PATENT DOCUMENTS

| | | |
|---|---|---|
| WO | WO 2016/100236 | 6/1916 |
| WO | WO 2016/100241 | 6/1916 |
| WO | WO 2016/123143 | 8/1916 |
| WO | WO 2017/106185 | 12/1916 |
| WO | WO 2018/106993 | 6/1918 |
| WO | WO 2018/208849 | 11/1918 |
| WO | WO 94/09699 | 5/1994 |
| WO | WO 94/018317 | 8/1994 |
| WO | WO 96/012796 | 5/1996 |
| WO | WO 01/083551 | 11/2001 |
| WO | WO 02/036769 | 5/2002 |
| WO | WO 04/073641 | 9/2004 |
| WO | WO 2005/044996 | 5/2005 |
| WO | WO 08/049113 | 4/2008 |
| WO | WO 2008/049113 | 4/2008 |
| WO | WO 09/061996 | 5/2009 |
| WO | WO 10/033949 | 5/2010 |
| WO | WO 11/130566 | 10/2011 |
| WO | WO 11/146862 | 11/2011 |
| WO | WO 2012/079000 | 6/2012 |
| WO | WO 2012/127464 | 9/2012 |
| WO | WO 2013/126720 | 8/2013 |
| WO | WO 13/154760 | 10/2013 |
| WO | WO 14/127261 | 8/2014 |
| WO | WO 14/151960 | 9/2014 |
| WO | WO 14/164348 | 10/2014 |
| WO | WO 14/197638 | 12/2014 |
| WO | WO 15/123527 | 8/2015 |
| WO | WO 2015/134877 | 9/2015 |
| WO | WO 16/036746 | 3/2016 |

OTHER PUBLICATIONS

Nelson et al., "Toll-like receptor agonist therapy can profoundly augment the antitumor activity of adoptively transferred CD8(+) T cells without host preconditioning" J. Immunother. Cancer (2016) 4:6.

Paulos et al., "Microbial translocation augments the function of adoptively transferred self/tumor-specific CD8+ T cells via TLR4 signaling" J. Clin. Invest. (2007) 117:2197-2204.

International Preliminary Report on Patentability dated Mar. 16, 2017 in International Application No. PCT/US2015/047957, filed on Sep. 1, 2015 and published as WO 2016/036749 on Mar. 10, 2016.

Office Action dated Aug. 7, 2017 in U.S. Appl. No. 14/622,018, filed Feb. 13, 2015 and published as US 2016-0046700 on Feb. 18, 2016.

Office Action dated Aug. 11, 2017 in U.S. Appl. No. 14/210,034, filed Mar. 13, 2014 and published as US 2014-0286987 on Sep. 25, 2014.

Chicaybam et al., "Chimeric Antigen Receptors in Cancer Immuno-Gene Therapy: Current Status and Future Directions" International Reviews of Immunology (2011) 30(5-6):294-311.

Koehler et al., "Engineered T Cells for the Adoptive Therapy of B-Cell Chronic Lymphocytic Leukaemia" Advances in Hematology (2012) 2012:595060. doi: 10.1155/2012/595060 1-13.

International Preliminary Report on Patentability dated Aug. 25, 2016 in International Application No. PCT/US2015/015829, filed on Feb. 13, 2015 and published as WO 2015/123527 on Aug. 20, 2015.

Extended European Search Report dated Sep. 21, 2016 in European Patent Application No. 14770399.5, filed on Mar. 13, 2014 and published as EP 2 968 502 on Jan. 20, 2016.

Search Report and Written Opinion dated Oct. 4, 2016 in Singapore Patent Application No. 11201506974X, filed on Mar. 13, 2014.

(56) References Cited

OTHER PUBLICATIONS

Curran et al., "Chimeric antigen receptors for T cell immunotherapy: current understanding and future directions" J. Gene Med. (2012) 14:405-415.
Ladanyi, "Prognostic and predictive significance of immune cells infiltrating cutaneous melanoma" Pigment Cell Melanoma Res. (2015) 28:490-500.
Office Action dated Jul. 7, 2016 in U.S. Appl. No. 14/210,034, filed Mar. 13, 2014 and published as US 2014-0286987 on Sep. 25, 2014.
Extended European Search Report dated Jul. 4, 2017 in European Patent Application No. 15748478.3, filed on Feb. 13, 2015 and published as EP 3 104 866 on Dec. 21, 2016.
Collinson-Pautz et al., "MyD88/CD40 Genetic Adjuvant Function in Cutaneous Atypical Antigen-Presenting Cells Contributes to DNA Vaccine Immunogenicity" PLOS ONE (2016) 11(10):e0164547.
Foster et al., "Regulated Expansion and Survival of Chimeric Antigen Receptor-Modified T Cells Using Small Molecule-Dependent Inducible MyD88/CD40" Molecular Therapy (2017) 25(9):1-13.
Office Action dated May 8, 2017 in U.S. Appl. No. 14/191,167, filed Feb. 26, 2014 and Published as 2014-0287490 on Sep. 25, 2014.
Hacker et al., "Specificity in Toll-like receptor signalling through distinct effector functions of TRAF3 and TRAF6" Nature (2006) 439:204-207.
Geng et al., "Amplifying TLR-MyD88 signals within tumor-specific T cells enhances antitumor activity to suboptimal levels of weakly immunogenic tumor antigens" Cancer Research (2010) 70(19):7442-7454.
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.
Adema et al., "Migration of dendritic cell based cancer vaccines: in vivo veritas?" Curr Opin Immunol. Apr. 2005;17(2):170-174.
Adema, G. J., et al., Nature, Jun. 12, 1997. 387: p. 713-7.
Albert et al., "Dendritic cell maturation is required for the cross-tolerization of CD8+ T cells." Nat Immunol. Nov. 2001;2(11):1010-1017.
Aliprantis et al., "The apoptotic signaling pathway activated by Toll-like receptor-2," EMBO J. 19(13):3325-3336, (2000).
Amara et al, "A versatile synthetic dimerizer for the regulation of protein-protein interactions." PNAS 1997;94:10618-10623.
Amara et al., "Cell surface tagging and a suicide mechanism in a single chimeric human protein" Hum. Gene Ther. (1999) 10(16):2651-5.
Anderson, D. M., et al., Nature, Nov. 13, 1997 390: p. 175-9.
Anurathapan, U. et al. Kinetics of tumor destruction by chimeric antigen receptor-modified T cells. Molecular therapy : the journal of the American Society of Gene Therapy 22, 623-633 (2014).
Arcone, et al., (1988) Nucl. Acids Res., 16(8), 3195-3207.
Ardeshna KM, et al., Blood. 2000;96:1039-1046.
Banchereau et al., "Dendritic cells as therapeutic vaccines against cancer." Nat Rev Immunol. Apr. 2005;5(4):296-306.
Banchereau J, et al., Ann N Y Acad Sci. 2003; 987:180-187.
Banchereau, J., & Steinman, R. M., Nature 392, 245-252 (1998).
Banchereau, J., et al., Annu Rev Immunol, 2000,. 18: p. 767-811.
Bander NH, et al., J Clin Oncol. 23: 4591-601, 2005.
Becker ML, Near R, Mudgett-Hunter M, et al: Expression of a hybrid immunoglobulin-T cell receptor protein in transgenic mice. Cell 58:911-21, 1989.
Belshaw et al. (Sep. 1996). "Controlling programmed cell death with a cyclophilin-cyclosporin-based chemical inducer of dimerization." Chemistry & Biology. 3(9): pp. 731-738.
Bennett et al., "Apoptosis of rat vascular smooth muscle cells is regulated by p53-dependent and -independent pathways." Circ Res. Aug. 1995;77(2):266-273.
Bennett, S. R., et al., Nature, Jun. 4, 1998, 393: p. 478-80.
Bernard et al., AIDS, 12(16):2125-2139, 1998.

Beutler B., "Inferences, questions and possibilities in Toll-like receptor signalling." Nature. Jul. 8, 2004;430(6996):257-263.
Bianco FJ, et al., Cancer Symposium: Abstract 278, 2005.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Blau, C. A. et al., Proc Natl Acad.Sci. USA 1997, 94:3076-3081.
Bloom, J.D. and F.H. Arnold, In the light of directed evolution: pathways of adaptive protein evolution. Proc Natl Acad Sci U S A, 2009. 106 Suppl 1: p. 9995-10000.
Boatright, K.M. and G.S. Salvesen, Mechanisms of Caspase activation. Curr Opin Cell Biol, 2003. 15(6): p. 725-31.
Boatright, K.M., et al., A unified model for apical Caspase activation. Mol Cell, 2003. 11(2): p. 529-41.
Bojak, A., et al., 2002. Vaccine 20:1975-79.
Boldin et al., "Involvement of MACH, a Novel MORT1/FADD-Interacting Protease, in Fas/APO-1- and TNF Receptor-Induced Cell Death," Cell vol. 85, 803-815, Jun. 14, 1996.
Bollard, C.J., et al., (2002) Blood 99:3179-3187.
Bollard, C.M., et al., (2004) J. Exptl. Med. 200:1623-1633.
Bonnert et al., GenBank Accession No. U84408, 1997.
Bonnert et al., GeneBank: AAC50954.1; GI: 1814020; Feb. 2, 1997.
Boss, W.F., et al., Basal signaling regulates plant growth and development. Plant Physiol, 2010. 154(2): p. 439-43.
Bowie et al, "Deciphering the message in protein sequences: tolerance to amino acid substitutions." Science Mar. 1990; 247:1306-1310.
Brady, S.C., L.A. Allan, and P.R. Clarke, Regulation of Caspase-9 through phosphorylation by protein kinase C zeta in response to hyperosmotic stress. Mol Cell Biol, 2005. 25(23): p. 10543-55.
Brentjens RJ, Davila ML, Riviere I, et al: CD19-targeted T cells rapidly induce molecular remissions in adults with chemotherapy-refractory acute lymphoblastic leukemia. Sci Transl Med 5:177ra38, 2013.
Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.
Cardone, M.H., et al., Regulation of cell death protease Caspase-9 by phosphorylation. Science, 1998. 282(5392): p. 1318-21.
Carpenito, et al: Control of large, established tumor xenografts with genetically retargeted human T cells containing CD28 and CD137 domains. Proc Natl Acad Sci U S A 106:3360-5, 2009.
Carter RE, et al., Proc Natl Acad Sci U S A. 93: 749-53, 1996.
Caux et al., "In vitro regulation of development and function of dendritic cells." Hematol Cell Ther. Oct. 1996;38(5):463.
Caux et al., "Activation of human dendritic cells through CD40 cross-linking" J. Exp. Med. (1994) 180:1263-72.
Caux, C. Adv Exp Med Biol. 1997, 417:21-5.
Cazeaux, N., et al., 2002. Vaccine 20:3322-31.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang SS, et al., Clin Cancer Res. 5: 2674-81, 1999.
Chang SS, et al., Urology. 57: 801-5, 2001.
Chang, W.C., et al., Modifying ligand-induced and constitutive signaling of the human 5-HT4 receptor. PLoS One, 2007. 2(12): p. e1317.
Chao, Y., et al., Engineering a dimeric Caspase-9: a re-evaluation of the induced proximity model for Caspase activation. PLoS Biol, 2005. 3(6):e183, 1079-1087.
Chatteijee, et al., (1995) Ann. N.Y. Acad. Sci., 770,79-90.
Chen and Okayama, Mol. Cell Biol., 7(8):2745-2752, 1987.
Chen et al PNAS 94: 1914-1918, 1997.
Cheung, Y.K., et al., 2004. Vaccine 23:629-38.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous

(56) References Cited

OTHER PUBLICATIONS

Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain." Science. Jul. 22, 2005;309(5734):581-585.
Christiansen JJ, et al., Mol Cancer Ther. 4: 704-14, 2005.
Ciceri, F. et al. Antitumor effects of HSV-TK-engineered donor lymphocytes after allogeneic stem-cell transplantation. Blood 109, 4698-4707 (2007).
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T (2006) Chem Biol Drug Des 67:440-2.
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke, S. R., J Leukoc Biol, 2000, May. 67: p. 607-14.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Cohen et al Nucleic Acid Res. 18:2807-2808, 1990.
Contin et al., "Membrane-anchored CD40 is processed by the tumor necrosis factor-alpha-converting enzyme. Implications for CD40 signaling." J Biol Chem. Aug. 29, 2003;278(35):32801-32809.
Coupar et al., Gene, 68:1-10, 1988.
Craddock JA, Lu A, Bear A, et al: Enhanced tumor trafficking of GD2 chimeric antigen receptor T cells by expression of the chemokine receptor CCR2b. J Immunother 33:780-8, 2010.
Cranmer et al., "Clinical applications of dendritic cell vaccination in the treatment of cancer." Cancer Immunol Immunother. Apr. 2004;54(4):275-306.
Crawford ED, et al., N Engl J Med. 321: 419-24, 1989.
Cremer et al., "Long-lived immature dendritic cells mediated by TRANCE-RANK interaction." Blood. Nov. 15, 2002;100(10):3646-3655.
Cristofanilli et al., "Circulating tumor cells, disease progression, and survival in metastatic breast cancer." N Engl J Med. Aug. 19, 2004;351(8):781-91.
Cyster JG., "Chemokines and cell migration in secondary lymphoid organs." Science. Dec. 10, 1999;286(5447):2098-2102.
Dallal RM, Lotze MT., "The dendritic cell and human cancer vaccines." Curr Opin Immunol. Oct. 2000;12(5):583-588.
Davis et al., "Crystal structure of prostate-specific membrane antigen, a tumor marker and peptidase." Proc Natl Acad Sci USA. Apr. 26, 2005;102(17):5981-5986.
De Becker et al., "The adjuvant monophosphoryl lipid A increases the function of antigen-presenting cells." Int Immunol. Jun. 2000;12(6):807-815.
De Gruijl et al, "Prolonged Maturation and Enhanced Transduction of Dendritic Cells Migrated from Human Skin Explants After in Situ Delivery of CD40-Targeted Adenoviral Vectors," The Journal of Immunology vol. 169,2002 PQS 5322-5331.
De la Taille A, et al., Cancer Detect Prev. 24: 579-88, 2000.
De Vries et al., "Effective migration of antigen-pulsed dendritic cells to lymph nodes in melanoma patients is determined by their maturation state." Cancer Res. Jan. 1, 2003;63(1):12-17.
Deml, L.A., et al., 2001. J. Virol. 75:1099-11001.
Deonarain, "Ligand-targeted receptor-mediated vectors for gene delivery," 1998, Expert Opin. Ther. Pat., vol. 8, pp. 53-69.
Di Stasi, A. et al. Inducible apoptosis as a safety switch for adoptive cell therapy. The New England journal of medicine 365, 1673-1683 (2011).

Diehl et al., "CD40 activation in vivo overcomes peptide-induced peripheral cytotoxic T-lymphocyte tolerance and augments antitumor vaccine efficacy." Nat Med. Jul. 1999;5(7):774-779.
Donnelly et al., "DNA vaccines." Annu Rev Immunol. 1997;15:617-48.
Donnelly, ML 2001, J. Gen. Virol. 82:1013-25.
Dotti, G., Gottschalk, S., Savoldo, B. & Brenner, M.K. Design and development of therapies using chimeric antigen receptor-expressing T cells. Immunological reviews 257, 107-126 (2014).
Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.
Elgueta et al., "Molecular mechanism and function of CD40/CD40L engagement in the immune system," Immunological Reviews, 229, (2009) 152-172.
Evel-Kabler et al., "SOCS1 restricts dendritic cells' ability to break self tolerance and induce antitumor immunity by regulating IL-12 production and signaling." J Clin Invest. Jan. 2006;116(1):90-100.
Fan et al., "Improved artificial death switches based on caspases and FADD." Hum Gene Ther. Sep. 20, 1999;10(14):2273-2285.
Farrar et al., "Activation of the Raf-1 kinase cascade by courmycin-induced dimerization," Nature 383, Sep. 12, 1996.
Fearon et al. "The instructive role of innate immunity in the acquired immune response," (1996) Science 272: 50-53.
Fechheimer et al., (1987) Proc. Nat'l Acad. Sci. USA, 84,8463-8467.
Fedorov, V.D., Themeli, M. & Sadelain, M. PD-1- and CTLA-4-based inhibitory chimeric antigen receptors (iCARs) divert off-target immunotherapy responses. Science translational medicine 5, 215ra172 (2013).
Fernandez, N. C., et al.,. Nat Med, Apr. 5, 1999: p. 405-11.
Ferrari et al., (1996) J. Virol., 70,3227-3234.
Ferraro, B. et al., Human Vaccines 7:120-127 (2011).
Finney HM, Akbar AN, Lawson AD: Activation of resting human primary T cells with chimeric receptors: costimulation from CD28, inducible costimulator, CD134, and CD137 in series with signals from the TCR zeta chain. J Immunol 172:104-13, 2004.
Finney HM, Lawson AD, Bebbington CR, et al: Chimeric receptors providing both primary and costimulatory signaling in T cells from a single gene product. J Immunol 161:2791-7, 1998.
Fisher et al., "Transduction with Recombinant Adeno-Associated Virus for Gene Therapy Is Limited by Leading-Strand Synthesis" (1996) J. Virol., 70,520-532.
Fisher, D.T. et al. IL-6 trans-signaling licenses mouse and human tumor microvascular gateways for trafficking of cytotoxic T cells. The Journal of clinical investigation 121, 3846-3859 (2011).
Flotte et al., Proc. Nat'l Acad. Sci. USA, 90,10613-10617, (1993).
Flotte TR, Carter BJ. "Adeno-associated virus vectors for gene therapy." Gene Ther. Aug. 1995;2(6):357-362.
Flotte, "Prospects for Virus-Based Gene Therapy for Cystic Fibrosis," Journal of Bioenergetics and Bioinformatics, vol. 25, No. 1, 1993.
Foster, A.E. et al. Autologous designer antigen-presenting cells by gene modification of T lymphocyte blasts with IL-7 and IL-12. Journal of immunotherapy 30, 506-516 (2007).
Freeman LM, et al., Q J Nucl Med. 46: 131-7, 2002.
Fujio Y, Walsh K., "Akt mediates cytoprotection of endothelial cells by vascular endothelial growth factor in an anchorage-dependent manner." J Biol Chem. Jun. 4, 1999;274(23):16349-16354.
Gaubert, G.; Wengel, J. Tetrahedron Letters 2004, 45, 5629.
Gauthier-Campbell et al., Molecular Biology of the Cell 15: 2205-2217 (2004).
Gay, N.J., Symmons, M.F., Gangloff, M. & Bryant, C.E. Assembly and localization of Toll-like receptor signalling complexes. Nature reviews. Immunology 14, 546-558 (2014).
Gefter et al., Somatic Cell Genet., 3:231-236, 1977.
GenBank Accession No. M29540, Human carcinoembryonic antigen mRNA (CEA), complete cds, Nov. 1, 1994.
Gestwicki, J.E., et al., Combinatorial Chem. & High Throughput Screening 10:667-675 (2007).
Gibson, D.G. et al. Enzymatic assembly of DNA molecules up to several hundred kilobases. Nature methods 6, 343-345 (2009).

(56) References Cited

OTHER PUBLICATIONS

Gilboa, E, Nat Rev Cancer 4, 401-11 (2004).
Gilboa, E. & Vieweg, J., Immunol Rev 199, 251-63 (2004).
Gittes RF, N Engl J Med. 324: 236-45, 1991.
Giudicelli et al., "IMGT/LIGM-DB, the IMGT comprehensive database of immunoglobulin and T cell receptor nucleotide sequences" Nucleic Acids Research (2006) 34:D781-4.
Galabati et al., Biochem. J. 303: 697-700 (1994).
Glode, "The case for adjuvant therapy for prostate cancer" Journal of Urology (2006) 176:S30-S33.
Goodman et al. (1994), Blood, 84,1492-1500.
Goodwin JS, Curr Opin Immunol. 1989;2:264-268.
Goodwin JS, et al., J Exp Med. 1977;146:1719-1734.
Gopal, T.V., Mol Cell Biol. May 1985;5(5):1188-90.
Gossen and Bujard, Proc. Natl. Acad. Sci. USA, 89:5547-5551, 1992.
Gossen et al., Science, 268:1766-1769, 1995.
Goverman J, Gomez SM, Segesman KD, et al: Chimeric immunoglobulin-T cell receptor proteins form functional receptors: implications for T cell receptor complex formation and activation. Cell 60:929-39, 1990.
Graham and van der Eb, (1973) Virology, 52, 456-467.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Gross G, Waks T, Eshhar Z: Expression of immunoglobulin-T-cell receptor chimeric molecules as functional receptors with antibody-type specificity. Proc Natl Acad Sci U S A 86:10024-8, 1989.
Gross, G., and Eshar, Z., FASEB Journal 6:3370-3378 (1992).
Grupp, S.A. et al. Chimeric antigen receptor-modified T cells for acute lymphoid leukemia. The New England journal of medicine 368, 1509-1518 (2013).
Guedan S, Chen X, Madar A, et al: ICOS-based chimeric antigen receptors program bipolar TH17/TH1 cells. Blood, 2014, 1070-1080.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.
Hanks BA, et al., Nat Med. 2005;11:130-137.
Harbury et al., "Crystal structure of an isoleucine-zipper trimer," Nature, vol. 371, Sep. 1, 1994, 80-83.
Hauer et al., PNAS 102(8): 2874-2879 (2005)).
Hay, R.T., et al., J Mol Biol. Jun. 5, 1984;175(4):493-510.
Haynes, N.M., et al. J. Immunol. 166:182-7 (2001).
He et al., "A simplified system for generating recombinant adenoviruses." Proc Natl Acad Sci USA. Mar. 3, 1998;95(5):2509-2514.
Hearing and Shenk, (1983) J. Mol. Biol. 167,809-822.
Hearing et al., J. (1987) Virol., 67, 2555-2558.
Hermans et al., "CD8+ T cell-dependent elimination of dendritic cells in vivo limits the induction of antitumor immunity." J Immunol. Mar. 15, 2000;164(6):3095-3101.
Ho, S. N. et al., Nature 1996, 382:822-826.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunologial Methods 237(2000) 159-173.
Hollstein et al Nucleic Acids Res. 22:3551-3555, 1994.
Holsinger, L. J. et al., Proc.Natl.Acad.Sci. USA 1995, 95:9810-9814.

Hombach A, Wieczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
Hong, T., et al., A simple theoretical framework for understanding heterogeneous differentiation of CD4+ T cells. BMC Syst Biol, 2012. 6: p. 66.
Horng et al., "*Drosophila* MyD88 is an adapter in the Toll signaling pathway," PNAS 98(22):12654-12658, Oct. 23, 2001.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hostager et al., "Different: CD40-mediated Signaling Events Require Distinct CD40 Structural features," J. Immunol. 157:1047-1053, Aug. 1, 1996.
Hou WS, Van Parijs L., "A Bcl-2-dependent molecular timer regulates the lifespan and immunogenicity of dendritic cells." Nat Immunol. Jun. 2004;5(6):583-589.
Hsiao, E.G., et al., Constitutive Gs activation using a single-construct tetracycline-inducible expression system in embryonic stem cells and mice. Stem Cell Res Ther, 2011. 2(2): p. 11.
Imai C, Mihara K, Andreansky M, et al: Chimeric receptors with 4-1BB signaling capacity provoke potent cytotoxicity against acute lymphoblastic leukemia. Leukemia 18:676-84, 2004.
Inaba et al., "Generation of large numbers of dendritic cells from mouse bone marrow cultures supplemented with granulocyte/macrophage colony-stimulating factor" J. Exp. Med. (1992) 176:1693-702.
Inman, B.A., Frigola, X., Dong, H. & Kwon, E.D. Costimulation, coinhibition and cancer. Current cancer drug targets 7, 15-30 (2007).
Introna, M. et al. Genetic modification of human T cells with CD20: a strategy to purify and lyse transduced cells with anti-CD20 antibodies. Human gene therapy 11, 611-620 (2000).
Ismaili J, et al., J Immunol. 2002;168:926-932.
Israeli et al Cancer Res. 53:227-230, 1993.
Israeli RS, et al., Cancer Res. 54: 1807-11, 1994.
Israeli RS, et al., Cancer Res. 54: 6306-10, 1994.
Iuliucci JD, et al., J Clin Pharmacol. 41: 870-9, 2001.
Jackson et al EMBOJ, 11:527-535, 1992.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Janeway et al. (1989) Cold Spring Harb. Symp. Quant. Biol., 54: 1-13; Medzhitov et al., Nature, 388:394-397, 1997.
Jemal A, et al., Cancer statistics, 2008. CA Cancer J Clin. 58: 71-96, 2008.
Jena, B., Moyes, J.S., Huls, H. & Cooper, L.J. Driving CAR-based T-cell therapy to success. Current hematologic malignancy reports 9, 50-56 (2014).
Jensen MC, Popplewell L, Cooper LJ, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.
Josien et al., "TRANCE, a tumor necrosis factor family member, enhances the longevity and adjuvant properties of dendritic cells in vivo." J Exp Med. Feb. 7, 2000;191(3):495-502.
Kadowaki N, et al., J Exp Med. 2001;194:863-869.
Kagan JC, Medzhitov R., "Phosphoinositide-mediated adaptor recruitment controls Toll-like receptor signaling." Cell. Jun. 2, 2006;125(5):943-955.
Kageyama et al., (1987) J. Biol. Chem., 262,2345-2351.
Kalams et al., "The critical need for CD4 help in maintaining effective cytotoxic T lymphocyte responses." J Exp Med. Dec. 21, 1998;188(12):2199-2204.

(56) References Cited

OTHER PUBLICATIONS

Kalinski et al., "Dendritic cells, obtained from peripheral blood precursors in the presence of PGE2, promote Th2 responses." Adv Exp Med Biol. 1997;417:363-367.
Kalinski P, Blood. 2001;97:3466-3469.
Kalinski P, Hilkens CM, Wierenga EA, et al: T-cell priming by type-1 and type-2 polarized dendritic cells: the concept of a third signal. Immunol Today 20:561-7, 1999.
Kalos, M. et al. T cells with chimeric antigen receptors have potent antitumor effects and can establish memory in patients with advanced leukemia. Science translational medicine 3, 95ra73 (2011).
Kamburov, A., Wierling, C., Lehrach, H. & Herwig, R. ConsensusPathDB—a database for integrating human functional interaction networks. Nucleic acids research 37, D623-628 (2009).
Kandel ES, Hay N., "The regulation and activities of the multi-functional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7)1099-105.
Kantoff et al., "Sipuleucel-T immunotherapy for castration-resistant prostate cancer." N Engl J Med. Jul. 29, 2010;363(5):411-22.
Kaplitt et al., (1994) Nat'l Genet., 8,148-153.
Kaplitt, M.G., et al., Ann Thorac Surg. Dec. 1996;62(6):1669-76.
Katari, U.L. et al. Engineered T cells for pancreatic cancer treatment. HPB : the official journal of the International Hepato Pancreato Biliary Association 13, 643-650 (2011).
Kawakami et al Proc. Nat'l Acad. Sci. USA 91:6458-6462, 1992.
Kawakarni et al, J. Exp. Med. 180:347-352, 1994.
Kehry, Marilyn R., "CD40-Mediated Signaling in B Cells, Balancing Cell Survival, Growth and Death," The American Association of Immunologists, 1996, 2345-2348.
Kelleher et al., "Lipopolysaccharide Modulation of Dendritic Cells is Insufficient to Mature Dendritic Cells to Generate CTLs from Native Polyclonal CD8+ T Cells in Vitro, Whereas CD40 Ligation is Essential," The Journal of Immunology, The American Society of Immunologists, vol. 167, No. 11, Jan. 1, 2001, pp. 6247-6255.
Kelly WK and Slovin SF, Curr Oncol Rep. 2: 394-401, 2000.
Kemnade JO, Seethammagari M, Narayanan P, et al: Off-the-shelf Adenoviral-mediated Immunotherapy via Bicistronic Expression of Tumor Antigen and iMyD88/CD40 Adjuvant. Mol Ther, 2012, 20(7):1462-71.
Kempf et al, "Improved stimulation of human dendritic cells by receptor engagement with surface-modified microparticles," J Drug Target vol. 11 No. 1, Jan. 2003 pp. 11-18.
Kershaw MH, Westwood JA, Parker LL, et al: A phase I study on adoptive immunotherapy using gene-modified T cells for ovarian cancer. Clin Cancer Res 12:6106-15, 2006.
Kessler et al., (1996) Proc. Nat'l Acad. Sci. USA, 93,14082-14087.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Kim et al., "High cleavage efficiency of a 2A peptide derived from porcine teschovirus-1 in human cell lines, zebrafish and mice" PLoS ONE (2011) 6(4):e18556.
Klein et al., (1987) Nature, 327, 70-73.
Kloss, C.C., Condomines, M., Cartellieri, M., Bachmann, M. & Sadelain, M. Combinatorial antigen recognition with balanced signaling promotes selective tumor eradication by engineered T cells. Nature biotechnology 31, 71-75 (2013).
Kobayashi et al., "IRAK-M is a negative regulator of Toll-like receptor signaling." Cell. Jul. 26, 2002;110(2)1 91-202.
Kochenderfer, J.N. et al. Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor. Journal of clinical oncology : official journal of the American Society of Clinical Oncology (2014) 540-549.
Koeberl et al., (1997) Proc. Nat'l Acad. Sci. USA, 94,1426-1431.
Kohler & Milstein, Eur. J. Immunol., 6:511-519, 1976.
Kohler & Milstein, Nature, 256:495-497, 1975.
Kopytek, S.J., et al., Chemistry & Biology 7:313-321 (2000).
Korst et al., "Effect of adenovirus gene transfer vectors on the immunologic functions of mouse dendritic cells." Mol Ther. Mar. 2002;5(3):307-315.
Kouskoff, V., et al., B cell receptor expression level determines the fate of developing B lymphocytes: receptor editing versus selection. Proc Natl Acad Sci U S A, 2000. 97(13): p. 7435-9.
Kraaij R, et al., Prostate. 62: 253-9, 2005.
Krug et al., "Toll-like receptor expression reveals CpG DNA as a unique microbial stimulus for plasmacytoid dendritic cells which synergizes with CD40 ligand to induce high amounts of IL-12." Eur J. Immunol. 31:3026-3037.
Kudo et al., "T lymphocytes expressing a CD16 signaling receptor exert antibody-dependent cancer cell killing" Cancer Research (2014) 74:93-103.
Kumar, S., et al., 2006. DNA Cell Biol. 25:383-92.
Kutzler, M.A., and Weiner, D.B., 2008. Nature Rev. Gen. 9:776-88.
Kutzler, M.A., et al., 2005. J. Immunol. 175:112-125.
Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
Kwon et al PNAS 84:7473-7477, 1987.
Labeur et al., "Generation of tumor immunity by bone marrow-derived dendritic cells correlates with dendritic cell maturation stage." J Immunol. Jan. 1, 1999;162(1):168-175.
Laddy, D.J., et al., 2008. PLoS.ONE 3 e2517.
Langenkamp et al., "Kinetics of dendritic cell activation: impact on priming of TH1, TH1 and nonpolarized T cells." Nat Immunol. Oct. 2000;1(4):311-316.
Lanitis, E. et al. Chimeric antigen receptor T Cells with dissociated signaling domains exhibit focused antitumor activity with reduced potential for toxicity in vivo. Cancer immunology research 1, 43-53 (2013).
Lanzavecchia A, Sallusto F., "Regulation of T cell immunity by dendritic cells." Cell. Aug. 10, 2001;106(3):263-266.
Lanzavecchia, A. and F. Sallusto, Science, 2000. 290: p. 92-96.
Lapointe R, et al., Eur J Immunol. 2000;30:3291-3298.
Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.
Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.
Lee DW, Gardner R, Porter DL, et al: Current concepts in the diagnosis and management of cytokine release syndrome. Blood 124:188-95, 2014.
Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.
Lee et al., "Cytoplasmic domain-mediated dimerizations of toll-like receptor 4 observed by beta-lactamase enzyme fragment complementation." J Biol Chem. Mar. 12, 2004;279(11):10564-10574.
Leo et al., "Partition coefficients and their uses." Chem Rev. Dec. 1971;71(6):525-616.
Levrero et al., Gene, 101:195-202, 1991.
Leyton, J.V. et al. Engineered humanized diabodies for microPET imaging of prostate stem cell antigen-expressing tumors. Protein engineering, design & selection: PEDS 22, 209-216 (2009).
Leyton, J.V. et al. Humanized radioiodinated minibody for imaging of prostate stem cell antigen-expressing tumors. Clinical cancer research: an official journal of the American Association for Cancer Research 14, 7488-7496 (2008).

(56) References Cited

OTHER PUBLICATIONS

Li et al., "A novel conditional Akt 'survival+A185 switch' reversibly protects cells from apoptosis." Gene Ther. Feb. 2002;9(4):233-244.
Li, V., et al., 2000. Virology 272:417-28.
Linette, G.P. et al. Cardiovascular toxicity and titin cross-reactivity of affinity-enhanced T cells in myeloma and melanoma. Blood 122, 863-871 (2013).
Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.
Liu H, et al., Cancer Res. 57: 3629-34, 1997.
Liu H, et al., Cancer Res. 58: 4055-60, 1998.
Livak et al., "Analysis of relative gene expression data using real-time quantitative PCR and the 2(-Delta Delta C(T)) Method." Methods. Dec. 2001;25(4):402-408.
Lodge et al., Dendridic Cell-based Immunotherapy of Prostate Cancer: Immune Monitoring of a Phase II Clincal Trial, Cancer Res. 60:829-833, 2000.
Loiarro et al., "Peptide-mediated interference of TIR domain dimerization in MyD88 inhibits interleukin-1-dependent activation of NF-{kappa}B." J Biol. Chem. Apr. 22, 2005;280(16)15809-15814.
Luft T, et al., Blood. 2002;100:1362-1372.
Luke et al., "The family of five: TIR-domain-containing adaptors in Toll-like receptors signaling" Nature Reviews Immunology (2007) 7:353-364.
Luning Prak, E.T., M. Monestier, and R.A. Eisenberg, B cell receptor editing in tolerance and autoimmunity. Ann N Y Acad Sci, 2011. 1217: p. 96-121.
Luo, Z. et al., Nature 1996,383:181-185.
MacCorkle, R. A. et al., Proc Natl Acad Sci USA 1998, 95:3655-3660.
Macejak and Sarnow, Nature, 353:90-94, 1991.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.
Maher J, Brentjens RJ, Gunset G, et al: Human T-lymphocyte cytotoxicity and proliferation directed by a single chimeric TCRzeta /CD28 receptor. Nat Biotechnol 20:70-5, 2002.
Malin, A.S., et al., 2000. Microbes Infect. 2:1677-85.
Malissen B, Ewbank JJ., "'TaiLoRing' the response of dendritic cells to pathogens." Nat Immunol. Aug. 2005;6(8):750-769.
Mann et al., (1983) Cell, 33,153-159.
Marsland et al., "CCL19 and CCL21 induce a potent proinflammatory differentiation program in licensed dendritic cells." Immunity. Apr. 2005;22(4):493-505.
Martin, M.C., et al., Protein kinase A regulates Caspase-9 activation by Apaf-1 downstream of cytochrome c. J Biol Chem, 2005. 280(15): p. 15449-55.
Martin S, Pahari S, Sudan R, et al: CD40 signaling in CD8+CD40+ T cells turns on contra-T regulatory cell functions. J Immunol 184:5510-8, 2010.
Martln-Fontecha et al., "Regulation of dendritic cell migration to the draining lymph node: impact on T lymphocyte traffic and priming." J Exp Med. Aug. 18, 2003;198(4):615-621.
Maude, S.L. et al. Chimeric antigen receptor T cells for sustained remissions in leukemia. The New England journal of medicine 371, 1507-1517 (2014).
Mazouz et al., "CD40 triggering increases the efficiency of dendritic cells for antitumoral immunization." Cancer Immun. Mar. 27, 2002;2:2.
McCown et al., (1996) Brain Res., 713, 99-107.
McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.
McWhirter, S. M., et al., Proc Natl Acad Sci U S A, Jul. 20, 1999. 96: p. 8408-13.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the *Drosophila* Toll protein signals activation of adaptive immunity." Nature. Jul. 24, 1997;388(6640):394-397.
Medzhitov et al., Molecular Cell, 2:253-258, 1998.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Meylan, E., et al., Nature (2006) 442:39-44.
Miga et al., "Dendritic cell longevity and T cell persistence is controlled by CD154-CD40 interactions." Eur J Immunol. Mar. 2001;31(3):959-965.
Milone MC, Fish JD, Carpenito C, et al: Chimeric receptors containing CD137 signal transduction domains mediate enhanced survival of T cells and increased antileukemic efficacy in vivo. Mol Ther 17:1453-64, 2009.
Mizukami et al., (1996) Virology, 217,124-130.
Mochizuki et al., "Akt protein kinase inhibits non-apoptotic programmed cell death induced by ceramide." J Biol Chem. Jan. 25, 2002;277(4):2790-2797.
Montgomery, D.L., et al., 1993. DNA Cell Biol. 12:777-83.
Morgan et al., "Cancer regression in patients after transfer of genetically engineered lymphocytes." Science. Oct. 6, 2006;314(5796):126-129.
Morgan, R.A., et al., (2010) Molecular Therapy 18:843-851.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., Science, 244(4910):1342-1344, 1989.
Nakagami et al., "Safety and efficacy of docetaxel, estramustine phosphate and hydrocortisone in hormone-refractory prostate cancer patients." Int J Urol. Jul. 2010;17(7):629-34.
Napolitani et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1534, and Supplementary Materials pp. 1-16.
Narayanan et al., Abstract: 4761 "The iCD40.MyD88 combovector: A new platform for enhanced DC tumor immunotherapy", Proceedings of the American Association for Cancer Research Annual Meeting, vol. 51, Apr. 15, 2010.
Narum, D.L., et al., 2001. 69:7250-55.
Nestle et al., "Dendritic cells: On the move from bench to bedside." Nat Med. Jul. 2001;7(7):761-765.
Ni, C., et al., PNAS, 2000, 97(19): 10395-10399.
Nicolau et al., (1987) Methods Enzymol., 149,157-176.
Nishiya et al., "Ligand-regulated chimeric receptor approach reveals distinctive subcellular localization and signaling properties of the Toll-like receptors," J. Biol, Chem. 279(18):19008-19017, 2004.
Nociari et al., J. Immunol. Methods, 213(2): 157-167, 1998.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve

(56) References Cited

OTHER PUBLICATIONS

Growth Factor Receptor Superfamily, Sequence Identity With the Fas Antigen*," The Journal of Biological Chemistry, vol. 267, No. 15, May 25, 1992 10709-10715.
Ohshima, Y., et al., J Immunol, Oct. 15, 1997. 159: p. 3838-48.
Oliviero et al., (1987) EMBO J., 6, 1905-1912.
O'Neill DW, et al., Blood. 2004;104:2235-2246.
O'Sullivan B, Thomas R., "CD40 and dendritic cell function." Crit Rev Immunol. 2003 ;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Page, B., et al., Anticancer Res. Jul.-Aug. 1998;18(4A):2313-6.
Palecek et al., "Integrin-ligand binding properties govern cell migration speed through cell-substratum adhesiveness." Nature. Feb. 6, 1997;385(6616):537-540.
Papworth, C., Bauer, J. C., Braman, J. and Wright, D. A., Site-directed mutagenesis in one day with >80% efficiency. Strategies, 1996. 9(3): p. 3-4.
Park et al, "An essential role for Akt1 in dendritic cell function and tumor immunotherapy," Nature Biology, vol. 24, No. 12, Dec. 2006, pp. 1581-1590.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Park JR, Digiusto DL, Slovak M, et al: Adoptive transfer of chimeric antigen receptor redirected cytolytic T lymphocyte clones in patients with neuroblastoma. Mol Ther 15:825-33, 2007.
Pasare C, Medzhitov R., "Toll pathway-dependent blockade of CD4+CD25+ T cell-mediated suppression by dendritic cells." Science. Feb. 14, 2003;299(5609)1033-1036.
Paskind et al., (1975) Virology, 67,242-248.
Pelletier and Sonenberg, Nature, 334:320-325, 1988.
Perales et al., Proc. Natl. Acad. Sci. USA, 91:4086-4090, 1994.
Philip, B. et al. A highly compact epitope-based marker/suicide gene for easier and safer T-cell therapy. Blood 124, 1277-1287 (2014).
Ping et al., (1996) Microcirculation, 3,225-228.
Pinto JT, et al., Clin Cancer Res. 2: 1445-51, 1996.
Poli and Cortese, (1989) Proc. Nat'l Acad. Sci. USA, 86,8202-8206.
Porter, D.L., Levine, B.L., Kalos, M., Bagg, A. & Jun., C.H. Chimeric antigen receptor-modified T cells in chronic lymphoid leukemia. The New England journal of medicine 365, 725-733 (2011).
Potter et al., (1984) Proc. Nat'l Acad. Sci. USA, 81, 7161-7165.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.
Prowse and Baumann, (1988) Mol Cell Biol, 8,42-51.
Pruschy et al., "Mechanistic Sutdies of a Signaling Pathway Activated by the Organic Dimerizer FK1012," Chemistry and Biology 1994 vol. 1, No. 3, 163-172.
Puccetti et al., "Effects of IL-12 and IL-23 on antigen-presenting cells at the interface between innate and adaptive immunity." Crit Rev Immunol. 2002;22(5-6):373-390.
Pule, et al: A chimeric T cell antigen receptor that augments cytokine release and supports clonal expansion of primary human T cells. Mol Ther 12:933-41, 2005.
Pule, et al: Virus-specific T cells engineered to coexpress tumor-specific receptors: persistence and antitumor activity in individuals with neuroblastoma. Nat Med 14:1264-70, 2008.
Pullen, S.S., et al., J Biol Chem, May 14, 1999.274: p. 14246-54.
Raina, D., et al., c-Abl tyrosine kinase regulates Caspase-9 autocleavage in the apoptotic response to DNA damage. J Biol Chem, 2005. 280(12): p. 11147-51.
Randall, K.L., et al., Dock8 mutations cripple B cell immunological synapses, germinal centers and long-lived antibody production. Nat Immunol, 2009. 10(12): p. 1283-91.

Ramos CA, Dotti G: Chimeric antigen receptor (CAR)-engineered lymphocytes for cancer therapy. Expert Opin Biol Ther 11:855-73, 2011.
Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.
Re F, Strominger JL., "Toll-Ike receptor 2(TLR2) and TLR4 differentially activate human dendritic cells." J Biol Chem. Oct. 5, 2001;276(40):37692-37699.
Reis e Sousa C., "Dendritic cells as sensors of infection." Immunity. May 2001;14(5):495-498.
Renan, M. J. (1990) Radiother Oncol., 19, 197-218.
Renatus, M., et al., Dimer formation drives the activation of the cell death protease Caspase-9. Proc Natl Acad Sci U S A, 2001. 98(25): p. 14250-5.
Rescigno M, et al., J Exp Med. 1998;188:2175-2180.
Resh et al., "Fatty acylation of proteins: new insights into membrane targeting of myristoylated and palmitoylated proteins" Biochim. Biophys. Acta. (1999) 1451:1-16.
Richard et al, "Expansion of Genetically modified Primary Human HemopOietic cells Using Chemical Inducers of Dimerization," Blood vol. 95, 2000 pp. 430-436.
Rickert, R.C., Jellusova, J. & Miletic, A.V. Signaling by the tumor necrosis factor receptor superfamily in B-cell biology and disease. Immunological reviews 244, 115-133 (2011).
Ridge, J. P., D. R. F, and P. Nature, Jun. 4, 1998. 393: p. 474-8.
Ridgway D., "The first 1000 dendritic cell vaccinees." Cancer Invest. 2003;21(6):873-886.
Riol-Blanco et al., "The chemokine receptor CCR7 activates in dendritic cells two signaling modules that independently regulate chemotaxis and migratory speed." J Immunol. Apr. 1, 2005;174(7):4070-4080.
Rippe et al., Mol. Cell Biol., 10:689-695, 1990.
Rivera, V. M. et al., Nat.Med. 1996, 2:1028-1032.
Rivera, V.M., "Controlling Gene Expression USing SynthetiC Ligands," Methods: A companion to Methods in Enzymology vol. 14,1998 pp. 421-429.
Riviere, I., Brose, K. & Mulligan, R.C. Effects of retroviral vector design on expression of human adenosine deaminase in murine bone marrow transplant recipients engrafted with genetically modified cells. Proceedings of the National Academy of Sciences of the United States of America 92, 6733-6737 (1995).
Ron, et al., (1991) Mol. Cell. Biol., 2887-2895.
Ronni et al., "Common interaction surfaces of the toll-like receptor 4 cytoplasmic domain stimulate multiple nuclear targets," Molecular and Cellular Biology, Apr. 2003, vol. 23, No. 7, pp. 2543-2555.
Roose, J.P., et al., T cell receptor-independent basal signaling via Erk and Abl kinases suppresses RAG gene expression. PLoS Biol, 2003. 1(2): p. E53.
Rosenberg SA, Immunity. 1999;10:281-287.
Roux et al., (1989) Proc. Nat'l Acad. Sci. USA, 86, 9079-9083.
Rudd, M.L., A. Tua-Smith, and D.B. Straus, Lck SH3 domain function is required for T-cell receptor signals regulating thymocyte development. Mol Cell Biol, 2006. 26(21): p. 7892-900.
Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.
Salkowski et al., "Lipopolysaccharide and monophosphoryl lipid a differentially regulate interleukin-12, gamma interferon, and interleukin-10 mRNA production in murine macrophages." Infect Immun. Aug. 1997;65(8):3239-3247.
Sallusto, F., et al., Eur J Immunol, Sep. 28, 1998: p. 2760-9.
Samulski et al., J. Virol., 61:3096-3101 (1987).
Sanchez-Sanchez et al., "The multiple personalities of the chemokine receptor CCR7 in dendritic cells." J Immunol. May 1, 2006;176(9):5153-5159.
Sardesai, N.Y., and Weiner, D.B., Current Opinion in Immunotherapy 23:421-9 (2011).

(56) References Cited

OTHER PUBLICATIONS

Sato et al., "Combination of monocyte-derived dendrinic cells and activated T cells which express CD40 ligand an new approach to cancer Immunotherapy," Cancer Imminol Immunther, vol. 53, No. 1, Jan. 2004, pp. 53-61.
Savoldo B, Ramos CA, Liu E, et al: CD28 costimulation improves expansion and persistence of chimeric antigen receptor-modified T cells in lymphoma patients. J Clin Invest 121:1822-6, 2011.
Scandella E, et al., Blood. 2002;100:1354-1361.
Scandella et al., "CCL19/CCL21-triggered signal transduction and migration of dendritic cells requires prostaglandin E2." Blood. Mar. 1, 2004;103(5)1595-1601.
Schellhammer PF, et al., J Urol. 157: 1731-5, 1997.
Schenten D, Nish SA, Yu S, et al: Signaling through the adaptor molecule MyD88 in CD4+ T cells is required to overcome suppression by regulatory T cells. Immunity 40:78-90, 2014.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7)1148-59.
Scher HI, et al., J Natl Cancer Inst. 88: 1623-34, 1996.
Scher, H.I. and Kelly, W.K., Journal of Clinical Oncology 11, 1566-72 (1993).
Schneider, R. M., et al., 1997. J. Virol. 71:4892-4903.
Schoenberger, S. P., et al., Nature, Jun. 4, 1998. 393: p. 480-3.
Schram, B.R., et al., B cell receptor basal signaling regulates antigen-induced Ig light chain rearrangements. J Immunol, 2008. 180(7): p. 4728-41.
Schuler et al., "Dendritic cells as adjuvants for immune-mediated resistance to tumors" J. Exp. Med. (1997) 186:1183-7.
Schuler et al., "The use of dendritic cells in cancer immunotherapy." Curr Opin Immunol. Apr. 2003; 15(2):138-147.
Schultz et al., "CD40 triggering of heterodimeric IL-12 p70 production by dendritic cells in vivo requires a microbial priming signal," Immunity, vol. 13, No. 4, Oct. 2000. pp. 453-462.
Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).
Schweitzer et al., J. Org. Chem., 59:7238-7242 (1994).
Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
Shaffer et al., "Circulating tumor cell analysis in patients with progressive castration-resistant prostate cancer." Clin Cancer Res. Apr. 1, 2007;13(7):2023-9.
Shen et al., "Silencing of SOCS1 enhances antigen presentation by dendritic cells and antigen-specific anti-tumor immunity." Nat Biotechnol. Dec. 2004;22(12):1546-1553.
Shiozaki, E.N., J. Chai, and Y. Shi, Oligomerization and activation of Caspase-9, induced by Apaf-1 CARD. Proc Natl Acad Sci U S A, 2002. 99(7): p. 4197-202.
Shiozaki, E.N., et al., Mechanism of XIAP-mediated inhibition of Caspase-9. Mol Cell, 2003. 11(2): p. 519-27.
Shi, Y., Mechanisms of Caspase activation and inhibition during apoptosis. Mol Cell, 2002. 9(3): p. 459-70.
Silver DA, et al., Clin Cancer Res. 3: 81-5, 1997.
Simpson et al., Gastroenterology, 115(4):849-855, 1998.
Small EJ and Srinivas S, Cancer. 76: 1428-34, 1995.
Small EJ and Vogelzang NJ, J Clin Oncol. 15: 382-8, 1997.
Smith et al., "Cognate CD4(+) T cell licensing of dendritic cells in CD8(+) T cell immunity." Nat Immunol. Nov. 2004;5(11):1142-1148.
Smith, J.M., et al., 2004. AIDS Res. Hum. Retroviruses 20:1335-47.
Snyder DS, Nature. 1982;299:163-165.
Song, D.G. et al. CD27 costimulation augments the survival and antitumor activity of redirected human T cells in vivo. Blood 119, 696-706 (2012).
Sonpavde, et al., "Vaccine therapy for prostate cancer", Urologic Oncology, Elsevier, NY, vol. 25, No. 6, Nov. 1, 2007, 451-459.
Sorensen et al., "Endostatin reduces cascularization, blood flow, and growth in a rat gliosarcoma." Neuro Oncol. Jan. 2002;4(1):1-8.
Sorkin, A. and M. von Zastrow, Endocytosis and signalling: intertwining molecular networks. Nat Rev Mol Cell Biol, 2009. 10(9): p. 609-22.
Spencer D. M. et al., Curr Biol 1996, 6:839-847.
Spencer D. M. et al., Proc.Natl.Acad.Sci. USA 1995, 92:9805-9809.
Spencer DM, et al., Science. 1993;262:1019-1024.
Spiegel, A.M., Defects in G protein-coupled signal transduction in human disease. Annu Rev Physiol, 1996. 58: p. 143-70.
Sporri R, Reis e Sousa C., "Inflammatory mediators are insufficient for full dendritic cell activation and promote expansion of CD4+ T cell populations lacking helper function." Nat Immunol. Feb. 2005;6(2):163-170.
Steinman RM, Annu Rev Immunol. 2003;21:685-711.
Steinman RM, Pope M., "Exploiting dendritic cells to improve vaccine efficacy." J Clin Invest. Jun. 2002;109(12):1519-1526.
Stennicke, H.R., et al., Caspase-9 can be activated without proteolytic processing. J Biol Chem, 1999. 274(13): p. 8359-62.
Straathof, K.C. et al. An inducible caspase 9 safety switch for T-cell therapy. Blood 105, 4247-4254 (2005).
Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.
Strober, W., et al., Nature Reviews (2006) 6:9-20.
Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.
Su SL, et al., Cancer Res. 55: 1441-3, 1995.
Suarez-Alvarez et al, Epigenetic Mechanisms Regulate MHC and Antigen Processing Moleculers in Human Embryonic and Induced Pluripotent Stem Cells. PLoS ONE (April) 5(4):e10192, 2010, pp. 1-12.
Subramanian, A. et al. Gene set enrichment analysis: a knowledge-based approach for interpreting genome-wide expression profiles. Proceedings of the National Academy of Sciences of the United States of America 102, 15545-15550 (2005).
Suda et al., "Molecular Cloning and Expression of the Fas Ligand, a Novel Member of the Tumor Necrosis Factor Family," Cell vol. 75, 1169-1176 Dec. 17, 1993.
Szymczak et al., "Correction of multi-gene deficiency in vivo using a single 'self-cleaving' 2A peptide-based retroviral vector" Nature Biotechnology (2004) 22:589-94.
Tai et al., Cancer Research 64, 2846-2852 (2004).
Tao, Y.X., Constitutive activation of G protein-coupled receptors and diseases: insights into mechanisms of activation and therapeutics. Pharmacol Ther, 2008. 120(2): p. 129-48.
Ten Klooster JP et al, Biology of the Cell (2007) 99, 1-12.
Tepler, I, et al. (1989) J. Biol. Chem. 264:5912.
Termeer, C. C., et al., J Immunol, Aug. 15, 2000. 165: p. 1863-70.
Thompson et al., "The low-toxicity versions of LPS, MPL adjuvant and RC529, are efficient adjuvants for CD4+ T Cells." J Leukoc Biol. Dec. 2005:78(6)1273-1280.
Tibbetts et. al. (1977) Cell, 12,243-249.
Till BG, Jensen MC, Wang J, et al: CD20-specific adoptive immunotherapy for lymphoma using a chimeric antigen receptor with both CD28 and 4-1BB domains: pilot clinical trial results. Blood 119:3940-50, 2012.
Timmerman et al., "Dendritic cell vaccines for cancer immunotherapy", Annu. Rev. Med. (1999) 50:507-29.
Tone, M., et al., Proc Natl Acad Sci U S A, 2001. 98(4): p. 1751-1756.
Tong et al, "Prospects for CD40-directed Experimental Therapy of Human Cancer," Cancer Gene Therapy vol. 10, 2003, pp. 1-13.
Troyer JK, et al., Int J Cancer. 62: 552-8, 1995.
Tur-Kaspa et al., (1986) Mol. Cell Biol., 6,716-718.
Tze, L.E., et al., Basal immunoglobulin signaling actively maintains developmental stage in immature B cells. PLoS Biol, 2005. 3(3): p. e82.

(56) References Cited

OTHER PUBLICATIONS

Van der Pouw Kraan TC, et al., J Exp Med. 1995;181:775-779.
Vassiliou et al., "Prostaglandin E2 promotes the survival of bone marrow-derived dendritic cells." J Immunol. Dec. 1, 2004;173(11):6955-6964.
Vera, J. et al. T lymphocytes redirected against the kappa light chain of human immunoglobulin efficiently kill mature B lymphocyte-derived malignant cells. Blood 108, 3890-3897 (2006).
Vidalain et al., "CD40 signaling in human dendritic cells is initiated within membrane rafts." EMBO J. 2000; 19:3304-3313.
Vieweg J, et al., Springer Semin Immunopathol. 2005;26:329-341.
Vieweg, "Immunotherapy for Advanced Prostate Cancer," vol. 9 Suppl. 1 (2007) Reviews in Urology S29-S38.
Vincent, S., et al., Nature Biotechnology 21:936-40, 1098 (2003).
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "IL-12p70-Dependent Th1 Induction by Human B Cells Requires Combined Activation with CD40 Ligand and CpG DNA", Journal of Immunology, vol. 172, 2004, 954-963.
Wagner et al., Proc. Natl. Acad. Sci. USA, 87(9):3410-3414, 1990.
Waldner, C., et al., Double conditional human embryonic kidney cell line based on FLP and PhiC31 mediated transgene integration. BMC Res Notes, 2011. 4: p. 420.
Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
Wang, S., et al., 2006. Vaccine 24:4531-40.
Werneburg et al., "Molecular Characterization of CD40 Signaling Intermediates," The Journal of Biological Chemistry, vol. 276, Nov. 16, 2001, 43334-43342.
Werts C., et al., Cell Death and Differentiation (2006) 13:798-815.
Wesemann et al., "Suppressor of cytokine signaling 1 inhibits cytokine induction of CD40 expression in macrophages." J Immunol. Sep. 1, 2002;169(5):2354-2360.
Wilson et al., (1990) Mol. Cell. Biol., 6181-6191.
Wilson et al., Science, 244:1344-1346, 1989.
Wolchok et al., "Guidelines for the Evaluation of Immune Therapy Activity in Solid Tumors: Immune-Related Response Criteria," Clin Cancer Res 2009;15(23) Dec. 1, 2009, pp. 7412-7420.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright GL, Jr., et al., Urology. 48: 326-34, 1996.
Wu and Wu, (1987) J. Biol. Chem., 262, 4429-4432.
Wu and Wu, Adv. Drug Delivery Rev., 12:159-167, 1993.
Wu, X., et al., 2004. Biochem. Biophys. Res. Commun. 313:89-96.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xiao et al., (1996) J. Virol., 70,8098-8108.
Xie et al., "Adenovirus-mediated tissue-targeted expression of a caspase-9-based artificial death switch for the treatment of prostate cancer." Cancer Res. Sep. 15, 2001;61(18):6795-6804.
Xu, Z.L., et al. 2001. Gene 272:149-56.
Yadava, A., and Ockenhouse, C.F., 2003. Infect. Immun. 71:4962-69.
Yan, J. et al., 2007. Mol. Ther. 15:411-21.
Yanagawa Y, Onoe K., "CCL19 induces rapid dendritic extension of murine dendritic cells." Blood. Sep. 15, 2002;100(6)1948-1956.
Yang et al., (1990) Proc. Nat'l Acad. Sci. USA, 87, 9568-9572.
Yang, J.S., et al., 2002. Emerg. Infect. Dis. 8:1379-84.
Yvon E, Del Vecchio M, Savoldo B, et al: Immunotherapy of metastatic melanoma using genetically engineered GD2-specific T cells. Clin Cancer Res 15:5852-60, 2009.
Zechner et al., Mol. Cell. Biol., 2394-2401, 1988.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "Anti-melanoma activity of T cells redirected with a TCR-like chimeric antigen receptor" Scientific Reports (2014) 4:3571.
Zhang et al., "Retargeting NK-92 for anti-melanoma activity by a TCR-like single-domain antibody" Immunol. Cell. Biol. (2013) 91(10):615-24.
Zhang, W., et al., 2006. Biochem. Biophys. Res. Commun. 349:69-78.
Zhang, Y., et al., PLOS Pathogens 6:1-13 (2010).
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zhao Y, Wang QJ, Yang S, et al: A herceptin-based chimeric antigen receptor with modified signaling domains leads to enhanced survival of transduced T lymphocytes and antitumor activity. J Immunol 183:5563-74, 2009.
Zhong XS, et al., Mol Ther. Feb. 2010; 18(2):413-20.
Zhou, W., et al., 2002. Vet. Microbiol. 88:127-51.
Zitvogel L, et al., J Exp Med 1996. 183:87-97.
Zlakine et al., J. Cell Science 110: 673-679 (1997).
Zur Medege et al., "Expression and immunogenicity of sequence-modified human immunodeficiency virus type 1 subtype B pot and gagpol DNA vaccines." J Virol. Jun. 2003;77(11):6197-6207.
Zur Megede, J., et al., 2000. J. Virol. 74:2628-2635.
International Search Report and Written Opinion dated Dec. 3, 2014 in International Application No. PCT/US2014/26734 filed Mar. 13, 2014 and published as: WO 2014/151960 on: Sep. 24, 2014.
International Search Report and Written Opinion dated Jun. 29, 2015 in International Application No. PCT/US2015/015829, filed on Feb. 13, 2015 and published as WO 2015/123527 on Aug. 20, 2015.
International Preliminary Report on Patentability dated Sep. 24, 2015 in International Application No. PCT/US2014/026734, filed on Mar. 13, 2014 and published as WO 2014/151960 on Sep. 25, 2014.
International Search Report and Written Opinion dated Dec. 28, 2015 in International Application No. PCT/US2015/047957, filed on Sep. 1, 2015 and published as WO 2016/036749 on Mar. 10, 2016.
Office Action dated Feb. 8, 2016 in U.S. Appl. No. 14/210,034, filed Mar. 13, 2014 and published as US 2014-0286987 on Sep. 25, 2014.
ARIAD Pharmaceuticals, Inc., "ARGENT Regulated Homodimerization Kit" Version 2.0, product brochure, Sep. 9, 2002.
Office Action dated Dec. 5, 2017 in U.S. Appl. No. 14/210,034, filed Mar. 13, 2014 and published as US 2014-0286987 on Sep. 25, 2014.
Office Action dated Feb. 1, 2018 in U.S. Appl. No. 14/622,018, filed Feb. 13, 2015 and published as US 2016-0046700 on Feb. 18, 2016.
Written Opinion dated Feb. 7, 2018 in Singapore Patent Application No. 11201506974X, filed on Mar. 13, 2014.
Extended European Search Report dated Apr. 5, 2018 in European Patent Application No. 15838927.0, filed on Sep. 1, 2015 and published as EP 3 189 148 on Jul. 12, 2017.
Office Action dated Sep. 14, 2018 in U.S. Appl. No. 14/622,018, filed Feb. 13, 2015 and published as US 2016-0046700 on Feb. 18, 2016.
Foster et al., "MyD88/CD40 Enhanced CD19-Specific CAR-T Cells Maintain Therapeutic Efficacy Following Resolution of Cytokine-Related Toxicity Using Inducible Caspase-9" Blood (2017) 130(S1):4615.
Office Action dated Dec. 17, 2018, in U.S. Appl. No. 15/399,512.
Response to Office Action filed Apr. 16, 2019, in U.S. Appl. No. 15/399,512.
Office Action dated May 25, 2018, in U.S. Appl. No. 15/399,512.

(56) References Cited

OTHER PUBLICATIONS

Response to Office Action filed Aug. 23, 2018, in U.S. Appl. No. 15/399,512.
Office Action dated May 20, 2019, in U.S. Appl. No. 14/622,018.
Response to Office Action filed Mar. 13, 2019, in U.S. Appl. No. 14/622,018.
Office Action dated Sep. 29, 2017, in U.S. Appl. No. 14/191,167.
Response to Office Action filed Aug. 30, 2017, in U.S. Appl. No. 14/191,167.
Response to Office Action filed Mar. 14, 2017, in U.S. Appl. No. 14/191,167.
Office Action dated Sep. 15, 2016, in U.S. Appl. No. 14/191,167.
Response to Office Action filed Jul. 26, 2016, in U.S. Appl. No. 14/191,167.
Office Action dated Apr. 18, 2016, in U.S. Appl. No. 14/191,167.
Response to Office Action filed Feb. 25, 2016, in U.S. Appl. No. 14/191,167.
Office Action dated Nov. 24, 2015, in U.S. Appl. No. 14/191,167.
Response to Office Action filed May 9, 2017, in U.S. Appl. No. 14/210,034.
Response to Office Action filed Jan. 6, 2017, in U.S. Appl. No. 14/210,034.
Response to Office Action filed Aug. 1, 2017 filed in U.S. Appl. No. 14/210,034.
Response to Office Action filed Nov. 9, 2017, in U.S. Appl. No. 14/210,034.
Response to Office Action filed Nov. 7, 2017, in U.S. Appl. No. 14/622,018.
Office Action dated Feb. 1, 2018, in U.S. Appl. No. 14/622,018.
Response to Office Action filed May 1, 2018, in U.S. Appl. No. 14/622,018.
Abraham and Weiss, 2004, "Jurkat T cells and development of the T-cell receptor signaling paradigm," Nat. Rev. Immunol., 4(4):301-308.
Breitbach et al., 2007, "Potential risks of bone marrow cell transplantation into infarcted hearts", Blood, 110(4):1362-9.
Collinson-Pautz et al., 2019, "Constitutively active MyD88/CD40 costimulation enhances expansion and efficacy of chimeric antigen receptor T cells targeting hematological malignancies", Leukemia: 13 pages.
Foster et al. 2014, "Inducible MyD88/CD40 allows AP1903-dependent costimulation to control proliferation and survival of chimeric antigen receptor-modified t cells", Blood Journal: 1121.
Foster et al. 2015, "Inducible MyD88/CD40 allows rimiducid-dependent activation to control proliferation and survival of chimeric antigen receptor-modified t cells", Blood Journal: 4295.
GenBank Accession No. AAA58476.1, FK506-binding protein 12 [*Homo sapiens*], Feb. 12, 2001 [retrieved Mar. 12, 2019]. Retrieved from the internet <URL: https://www.ncbi.nlm.nih.gov/protein/182649?sat=4&satkey=34 1111 66>.
Kuby, J., 1997, Immunology, New York, W. H. Freeman and Company, p. 47-83.
Leriche et al., 2012, "Cleavable linkers in chemical biology," Bioorg. & Med. Chem., 20:571-582.
Iuliucci et al., 2001, "Intravenous safety and pharmacokinetics of a novel dimerizer drug, AP1903, in healthy volunteers", J Clin Pharmacol., 41:870-879.
Mata et al., 2017, "Inducible activation of MyD88 and CD40 in CAR T cells result in controllable and potent antitumor activity in preclinical solid tumor models", Cancer Discovery, 7(11):1306-1319.
Nakagawa et al., 2013, "Development of next-generation adoptive immunotherapy using cytotoxic T-lymphocyte (CTL) expressing chimeric antigen-receptor (CAR)," Drug Delivery System, 28(1):35-44, in Japanese with an English abstract.
Temin et al., 1986, In: Gene Transfer, Kucherlapati (ed.), New York: Plenum Press, pp. 149-188.

\* cited by examiner

Example 12. Constitutively active MyD88/CD40 for CAR-T costimulation

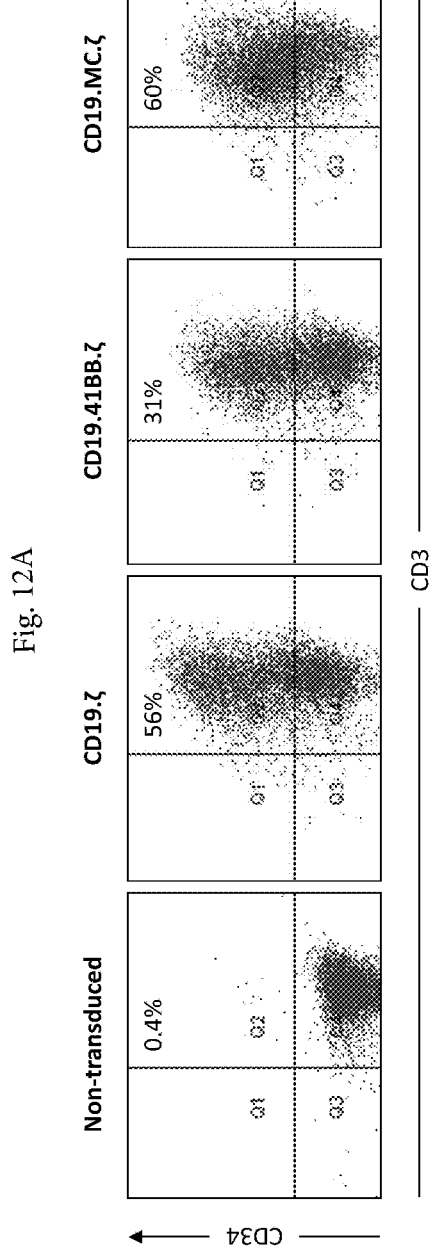
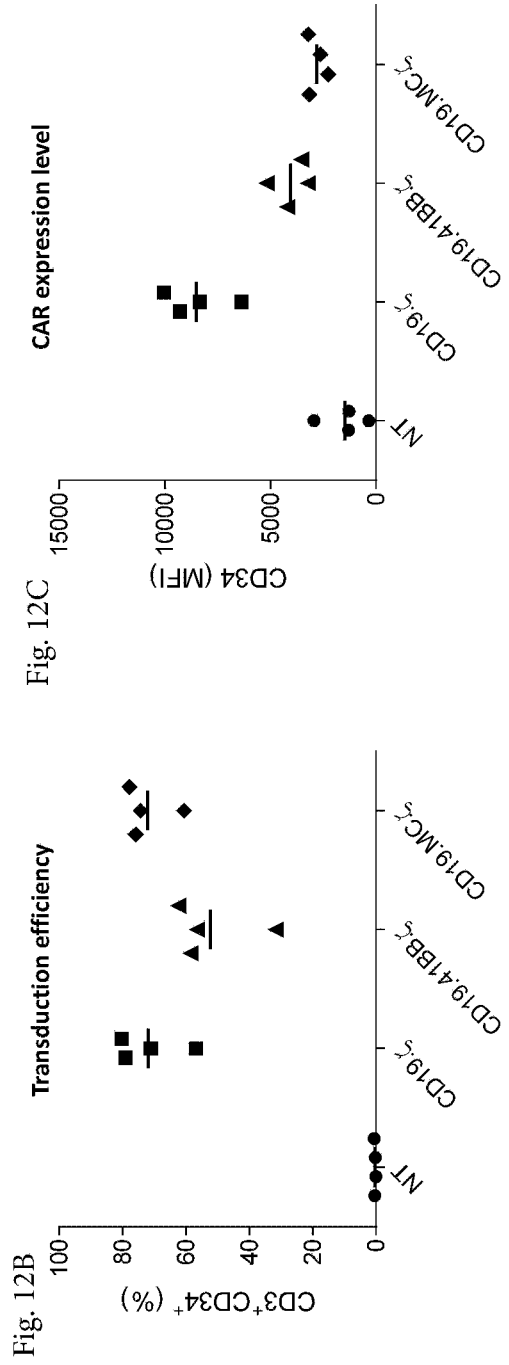
Fig. 12A
Fig. 12B
Fig. 12C

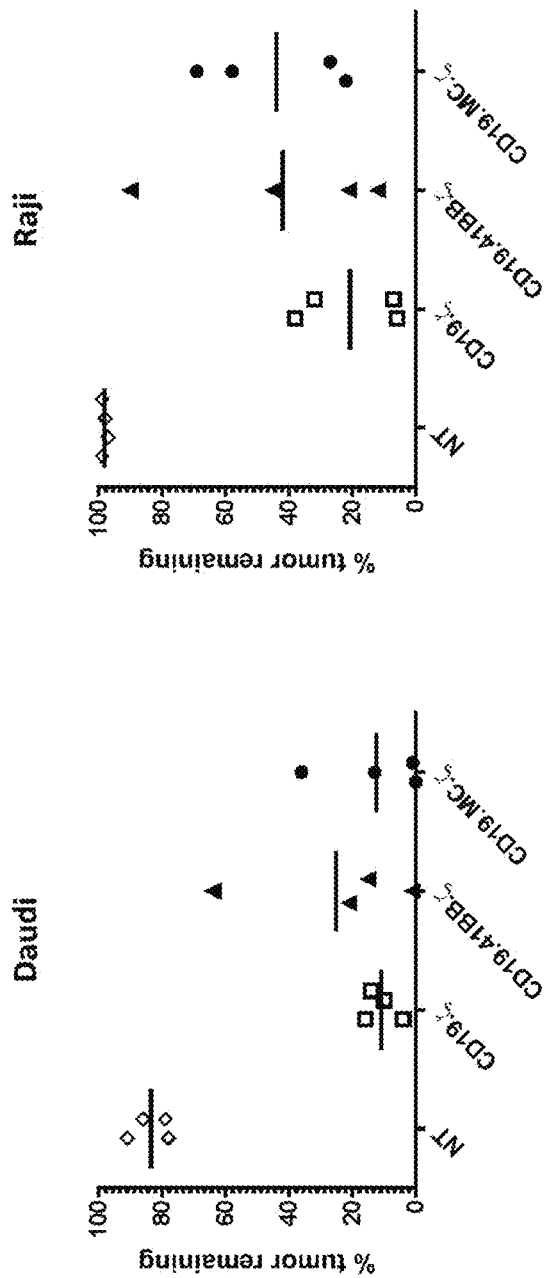

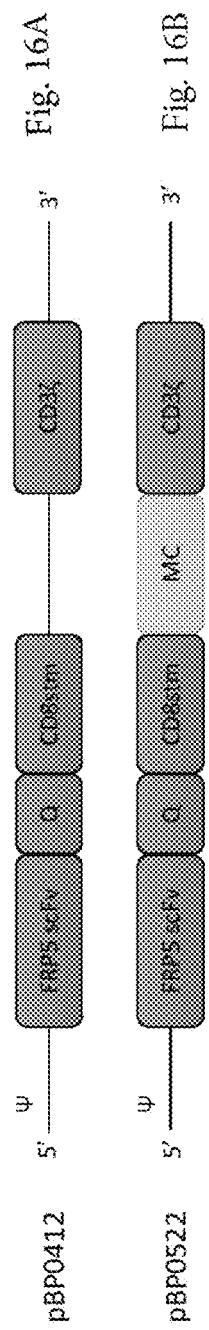

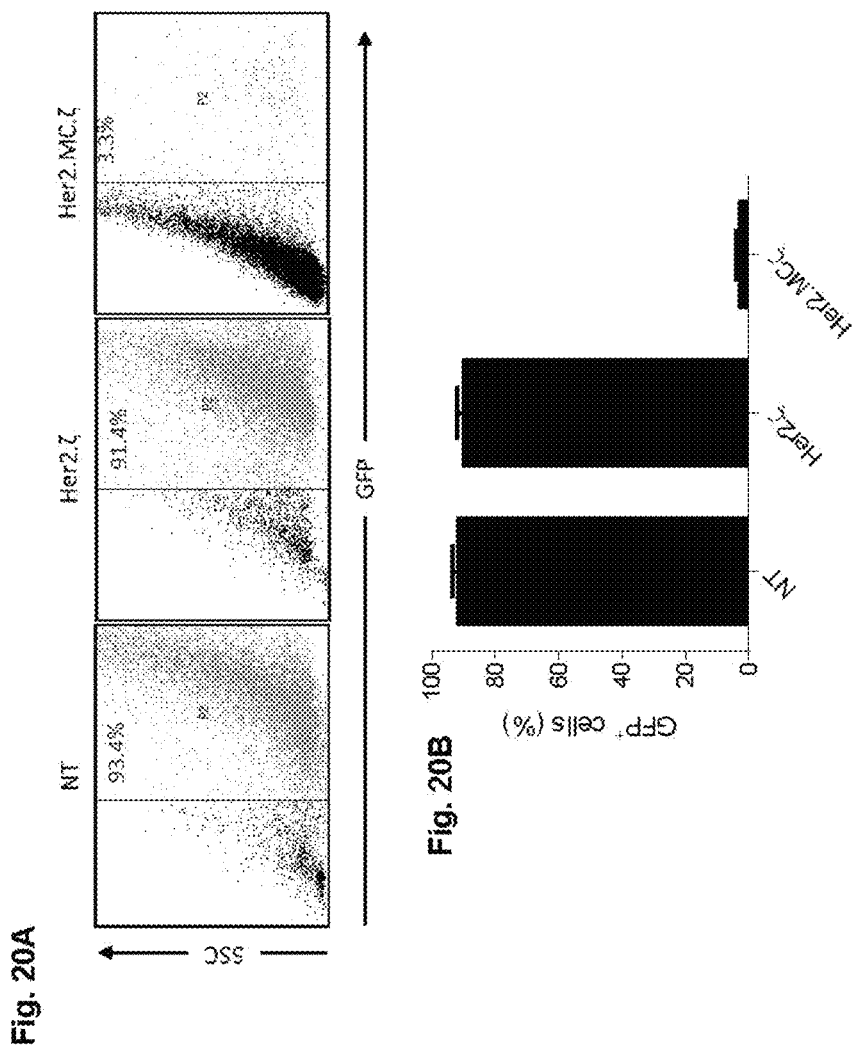

SFG-Myr.MC-2A-CD19scFv.CD34e.CD8stm.zeta
8589 bp

Fig. 26A  SFG-iCasp9.2A.CD19.ζ
Fig. 26B  SFG-iCasp9.2A.CD19.28.ζ
Fig. 26C  SFG-iCasp9.2A.CD19.MC.ζ
Fig. 26D  SFG-iCasp9.2A.CD19.ζ.2A.MC

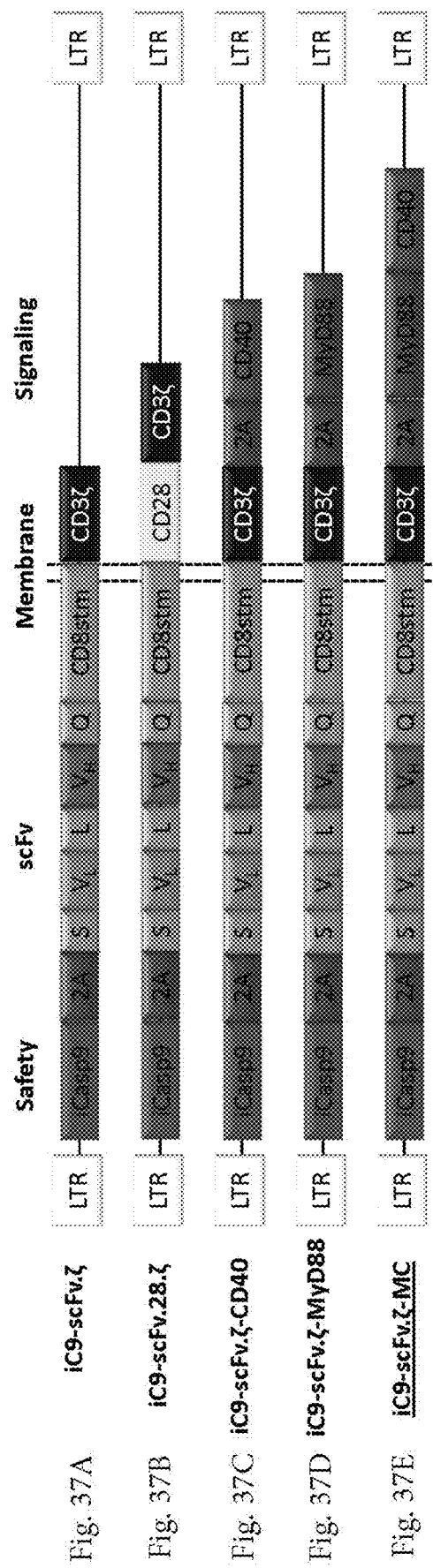

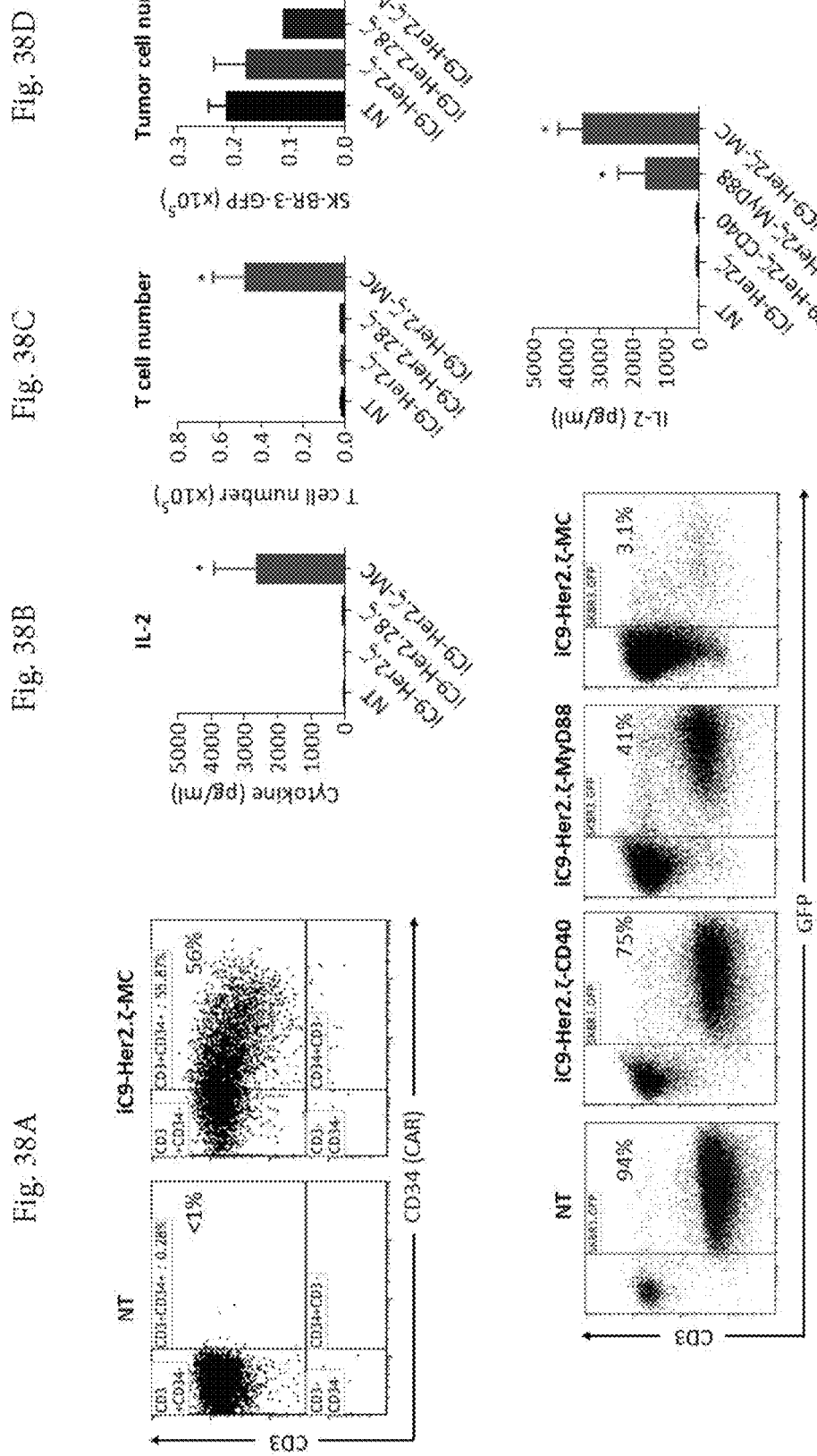

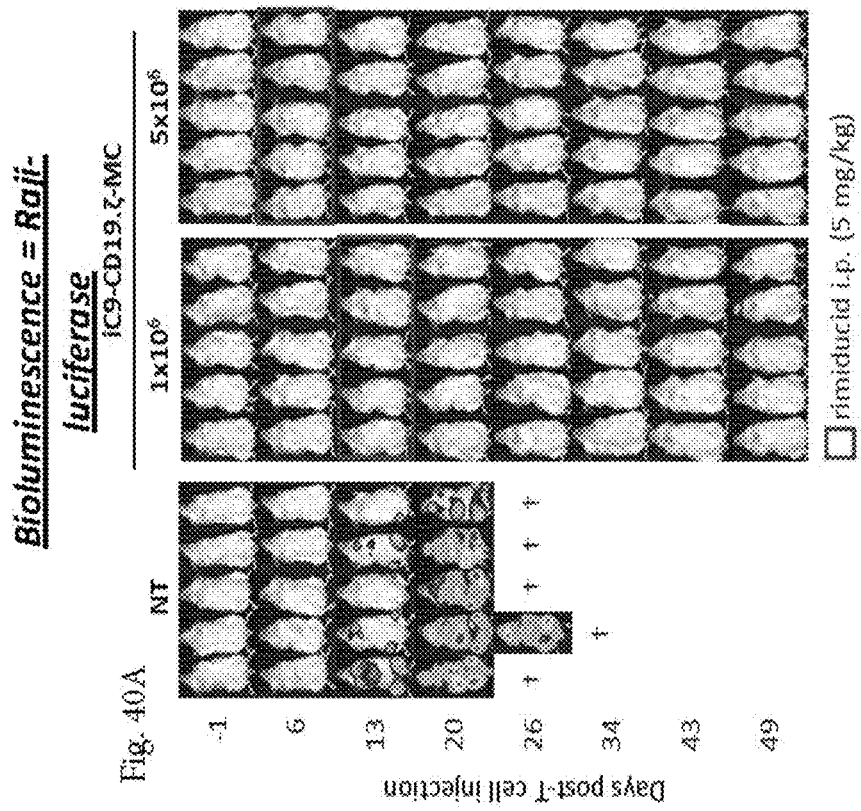

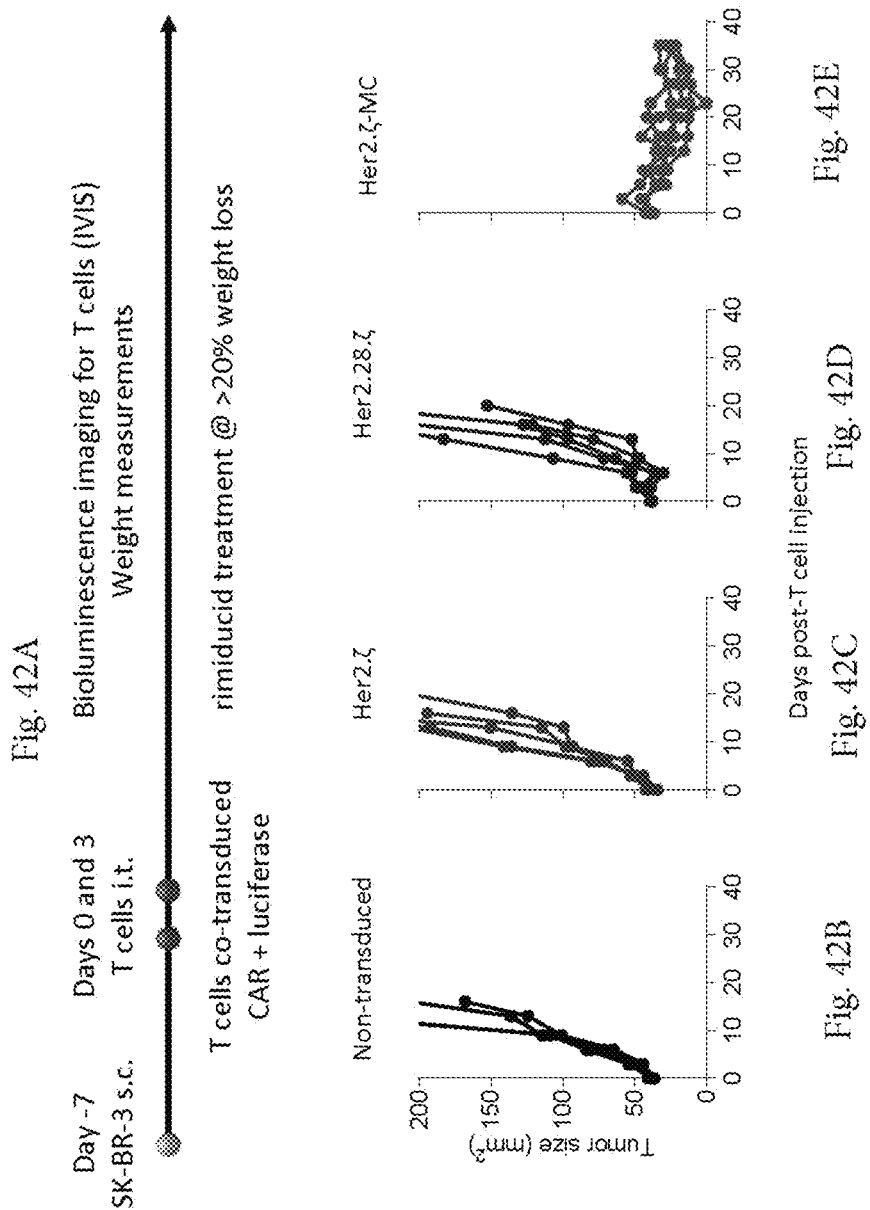

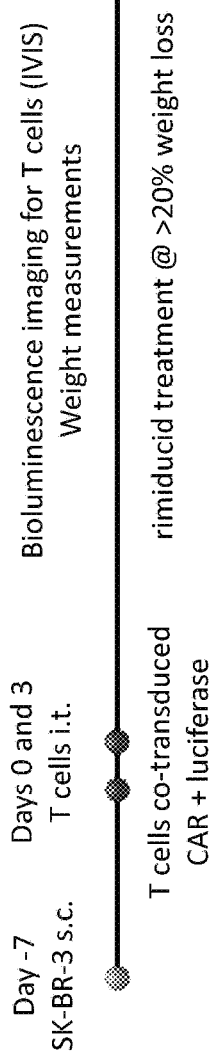
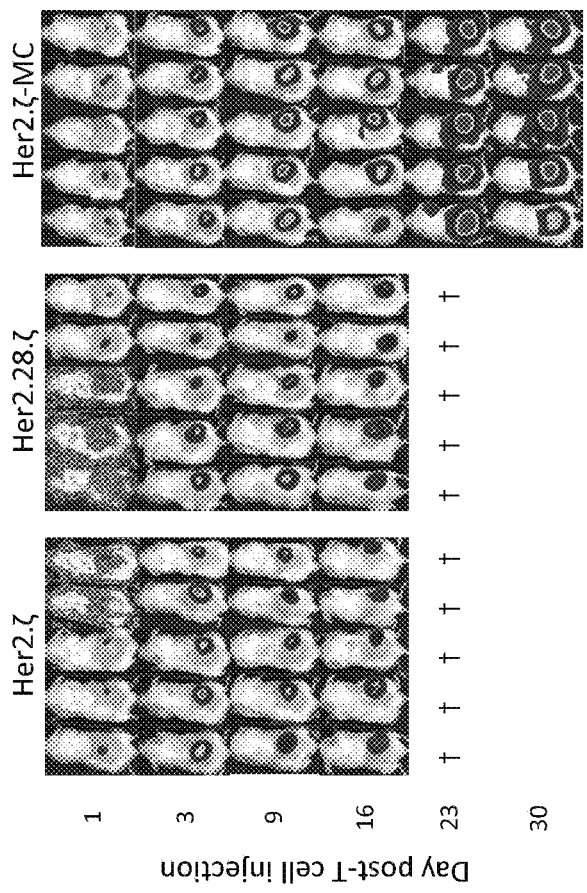
Fig. 43A
Fig. 43B
Fig. 43C

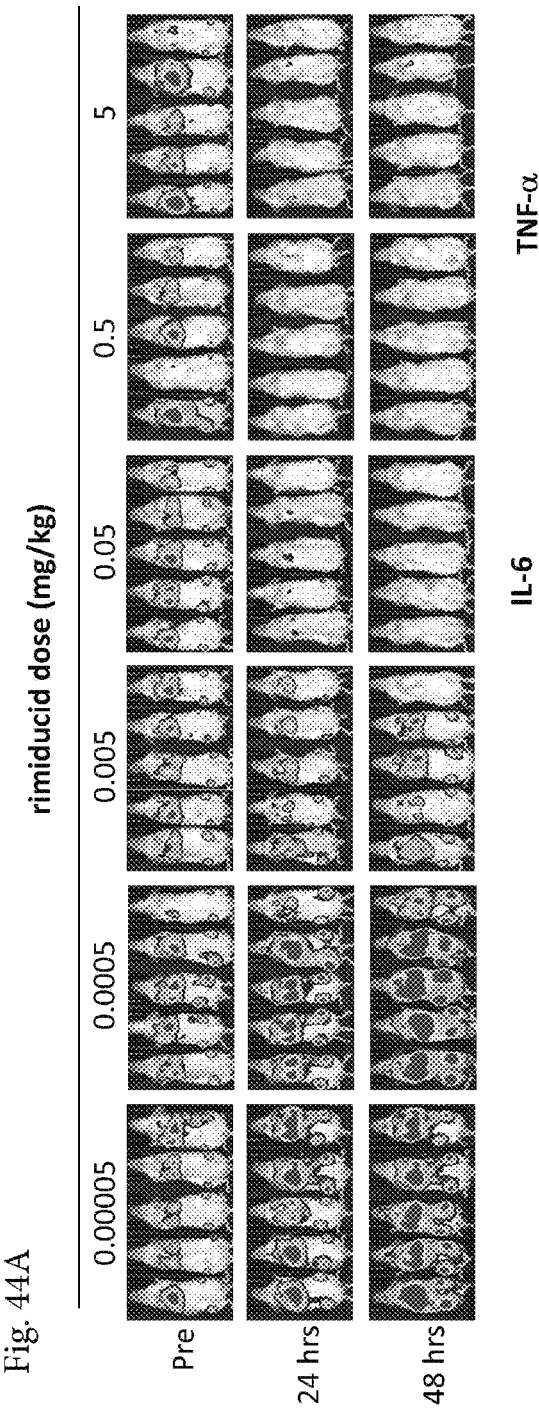
Fig. 44A
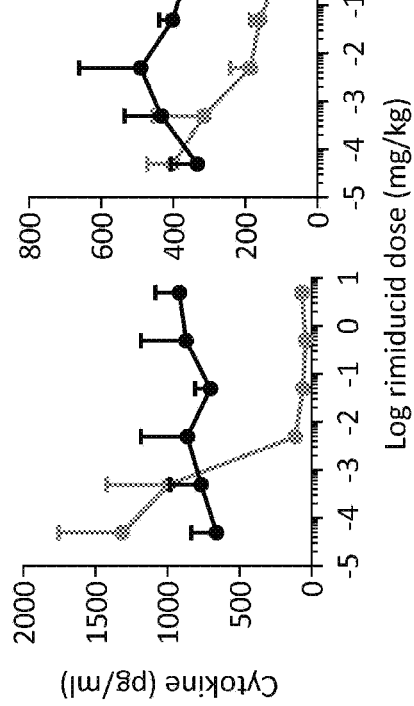
Fig. 44C
Fig. 44D
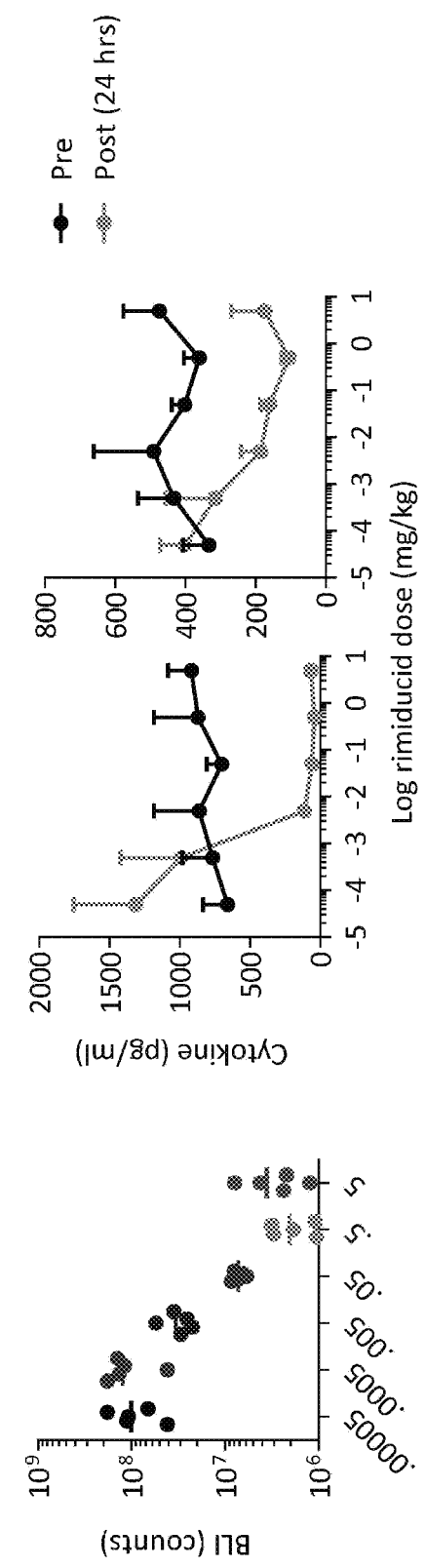
Fig. 44B

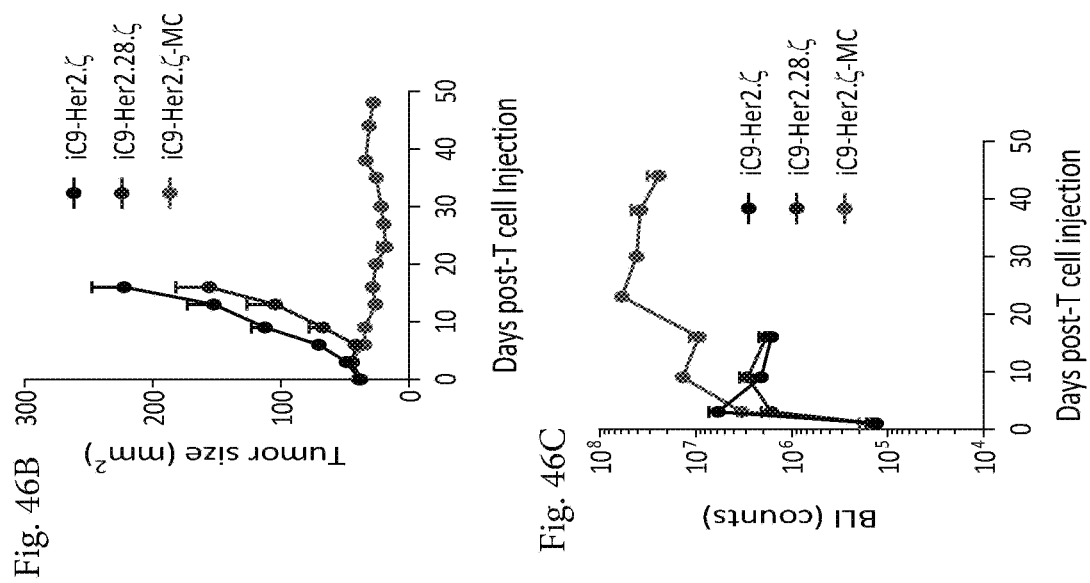
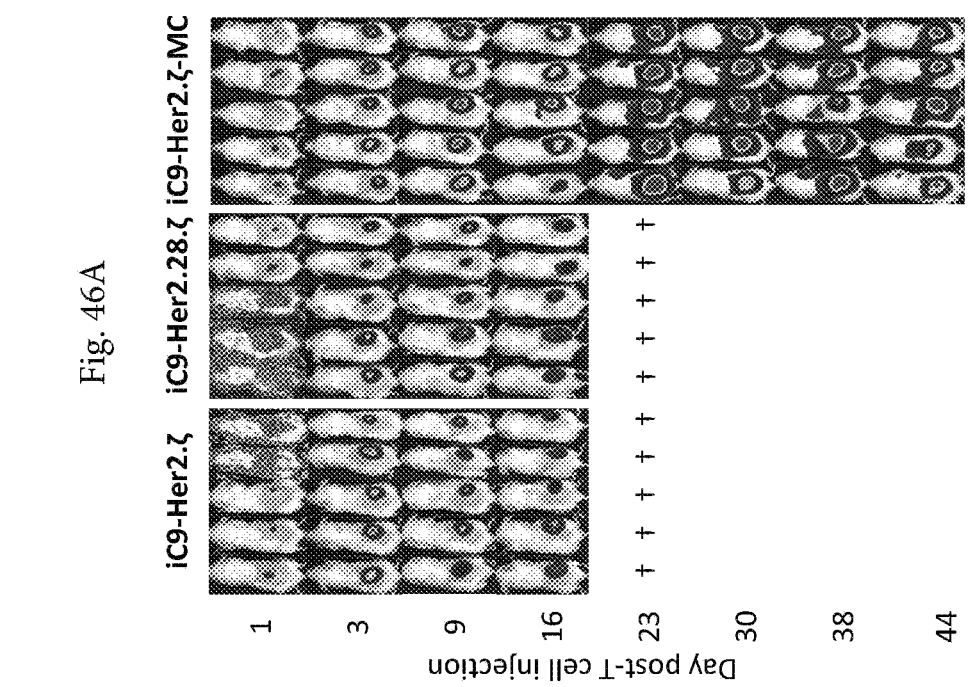
Fig. 46A
Fig. 46B
Fig. 46C

COSTIMULATION OF CHIMERIC ANTIGEN RECEPTORS BY MYD88 AND CD40 POLYPEPTIDES

RELATED APPLICATIONS

Priority is claimed to U.S. Provisional Patent Application Ser. No. 62/044,885, filed Sep. 2, 2014, entitled "Costimulation of Chimeric Antigen Receptors by MyD88 and CD40 Polypeptides," to U.S. Provisional Patent Application Ser. No. 62/115,735, filed Feb. 13, 2015, entitled "Costimulation of Chimeric Antigen Receptors by MyD88 and CD40 Polypeptides," and to U.S. Provisional Patent Application Ser. No. 62/143,503, filed Apr. 6, 2015, entitled "Costimulation of Chimeric Antigen Receptors by MyD88 and CD40 Polypeptides." The entire content of the foregoing applications are incorporated herein by reference in their entireties, including all text, tables and drawings, for all purposes.

SEQUENCE LISTING

The instant application contains a Sequence Listing which has been submitted electronically in ASCII format and is hereby incorporated by reference in its entirety. Said ASCII copy, created on Oct. 29, 2015, is named BEL-2016-UT_SL.txt and is 228,864 bytes in size.

FIELD

The technology relates generally to the field of immunology and relates in part to methods for activating T cells and other cells resulting in an immune response against a target antigen. The technology also relates to costimulation of therapeutic cells that express chimeric antigen receptors that recognize target antigens using chimeric MyD88- and CD40-derived polypeptides. The technology further relates in part to therapeutic cells that express chimeric antigen receptors, wherein the chimeric antigen receptors have an endodomain that includes MyD88- and CD40-derived polypeptides, and methods for treating patients using the modified therapeutic cells.

BACKGROUND

T cell activation is an important step in the protective immunity against pathogenic microorganisms (e.g., viruses, bacteria, and parasites), foreign proteins, and harmful chemicals in the environment, and also as immunity against cancer and other hyperproliferative diseases. T cells express receptors on their surfaces (i.e., T cell receptors) that recognize antigens presented on the surface of cells. During a normal immune response, binding of these antigens to the T cell receptor, in the context of MHC antigen presentation, initiates intracellular changes leading to T cell activation.

Chimeric antigen receptors (CARs) are artificial receptors designed to convey antigen specificity to T cells without the requirement for MHC antigen presentation. They include an antigen-specific component, a transmembrane component, and an intracellular component selected to activate the T cell and provide specific immunity. Chimeric antigen receptor-expressing T cells may be used in various therapies, including cancer therapies. Costimulating polypeptides may be used to enhance the activation of CAR-expressing T cells against target antigens, and therefore increase the potency of adoptive immunotherapy.

SUMMARY

Transduced or transfected T cells and other cells may express a chimeric antigen receptor, resulting in activation of T cell immunity in the presence of a target antigen. Chimeric antigen receptors (CARs) are artificial receptors designed to convey antigen specificity to T cells. They generally include an antigen-specific component, a transmembrane component, and an intracellular component selected to activate the T cell and provide specific immunity. Chimeric antigen receptor-expressing T cells may be used in various therapies, including cancer therapies.

The chimeric antigen receptor polypeptides may include endogenous signaling or activation domains to increase the potency of the chimeric antigen receptor modified cell. In other examples, the signaling or activation domains may be incorporated into a separate polypeptide, a chimeric stimulating molecule, which may be co-expressed with a chimeric antigen receptor, for example, a first-generation CAR, in the modified cell. T cell activation may be observed, for example, by the expression and secretion of inflammatory cytokines and chemokines. The activated cells may be used to increase the immune response against a disease, or to treat cancer by, for example, reducing the size of a tumor. The therapeutic course of treatment may be monitored by determining the size and vascularity of tumors by various imaging modalities (e.g. CT, bone scan, MRI, PET scans, TRO-FEX scans), by various standard blood biomarkers (e.g. PSA, circulating tumor cells (CTCs)), or by serum levels of various inflammatory, hypoxic cytokines, or other factors in the treated patient.

In some therapeutic instances, a patient might experience a negative symptom during therapy using chimeric antigen receptor-modified cells. In some cases these therapies have led to side effects due, in part, to non-specific attacks on healthy tissue. Therefore, in some embodiments are provided nucleic acids, cells, and methods wherein the modified T cell also expresses an inducible Caspase-9 polypeptide. If there is a need, for example, to reduce the number of chimeric antigen receptor modified T cells, an inducible ligand may be administered to the patient, thereby inducing apoptosis of the modified T cells.

The antitumor efficacy from immunotherapy with T cells engineered to express chimeric antigen receptors (CARs) has steadily improved as CAR molecules have incorporated additional signaling domains to increase their potency. T cells transduced with first generation CARs, containing only the CD3ζ intracellular signaling molecule, have demonstrated poor persistence and expansion in vivo following adoptive transfer (Till B G, Jensen M C, Wang J, et al: CD20-specific adoptive immunotherapy for lymphoma using a chimeric antigen receptor with both CD28 and 4-1BB domains: pilot clinical trial results. Blood 119:3940-50, 2012; Pule M A, Savoldo B, Myers G D, et al: Virus-specific T cells engineered to coexpress tumor-specific receptors: persistence and antitumor activity in individuals with neuroblastoma. Nat Med 14:1264-70, 2008; Kershaw M H, Westwood J A, Parker L L, et al: A phase I study on adoptive immunotherapy using gene-modified T cells for ovarian cancer. Clin Cancer Res 12:6106-15, 2006), as tumor cells often lack the requisite costimulating molecules necessary for complete T cell activation. Second generation CAR T cells were designed to improve proliferation and survival of the cells. Second generation CAR T cells that incorporate the intracellular costimulating domains from either CD28 or 4-1BB (Carpenito C, Milone M C, Hassan R, et al: Control of large, established tumor xenografts with genetically retargeted human T cells containing CD28 and CD137 domains. Proc Natl Acad Sci USA 106:3360-5, 2009; Song D G, Ye Q, Poussin M, et al: CD27 costimulation augments the survival and antitumor activity of redirected human T cells in vivo. Blood 119:696-706, 2012), show improved survival and in vivo expansion following adoptive transfer, and more recent clinical trials using anti-CD19 CAR-modified T cells containing these costimulating molecules have shown remarkable efficacy for the treatment of CD19+ leukemia. (Kalos M, Levine B L, Porter D L, et al: T cells with chimeric antigen receptors have potent antitumor effects and can establish memory in patients with advanced leukemia. Sci Transl Med 3:95ra73, 2011; Porter D L, Levine B L, Kalos M, et al: Chimeric antigen receptor-modified T cells in chronic lymphoid leukemia. N Engl J Med 365:725-33, 2011; Brentjens R J, Davila M L, Riviere I, et al: CD19-targeted T cells rapidly induce molecular remissions in adults with chemotherapy-refractory acute lymphoblastic leukemia. Sci Transl Med 5:177ra38, 2013).

While others have explored additional signaling molecules from tumor necrosis factor (TNF)-family proteins, such as OX40 and 4-1BB, called "third generation" CART cells, (Finney H M, Akbar A N, Lawson A D: Activation of resting human primary T cells with chimeric receptors: costimulation from CD28, inducible costimulator, CD134, and CD137 in series with signals from the TCR zeta chain. J Immunol 172:104-13, 2004; Guedan S, Chen X, Madar A, et al: ICOS-based chimeric antigen receptors program bipolar TH17/TH1 cells. Blood, 2014), other molecules which induce T cell signaling distinct from the CD3ζ nuclear factor of activated T cells (NFAT) pathway may provide necessary costimulation for T cell survival and proliferation, and possibly endow CAR T cells with additional, valuable functions, not supplied by more conventional costimulating molecules. Some second and third-generation CAR T cells have been implicated in patient deaths, due to cytokine storm and tumor lysis syndrome caused by highly activated T cells.

A novel T cell costimulating molecule, inducible MyD88/CD40 (iMC) (Narayanan P, Lapteva N, Seethammagari M, et al: A composite MyD88/CD40 switch synergistically activates mouse and human dendritic cells for enhanced antitumor efficacy. J Clin Invest 121:1524-34, 2011), has been found to provide controlled costimulation to human T cells. iMC is a potent, dimerizer drug (AP1903)-inducible molecule comprising the signaling elements from both the "universal" Toll-like receptor adapter, MyD88, and the TNF family member, CD40. In these studies, retroviral transduction of T cells with iMC allows AP1903-dependent signaling, but this costimulating signal alone was not sufficient to drive IL-2 production and T cell proliferation. However, complementing iMC with a first generation CAR (CD3ζ signaling domain only) allowed complete T cell activation that required both iMC and tumor recognition through the CAR, resulting in IL-2 production, CD25 receptor upregulation and T cell expansion, and the therapeutic efficacy was controlled by AP1903 in vivo. Further, cells comprising iMC, in the absence of dimerizing ligand, still maintain a level of basal activity, which, in the presence of a co-expressed CAR molecule and antigen, for example tumor antigen, recognition, provides T cell activation. Therefore, these studies indicate that the chimeric MyD88/CD40 (MC) element is a powerful costimulatory molecule for T cells receiving CD3ζ activation following recognition of tumor antigen via an extracellular CAR domain.

To extend these initial observations using a binary iMC/CAR system, MC was assessed for its ability to be included as an intracellular signaling moiety to provide costimulation to CAR-modified T cells in place of CD28 or 4-1BB, to provide requisite signaling to enhance T cell survival and proliferation. Here, it is shown that MC can be stably incorporated into the cytoplasmic region of a CAR recognizing prostate stem cell antigen (PSCA), CD19 antigen, or Her2/Neu antigen, and signaling from this costimulatory molecule enhances tumor cell killing as well as T cell survival and proliferation following tumor cell recognition.

Further, the chimeric costimulating molecule, MyD88/CD40 (MC), in the absence of a multimeric ligand-binding region is an intracellular signaling moiety that activates CAR-expressing cells, such as CAR-T cells, when expressed as a separate polypeptide from the CAR molecule. Transduction of CAR-T cells with a nucleic acid coding for a MyD88/CD40 chimeric stimulating molecule activates the CAR-expressing cells. This effect is observed with a cytoplasmic MyD88/CD40 chimeric stimulating molecule, lacking a membrane targeting region, and with a chimeric stimulating molecule comprising MyD88/CD40 and a membrane targeting region, such as, for example, a myristoylation region.

Thus provided in some embodiments is a nucleic acid comprising a promoter operably linked to a polynucleotide encoding a chimeric stimulating molecule, wherein the chimeric stimulating molecule comprises a MyD88 polypeptide or a truncated MyD88 polypeptide lacking the TIR domain; (ii) a CD40 cytoplasmic polypeptide region lacking the CD40 extracellular domain; and (iii) a membrane targeting region. Also provided is a nucleic acid comprising a promoter operably linked to a polynucleotide encoding a cytoplasmic chimeric stimulating molecule, wherein the cytoplasmic chimeric stimulating molecule comprises a MyD88 polypeptide or a truncated MyD88 polypeptide lacking the TIR domain; and a CD40 cytoplasmic polypeptide region lacking the CD40 extracellular domain. The chimeric stimulating molecules of the present application are not capable of ligand-induced multimerization or dimerization caused by the binding of ligand directly to the chimeric stimulating molecules, and do not include mutimerizing or dimerizing ligand binding sites, such as, for example, FKBP regions. Also provided in some embodiments, is a nucleic acid comprising a promoter operably linked to a polynucleotide encoding a chimeric stimulating molecule, wherein the chimeric stimulating molecule consists essentially of (i) a MyD88 polypeptide or a truncated MyD88 polypeptide lacking the TIR domain; (ii) a CD40 cytoplasmic polypeptide region lacking the CD40 extracellular domain; and (iii) a membrane targeting region. Also provided in some embodiments is a nucleic acid comprising a promoter operably linked to a polynucleotide encoding a cytoplasmic chimeric stimulating molecule, wherein the cytoplasmic chimeric stimulating molecule consists essentially of (i) a MyD88 polypeptide or a truncated MyD88 polypeptide lacking the TIR domain; and (ii) a CD40 cytoplasmic polypeptide region lacking the CD40 extracellular domain. By "consists essentially of" in the context of the chimeric stimulating molecule is meant that the chimeric stimulating molecule may further include additional sequences or regions such as, for example, a linker region, that do not modify the functionality of the (i), (ii), or (iii) regions, and do not include a ligand-induced multimerizing or dimerizing region.

In some embodiments, nucleic acids are provided comprising a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; (ii) a CD40 cytoplasmic polypeptide region lacking the CD40 extracellular domain; and (iii) a membrane targeting region; and a second polynucleotide encoding a chimeric antigen receptor. In some embodiments, nucleic acids are provided comprising a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and a second polynucleotide encoding a chimeric antigen receptor.

In some embodiments, nucleic acids are provided comprising a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; (ii) a CD40 cytoplasmic polypeptide region lacking the CD40 extracellular domain; and (iii) a membrane targeting region; and a second polynucleotide encoding a T cell receptor or a T cell receptor based-chimeric antigen receptor. In some embodiments, nucleic acids are provided comprising a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and a second polynucleotide encoding a T cell receptor or a T cell receptor based chimeric antigen receptor.

In some embodiments, nucleic acids are provided comprising a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; (ii) a CD40 cytoplasmic polypeptide region lacking the CD40 extracellular domain; and (iii) a membrane targeting region; and a second polynucleotide encoding a chimeric Caspase-9 polypeptide comprising a multimeric ligand binding region and a Caspase-9 polypeptide. In some embodiments, nucleic acids are provided comprising a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and a second polynucleotide encoding a chimeric Caspase-9 polypeptide comprising a multimeric ligand binding region and a Caspase-9 polypeptide. In some embodiments, nucleic acids are provided comprising a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; (ii) a CD40 cytoplasmic polypeptide region lacking the CD40 extracellular domain; and (iii) a membrane targeting region; a second polynucleotide encoding a chimeric antigen receptor, a T cell receptor, or a T cell receptor based chimeric antigen receptor; and a third polynucleotide encoding a chimeric Caspase-9 polypeptide comprising a multimeric ligand binding region and a Caspase-9 polypeptide.

In some embodiments, nucleic acids are provided comprising a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and a second polynucleotide encoding a chimeric antigen receptor, a T cell receptor, or a T cell receptor based chimeric antigen receptor; and a third polynucleotide encoding a chimeric Caspase-9 polypeptide comprising a multimeric ligand binding region and a Caspase-9 polypeptide.

In certain embodiments, the nucleic acid encodes a chimeric stimulating molecule that does not include a membrane targeting region. In certain embodiments, the nucleic acid further comprises a second promoter operably linked to the second polynucleotide. In certain embodiments, the nucleic acid further comprises a second promoter operably linked to the second polynucleotide and a third promoter operably linked to the third polynucleotide. In other embodiments, one promoter is operably linked to both the first and second polynucleotides, or is operably linked to the first, second, and third polynucleotides.

In some embodiments, the nucleic acid further comprises a linker polynucleotide encoding a linker polypeptide between the first and second polynucleotides, wherein the linker polypeptide separates the translation products of the first and second polynucleotides during or after translation. In other embodiments, the nucleic acid further comprises polynucleotides encoding linker polypeptides between the three polynucleotides, wherein the three polynucleotides comprise the first, second, and third polynucleotides, wherein the linker polypeptides separate the translation products of the three polynucleotides during or after translation. In some embodiments, the linker polypeptide is a 2A polypeptide.

In some embodiments of the present application, a nucleic acid is provided, comprising a promoter operably linked to a polynucleotide encoding a chimeric antigen receptor, wherein the chimeric antigen receptor comprises (i) a transmembrane region; (ii) a MyD88 polypeptide or a truncated MyD88 polypeptide lacking a TIR domain; (iii) a CD40 cytoplasmic polypeptide region lacking a CD40 extracellular domain; (iv) a T cell activation molecule; and (v) an antigen recognition moiety. In some embodiments, the chimeric antigen receptor further comprises a stalk polypeptide. In some embodiments, a nucleic acid is provided, comprising a promoter operably linked to a first polynucleotide encoding a chimeric antigen receptor, wherein the chimeric antigen receptor comprises (i) a transmembrane region; (ii) a MyD88 polypeptide or a truncated MyD88 polypeptide lacking a TIR domain; (iii) a CD40 cytoplasmic polypeptide region lacking a CD40 extracellular domain; (iv) a T cell activation molecule; and (v) an antigen recognition moiety; and a second polynucleotide encoding a chimeric Caspase-9 polypeptide comprising a multimeric ligand binding region and a Caspase-9 polypeptide. In some embodiments, one promoter is operably linked to both the first and second polynucleotides. In some embodiments, the nucleic acid further comprises a linker polynucleotide encoding a linker polypeptide between the first and second polynucleotides, wherein the linker polypeptide separates the translation products of the first and second polynucleotides during or after translation. In some embodiments, the linker polypeptide is a 2A polypeptide. In some embodiments, the nucleic acid further comprises a second promoter operably linked to the second polynucleotide.

In certain embodiments, the membrane targeting region is selected from the group consisting of a myristoylation region, palmitoylation region, prenylation region, and transmembrane sequences of receptors. In certain embodiments, the membrane targeting region is a myristoylation region.

In certain embodiments, the truncated MyD88 polypeptide has the amino acid sequence of SEQ ID NO: 147, or a functional fragment thereof. IN certain embodiments, the MyD88 polypeptide has the amino acid sequence of SEQ ID NO: 282, or a functional fragment thereof. In certain embodiments, the cytoplasmic CD40 polypeptide has the amino acid sequence of SEQ ID NO: 149, or a functional fragment thereof.

In some embodiments, the nucleic acid is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and Vaccinia virus vectors. In some embodiments, the nucleic acid is contained within a plasmid.

Also provided are chimeric stimulating molecule polypeptides encoded by the nucleic acids of the present application. Thus in some embodiments, chimeric stimulating molecule polypeptides are provided comprising (i) a MyD88 polypeptide or a truncated MyD88 polypeptide lacking the TIR domain; (ii) a CD40 cytoplasmic polypeptide region lacking the CD40 extracellular domain; and (iii) a membrane targeting region. The polypeptides may be associated with or bound to a membrane in some embodiments. In other embodiments, the polypeptides may be isolated. In other embodiments, the polypeptides may comprise a membrane targeting region but not be associated with a membrane. In some embodiments, chimeric stimulating molecule polypeptides are provided comprising a MyD88 polypeptide or a truncated MyD88 polypeptide lacking the TIR domain; and a CD40 cytoplasmic polypeptide region lacking the CD40 extracellular domain. The chimeric stimulating molecule polypeptides may be isolated, or may, in some embodiments, be present in the cytoplasm of a cell.

Also provided in some embodiments is a chimeric antigen receptor comprising a MyD88 polypeptide or a truncated MyD88 polypeptide lacking a TIR domain and a CD40 cytoplasmic polypeptide region lacking a CD40 extracellular domain encoded by a nucleic acid of the present application. The chimeric antigen receptor may be isolated in some embodiments. In other embodiments, the chimeric antigen receptor may be associated with or bound to a membrane.

Also provided in some embodiments is a modified cell transfected or transduced with a nucleic acid encoding a chimeric stimulating molecule of the present application. In some embodiments, the chimeric stimulating molecule is constitutively expressed. In some embodiments, the chimeric stimulating molecule is constitutively active. In some embodiments, the nucleic acid further comprises a polynucleotide encoding a chimeric antigen receptor.

Also provided in some embodiments is a modified cell transfected or transduced with a nucleic acid encoding a chimeric stimulating molecule of the present application wherein the nucleic acid does not encode a chimeric antigen receptor; and the modified cell further comprises a nucleic acid comprising a polynucleotide encoding a chimeric antigen receptor.

Also provided in some embodiments, is a modified cell transfected or transduced with a nucleic acid encoding a chimeric stimulating molecule of the present application wherein the nucleic acid does not encode a T cell receptor or a T cell receptor based chimeric antigen receptor; and the modified cell further comprises a nucleic acid comprising a polynucleotide encoding a T cell receptor or a T cell receptor based-chimeric antigen receptor.

In some embodiments, the modified cells of the present application further comprise a nucleic acid comprising a polynucleotide encoding a chimeric Caspase-9 polypeptide, wherein the chimeric Caspase-9 polypeptide comprises a multimeric ligand binding region and a Caspase-9 polypeptide.

In some embodiments, the modified cell is a T cell, tumor infiltrating lymphocyte, NK-T cell, TCR-expressing cell, or NK cell. In some embodiments, the cell is a T cell. In some embodiments, the cell is obtained or prepared from bone marrow. In some embodiments, the cell is obtained or prepared from umbilical cord blood. In some embodiments, the cell is obtained or prepared from peripheral blood. In some embodiments, the cell is obtained or prepared from peripheral blood mononuclear cells. In some embodiments, the cell is a human cell. In some embodiments, the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

In some embodiments, the chimeric Caspase-9 polypeptide comprises a Caspase-9 polypeptide that lacks the CARD domain. In some embodiments, the Caspase-9 polypeptide comprises the amino acid sequence of SEQ ID NO: 153. In some embodiments, the Caspase-9 polypeptide consists essentially of the amino acid sequence of SEQ ID NO: 153. In certain embodiments, the Caspase-9 polypeptide comprises the amino acid sequence of SEQ ID NO: 153, and further comprises an amino acid substitution selected from the group consisting of the caspase variants in Table 1. In certain embodiments, the Caspase-9 polypeptide consists essentially of the amino acid sequence of SEQ ID NO: 153, and further comprises an amino acid substitution selected from the group consisting of the caspase variants in Table 1. In certain embodiments, the Caspase-9 polypeptide has a substituted amino acid residue of N405Q. In certain embodiments, the Caspase-9 polypeptide consists essentially of the amino acid sequence of SEQ ID NO: 153, and further comprises a substituted amino acid residue of N405Q.

In some embodiments, the multimeric ligand binding domain of the chimeric Caspase-9 polypeptide is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof. In some embodiments, the ligand binding region is an FKBP12 region. In some embodiments, the FKBP12 region is an FKBP12v36 region. In some embodiments, the FKBP region is Fv'Fvls. In some embodiments, the ligand is an FK506 dimer or a dimeric FK506 analog ligand. In some embodiments, the ligand is AP1903 (rimiducid) or AP20187.

The nucleic acids of the present application may comprise polynucleotides coding for chimeric antigen receptors in some embodiments. In some embodiments, chimeric antigen receptors are expressed in the modified cells that comprise the nucleic acids of the present application. In other embodiments, chimeric antigen receptors are provided that comprise MyD88 or truncated MyD88 polypeptides and a CD40 cytoplasmic region polypeptide. These chimeric antigen receptors of the present application may comprise, in some embodiments, (i) a transmembrane region; (ii) a T cell activation molecule; and (iii) an antigen recognition moiety. In some embodiments, the chimeric antigen receptor further comprises a co-stimulatory molecule selected from the group consisting of CD28, OX40, and 4-1BB. In some embodiments, the T cell activation molecule is selected from the group consisting of an ITAM-containing, Signal 1 conferring molecule, a CD3ζ polypeptide, and an Fc epsilon receptor gamma (FcεR1γ) subunit polypeptide. In some embodiments, the antigen recognition moiety binds to an antigen on a tumor cell. In some embodiments, the antigen recognition moiety binds to an antigen on a cell involved in a hyperproliferative disease or to a viral or bacterial antigen. In some embodiments, the antigen recognition moiety binds to an antigen selected from the group consisting of PSMA, PSCA, MUC1, CD19, ROR1, Mesothelin, GD2, CD123, MUC16, Her2/Neu, CD20, CD30, PRAME, NY-ESO-1, and EGFRvIII. In some embodiments, the antigen recognition moiety binds to an antigen selected from the group consisting of PSMA, PSCA, MUC1, CD19, ROR1, Mesothelin, GD2, CD123, MUC16, and Her2/Neu. In some embodiments, the antigen recognition moiety binds to PSMA. In some embodiments, the antigen recognition moiety binds to CD19. In some embodiments, the antigen recognition moiety binds to Her2/Neu.

In some embodiments, the antigen recognition moiety is a single chain variable fragment. In some embodiments, the transmembrane region is a CD28 transmembrane region or a CD8 transmembrane region. In some embodiments, the chimeric antigen receptor further comprises a CD8 stalk region.

Methods are provided in some embodiments for stimulating a T cell-mediated immune response in a subject, comprising administering an effective amount of modified cells of the present application to the subject. In some embodiments, the T cell-mediated immune response is directed against a target cell. In some embodiments, the modified cell comprises a chimeric antigen receptor, a T cell receptor, or a T cell receptor based chimeric antigen receptor that binds to an antigen on a target cell. In some embodiments, the target cell is a tumor cell. In some embodiments, the number or concentration of target cells in the subject is reduced following administration of the modified cells.

In some embodiments, the method further comprises measuring the number or concentration of target cells in a first sample obtained from the subject before administering the modified cell, measuring the number concentration of target cells in a second sample obtained from the subject after administration of the modified cell, and determining an increase or decrease of the number or concentration of target cells in the second sample compared to the number or concentration of target cells in the first sample. In some embodiments, the concentration of target cells in the second sample is decreased compared to the concentration of target cells in the first sample. In other embodiments, the concentration of target cells in the second sample is increased compared to the concentration or target cells in the first sample. In some embodiments, an additional dose of modified cells is administered to the subject.

Also provided are methods for providing anti-tumor immunity to a subject, comprising administering to the subject an effective amount of a modified cell of the present application. Also provided are methods for treating a subject having a disease or condition associated with an elevated expression of a target antigen, comprising administering to the subject an effective amount of a modified cell of the present application. In some embodiments, the target antigen is a tumor antigen.

Also provided in some embodiments are methods for reducing the size of a tumor in a subject, comprising administering a modified cell of the present application to the subject, wherein the cell comprises a chimeric antigen receptor, a T cell receptor, or a T cell receptor based chimeric antigen receptor comprising an antigen recognition moiety binds to an antigen on the tumor.

In some embodiments, the subject has been diagnosed as having a tumor. In some embodiments, the subject has cancer. In some embodiments, the subject has a solid tumor or leukemia. In some embodiments, the modified cell is a tumor infiltrating lymphocyte or a T cell. In some embodiments, the modified cell is delivered to a tumor bed. In some embodiments, the cancer is present in the blood or bone marrow of the subject. In some embodiments the subject has a blood or bone marrow disease. In some embodiments, the subject has been diagnosed with any condition or condition that can be alleviated by stem cell transplantation. In some embodiments, the subject has been diagnosed with sickle cell anemia or metachromatic leukodystrophy. In some embodiments, the subject has been diagnosed with a condition selected from the group consisting of a primary immune deficiency condition, hemophagocytosis lymphohistiocytosis (HLH) or other hemophagocytic condition, an inherited marrow failure condition, a hemoglobinopathy, a metabolic condition, and an osteoclast condition. In some embodiments, the subject has been diagnosed with a disease or condition selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

In some embodiments, the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

Also provided are methods of the present application further comprising determining whether an additional dose of the modified cell should be administered to the subject. In some embodiments, the methods further comprise administering an additional dose of the modified cell to the subject, wherein the disease or condition symptoms remain or are detected following a reduction in symptoms. In some embodiments, the methods further comprise identifying the presence, absence or stage of a condition or disease in a subject; and transmitting an indication to administer modified cell of the present application, maintain a subsequent dosage of the modified cell, or adjust a subsequent dosage of the modified cell administered to the patient based on the presence, absence or stage of the condition or disease identified in the subject.

In some embodiments, the methods of the present application comprise administering a modified cell to a subject that comprises a chimeric Caspase-9 polypeptide comprising a multimeric ligand binding region and a Caspase-9 polypeptide. In some embodiments the methods further comprise administering a multimeric ligand that binds to the multimeric ligand binding region to the subject following administration of the modified cells to the subject. In some embodiments, after administration of the multimeric ligand, the number of modified cells comprising the chimeric Caspase-9 polypeptide is reduced. In some embodiments, the number of modified cells comprising the chimeric Caspase-9 polypeptide is reduced by 50, 60, 70, 80, 90, 95, or 99% following administration of the multimeric ligand to the subject. In some embodiments, the methods comprise determining that the subject is experiencing a negative symptom following administration of the modified cells to the subject, and administering the ligand to reduce or alleviate the negative symptom. In some embodiments, the ligand is AP1903 or AP20187. In some embodiments, the modified cells are autologous T cells. In some embodiments, the modified cells are allogeneic T cells.

In some embodiments, the modified cells of the present application are transfected or transduced in vivo. In some embodiments, the modified cells are transfected or transduced ex vivo.

Also provided in certain embodiments are methods for expressing a chimeric stimulating molecule or a chimeric antigen receptor comprising a MyD88 polypeptide and a CD40 cytoplasmic polypeptide in a cell, comprising contacting a nucleic acid of the present application with a cell under conditions in which the nucleic acid is incorporated into the cell, whereby the cell expresses the chimeric stimulating molecule or the chimeric antigen receptor from the incorporated nucleic acid. In some embodiments, the nucleic acid is contacted with the cell ex vivo. In some embodiments, the nucleic acid is contacted with the cell in vivo.

In some embodiments, the methods further comprise administering a chemotherapeutic. In certain embodiments, the chemotherapeutic selected is a lymphodepleting chemotherapeutic. In some embodiments, the modified cells, or the nucleic acid, and the chemotherapeutic agent are administered in an amount effective to treat the disease or condition in the subject. In some embodiments, the chemotherapeutic agent is selected from the group consisting of carboplatin, estramustine phosphate (EMCYT), and thalidomide. In some embodiments, the chemotherapeutic agent is a taxane. The taxane may be, for example, selected from the group consisting of docetaxel (TAXOTERE), paclitaxel, and cabazitaxel. In some embodiments, the taxane is docetaxel. In some embodiments, the chemotherapeutic agent is administered at the same time or within one week after the administration of the modified cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the modified cell or nucleic acid. In some embodiments, the chemotherapeutic agent is administered at least 1 month before administering the cell or nucleic acid.

In some embodiments, the methods further comprise administering two or more chemotherapeutic agents. In some embodiments, the chemotherapeutic agents are selected from the group consisting of carboplatin, Estramustine phosphate, and thalidomide. In some embodiments, at least one chemotherapeutic agent is a taxane. The taxane may be, for example, selected from the group consisting of docetaxel, paclitaxel, and cabazitaxel. In some embodiments, the taxane is docetaxel. In some embodiments, the chemotherapeutic agents are administered at the same time or within one week after the administration of the modified cell or nucleic acid. In other embodiments, the chemotherapeutic agents are administered from 1 to 4 weeks or from 1 week to 1 month, 1 week to 2 months, 1 week to 3 months, 1 week to 6 months, 1 week to 9 months, or 1 week to 123 months after the administration of the cell or nucleic acid. In other embodiments, the methods further comprise administering the chemotherapeutic agents from 1 to 4 weeks or from 1 week to 1 month, 1 week to 2 months, 1 week to 3 months, 1 week to 6 months, 1 week to 9 months, or 1 week to 123 months before the administration of the cell or nucleic acid.

In some embodiments, the subject is a mammal. In some embodiments, the subject is a human.

This application incorporates by reference U.S. patent application Ser. No. 14/210,034, titled METHODS FOR CONTROLLING T CELL PROLIFERATION, filed Mar. 13, 2014; U.S. patent application Ser. No. 14/622,018, filed Feb. 13, 2015, titled METHODS FOR ACTIVATING T CELLS USING AN INDUCIBLE CHIMERIC POLYPEPTIDE; U.S. patent application Ser. No. 13/112,739, filed May 20, 2011, titled METHODS FOR INDUCING SELECTIVE APOPTOSIS; U.S. patent application Ser. No. 13/792, 135, filed Mar. 10, 2013, titled MODIFIED CASPASE POLYPEPTIDES AND USES THEREOF; AND U.S. patent application Ser. No. 14/296,404, filed Jun. 4, 2014, titled METHODS FOR INDUCING PARTIAL APOPTOSIS USING CASPASE POLYPEPTIDES; which are all hereby incorporated by reference herein in their entirety.

Also incorporated by reference in their entirety are U.S. Pat. No. 7,404,950, issued Jul. 29, 2008, to Spencer, D. et al.; U.S. Pat. No. 8,691,210, issued Apr. 8, 2004 to Spencer, et al.; U.S. patent application Ser. No. 12/532,196 by Spencer et al., filed Sep. 21, 2009; PCT application PCT/US2009/057738 to Spencer et al., published on Apr. 24, 2008 as WO2010/033949; U.S. patent application Ser. No. 13/087, 329 by Slawin et al., filed Apr. 14, 2011; PCT application PCT/US2011/032572, published on Oct. 20, 2011 as WO2011/130566; U.S. patent application Ser. No. 14/210, 324 by Spencer et al., filed Mar. 13, 2014; PCT application number PCT/US2014/026734 by Spencer et al., published as WO2014/251960 on Feb. 5, 2015; U.S. application Ser. No. 14/622,018, by Foster et al., filed Feb. 13, 2015; PCT application number PCT/US2015/015829 by Foster et al., published as WO2015/123527 on Aug. 20, 2015

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

Figure 1:
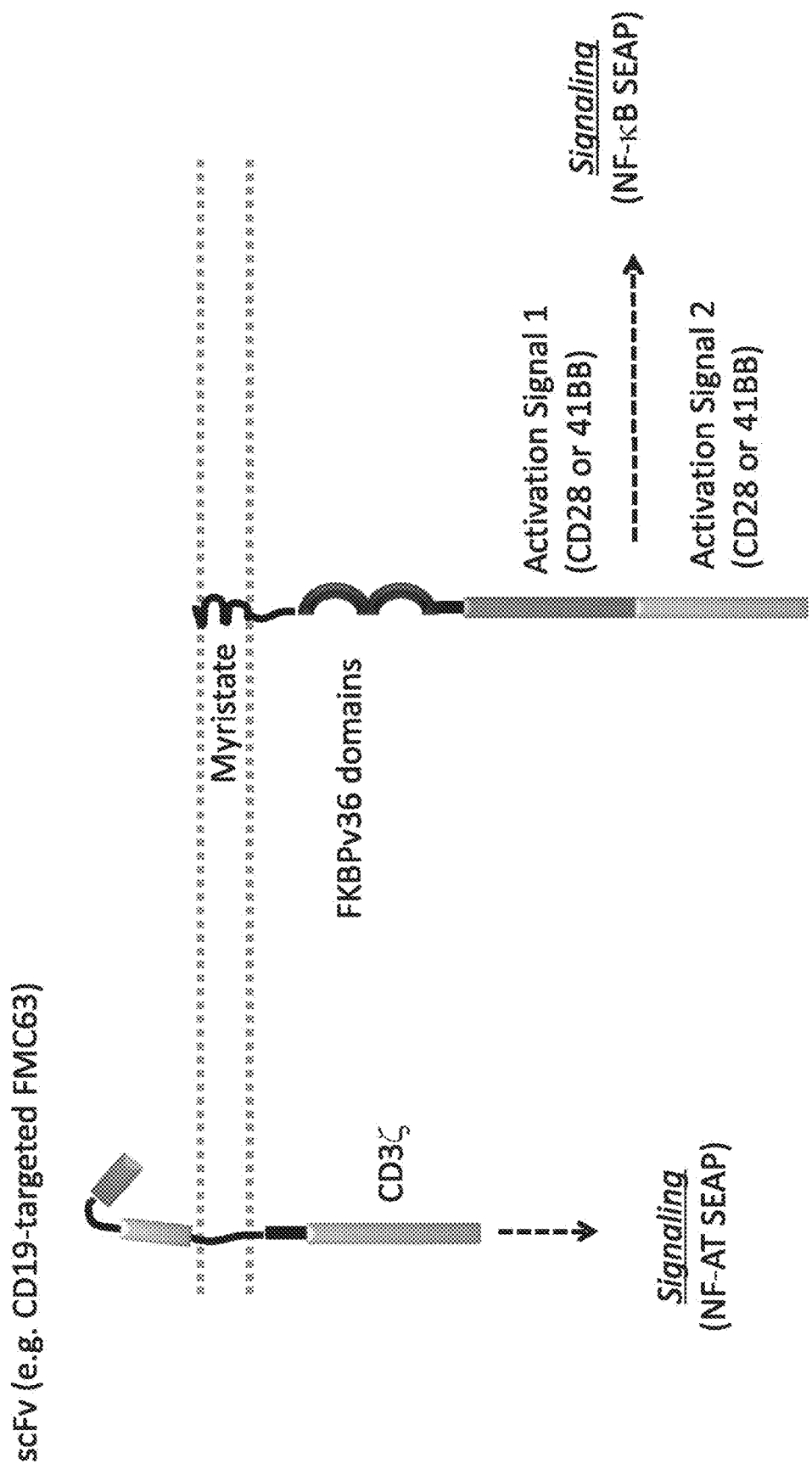

FIG. 1 is a schematic of a partial view of a cell membrane of a cell transduced or transfected with a chimeric antigen receptor and an example of a chimeric stimulating molecule comprising CD28 and 4-1BB polypeptides.

Figure 2:
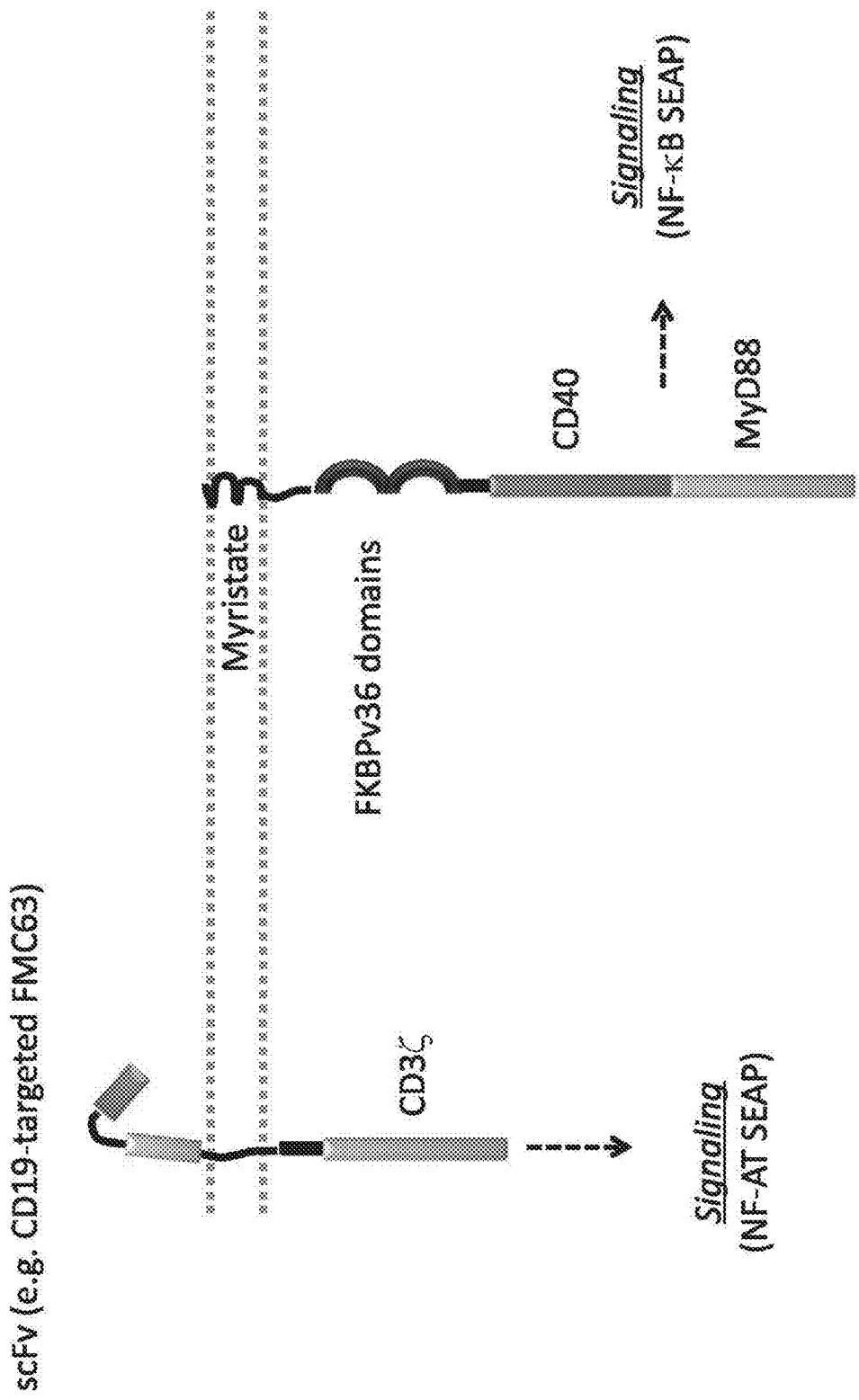

FIG. 2 is a schematic of a partial view of a cell membrane of a cell transduced or transfected with a chimeric antigen receptor and an example of a chimeric signaling molecule comprising an inducible chimeric CD40/MyD88 polypeptide.

Figure 3A:
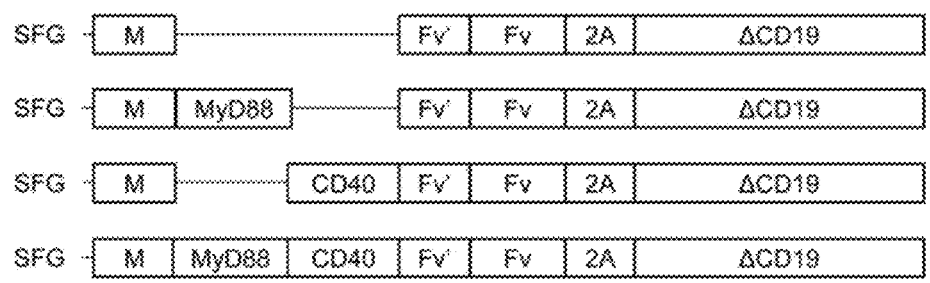
Figure 3B:
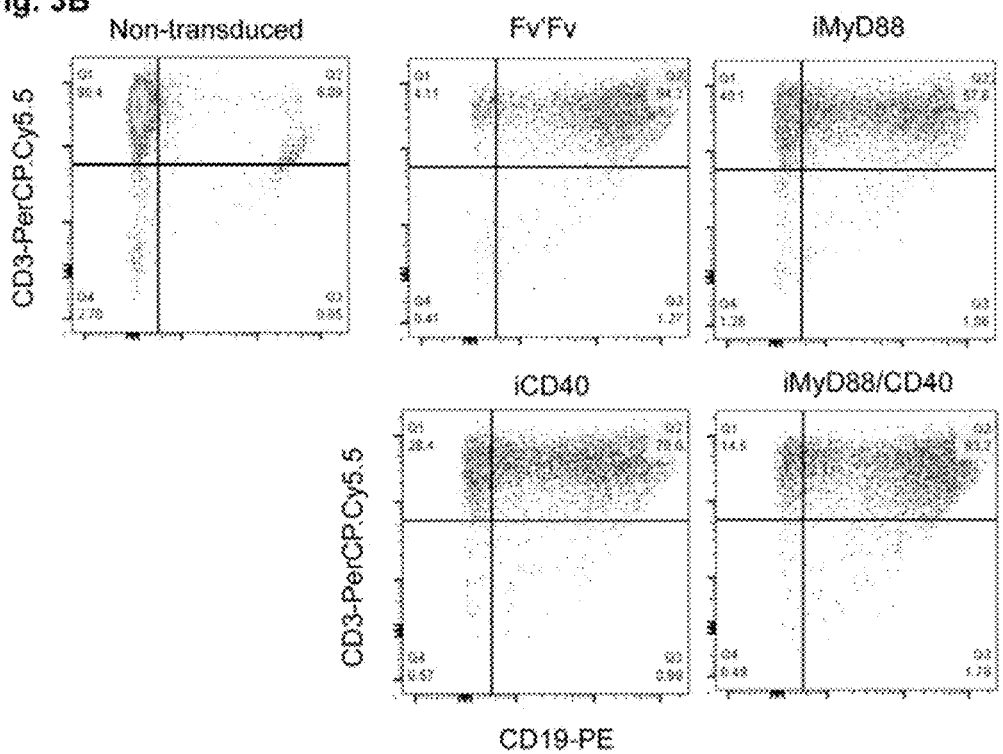
Figure 3C:
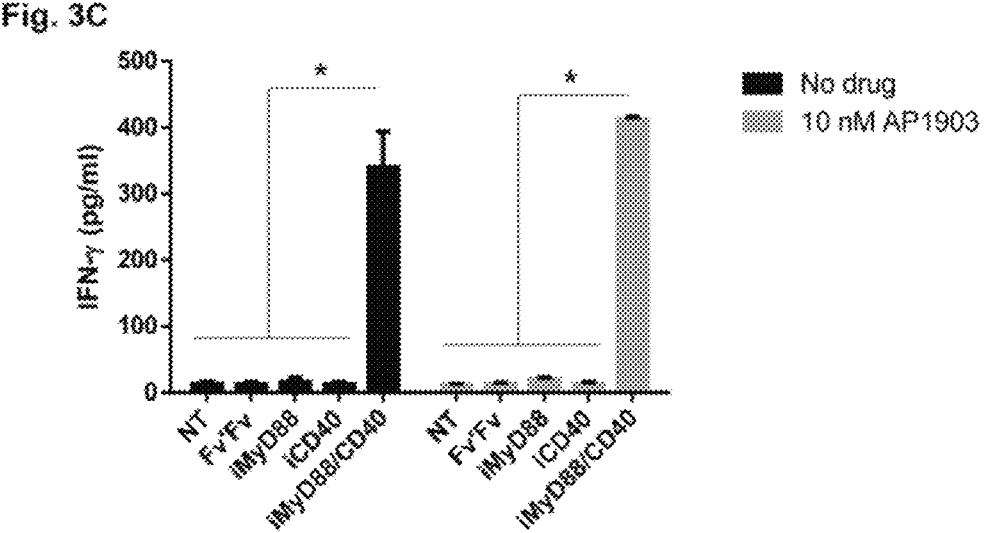
Figure 3D:
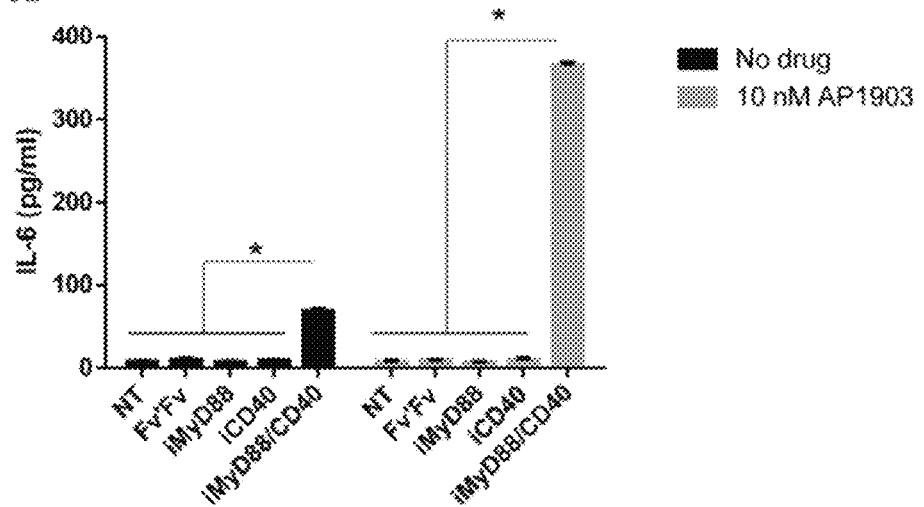

FIG. 3A-FIG. 3D provide examples of inducible chimeric stimulating molecules comprising CD40 and MyD88 polypeptides. FIG. 3A provides a graphic illustration of the general polypeptide elements of the inducible chimeric stimulating molecules. FIG. 3B provides flow cytometry results of CD19 marker detection in T cells that express the chimeric stimulating molecules. FIG. 3C is a bar graph of IFN γ production in T cells that express the chimeric stimulating molecules. FIG. 3D is a bar graph of IL-6 production in T cells that express the chimeric stimulating molecules.

Figure 4A:
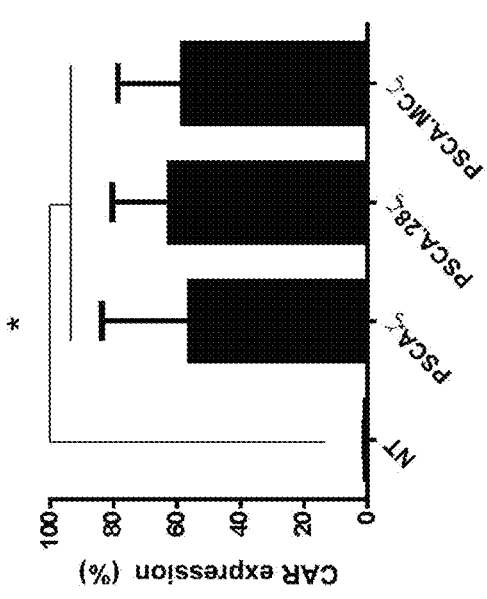
Figure 4B:
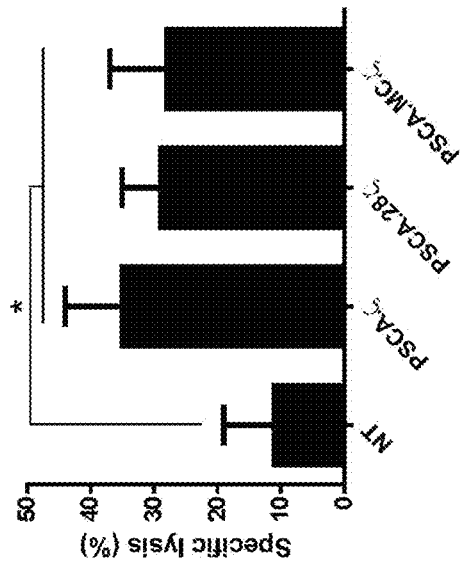
Figure 4C:
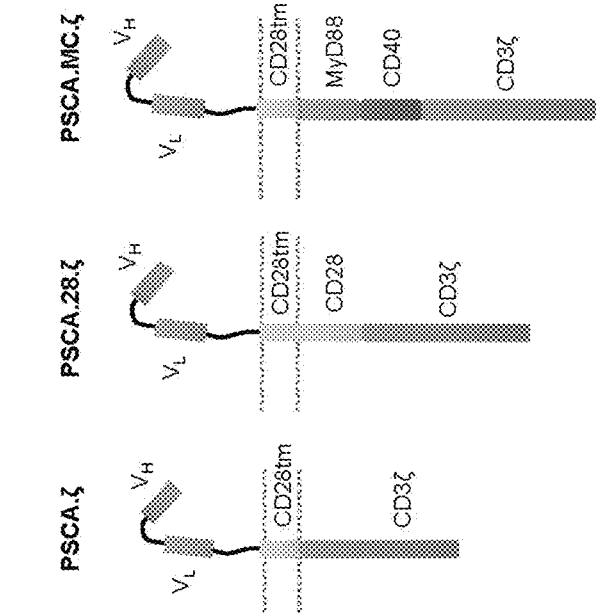
Figure 4D:
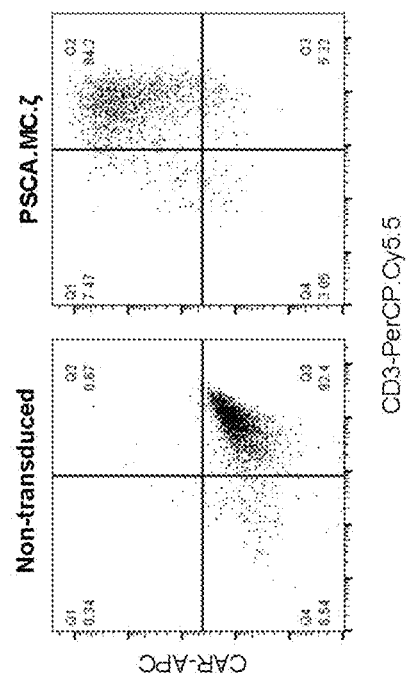

FIG. 4A-FIG. 4D provide examples of chimeric antigen receptors. FIG. 4A provides a graphic illustration of chimeric antigen receptors comprising MyD88 and CD40 polypeptides in the general context of a cell membrane. FIG. 4B is a bar graph of CAR expression in the transduced cells. FIG. 4C provides flow cytometry results showing CAR expression in the transduced cells. FIG. 4D is a bar graph showing specific lysis of PSCA$^+$ tumor cells by the CAR-expressing T cells.

Figure 5A:
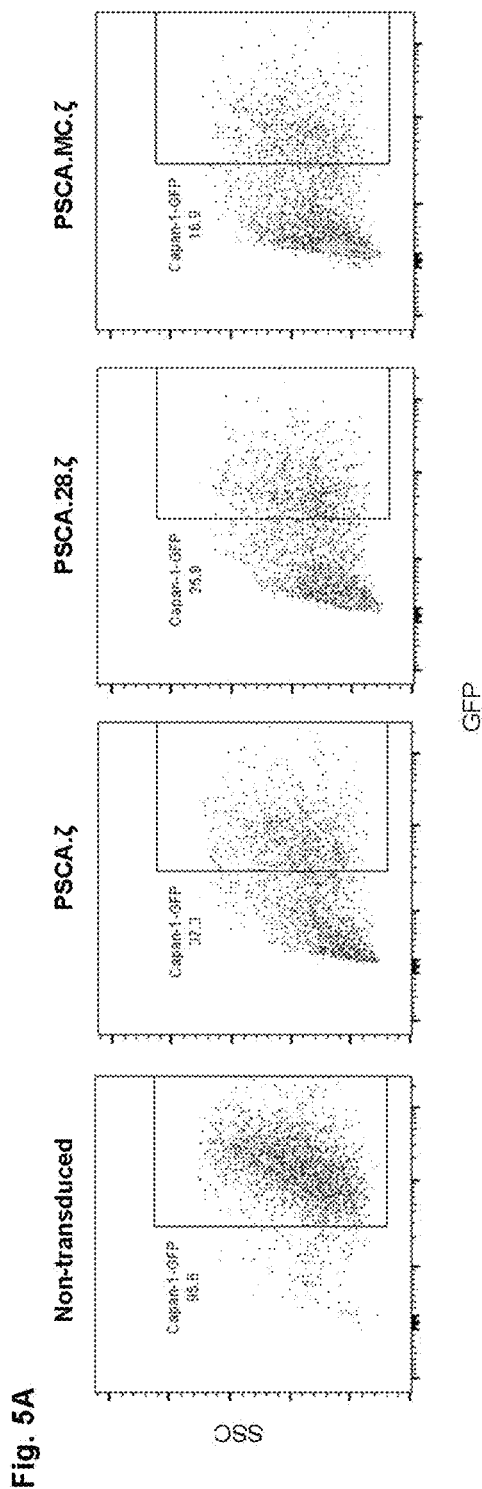
Figure 5B:
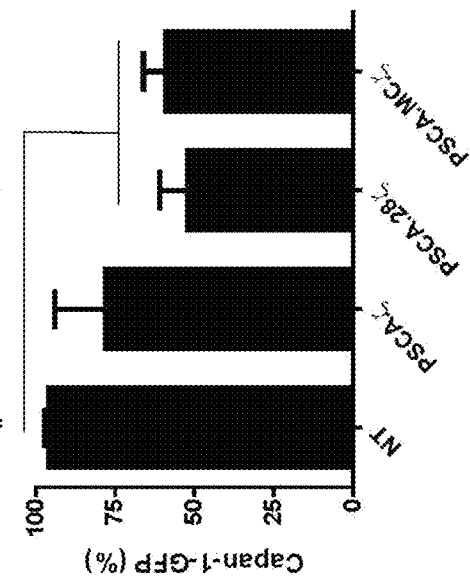
Figure 5C:
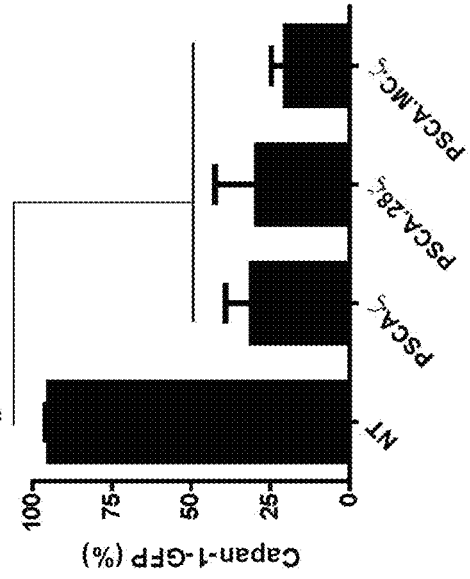

FIG. 5A-FIG. 5C provide examples of endogenous costimulation of the CAR molecule by MyD88 and CD40 polypeptides. FIG. 5A provides flow cytometry results measuring the killing of Capan-1-GFP cells by cells expressing the chimeric antigen receptor. FIG. 5B is a bar graph of the killing of Capan-1-GFP cells at a 1:1 ratio of CART cells to tumor cells. FIG. 5C is a bar graph of the killing of Capan-1-GFP cells at a 1:10 ratio of CAR T cells to tumor cells.

Figure 6B:
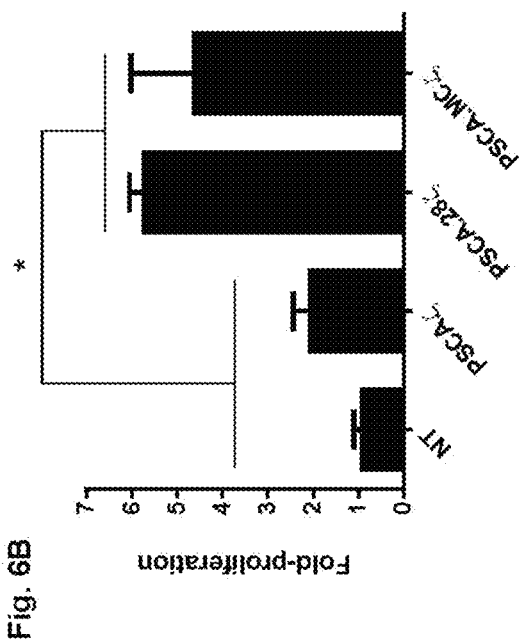
Figure 6D:
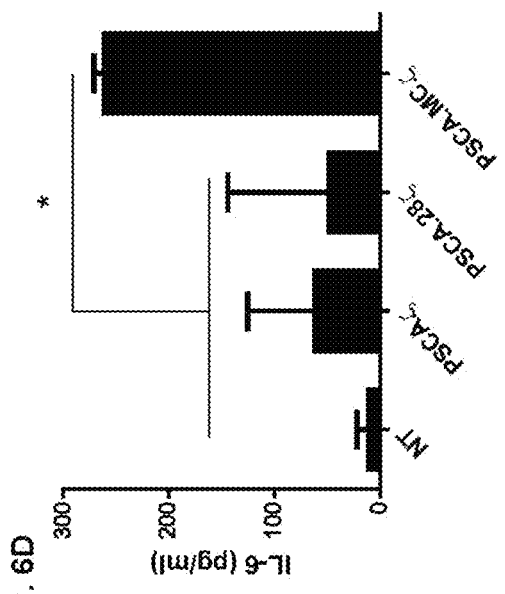
Figure 6A:
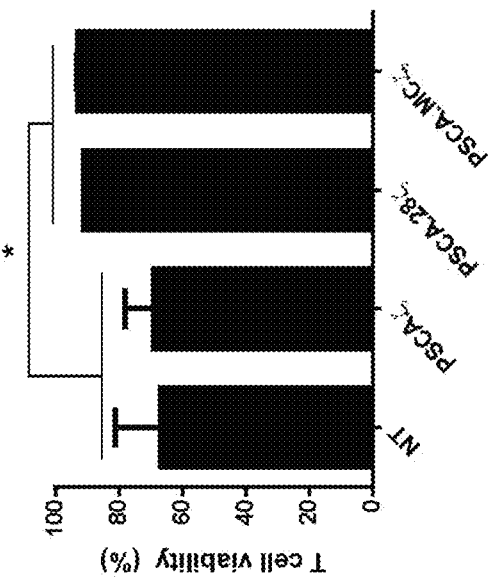
Figure 6C:
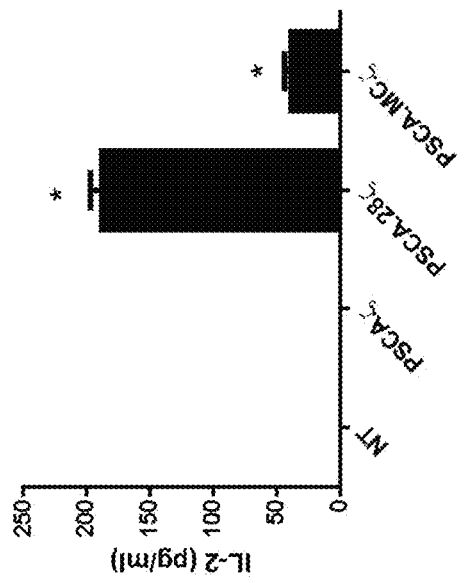

FIG. 6A-FIG. 6D provide results of cell viability and proliferation of cells that express the MyD88/CD40 chimeric antigen receptor. FIG. 6A is a graph of T cell viability. FIG. 6B is a graph of cell proliferation. FIG. 6C is a graph of IL-2 production. FIG. 6D is a graph of IL-6 production.

Figure 7:
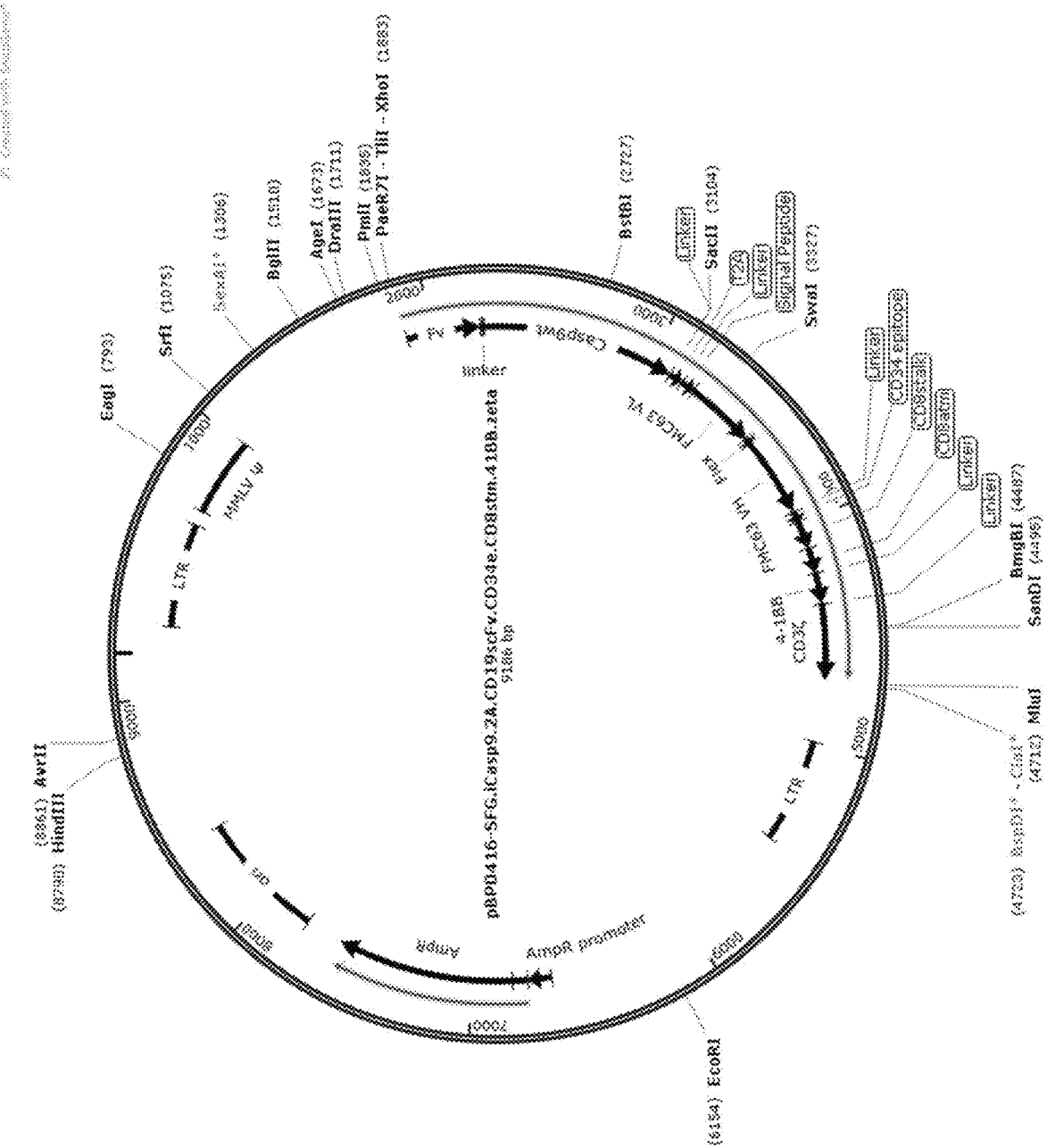

FIG. 7 is a plasmid map coding for a chimeric antigen receptor co-expressed with an inducible caspase molecule.

Figure 8:

FIG. 8 is a plasmid map coding for a chimeric stimulating molecule and a CD19 polypeptide marker.

Figure 9:
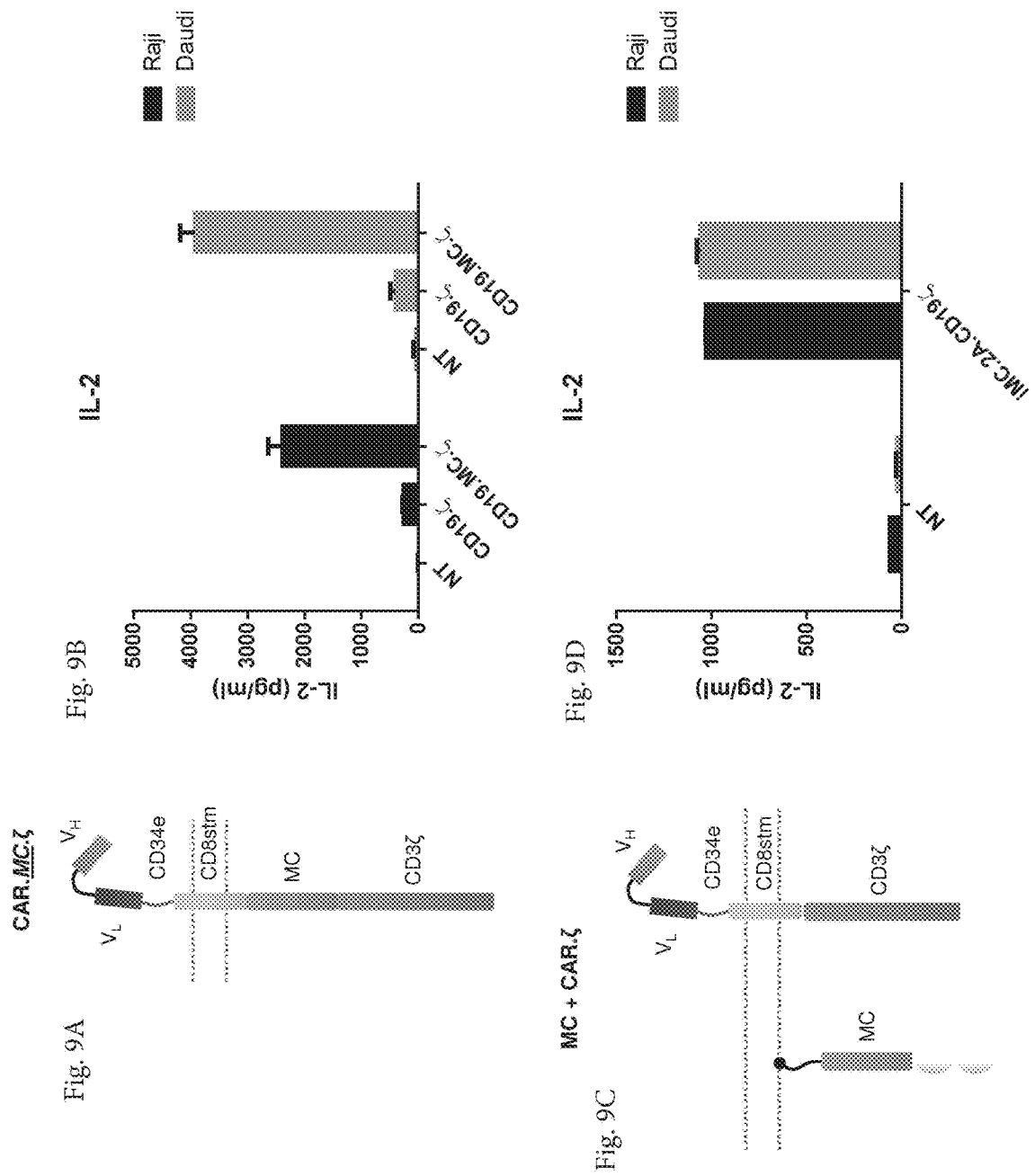

FIG. 9A-FIG. 9D: FIG. 9A is a schematic of a chimeric antigen receptor comprising MyD88 and CD40 polypeptides. FIG. 9B is a bar graph of an IL-2 assay of cells transfected with a plasmid encoding a chimeric antigen receptor comprising MyD88 and CD40 polypeptides. FIG. 9C is a schematic of a MyD88/CD40 costimulating molecule co-expressed with a first generation chimeric antigen receptor. FIG. 9D is a bar graph of an IL-2 assay of cells that express both a MyD88 costimulating molecule and a chimeric antigen receptor.

Figure 10:

FIG. 10 is a plasmid map coding for a MyD88/CD40 chimeric antigen receptor co-expressed with an inducible caspase-9 polypeptide.

Figure 11:
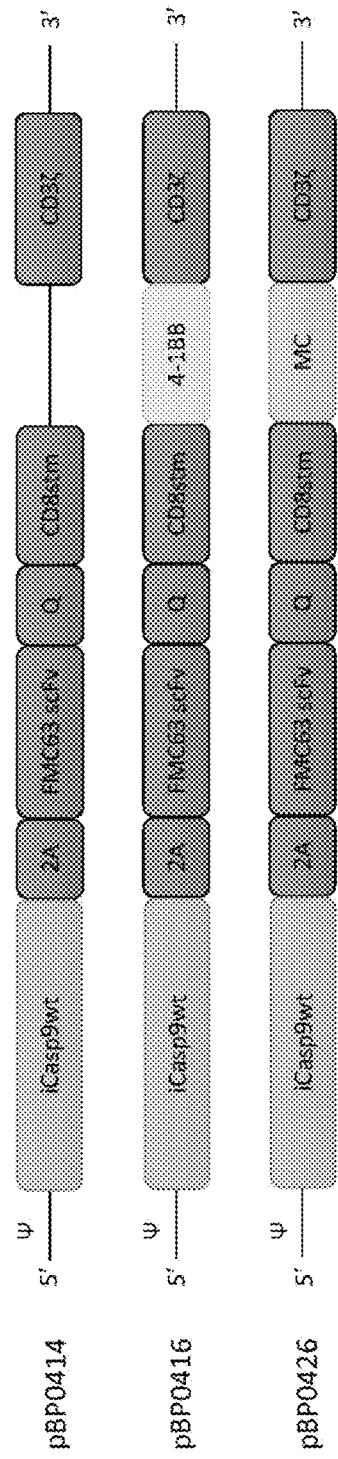

FIG. 11 is a schematic for a transgene of the MyD88/CD40 CAR co-expressed with an inducible caspase-9 polypeptide.

FIG. 12A-FIG. 12C provide results of experiments comparing a first generation CAR (CD19ζ), a CAR including the CD3ζ and 4-1BB polypeptides, and a CAR including the CD3ζ and MyD88/CD40 polypeptides. FIG. 12A provides flow cytometry results of transduction efficiency. FIG. 12B is a graph of transduction efficiency. FIG. 12C is a graph of CAR expression level.

Figures 13A, 13B:
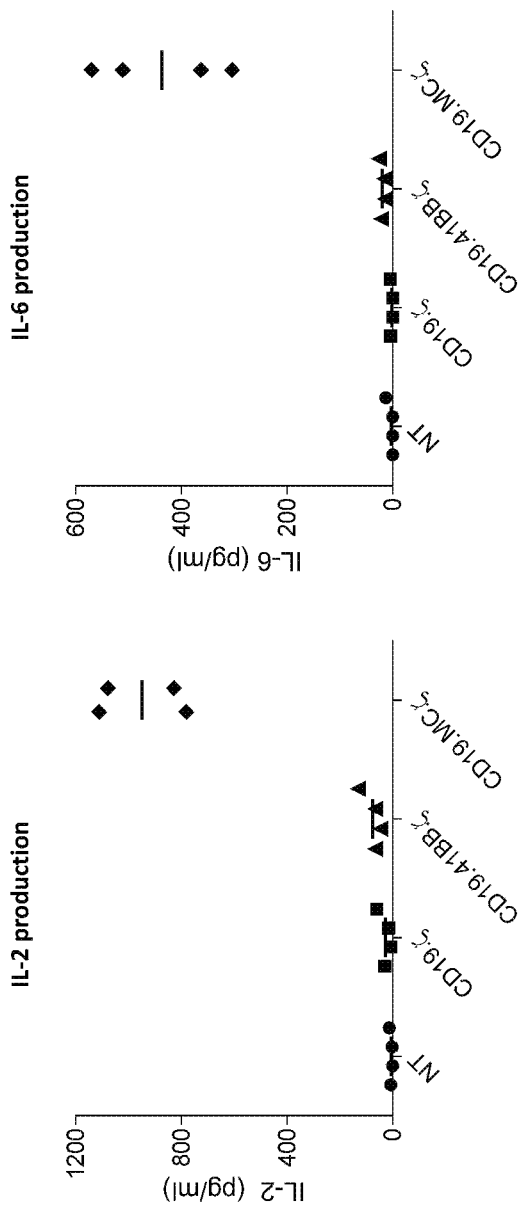

FIG. 13A-FIG. 13B provide results of experiments comparing a first generation CAR (CD19ζ), a CAR including the CD3ζ and 4-1BB polypeptides, and a CAR including the CD3ζ and MyD88/CD40 polypeptides for IL-2 production and IL-6 production following co-culture with CD19$^+$ Daudi Burkitt's lymphoma cells. NT denotes non-transformed cells. FIG. 13A is a graph of IL-2 production. FIG. 13B is a graph of IL-6 production.

Figures 14A, 14B:
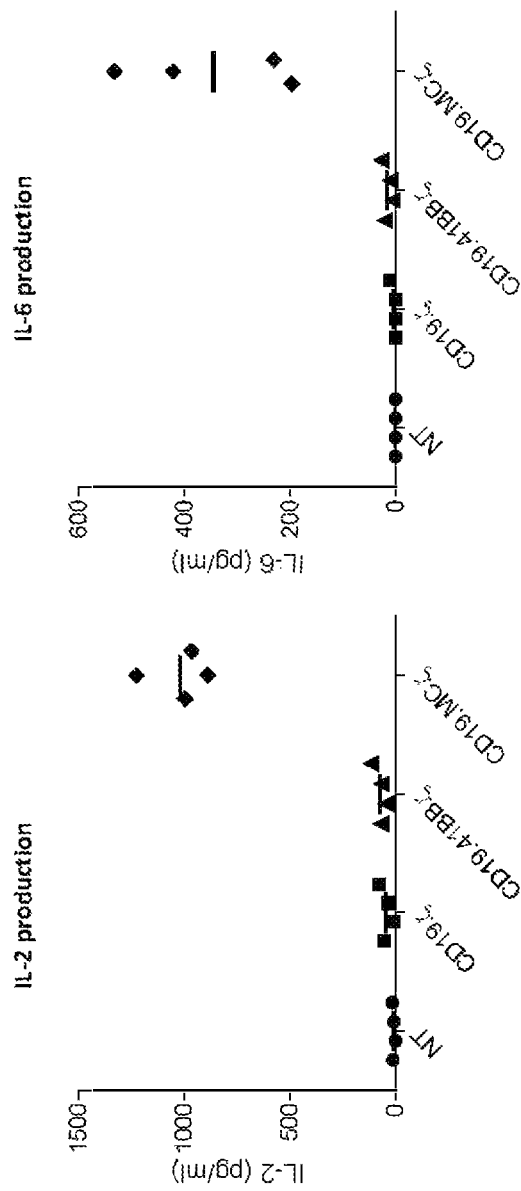

FIG. 14A-FIG. 14B provide results of experiments comparing a first generation CAR (CD19ζ), a CAR including the CD3ζ and 4-1BB polypeptides, and a CAR including the CD3ζ and MyD88/CD40 polypeptides for IL-2 production and IL-6 production following co-culture with CD19$^+$ Raji Burkitt's lymphoma cells. NT denotes non-transformed cells. FIG. 14A is a graph of IL-2 production. FIG. 14B is a graph of IL-6 production.

FIG. 15A-FIG. 15B provide results of tumor cell killing experiments comparing a first generation CAR (CD19ζ), a CAR including the CD3ζ and 4-1BB polypeptides, and a CAR including the CD3ζ and MyD88/CD40 polypeptides following 6 days of co-culture with FIG. 15A CD19$^+$ Daudi Burkitt's lymphoma cells and FIG. 15B CD19$^+$ Raji Burkitt's lymphoma cells. NT denotes non-transformed cells.

FIG. 16A-FIG. 16B provide schematics of a first generation-type chimeric antigen receptor (FIG. 16A), and a MyD88/CD40 chimeric antigen receptor (FIG. 16B).

Figure 17:
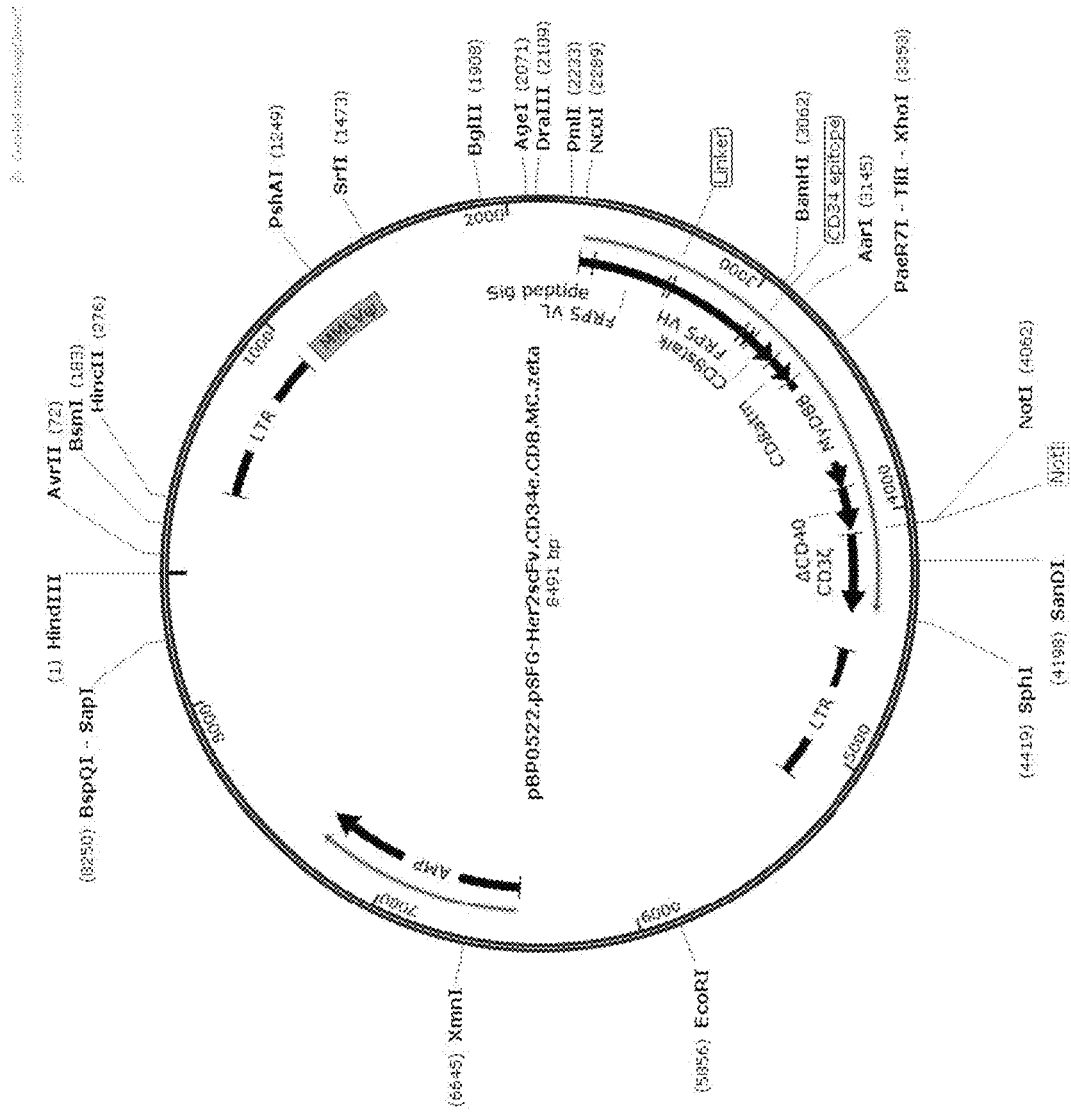

FIG. 17 is a plasmid map coding for a MyD88/CD40 chimeric antigen receptor comprising an antigen recognition moiety that recognizes Her2/Neu antigen.

Figure 18B:
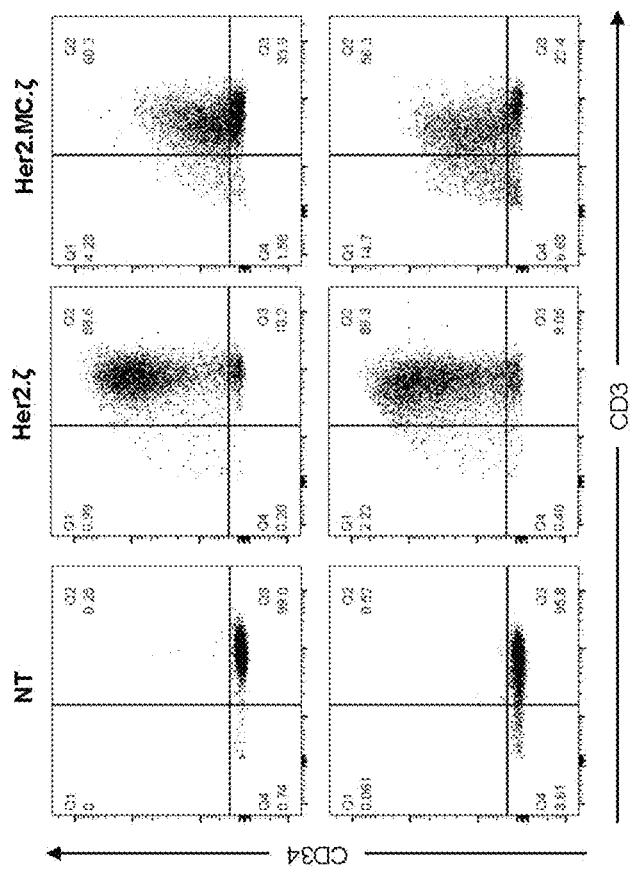
Figure 18A:
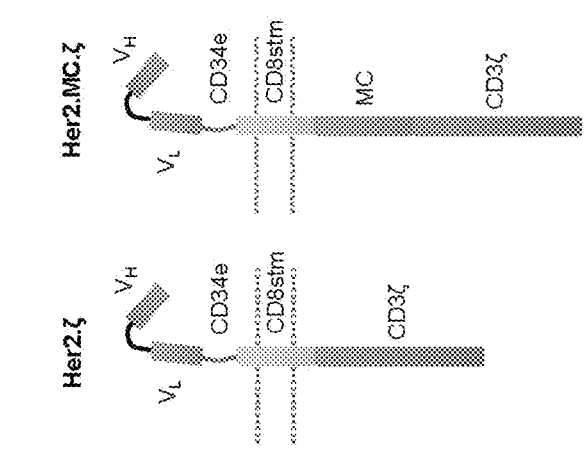

FIG. 18A-FIG. 18B provide examples of a Her2/New targeted chimeric antigen receptor. FIG. 18A provides a schematic of a Her2/Neu targeted CAR with and without the MC signaling domain; FIG. 18B provides sorting map results of the transduction of T cells and subsequent measurement of CAR expressed on the T cells using the CD34 epitope as a marker by flow cytometry.

Figure 19A:
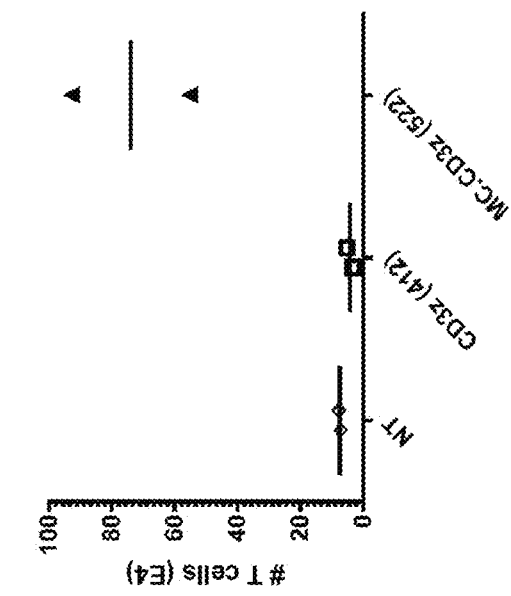
Figure 19B:
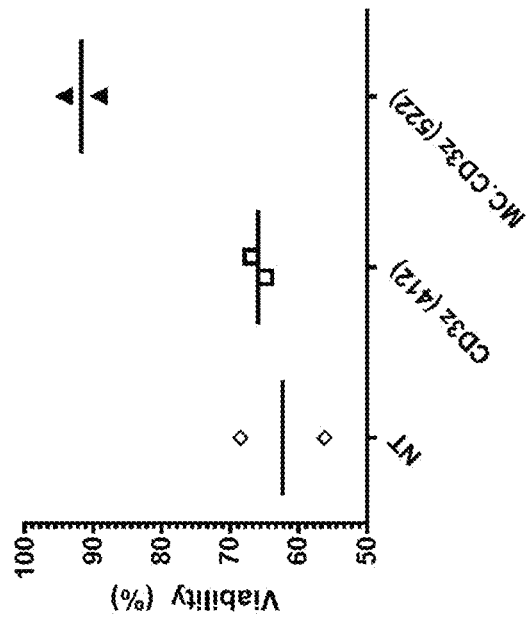

FIG. 19A-FIG. 19B provide graphs of T cell viability and T cell count following co-culturing of CAR T cells wherein the antigen recognition moiety of the chimeric antigen receptor recognizes the Her2/Neu antigen, with the Her2$^+$ breast cancer cell line MCF-7 for 7 days. These graphs show the viability of T cells after coculture and the total T cell number, indicating that CARs containing the MC molecule have better survival and enhanced proliferation. FIG. 19A is a graph of T cell viability.

FIG. 19B is a graph of T cell count.

FIG. 20A-FIG. 20B provide data showing the results of a co-culture assay with CAR-modified T cells, where the antigen recognition moiety of the chimeric antigen receptor recognizes the Her2/Neu antigen. FIG. 20A T cells were cultured with Her2$^+$ MCF-7-GFP tumor cells and tumor killing was assessed by measuring the percentage of GFP cells remaining in the culture after 7 days. FIG. 20B is a graph of cumulative data from two separate experiments.

Figure 21A:
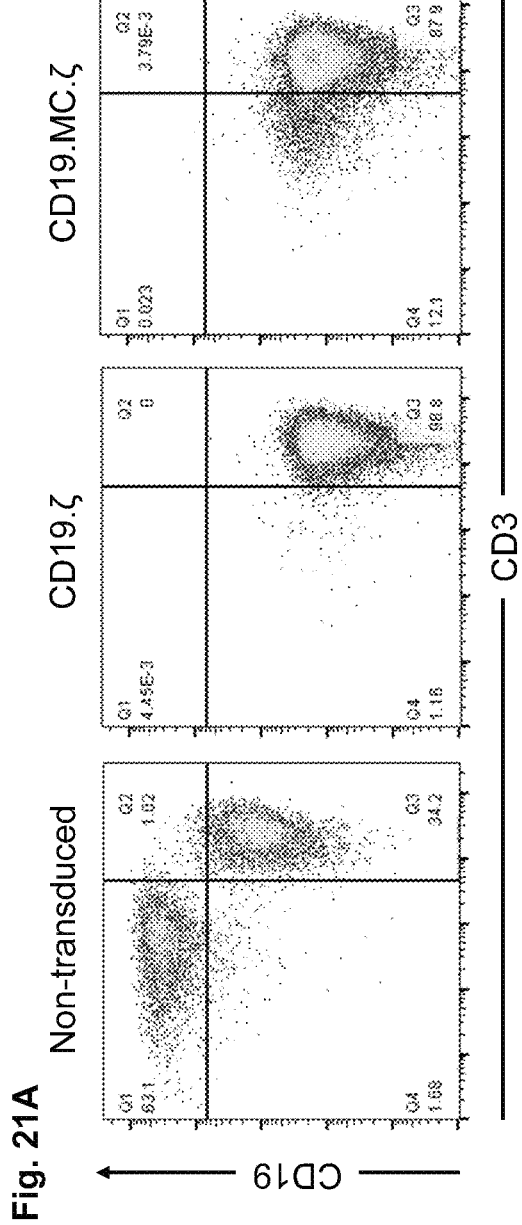
Figure 21E:
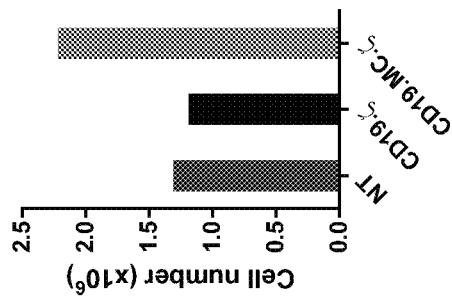
Figure 21D:
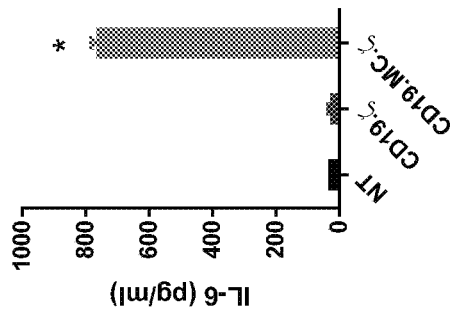
Figure 21C:
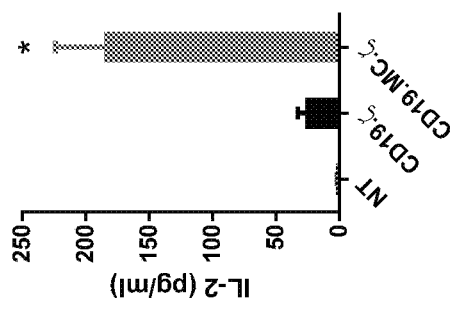
Figure 21B:
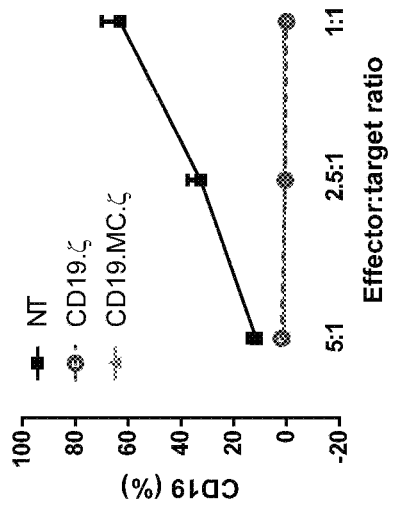

FIG. 21A-FIG. 21E provide data showing that the MyD88/CD40 signaling domain enhances T cell activity in a CD19 CAR. FIG. 21A provides flow cytometry data of cytotoxicity of non-transduced (NT), CD19.ζ and CD19.MC.ζ CAR modified T cells against CD19+ Raji tumor cells a 5:1 effector to target (E:T) ratio. FIG. 21B is a line graph of cytotoxicity dilution of CAR constructs against Raji tumor cells. FIG. 21C is a bar graph of IL-2 production after 48 hours of coculture with Raji tumor cells. FIG. 21D is a bar graph of IL-6 production after 48 hours of coculture with Raji tumor cells. FIG. 21E is a bar graph of cell number of CAR modified T cells after 4 days of culture with Raji tumor cells.

Figure 22:
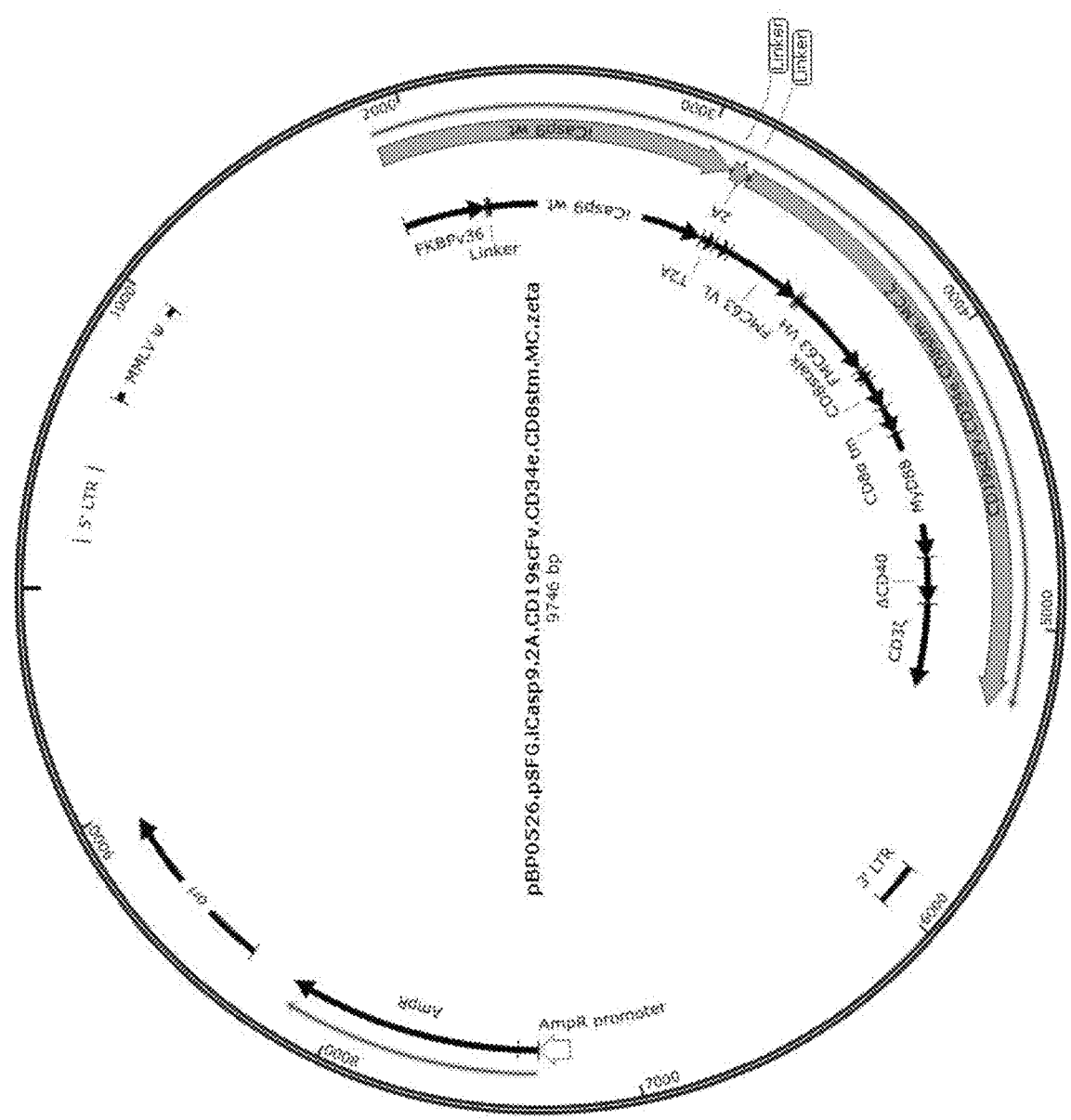

FIG. 22 is a plasmid map coding for a MyD88/CD40 chimeric antigen receptor comprising an antigen recognition moiety that recognizes CD19, and an inducible caspase-9 polypeptide.

Figure 23:
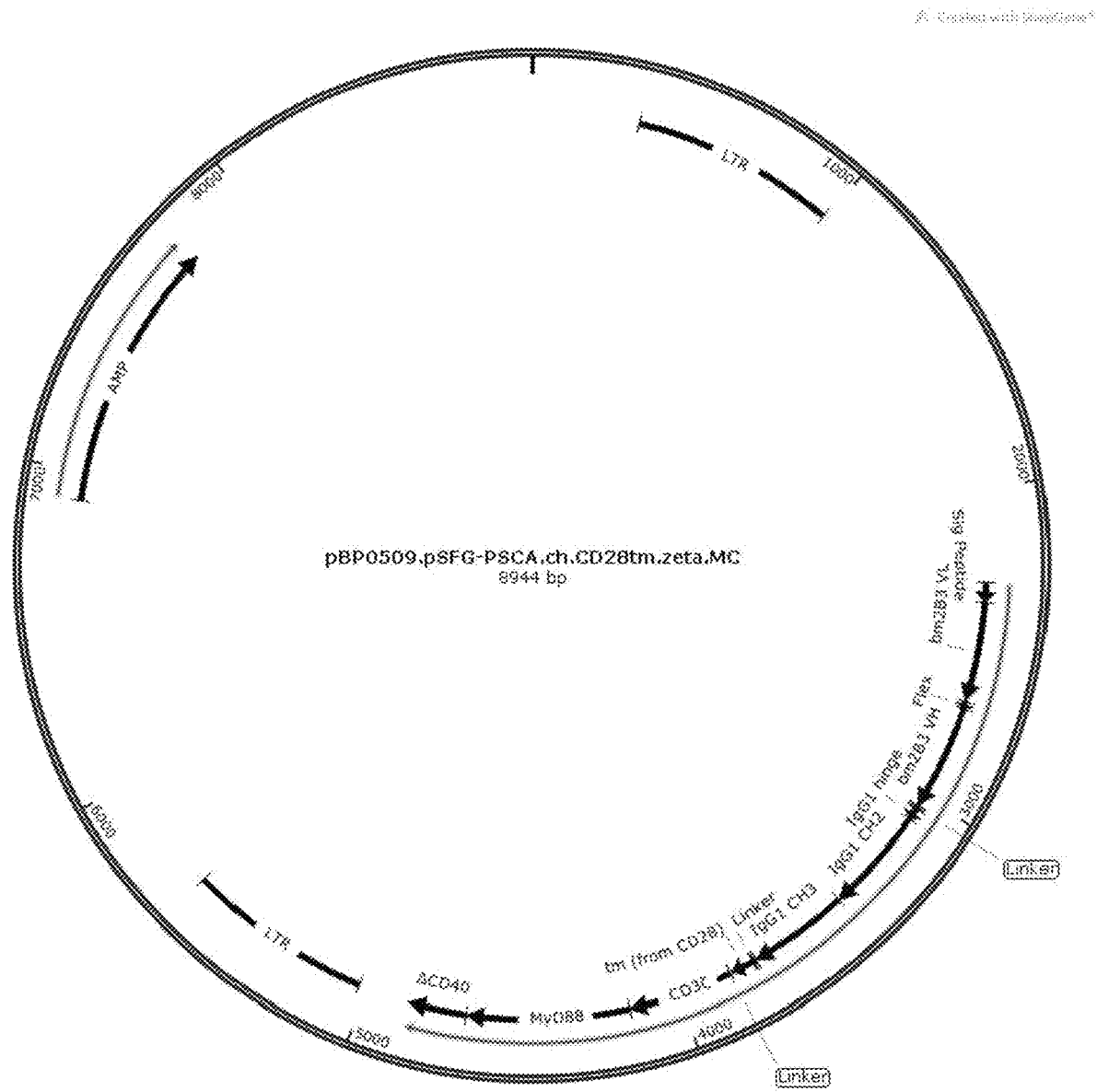

FIG. 23 is a plasmid map coding for a MyD88/CD40 chimeric antigen receptor comprising an antigen recognition moiety that recognizes PSCA.

Figure 24:
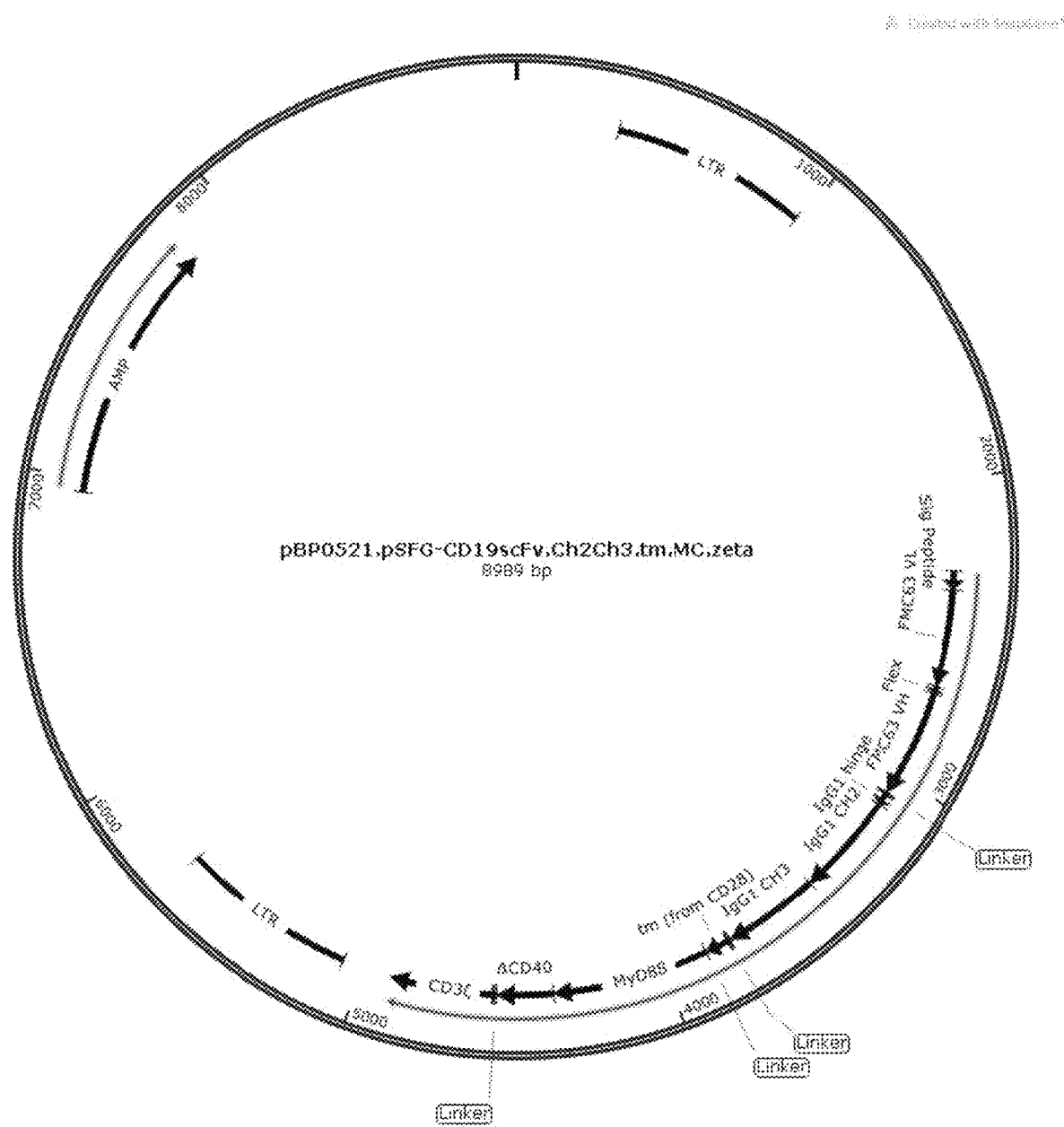

FIG. 24 is a plasmid map coding for a MyD88/CD40 chimeric antigen receptor comprising and antigen recognition moiety that recognizes CD19.

Figure 25:
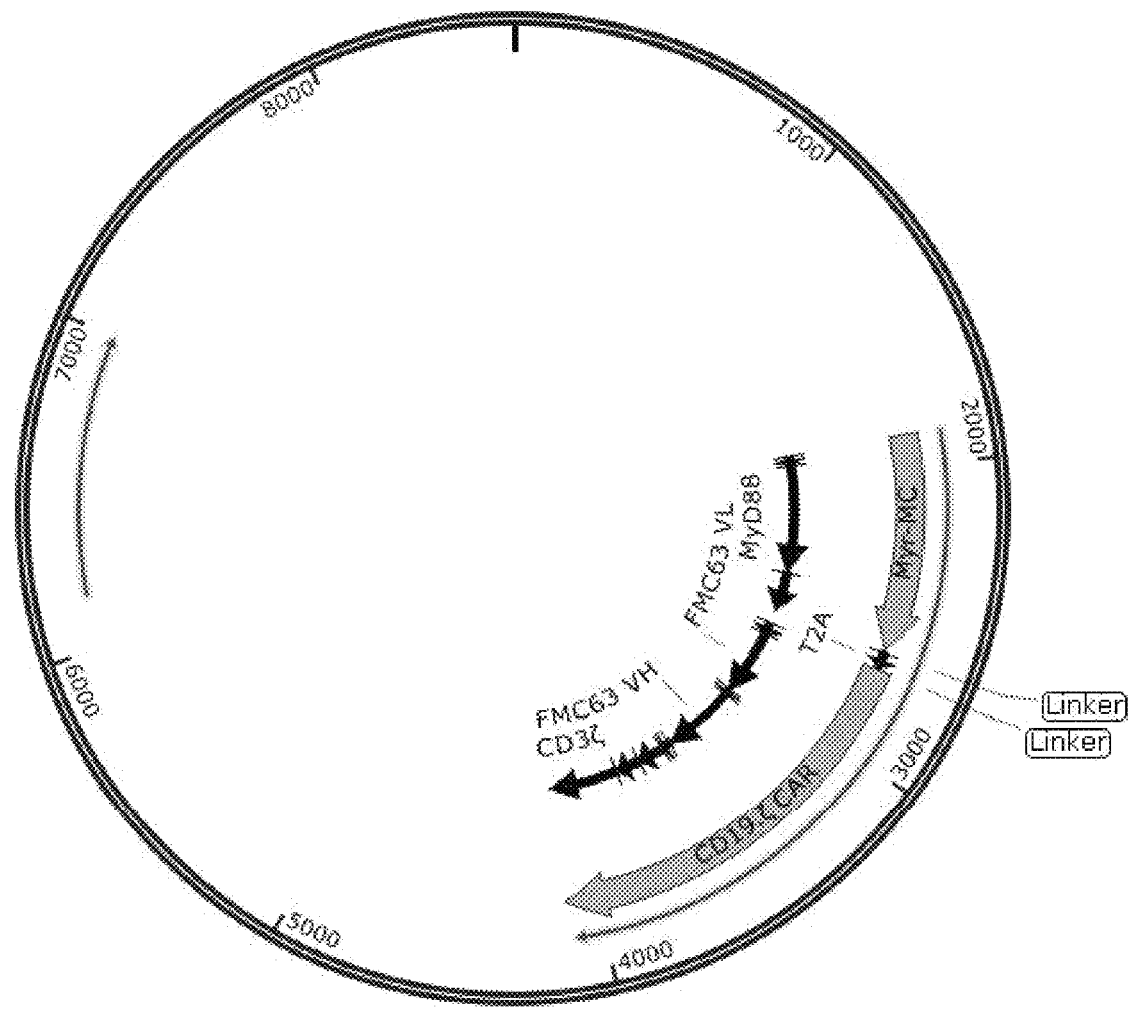

FIG. 25 is a plasmid map coding for a MyD88/CD40 chimeric stimulating molecule that is co-expressed with a chimeric antigen receptor.

FIG. 26A-FIG. 26D are schematics showing the CAR vector design discussed in Example 17. Four vectors were constructed bearing the iCaspase-9 suicide gene (iCasp9). FIG. 26A represents a standard 1st generation CAR molecule. FIG. 26B depicts a CAR that includes the CD28 endodomain. FIG. 26C: MC is expressed within the CAR molecule or as a constitutively expressed protein using a second 2A (FIG. 26D).

Figures 27A, 27B:
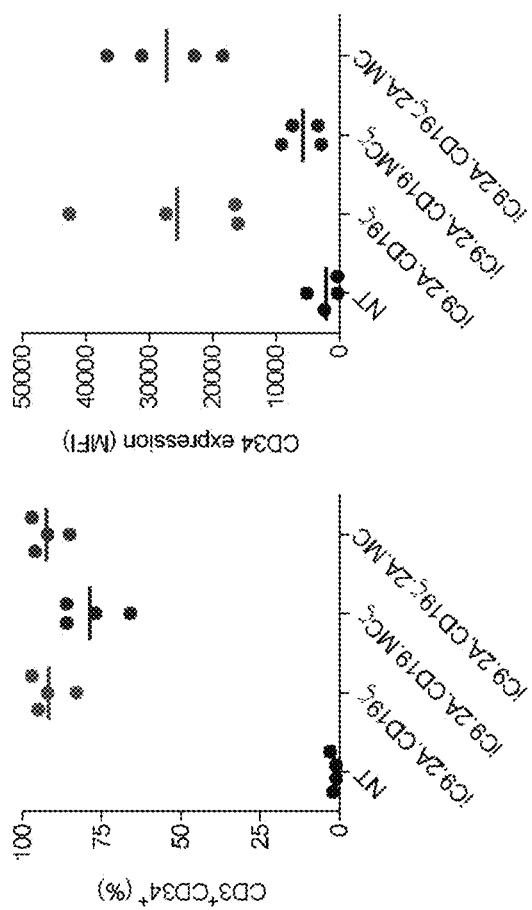

FIG. 27A and FIG. 27B provide graphs of CD3$^+$CD34$^+$% (FIG. 27A) and MFI (FIG. 27B) in T cells transduced with CAR molecules with different MC formats. T cells were transduced with each of the four vectors and compared to non-transduced T cells (NT) for CAR transduction efficiency (FIG. 27A) and CAR expression level (FIG. 27B) using mean fluorescence intensity (MFI) following CD3 and CD34 antibody labeling.

Figures 28A, 28B:
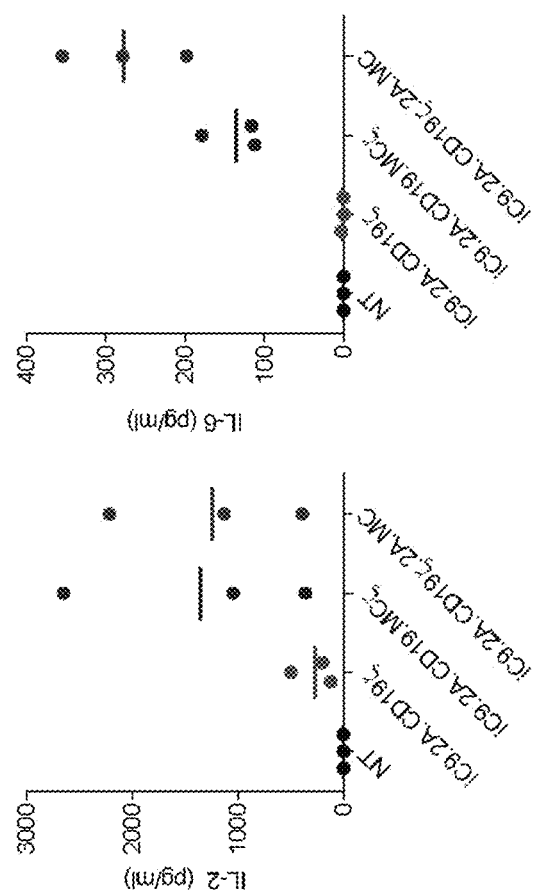

FIG. 28A and FIG. 28B provide graphs of IL-2 (FIG. 28A) and IL-6 (FIG. 28B) production following CD19\+ Raji coculture. T cells were transduced with each of the 4 vectors and compared to non-transduced T cells for cytokine production after a 1:1 T cell to tumor cell ratio coculture assay using Raji tumor cells. Supernatants were harvested at 48 hours and measured for IL-2 and IL-6 by ELISA.

Figures 29A, 29B:
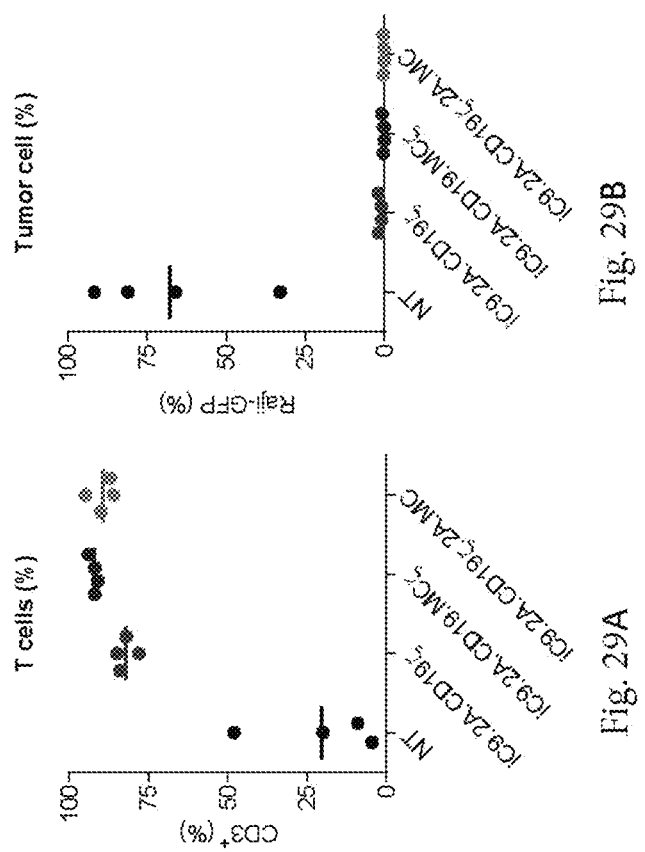

FIG. 29A and FIG. 29B are graphs of CD3$^+$% (FIG. 29A) and Raji-GFP % (FIG. 29B), assaying antitumor activity of different MC formats. T cells were transduced with each of the 4 vectors and compared to non-transduced T cells for tumor killing following coculture at a 1:1 T cell to tumor cell ratio using Raji-GFP tumor cells. After 14 days, the culture was harvested and analyzed by flow cytometry for CD3+ T cells and GFP+ tumor cells.

Figures 30A, 30B:
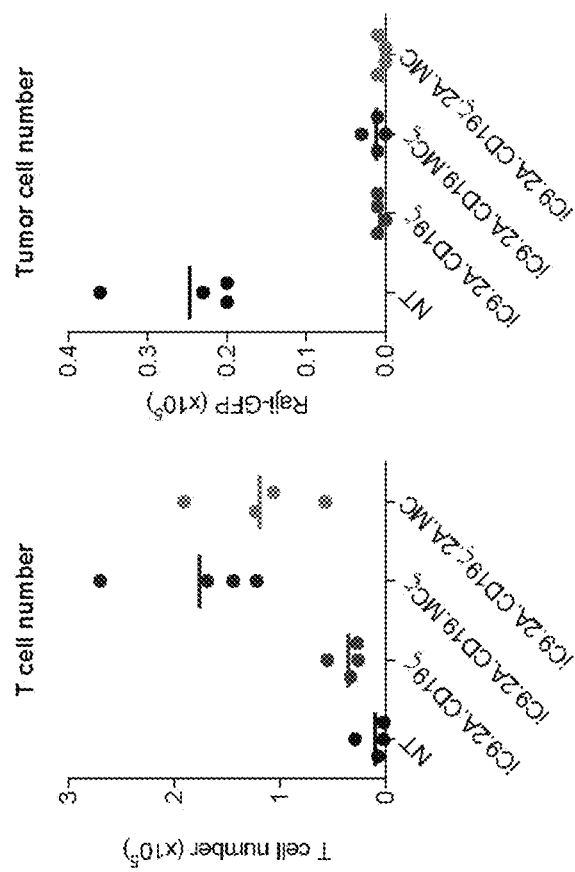

FIG. 30A and FIG. 30B are graphs of T cell number (FIG. 30A) and Raji-GFP (FIG. 30B) following MC costimulation of CD19-targeted CAR T cells. T cells were transduced with each of the 4 vectors and compared to non-transduced T cells for tumor killing following coculture at a 1:1 T cell to tumor cell ratio using Raji-GFP tumor cells. After 14 days, the culture was harvested and analyzed by flow cytometry for CD3+ T cells and GFP+ tumor cells and the cell numbers calculated base off total cell numbers.

Figure 31:
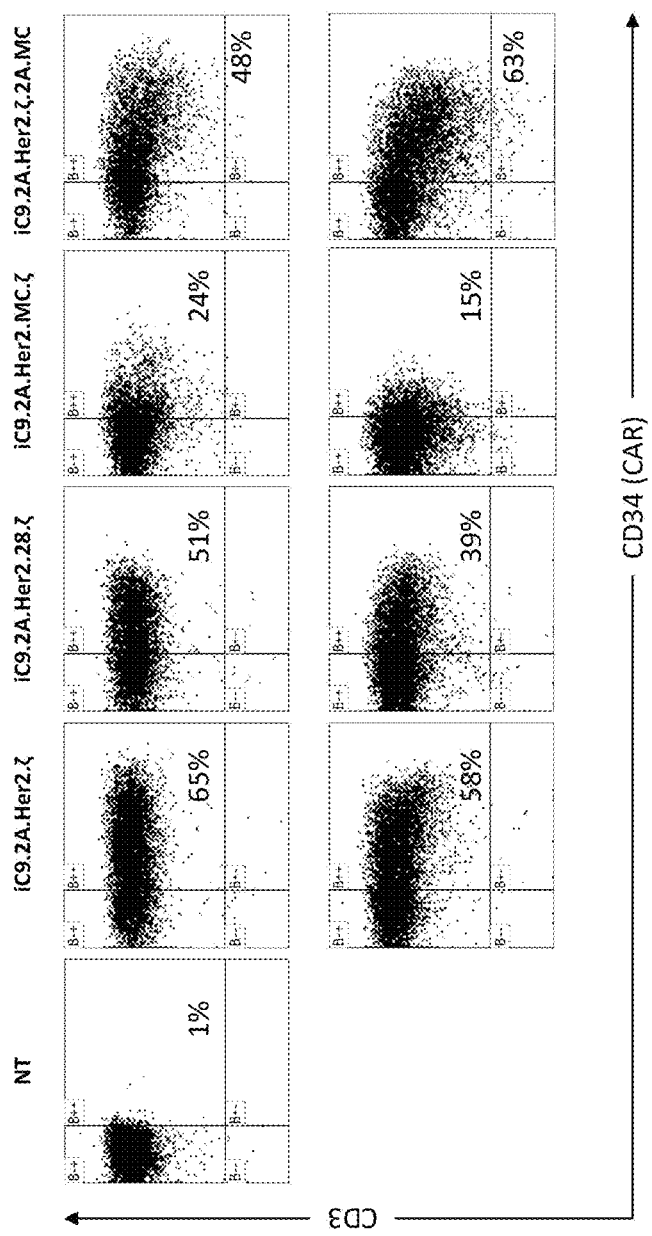

FIG. 31 is a FACs plot of expression of the CAR molecule with different MC formats using a Her2-targeted CAR. T cells were transduced with five different vectors targeting Her2 and subsequently analyzed by flow cytometry for CAR expression on days 4 and 8 post-transduction using CD3 and CD34 antibodies.

Figures 32A, 32B:
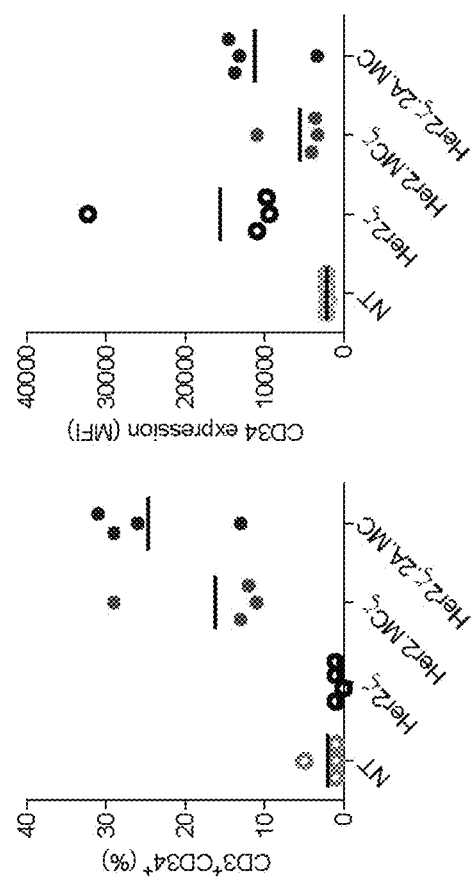

FIG. 32A and FIG. 32B are graphs of CAR transduction percent and MFI for HER2 CAR constructs of CD3$^+$CD34$^+$% (FIG. 32A) and MFI (FIG. 32B).

Figures 33A, 33B:
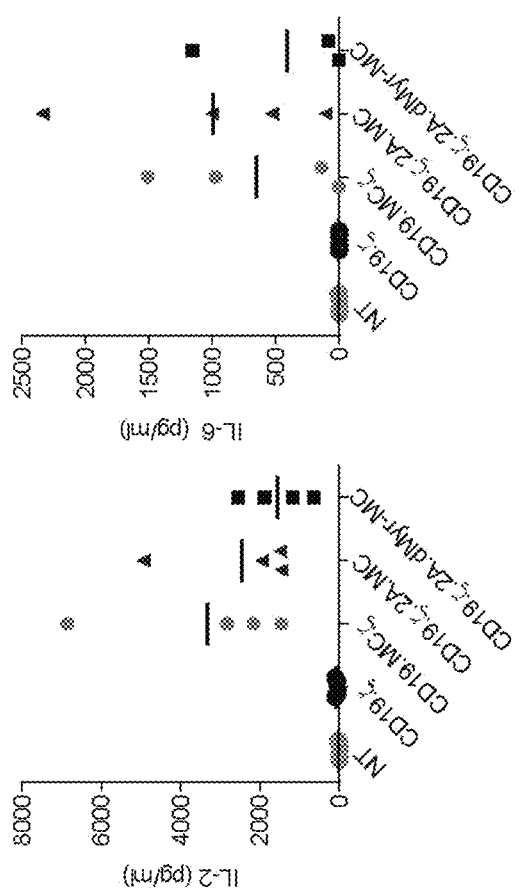

FIG. 33A and FIG. 33B are graphs of IL-2 (FIG. 33A) and IL-6 (FIG. 33B) production for HER2 CAR constructs.

Figures 34A, 34B:
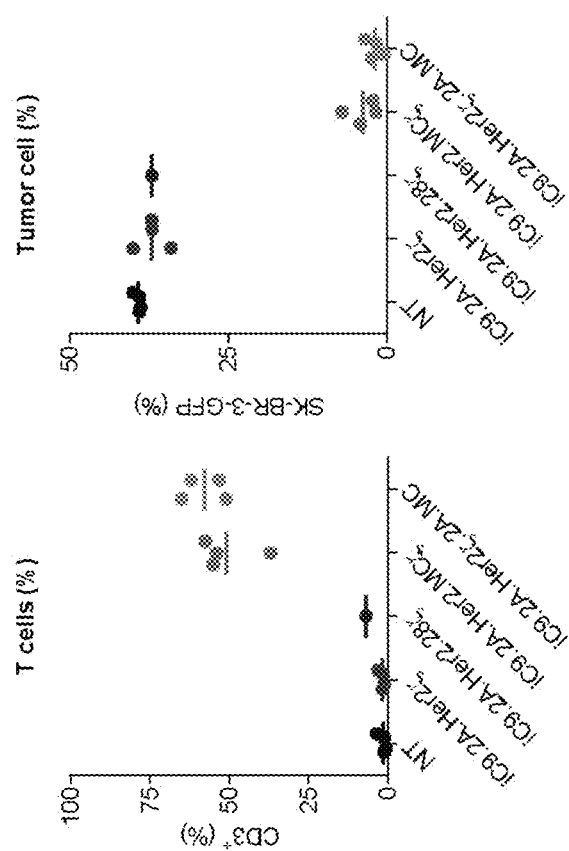

FIG. 34A and FIG. 34B provide graphs of antitumor activity of different MC formats; FIG. 34A: CD3+%, FIG. 34B: SK-BR-3-GFP %. T cells were transduced with each of the 5 vectors and compared to non-transduced T cells for tumor killing following coculture at a 1:1 T cell to tumor cell ratio using Her2+ SK-BR-3-GFP tumor cells. After 14 days, the culture was harvested and analyzed by flow cytometry for CD3+ T cells and GFP+ tumor cells.

Figures 35A, 35B:
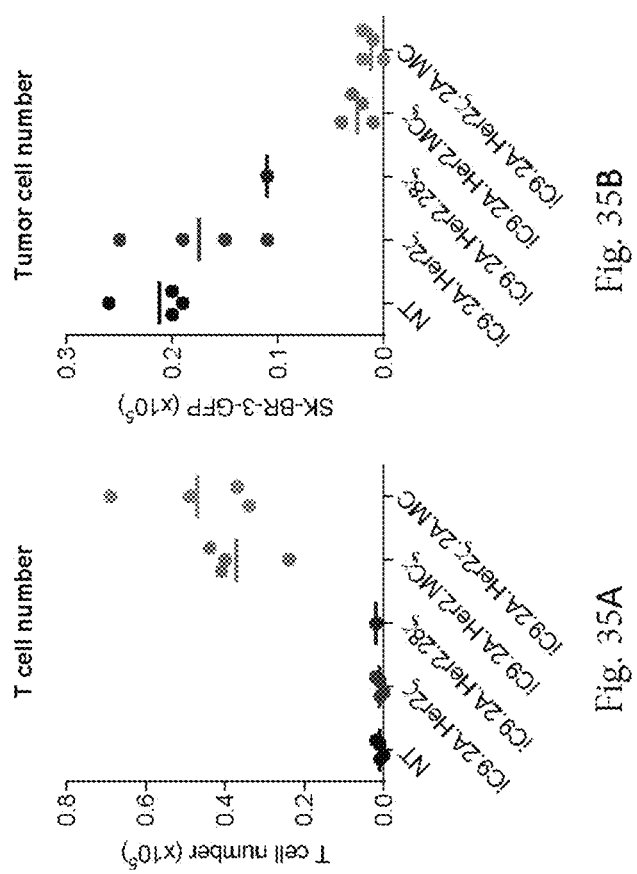

FIG. 35A and FIG. 35B provide graphs showing MC costimulation enhances T cell proliferation of Her2-targeted CAR-T cells. FIG. 35A: T cell number, FIG. 35B: SK-BR-3-GFP. T cells were transduced with each of the 4 vectors and compared to non-transduced T cells for tumor killing following coculture at a 1:1 T cell to tumor cell ratio using SK-BR-3-GFP tumor cells. After 14 days, the culture was harvested and analyzed by flow cytometry for CD3+ T cells and GFP+ tumor cells and the cell numbers calculated base off total cell numbers.

Figures 36A, 36B:
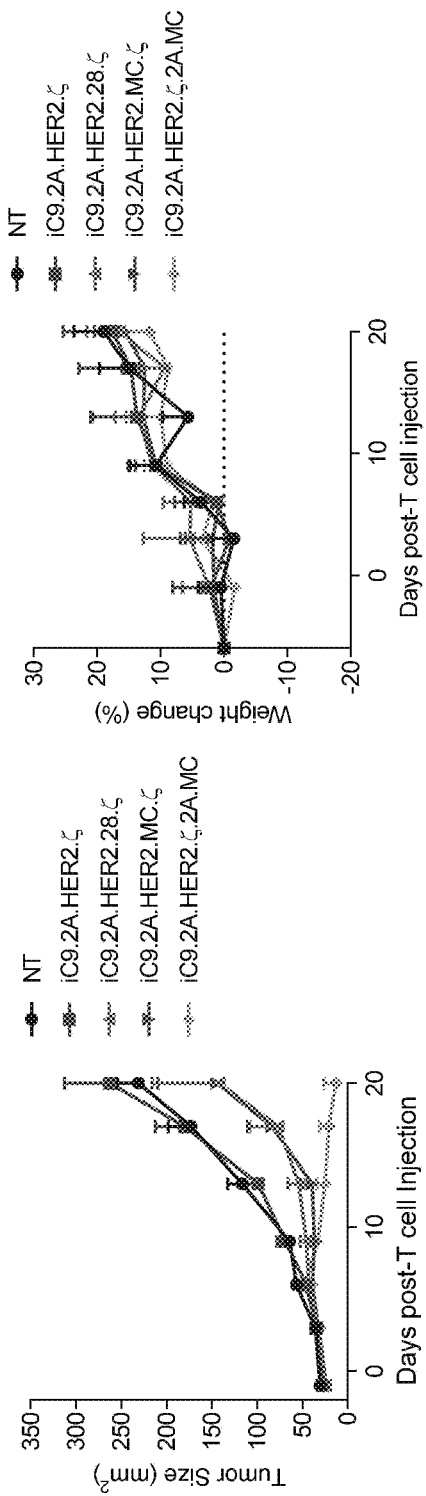

FIG. 36A and FIG. 36B provide graphs showing that constitutively expressed MC using a 2A polypeptide demonstrates enhanced antitumor activity in vivo. FIG. 36A: Tumor size, FIG. 36B: Weight change %. Immune deficient mice (NSG) were injected s.c. with 1×106 SK-BR-3-EGFPluciferase tumor cells in the right flank. After 7 days, the tumors were treated with 2 intratumoral injections on days 7 and 10 with 1×107 Her2-specific CAR-modified T cells, or non-transduced (NT). Tumor size and weight was measured twice weekly for each of the groups.

FIG. 37A-FIG. 37E provide schematics of retrovirus constructs used to express chimeric antigen receptors containing single chain variable fragments specific for CD19 and Her2. The constructs also included polynucleotides coding for various costimulating molecules such as the CD28 costimulatory domain, or MyD88, CD40, or MyD88/CD40 (MC). The constructs also include a polynucleotide sequence coding for a Caspase-9 safety switch (iC9). FIG. 37A: iC9-scFv.ζ. FIG. 37B: iC9-scFv.28.ζ. FIG. 37C: iC9-scFv.-CD40. FIG. 37D: iC9-scFv.ζ-MyD88. FIG. 37E: iC9-scFv.ζ-MC.

FIG. 38A-FIG. 38F provide results of MyD88/CD40 (MC) costimulation assays using the constructs of FIG. 37A-FIG. 37E. FIG. 38A provides flow cytometry results showing expression of the CAR/chimeric costimulating molecule construct in T cells. FIG. 38B provides a bar graph of IL-2 production in T cells expressing the various constructs. FIG. 38C provides a bar graph of the number of T cells from a coculture experiment with different CAR constructs. FIG. 38D provides a bar graph tumor cell number from a coculture experiment with different CAR constructs. FIG. 38E provides flow cytometry results showing efficacy of tumor cell elimination following coculture with T cells expressing the various constructs. FIG. 38F provides a bar graph of IL-2 production from a coculture assay using the various constructs.

Figure 39A:
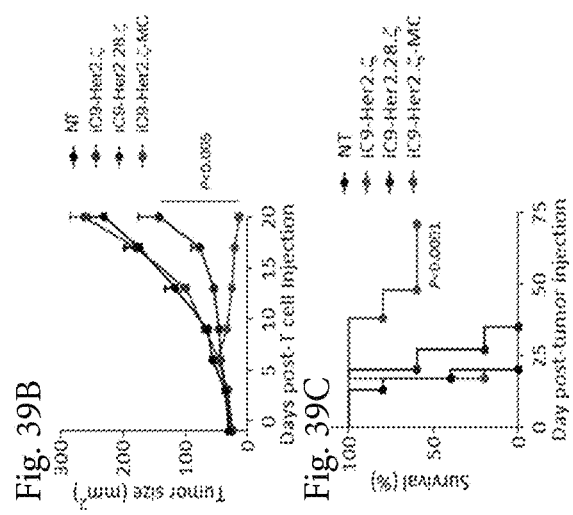
Figure 39B:
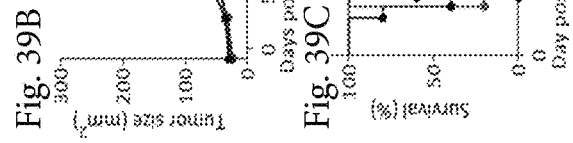
Figure 39C:
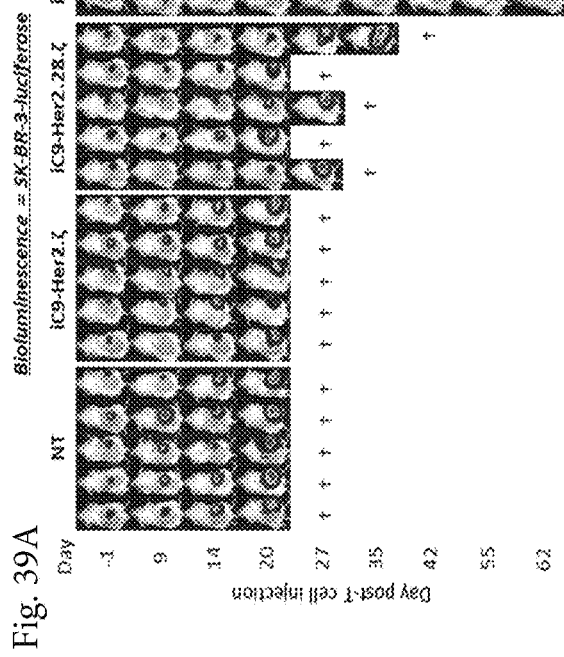
Figure 39D:
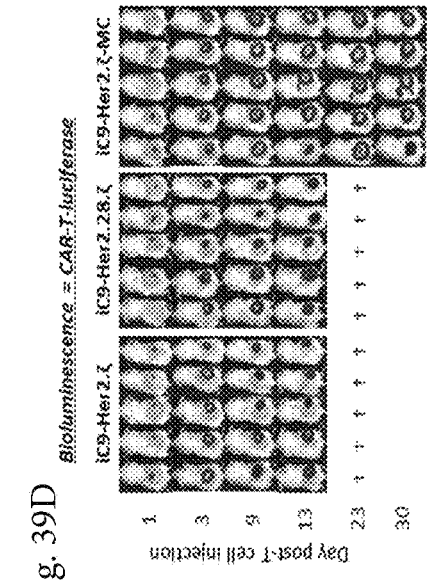
Figure 39E:
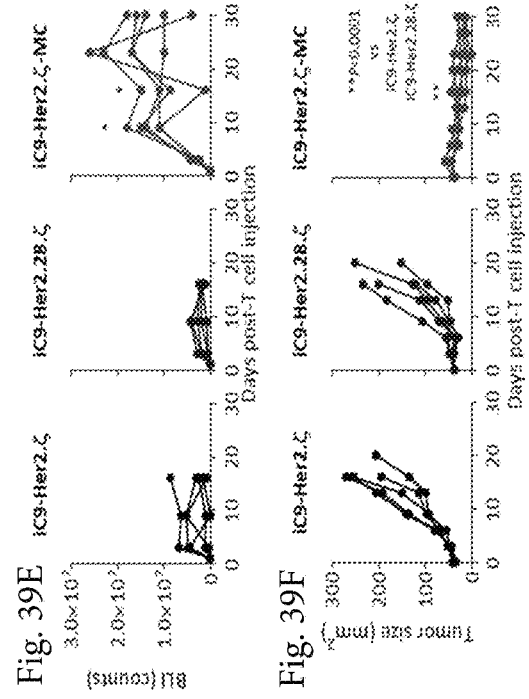
Figure 39F:
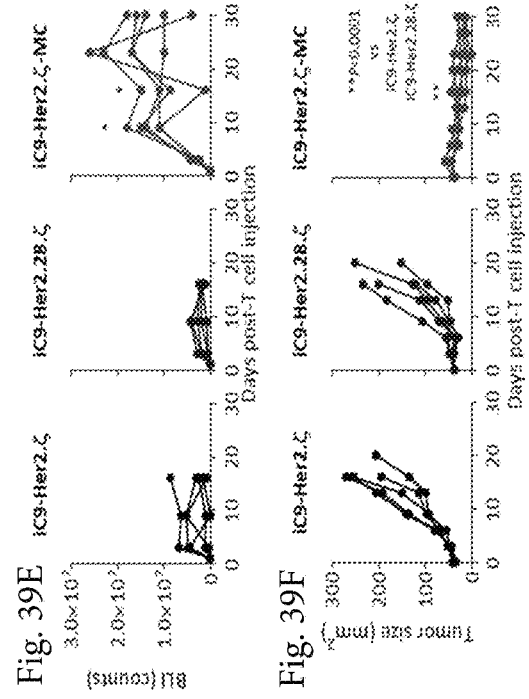

FIG. 39A-FIG. 39F provide results of the enhancement of Her2CAR-T cell efficacy in vivo by the MyD88/CD40 chimeric costimulatory molecule using the constructs of FIG. 37A-FIG. 37E. FIG. 39A T cells were transduced with Her2.ζ, Her2.28.∂ or Her2.ζ-MC CARs and injected directly into luciferase-expressing s.c. Her2+ SK-BR-3 tumors engrafted into NSG mice (n=5). Bioluminescence (BLI), as shown in FIG. 39A photos, of tumor cells was measured by IVIS. FIG. 39B is a graph of tumor size, which was measured by calipers and survival. FIG. 39C is a graph of tumor size calculated over 75 days. FIG. 39D is a photo showing bioluminescence following subsequent co-transduction of T cells with CAR and luciferase and injected directly into s.c. Her2$^+$ SK-BR-3 tumors engrafted into NSG mice (n=5). FIG. 39E is a graph of CAR-T cell expansion which was calculated by region-of-interest ROI using IVIS imaging. FIG. 39F is a graph of tumor size, which was calculated by caliper measurements and shows individual mice in each treatment group. *P-value=<0.05.

FIG. 40A-FIG. 40C provide results of the enhancement of CD19 CAR-T cell efficacy in vivo by the MyD88/CD40 chimeric costimulatory molecule using the constructs of FIG. 37A-FIG. 37E. FIG. 40A: NSG mice (n=5 per group) were engrafted with Raji-luciferase tumor cells and then treated with non-transduced (NT) or iC9-CD19.ζ-MC CAR-modified T cells on day 3. Tumor growth was measured by IVIS imaging and calculated by whole-body BLI, as shown in photos. FIG. 40B provides a graph of bioluminescent counts (BLI counts) and FIG. 40C provides a graph of (Kaplan-Meier analysis from (A)). At objective evidence of sCRS, rimiducid (AP1903) was administered (gray boxes, FIG. 40A; third row middle column, second row right column), leading to normalization of cytokines within 24 hrs and complete resolution of clinical sCRS without compromising tumor control.

Figure 41A:
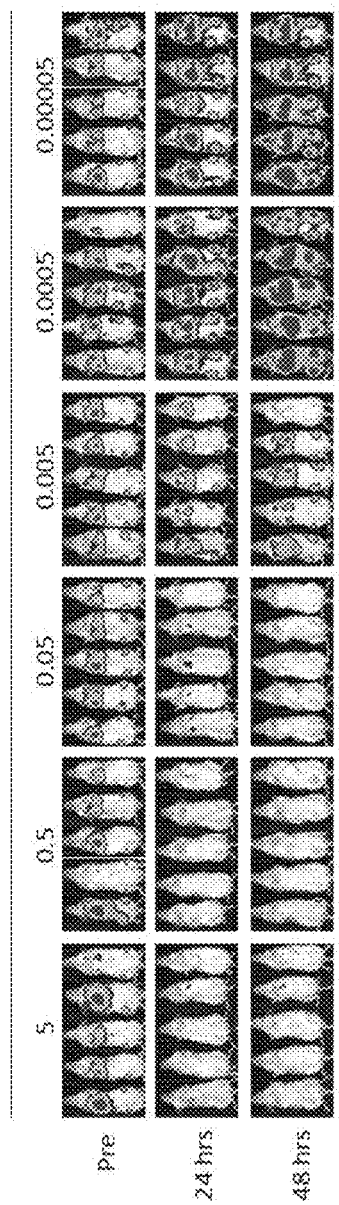
Figure 41B:
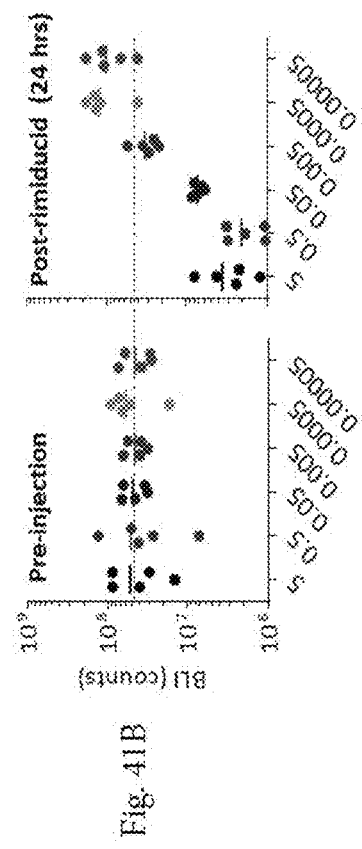
Figure 41C:
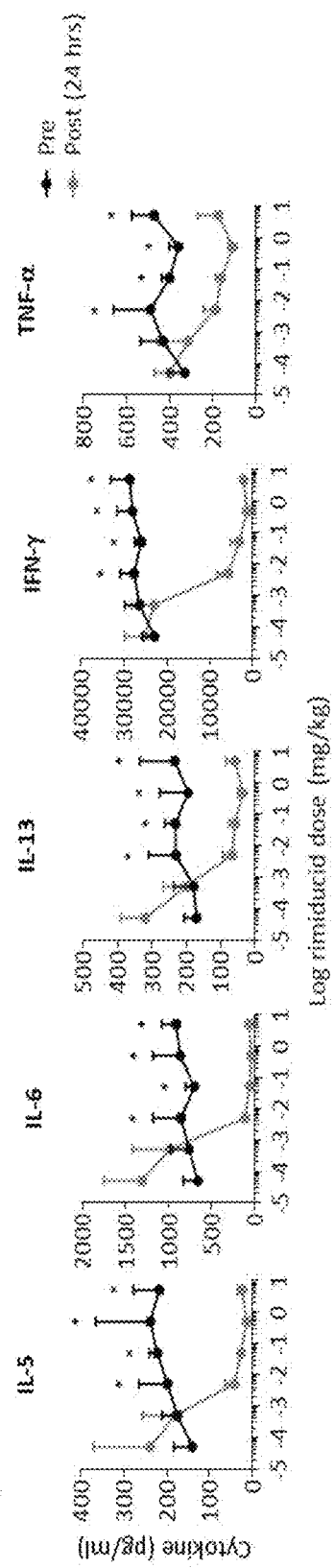

FIG. 41A-FIG. 41C provide results of assays of the titration of inducible chimeric Caspase-9 expressing cells, using the constructs of FIG. 37A-FIG. 37E, with rimiducid. FIG. 41A and FIG. 41B: NSG mice (n=5 per group) were engrafted with CD19+ Raji lymphoma cells and treated with 5×10$^6$ iC9-CD19.ζ-MC/luciferase-transduced T cells at day 3. After 6 days, mice were treated i.p. with log dilutions of rimiducid (0.00005-5 mg/kg). BLI of CAR-T cells was assessed prior to rimiducid treatment and at 24 and 48 hours post-injection. FIG. 41A provides photos showing bioluminescence, and FIG. 41B provides graphs of the results of the assay. FIG. 41C provides graphs of serum cytokine levels, which were measured from each group before (black line) and 24 hours post-administration (gray line) of rimiducid. *P-value=<0.01.

FIG. 42A-FIG. 42E provide the results of efficacy and safety assays of various Her2-chimeric antigen receptor constructs of FIG. 37A-FIG. 37E. FIG. 42A provides a timeline of the assays. FIG. 42B-FIG. 42E provide graphs showing tumor size in mice following administration of control T cells (FIG. 42B) and transduced T cells. FIG. 42C: Her2.ζ. FIG. 42D: Her2.28.ζ. FIG. 42E: Her2.ζ-MC.

FIG. 43A-FIG. 43C provide the results of efficacy and safety assays of various Her2-chimeric antigen receptor constructs of FIG. 37A-FIG. 37E. FIG. 43A provides a timeline of the assays. FIG. 43B provides photographs showing bioluminescence in mice following administration of the transduced T cells. FIG. 43C is a graph of the bioluminescence assay.

FIG. 44A-FIG. 44D provide results of assays of the titration of inducible chimeric Caspase-9 expressing cells, using the CD19-specific CAR constructs of FIG. 37A-FIG. 37E, with rimiducid.

FIG. 44A provides photographs showing bioluminescence in mice following administration of the transduced T cells. FIG. 44B is a graph of bioluminescence in mice following administration of rimiducid to induce Caspase-9 activity. FIG. 44C is a graph of IL-6 secretion, and FIG. 44D is a graph of TNF-alpha secretion following administration of rimiducid.

Figures 45A, 45B, 45C, 45D:
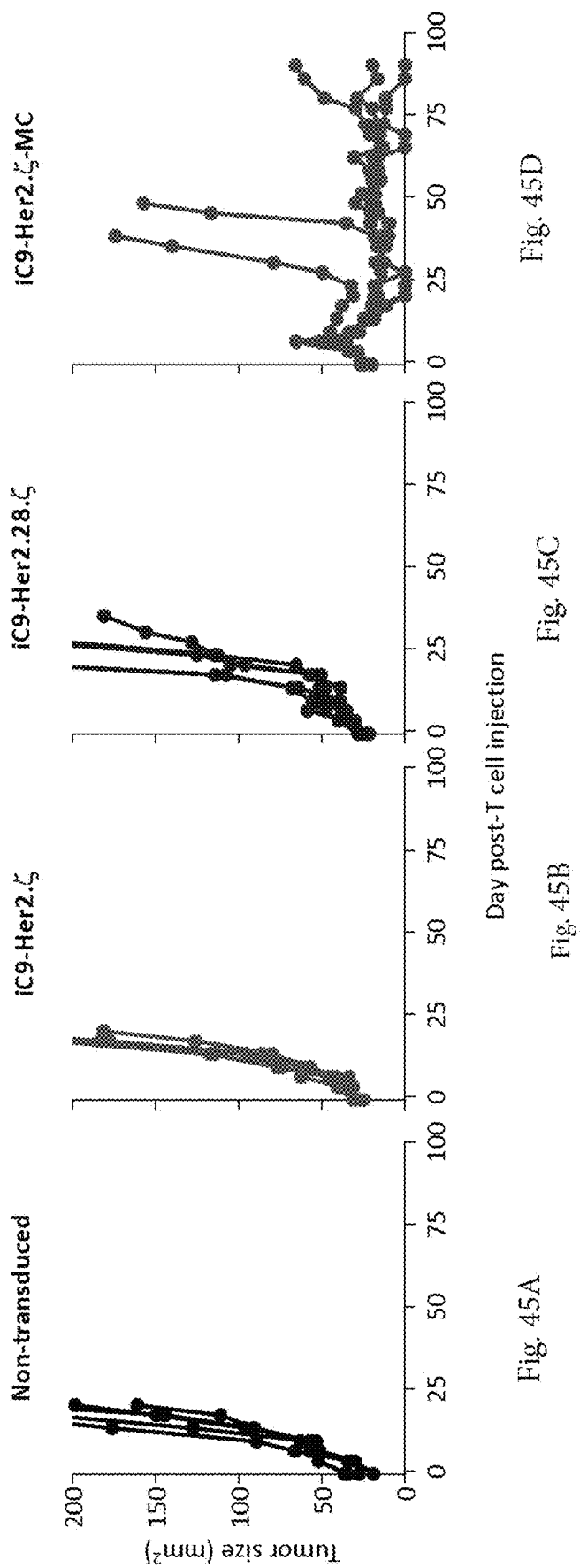

FIG. 45A-FIG. 45D provide graphs of tumor size in days post administration of Her2-specific CAR constructs. FIG. 45A: non-transduced T cell control. FIG. 45B: iC9-Her2. FIG. 45C: iC9-Her2.28. FIG. 45D: iC9-Her2.ζ-MC.

FIG. 46A-FIG. 46C provide results of assays of in vivo expansion of MC-enabled Her2 CAR-T cells. FIG. 46A provides photographs showing bioluminescence in mice following administration of the transduced T cells. FIG. 46B provides a graph of tumor size in days post-administration. FIG. 46C provides a graph of bioluminescence in days post-administration.

Figure 47C:
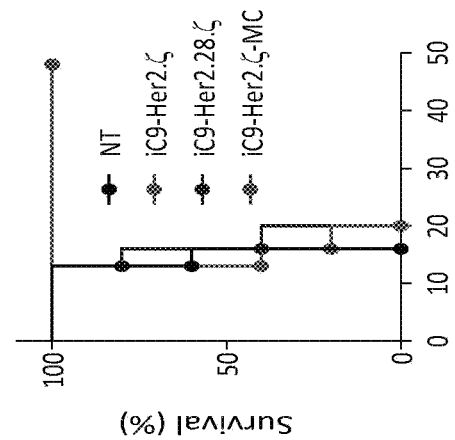
Figure 47B:
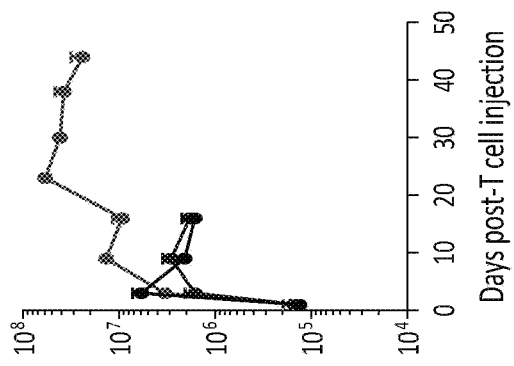
Figure 47A:
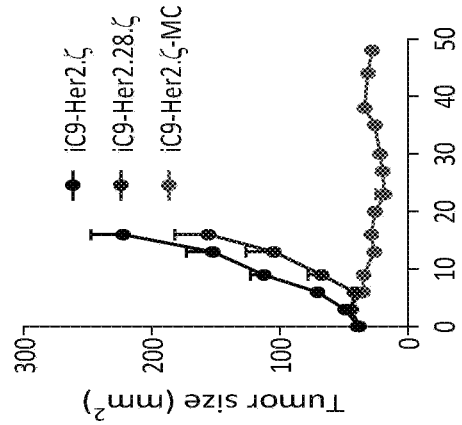

FIG. 47A-FIG. 47C provide results of assays of survival of mice following administration of MC-enabled Her2 CAR-T cells. FIG. 47A provides a graph of tumor size. FIG. 47B provides a graph of bioluminescence, and FIG. 47C provides a graph of percent survival in days post-injection of T cells.

FIG. 48A-FIG. 48F provide schematic representations of the DNA constructs used to express MyD88/CD40 chimeric stimulating molecules. FIG. 48A: construct encodes a CD19-specific chimeric antigen receptor, a chimeric inducible Caspase-9 polypeptide, and a MyD88/CD40 costimulatory molecule. FIG. 48B: construct encodes a CD19-specific chimeric antigen receptor and a chimeric inducible Caspase-9 polypeptide. FIG. 48C: construct encodes a CD19-specific chimeric antigen receptor. FIG. 48D: construct encodes a membrane-targeted MyD88/CD40 costimulatory molecule and a CD19-specific chimeric antigen receptor. FIG. 48E construct encodes a membrane-targeted MyD88/CD40 costimulatory molecule comprising an epitope for the QBEND10 antibody directed to CD34 (Q epitope). FIG. 48F: construct encodes a membrane-targeted inducible MyD88/CD40 costimulatory molecule comprising a multimeric ligand binding site and a CD19-specific chimeric antigen receptor.

Figure 49:
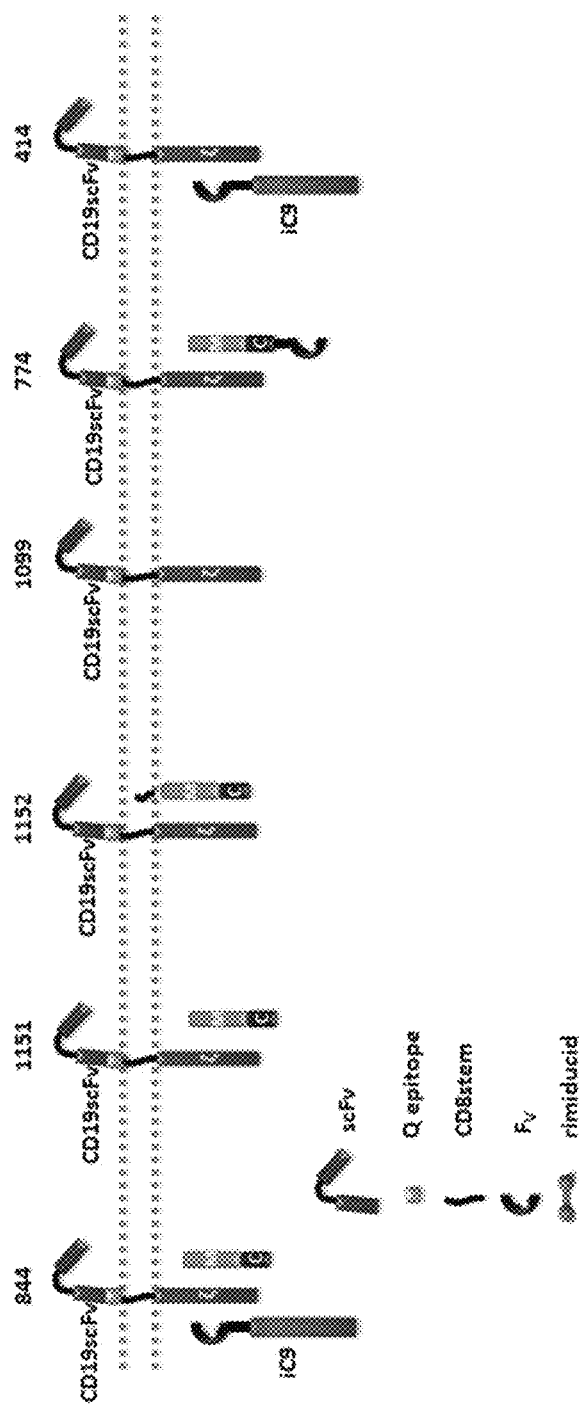

FIG. 49 provides a schematic representation of the proteins produced by the constructs in FIG. 48. Dots represent the plasma membrane with MC in 1152 tethered to the membrane with an N-terminal myristate.

Figure 50A:
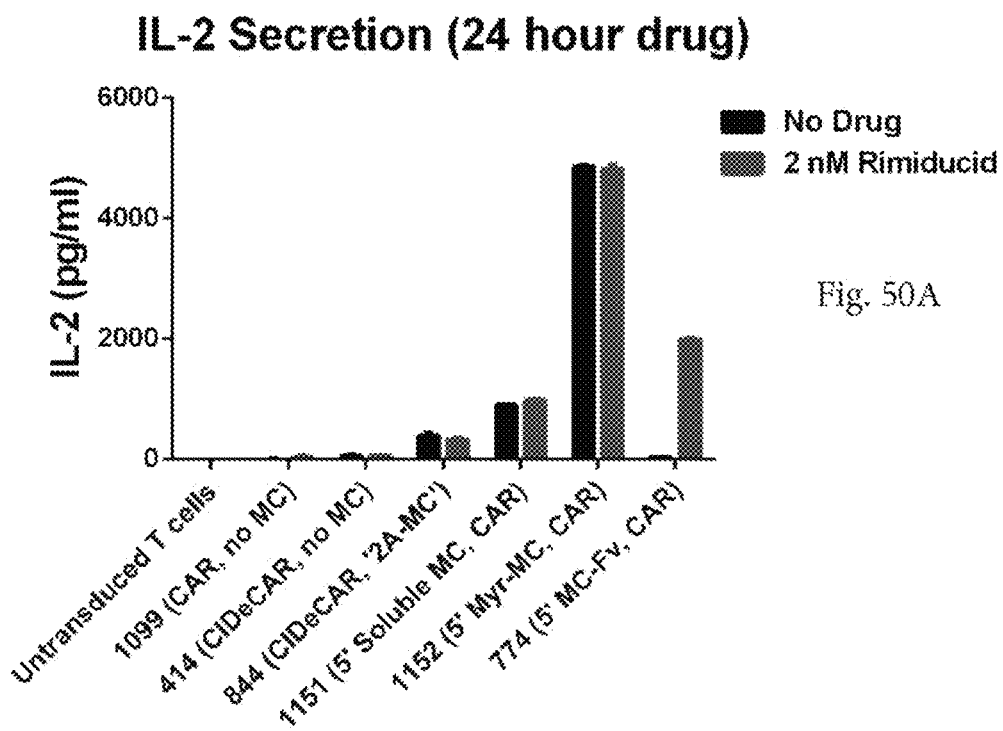
Figure 50B:
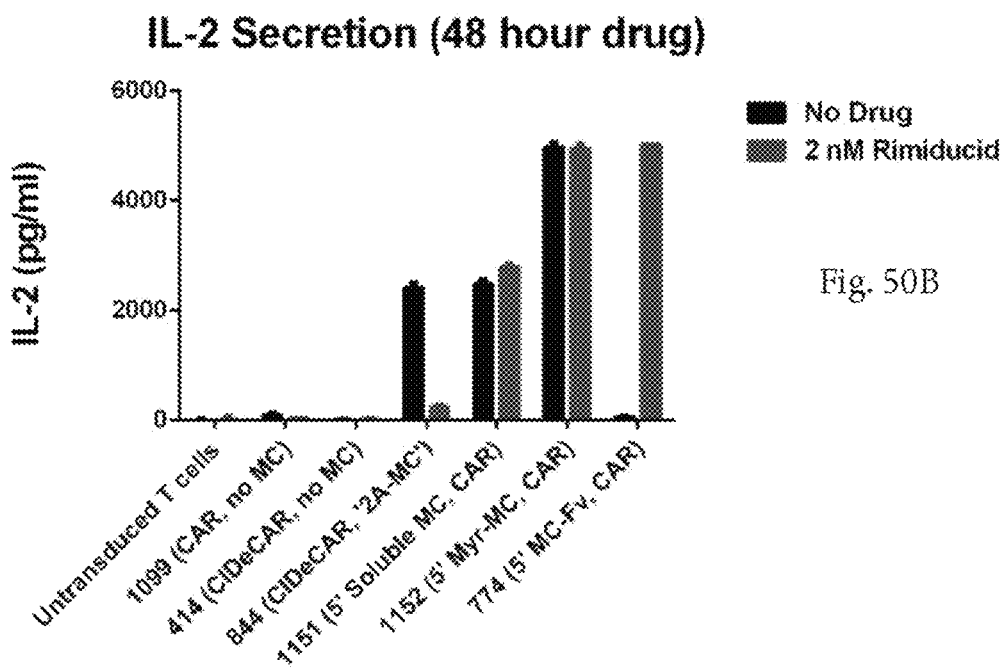

FIG. 50A and FIG. 50B are graphs of IL-2 secretion from T cells transduced with the indicated recombinant retroviruses. FIG. 50A: assay performed at 24 hours post transduction. FIG. 50B: assay performed at 48 hours post transduction.

Figure 51A:
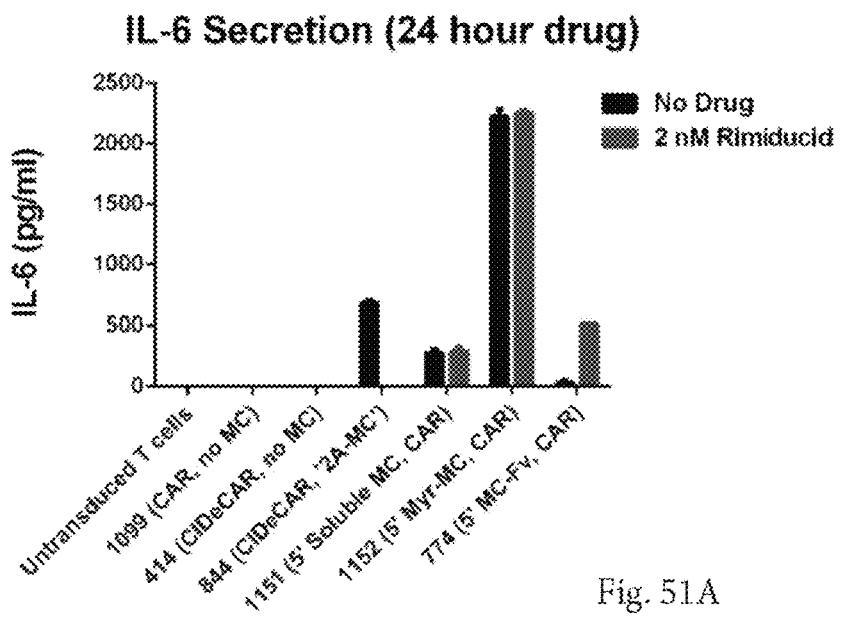
Figure 51B:
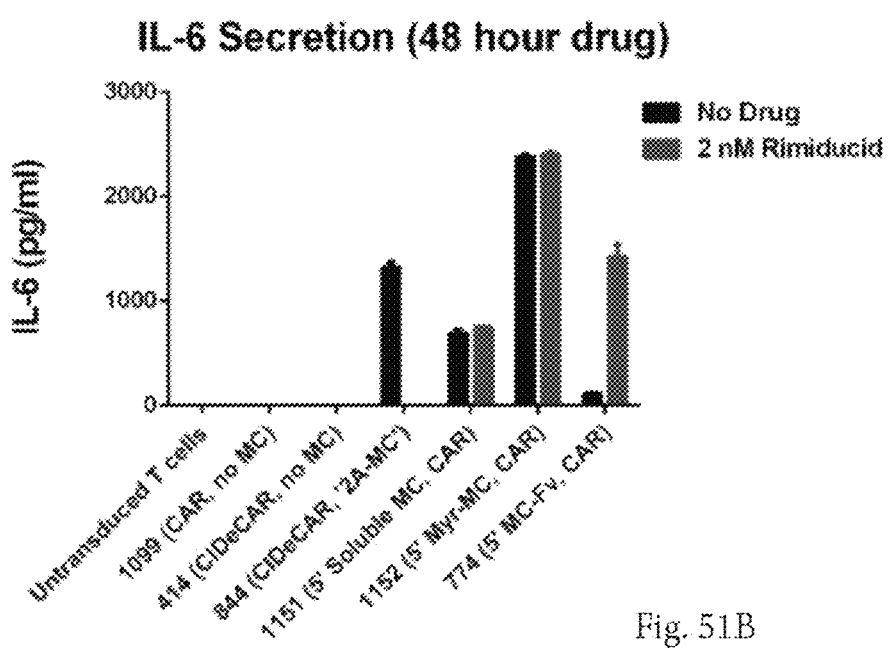

FIG. 51A and FIG. 51B are graphs of IL-6 secretion from T cells transduced with the indicated recombinant retroviruses. FIG. 51A: assay performed at 24 hours post transduction. FIG. 51B: assay performed at 48 hours post transduction.

DETAILED DESCRIPTION

Adoptive transfer of T cells genetically engineered to express chimeric antigen receptors (CARs) that recognize antigens expressed on tumor cells have begun to show promise in clinical studies. CARs are comprised of an antigen binding region, for example, a single-chain variable fragment (scFv) derived from an antigen-specific monoclonal antibody and a T cell activation molecule, such as the ζ-chain from the T cell receptor (CD3).

The basic components of a chimeric antigen receptor (CAR) include the following. The variable heavy (VH) and light (VL) chains for a tumor-specific monoclonal antibody are fused in-frame with the CD3ζ chain (ζ) from the T cell receptor complex. The VH and VL are generally connected together using a flexible glycine-serine linker, and then attached to the transmembrane domain by a spacer ($CH_2CH_3$) to extend the scFv away from the cell surface so that it can interact with tumor antigens.

Following transduction, T cells now express the CAR on their surface, and upon contact and ligation with a tumor antigen, signal through the CD3ζ chain inducing cytotoxicity and cellular activation.

Investigators have noted that activation of T cells through CD3ζ is sufficient to induce a tumor-specific killing, but is insufficient to induce T cell proliferation and survival. Early clinical trials using T cells modified with CARs expressing only the ζ chain showed that gene-modified T cells exhibited poor survival and proliferation in vivo. These constructs are termed 1st generation CARs.

As co-stimulation through the B7 axis is necessary for complete T cell activation, investigators added the co-stimulating polypeptide CD28 signaling domain to the CAR construct. This region generally contains the transmembrane region (in place of the CD3ζ version) and the YMNM motif for binding PI3K and Lck. In vivo comparisons between T cells expressing CARs with only ζ or CARs with both ζ and CD28 demonstrated that CD28 enhanced expansion in vivo, in part due to increased IL-2 production following activation. The inclusion of CD28 is called a 2nd generation CAR. The most commonly used costimulating molecules include CD28 and 4-1BB, which, following tumor recognition, can initiate a signaling cascade resulting in NF-ζB activation, which promotes both T cell proliferation and cell survival.

The use of co-stimulating polypeptides 4-1BB or OX40 in CAR design has further improved T cell survival and efficacy. 4-1BB in particular appears to greatly enhance T cell proliferation and survival. This 3rd generation design (with 3 signaling domains) has been used in PSMA CARs (Zhong X S, et al., Mol Ther. 2010 February; 18(2):413-20) and in CD19 CARs, most notably for the treatment of CLL (Milone, M. C., et al., (2009) Mol. Ther. 17:1453-1464; Kalos, M., et al., Sci. Transl. Med. (2011) 3:95ra73; Porter, D., et al., (2011) N. Engl. J. Med. 365: 725-533). These cells showed impressive function in 3 patients, expanding more than a 1000-fold in vivo, and resulted in sustained remission in all three patients.

T cell receptor signaling can be induced using a chemical inducer of dimerization (CID) in combination with a chimeric receptor that includes a multimerization region that binds to the CID, T cells were engineered to express the CD3ζ chain, which was linked with 1, 2, or 3 FKBP fragments. The cells expressed the chimeric receptor, and demonstrated CID-dependent T cell activation (Spencer, D. M., et al., Science, 1993. 262: p. 1019-1024). An inducible MyD88/CD40 (iMC) molecule for the activation of CAR-modified T cells was tested, and it was found that activation of iMC by AP1903 (rimiducid) provides powerful costimulation that increases T cell survival, proliferation, activation and tumor cell killing.

An inducible MyD88/CD40 (MC) molecule, when co-expressed in a T cell with a CAR molecule comprising CD3ζ, was found to provide costimulation. In this assay, the MyD88/CD40 molecule also included a multimerization region, and was inducible in the presence of the AP1903 ligand. The inducible MyD88/CD40 polypeptide was coexpressed with a CD19-binding chimeric antigen receptor. In the absence of dimerizing ligand, basal activity was observed, allowing high IL-2 production.

Next, a MyD88/CD40 molecule was assayed to determine whether it could also be used to replace CD28 or 4-1BB costimulation in CAR designs. The functionality of MyD88/CD40 as a costimulating molecule to prostate stem cell antigen (PSCA)-targeted CARs was assayed with either CD3ζ (PSCA.ζ) or CD28.CD3ζ (PSCA.28.ζ) endodomains and the data showed that incorporation of MC promoted T cell survival and proliferation, enhanced tumor killing in co-culture assays against a PSCA+ tumor cell line (Capan-1) and improved cytokine production (e.g., IL-2 and IL-6) compared to T cells transduced with only PSCA.ζ. MyD88/CD40 can therefore be used, for example, as a costimulatory endodomain to enhance the function of CAR T cells.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct between the host and donor cells.

Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorferi, Plasmodium*, herpes simplex viruses, human immunodeficiency virus, papillomavirus, *Vibrio cholera, E. coli*, measles virus, rotavirus, *shigella, Salmonella typhi, Neisseria* gonorrhea. Therefore, any macromolecules, including virtually all proteins or peptides, can serve as antigens. Furthermore, antigens can be derived from recombinant or genomic DNA. Any DNA that contains nucleotide sequences or partial nucleotide sequences of a pathogenic genome or a gene or a fragment of a gene for a protein that elicits an immune response results in synthesis of an antigen. Furthermore, the present methods are not limited to the use of the entire nucleic acid sequence of a gene or genome. The present compositions and methods include, but are not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "cell" can be any cell that accomplishes the goal of aiding the enhancement of an immune response (i.e., from the T-cell or -B-cell arms of the immune system) against an antigen or antigenic composition. As discussed in Kuby, 2000, Immunology, .supp. 4th edition, W.H. Freeman and company, for example, (incorporated herein by reference), and used herein in certain embodiments, a cell that displays or presents an antigen normally or with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fusion of two or more cells are discussed in, for example, Goding, J. W., Monoclonal Antibodies: Principles and Practice, pp. 65-66, 71-74 (Academic Press, 1986); Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Kohler & Milstein, Nature, 256:495-497, 1975; Kohler & Milstein, Eur. J. Immunol., 6:511-519, 1976, Gefter et al., Somatic Cell Genet., 3:231-236, 1977, each incorporated herein by reference. In some cases, the immune cell to which a cell displays or presents an antigen to is a CD4+TH cell. Additional molecules expressed on the APC or other immune cells may aid or improve the enhancement of an immune response. Secreted or soluble molecules, such as for example, cytokines and adjuvants, may also aid or enhance the immune response against an antigen. Various examples are discussed herein.

An "antigen recognition moiety" may be any polypeptide or fragment thereof, such as, for example, an antibody fragment variable domain, either naturally derived, or synthetic, which binds to an antigen. Examples of antigen recognition moieties include, but are not limited to, polypeptides derived from antibodies, such as, for example, single chain variable fragments (scFv), Fab, Fab', F(ab')$_2$, and Fv fragments; polypeptides derived from T Cell receptors, such as, for example, TCR variable domains; secreted factors (e.g., cytokines, growth factors) that can be artificially fused to signaling domains (e.g., "zytokines"), and any ligand or receptor fragment (e.g., CD27, NKG2D) that binds to the extracellular cognate protein. Combinatorial libraries could also be used to identify peptides binding with high affinity to tumor-associated targets. Moreover, "universal" CARs can be made by fusing aviden to the signaling domains in combination with biotinylated tumor-targeting antibodies (Urbanska (12) Ca Res) or by using Fc gamma receptor/CD16 to bind to IgG-targeted tumors (Kudo K (13) Ca Res).

The term "autologous" means a cell, nucleic acid, protein, polypeptide, or the like derived from the same individual to which it is later administered. The modified cells of the present methods may, for example, be autologous cells, such as, for example, autologous T cells.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

By "chimeric antigen receptor" or "CAR" is meant, for example, a chimeric polypeptide which comprises a polypeptide sequence that recognizes a target antigen (an antigen-recognition domain) linked to a transmembrane polypeptide and intracellular domain polypeptide selected to activate the T cell and provide specific immunity. The antigen-recognition domain may be a single-chain variable fragment (ScFv), or may, for example, be derived from other molecules such as, for example, a T cell receptor or Pattern Recognition Receptor. The intracellular domain comprises at least one polypeptide which causes activation of the T cell, such as, for example, but not limited to, CD3 zeta, and, for example, co-stimulatory molecules, for example, but not limited to, CD28, OX40 and 4-1BB. The term "chimeric antigen receptor" may also refer to chimeric receptors that are not derived from antibodies, but are chimeric T cell receptors. These chimeric T cell receptors may comprise a polypeptide sequence that recognizes a target antigen, where the recognition sequence may be, for example, but not limited to, the recognition sequence derived from a T cell receptor or an scFv. The intracellular domain polypeptides are those that act to activate the T cell. Chimeric T cell receptors are discussed in, for example, Gross, G., and Eshhar, Z., FASEB Journal 6:3370-3378 (1992), and Zhang, Y., et al., PLOS Pathogens 6:1-13 (2010).

In one type of chimeric antigen receptor (CAR), the variable heavy (VH) and light (VL) chains for a tumor-specific monoclonal antibody are fused in-frame with the CD3 zeta chain (ζ) from the T cell receptor complex. The VH and VL are generally connected together using a flexible glycine-serine linker, and then attached to the transmembrane domain by a spacer (CH2CH3) to extend the scFv away from the cell surface so that it can interact with tumor antigens. Following transduction, T cells now express the CAR on their surface, and upon contact and ligation with a tumor antigen, signal through the CD3 zeta chain inducing cytotoxicity and cellular activation.

Investigators have noted that activation of T cells through CD3 zeta is sufficient to induce a tumor-specific killing, but is insufficient to induce T cell proliferation and survival. Early clinical trials using T cells modified with first generation CARs expressing only the zeta chain showed that gene-modified T cells exhibited poor survival and proliferation in vivo.

An "antigen recognition moiety" may be any polypeptide or fragment thereof, such as, for example, an antibody fragment variable domain, either naturally-derived, or synthetic, which binds to an antigen. Examples of antigen recognition moieties include, but are not limited to, polypeptides derived from antibodies, such as, for example, single chain variable fragments (scFv), Fab, Fab', F(ab')2, and Fv fragments; polypeptides derived from T Cell receptors, such as, for example, TCR variable domains; and any ligand or receptor fragment that binds to the extracellular cognate protein.

As used herein, the term "cDNA" is intended to refer to DNA prepared using messenger RNA (mRNA) as template. The advantage of using a cDNA, as opposed to genomic DNA or DNA polymerized from a genomic, non- or partially processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

By "constitutively active" is meant that the chimeric stimulating molecule's T cell activation activity, as demonstrated herein, is active in the absence of an inducer. Constitutively active chimeric stimulating molecules in the present application do not comprise a multimeric ligand binding region, or a functional multimeric ligand binding region, and are not inducible by AP1903, AP20187, or other CID.

As used herein, the term "ex vivo" refers to "outside" the body. The terms "ex vivo" and "in vitro" can be used interchangeably herein.

As used herein, the term "functionally equivalent," as it relates to CD40, for example, refers to a CD40 nucleic acid fragment, variant, or analog, refers to a nucleic acid that codes for a CD40 polypeptide, or a CD40 polypeptide, that stimulates an immune response to destroy tumors or hyperproliferative disease. "Functionally equivalent" or "a functional fragment" of a CD40 polypeptide refers, for example, to a CD40 polypeptide that is lacking the extracellular domain, but is capable of amplifying the T cell-mediated tumor killing response by upregulating dendritic cell expression of antigen presentation molecules. When the term "functionally equivalent" is applied to other nucleic acids or polypeptides, such as, for example, PSA peptide, PSMA peptide, MyD88, or truncated MyD88, it refers to fragments, variants, and the like that have the same or similar activity as the reference polypeptides of the methods herein. For example, a functional fragment of a tumor antigen polypeptide, such as, for example, PSMA may be antigenic, allowing for antibodies to be produced that recognize the particular tumor antigen. A functional fragment of a ligand binding region, for example, Fvls, would include a sufficient portion of the ligand binding region polypeptide to bind the appropriate ligand. "Functionally equivalent" refers, for example, to a co-stimulatory polypeptide that is lacking the extracellular domain, but is capable of amplifying the T cell-mediated tumor killing response when expressed in T cells.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions. In some embodiments, the subject is a mammal. In some embodiments, the subject is a human.

As used herein, the term "polynucleotide" is defined as a chain of nucleotides. Furthermore, nucleic acids are polymers of nucleotides. Thus, nucleic acids and polynucleotides as used herein are interchangeable. Nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PORT", and the like, and by synthetic means. Furthermore, polynucleotides include mutations of the polynucleotides, include but are not limited to, mutation of the nucleotides, or nucleosides by methods well known in the art. A nucleic acid may comprise one or more polynucleotides.

As used herein, the term "polypeptide" is defined as a chain of amino acid residues, usually having a defined sequence. As used herein the term polypeptide may be interchangeable with the term "proteins".

As used herein, the term "promoter" is defined as a DNA sequence recognized by the synthetic machinery of the cell, or introduced synthetic machinery, required to initiate the specific transcription of a gene.

As used herein, the terms "regulate an immune response," "modulate an immune response," or "control an immune response," refer to the ability to modify the immune response. For example, the composition is capable of enhancing and/or activating the immune response. Still further, the composition is also capable of inhibiting the immune response. The form of regulation is determined by the ligand that is used with the composition. For example, a dimeric analog of the chemical results in dimerization of the co-stimulating polypeptide leading to activation of the T cell, however, a monomeric analog of the chemical does not result in dimerization of the co-stimulating polypeptide, which would not activate the T cells.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeably.

The term "terms "patient" or "subject"" are interchangeable, and, as used herein include, but are not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "vaccine" refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

As used herein, the term "under transcriptional control" or "operatively linked" is defined as the promoter is in the correct location and orientation in relation to the nucleic acid to control RNA polymerase initiation and expression of the gene.

By "T cell activation molecule" is meant a polypeptide that, when incorporated into a T cell expressing a chimeric antigen receptor, enhances activation of the T cell. Examples include, but are not limited to, ITAM-containing, Signal 1 conferring molecules such as, for example, CD3ζ polypeptide, and Fc receptor gamma, such as, for example. Fc epsilon receptor gamma (FcεR1γ) subunit (Haynes, N. M., et al. J. Immunol. 166:182-7 (2001)). J. Immunology).

As used herein, the terms "treatment", "treat", "treated", or "treating" refer to prophylaxis and/or therapy. When used with respect to a solid tumor, such as a cancerous solid tumor, for example, the term refers to prevention by prophylactic treatment, which increases the subject's resistance to solid tumors or cancer. In some examples, the subject may be treated to prevent cancer, where the cancer is familial, or is genetically associated. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, for example, reduce or eliminate the infection or prevent it from becoming worse.

The methods provided herein may be used, for example, to treat a disease, disorder, or condition wherein there is an elevated expression of a tumor antigen.

As used herein, the term "vaccine" refers to a formulation which contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

Blood disease: The terms "blood disease", "blood disease" and/or "diseases of the blood" as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

Bone marrow disease: The term "bone marrow disease" as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnocytopenia, anemia, multiple myeloma and the like.

T cells and Activated T cells: T cells (also referred to as T lymphocytes) belong to a group of white blood cells referred to as lymphocytes. Lymphocytes generally are involved in cell-mediated immunity. The "T" in "T cells" refers to cells derived from or whose maturation is influenced by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histo-compatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD 4 expression are referred to as $CD3^+$ or $CD4^+$). CD3 and CD4 proteins are cell surface receptors or co-receptors that may be directly and/or indirectly involved in signal transduction in T cells.

Peripheral blood: The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

By "kill" or "killing" as in a percent of cells killed, is meant the death of a cell through apoptosis, as measured using any method known for measuring apoptosis. The term may also refer to cell ablation.

Donor T cell: The term "donor T cell" as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GvHD). Certain activated donor T cells can cause a higher or lower GvHD response than other activated T cells. Donor T cells may also be reactive against recipient tumor cells, causing a beneficial graft vs. tumor effect.

Function-conservative variants are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, for example, at least 80%, for example, at least 90%, and for example, at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the settings used in certain embodiments are those that results in the highest sequence similarity.

Mesenchymal stromal cell: The terms "mesenchymal stromal cell" or "bone marrow derived mesenchymal stromal cell" as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

Embryonic stem cell: The term "embryonic stem cell" as used herein, refers to pluripotent stem cells derived from the inner cell mass of the blastocyst, an early stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from multipotent in that pluripotent cells can generate all cell types, while multipotent cells (e.g., adult stem cells) can only produce a limited number of cell types.

Inducible pluripotent stem cell: The terms "inducible pluripotent stem cell" or "induced pluripotent stem cell" as used herein refers to adult, or differentiated cells, that are "reprogrammed" or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells.

$CD34^+$ cell: The term "$CD34^+$ cell" as used herein refers to a cell expressing the CD34 protein on its cell surface. "CD34" as used herein refers to a cell surface glycoprotein (e.g., sialomucin protein) that often acts as a cell-cell adhesion factor and is involved in T cell entrance into lymph nodes, and is a member of the "cluster of differentiation" gene family. CD34 also may mediate the attachment of stem cells to bone marrow, extracellular matrix or directly to stromal cells. $CD34^+$ cells often are found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population of dendritic cells (which are factor XIIIa negative) in the interstitium and around the adnexa of dermis of skin, as well as cells in certain soft tissue tumors (e.g., alveolar soft part sarcoma, pre-B acute lymphoblastic leukemia (Pre-B-ALL), acute myelogenous leukemia (AML), AML-M7, dermatofibrosarcoma protuberans, gastrointestinal stromal tumors, giant cell fibroblastoma, granulocytic sarcoma, Kaposi's sarcoma, liposarcoma, malignant fibrous histiocytoma, malignant peripheral nerve sheath tumors, mengingeal hemangiopericytomas, meningiomas, neurofibromas, schwannomas, and papillary thyroid carcinoma).

Tumor infiltrating lymphocytes (TILs) refer to T cells having various receptors which infiltrate tumors and kill tumor cells in a targeted manor. Regulating the activity of the TILs using the methods of the present application would allow for more direct control of the elimination of tumor cells.

Gene expression vector: The terms "gene expression vector", "nucleic acid expression vector", or "expression vector" as used herein, which can be used interchangeably throughout the document, generally refers to a nucleic acid molecule (e.g., a plasmid, phage, autonomously replicating sequence (ARS), artificial chromosome, yeast artificial chromosome (e.g., YAC)) that can be replicated in a host cell and be utilized to introduce a gene or genes into a host cell. The genes introduced on the expression vector can be endogenous genes (e.g., a gene normally found in the host cell or organism) or heterologous genes (e.g., genes not normally found in the genome or on extra-chromosomal nucleic acids of the host cell or organism). The genes introduced into a cell by an expression vector can be native genes or genes that have been modified or engineered. The gene expression vector also can be engineered to contain 5' and 3' untranslated regulatory sequences that sometimes can function as enhancer sequences, promoter regions and/or terminator sequences that can facilitate or enhance efficient transcription of the gene or genes carried on the expression vector. A gene expression vector sometimes also is engineered for replication and/or expression functionality (e.g., transcription and translation) in a particular cell type, cell location, or tissue type. Expression vectors sometimes include a selectable marker for maintenance of the vector in the host or recipient cell.

Developmentally regulated promoter: The term "developmentally regulated promoter" as used herein refers to a promoter that acts as the initial binding site for RNA polymerase to transcribe a gene which is expressed under certain conditions that are controlled, initiated by or influenced by a developmental program or pathway. Developmentally regulated promoters often have additional control regions at or near the promoter region for binding activators or repressors of transcription that can influence transcription of a gene that is part of a development program or pathway. Developmentally regulated promoters sometimes are involved in transcribing genes whose gene products influence the developmental differentiation of cells.

Developmentally differentiated cells: The term "developmentally differentiated cells", as used herein refers to cells that have undergone a process, often involving expression of specific developmentally regulated genes, by which the cell evolves from a less specialized form to a more specialized form in order to perform a specific function. Non-limiting examples of developmentally differentiated cells are liver cells, lung cells, skin cells, nerve cells, blood cells, and the like. Changes in developmental differentiation generally involve changes in gene expression (e.g., changes in patterns of gene expression), genetic re-organization (e.g., remodeling or chromatin to hide or expose genes that will be silenced or expressed, respectively), and occasionally involve changes in DNA sequences (e.g., immune diversity differentiation). Cellular differentiation during development can be understood as the result of a gene regulatory network. A regulatory gene and its cis-regulatory modules are nodes in a gene regulatory network that receive input (e.g., protein expressed upstream in a development pathway or program) and create output elsewhere in the network (e.g., the expressed gene product acts on other genes downstream in the developmental pathway or program).

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

In some embodiments, the nucleic acid is contained within a viral vector. In certain embodiments, the viral vector is an adenoviral vector, or a retroviral or lentiviral vector. It is understood that in some embodiments, the cell is contacted with the viral vector ex vivo, and in some embodiments, the cell is contacted with the viral vector in vivo.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

By MyD88, or MyD88 polypeptide, is meant the polypeptide product of the myeloid differentiation primary response gene 88, for example, but not limited to the human version, cited as NCBI Gene ID 4615. One example of a MyD88 polypeptide is presented as SEQ ID NO: 282. By "truncated," is meant that the protein is not full length and may lack, for example, a domain. For example, a truncated MyD88 is not full length and may, for example, be missing the TIR domain. One example of a truncated MyD88 is indicated as MyD88L herein, and is also presented as SEQ ID NOS: 5 (nucleic acid sequence) and 6 (peptide sequence). SEQ ID NO: 5 includes the linkers added during subcloning. By a nucleic acid sequence coding for "truncated MyD88" is meant the nucleic acid sequence coding for the truncated MyD88 peptide, the term may also refer to the nucleic acid sequence including the portion coding for any amino acids added as an artifact of cloning, including any amino acids coded for by the linkers. It is understood that where a method or construct refers to a truncated MyD88 polypeptide, the method may also be used, or the construct designed to refer to another MyD88 polypeptide, such as a full length MyD88 polypeptide. Where a method or construct refers to a full length MyD88 polypeptide, the method may also be used, or the construct designed to refer to a truncated MyD88 polypeptide.

In the methods herein, the CD40 portion of the peptide may be located either upstream or downstream from the MyD88 or truncated MyD88 polypeptide portion.

The cell in some embodiments is contacted with an antigen, sometimes ex vivo. In certain embodiments the cell is in a subject and an immune response is generated against the antigen, such as a cytotoxic T-lymphocyte (CTL) immune response. In certain embodiments, an immune response is generated against a tumor antigen (e.g., PSMA). In some embodiments, the nucleic acid is prepared ex vivo and administered to the subject by intradermal administration or by subcutaneous administration, for example. Sometimes the cell is transduced or transfected with the nucleic acid ex vivo or in vivo.

In some embodiments, the nucleic acid comprises a promoter sequence operably linked to the polynucleotide sequence. Alternatively, the nucleic acid comprises an ex vivo-transcribed RNA, containing the protein-coding region of the chimeric protein.

By "reducing tumor size" or "inhibiting tumor growth" of a solid tumor is meant a response to treatment, or stabilization of disease, according to standard guidelines, such as, for example, the Response Evaluation Criteria in Solid Tumors (RECIST) criteria. For example, this may include a reduction in the diameter of a solid tumor of about 5%, 10%, 20%, 30%, 40%, 50%, 60%, 70%, 80%, 90%, or 100%, or the reduction in the number of tumors, circulating tumor cells, or tumor markers, of about 5%, 10%, 20%, 30%, 40%, 50%, 60%, 70%, 80%, 90%, or 100%. The size of tumors may be analyzed by any method, including, for example, CT scan, MRI, for example, CT-MRI, chest X-ray (for tumors of the lung), or molecular imaging, for example, PET scan, such as, for example, a PET scan after administering an iodine 123-labelled PSA, for example, PSMA ligand, such as, for example, where the inhibitor is TROFEX™/MIP-1072/1095, or molecular imaging, for example, SPECT, or a PET scan using PSA, for example, PSMA antibody, such as, for example, capromad pendetide (PROSTASCINT), a 111-iridium labeled PSMA antibody.

By "reducing, slowing, or inhibiting tumor vascularization" is meant a reduction in tumor vascularization of about 5%, 10%, 20%, 30%, 40%, 50%, 60%, 70%, 80%, 90%, or 100%, or a reduction in the appearance of new vasculature of about 5%, 10%, 20%, 30%, 40%, 50%, 60%, 70%, 80%, 90%, or 100%, when compared to the amount of tumor vascularization before treatment. The reduction may refer to one tumor, or may be a sum or an average of the vascularization in more than one tumor. Methods of measuring tumor vascularization include, for example, CAT scan, MRI, for example, CT-MRI, or molecular imaging, for example, SPECT, or a PET scan, such as, for example, a PET scan after administering an iodine 123-labelled PSA, for example, PSMA ligand, such as, for example, where the inhibitor is TROFEX™/MIP-1072/1095, or a PET scan using PSA, for example, PSMA antibody, such as, for example, capromad pendetide (PROSTASCINT), a 111-iridium labeled PSMA antibody.

A tumor is classified, or named as part of an organ, such as a prostate cancer tumor when, for example, the tumor is present in the prostate gland, or has derived from or metastasized from a tumor in the prostate gland, or produces PSA. A tumor has metastasized from a tumor in the prostate gland, when, for example, it is determined that the tumor has chromosomal breakpoints that are the same as, or similar to, a tumor in the prostate gland of the subject.

Prostate Cancer

In the United States, prostate cancer is the most common solid tumor malignancy in men. It was expected to account for an estimated 186,320 new cases of prostate cancer in 2008 and 28,660 deaths. Jemal A, et al., Cancer statistics, 2008. CA Cancer J Clin. 58: 71-96, 2008. Approximately 70% of patients who experience PSA-progression after primary therapy will have metastases at some time during the course of their disease. Gittes R F, N Engl J Med. 324: 236-45, 1991. Androgen deprivation therapy (ADT) is the standard therapy for metastatic prostate cancer and achieves temporary tumor control or regression in 80-85% of patients. Crawford E D, et al., N Engl J Med. 321: 419-24, 1989; Schellhammer P F, et al., J Urol. 157: 1731-5, 1997; Scher H I and Kelly W K, J Clin Oncol. 11: 1566-72, 1993; Small E J and Srinivas S, Cancer. 76: 1428-34, 1995. Duration of response to hormone therapy, as well as survival after the initiation of hormone therapy, has been shown to be dependent on a number of factors, including the Gleason Sum of the original tumor, the ability to achieve an undetectable nadir PSA after initiation of ADT, and the PSA doubling time prior to initiation of ADT. Despite hormonal therapy, virtually all patients with metastatic prostate cancer ultimately develop progressive disease. Kelly W K and Slovin S F, Curr Oncol Rep. 2: 394-401, 2000; Scher H I, et al., J Natl Cancer Inst. 88: 1623-34, 1996; Small E J and Vogelzang N J, J Clin Oncol. 15: 382-8, 1997. The Gleason Sum of the original tumor, or the Gleason score, is used to grade levels of prostate cancer in men, based on the microscopic evaluation of the tumor. A higher Gleason score denotes a cancer that has a worse prognosis as it is more aggressive, and is more likely to spread. An example of the grading system is discussed in Gleason D F., The Veteran's Administration Cooperative Urologic Research Group: histologic grading and clinical staging of prostatic carcinoma. In Tannenbaum M (ed.) Urologic Pathology: The Prostate. Lea and Febiger, Philadelphia, 1977; 171-198.

Most patients with prostate cancer who have been started on ADT are treated for a rising PSA after failure of primary therapy (e.g. radical prostatectomy, brachytherapy, external beam radiation therapy, cryo-ablation, etc.). In the absence of clinical metastases, these patients experience a relatively long disease-free interval in the range of 7-11 years; however, the majority of these patients eventually develop hormone-resistant disease as evidenced by the return of a rising PSA level in the face of castrate levels of serum testosterone. These patients, too, have a poor prognosis, with the majority developing clinical metastases within 9 months and a median survival of 24 months. Bianco F J, et al., Cancer Symposium: Abstract 278, 2005. The term "prostate cancer" includes different forms or stages, including, for example, metastatic, metastatic castration resistant, metastatic castration sensitive, regionally advanced, and localized prostate cancer.

Engineering Expression Constructs

Expression constructs that express the present chimeric stimulating molecules comprise the chimeric stimulating molecule coding region and a promoter sequence, all operatively linked. Expression constructs that express the present MyD88/CD40-encoding chimeric antigen receptors comprise the MyD88/CD40 chimeric antigen receptor coding region and a promoter sequence, all operatively linked. In general, the term "operably linked" is meant to indicate that the promoter sequence is functionally linked to a second sequence, wherein the promoter sequence initiates and mediates transcription of the DNA corresponding to the second sequence.

In certain examples, the polynucleotide coding for the chimeric stimulating molecule or the MyD88/CD40 chimeric antigen receptor coding region is included in the same vector, such as, for example, a viral or plasmid vector, as a polynucleotide coding for the second polypeptide. This second polypeptide may be, for example, a caspase polypeptide, as discussed herein, or a marker polypeptide. Where the vector expresses a chimeric stimulating molecule, the second polypeptide may also be, for example, a non-MyD88/CD40-containing chimeric antigen receptor. In these examples, the construct may be designed with one promoter operably linked to a nucleic acid comprising a polynucleotide coding for the two polypeptides, linked by a cleavable 2A polypeptide. In this example, the first and second polypeptides are separated during translation, resulting in either a chimeric stimulating molecule or a MyD88/CD40 chimeric antigen receptor polypeptide, and the second polypeptide. In other examples, the two polypeptides may be expressed separately from the same vector, where each nucleic acid comprising a polynucleotide coding for one of the polypeptides is operably linked to a separate promoter. In yet other examples, one promoter may be operably linked to the two polynucleotides, directing the production of two separate RNA transcripts, and thus two polypeptides; in one example, the promoter may be bi-directional, and the coding regions may be in opposite directions 5'-3'. Therefore, the expression constructs discussed herein may comprise at least one, or at least two promoters.

In yet other examples, two polypeptides, such as, for example, the chimeric stimulating molecule or a MyD88/CD40 chimeric antigen receptor polypeptide, and the second polypeptide, may be expressed in a cell using two separate vectors. The cells may be co-transfected or co-transformed with the vectors, or the vectors may be introduced to the cells at different times.

The polypeptides may vary in their order, from the amino terminus to the carboxy terminus. For example, in the chimeric stimulating molecule, the order of the MyD88 polypeptide, CD40 polypeptide, and any additional polypeptide, may vary. In the chimeric antigen receptor, the order of the MyD88 polypeptide, CD40 polypeptide, and any additional polypeptide, such as, for example, the CD3ζ polypeptide may vary. The order of the various domains may be assayed using methods such as, for example, those discussed herein, to obtain the optimal expression and activity.

In certain embodiments, a nucleic acid molecule is provided that comprises a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, and wherein the chimeric stimulating molecule does not include a membrane targeting region; and b) a second polynucleotide encoding a T cell receptor, a T cell receptor-based chimeric antigen receptor, or a chimeric antigen receptor; and c) a third polynucleotide encoding a chimeric Caspase-9 polypeptide comprising a multimeric ligand binding region and a Caspase-9 polypeptide. It is understood that the order of the polynucleotides may vary, and may be tested to determine the suitability of the construct for any particular method, thus, the nucleic acid may include the polynucleotides in the varying orders, which also take into account a variation in the order of the MyD88 polypeptide or truncated MyD88 polypeptide-encoding sequence and the CD40 cytoplasmic polypeptide region-encoding sequence in the first polynucleotide. Thus the first polynucleotide may encode a polypeptide having and order of MyD88/CD40, truncatedMyD88/CD40, CD40/MyD88, or CD40/truncated MyD88. And, the nucleic acid may include the first through third polynucleotides in any of the following orders, where 1, 2, 3, indicate a first, second, or third order of the polynucleotide in the nucleic acid from 5' to 3'. It is understood that other polynucleotides, such as those that code for a 2A polypeptide, for example, may be present between the three listed polynucleotides; this Table is meant to designate the order of the first through third polynucleotides:

TABLE A

| First polynucleotide encoding a Chimeric stimulating molecule comprising MyD88 or truncated MyD88 and CD40 cytoplasmic polypeptide region. | Second polynucleotide encoding a T cell receptor, a T cell receptor-based chimeric antigen receptor, or a chimeric antigen receptor. | Third polynucleotide encoding a chimeric caspse-9 polypeptide. |
|---|---|---|
| 1 | 2 | 3 |
| 1 | 3 | 2 |
| 2 | 1 | 3 |
| 3 | 1 | 2 |
| 2 | 3 | 1 |
| 3 | 2 | 1 |

Similarly, the nucleic acids may include only two of the polynucleotides, coding for two of the polypeptides provided in the table above. In some examples, a cell is transfected or transduced with a nucleic acid comprising the three polynucleotides included in Table A above. In other examples, a cell is transfected or transduced with a nucleic acid that encodes two of the polynucleotides, coding for two of the polypeptides, as provided, for example, in Table B.

TABLE B

| First polynucleotide encoding a Chimeric stimulating molecule comprising MyD88 or truncated MyD88 and CD40 cytoplasmic polypeptide region. | Second polynucleotide encoding a T cell receptor, a T cell receptor-based chimeric antigen receptor, or a chimeric antigen receptor. | Third polynucleotide encoding a chimeric caspse-9 polypeptide. |
|---|---|---|
| 1 | 2 | |
| 1 | | 2 |
| 2 | 1 | |
| | 1 | 2 |
| 2 | | 1 |
| | 2 | 1 |

In some embodiments, the cell is transfected or transduced with the nucleic acid that encodes two of the polynucleotides, and the cell also comprises a nucleic acid comprising a polynucleotide coding for the third polypeptide. For example, a cell may comprise a nucleic acid comprising the first and second polynucleotides, and the cell may also comprise a nucleic acid comprising a polynucleotide coding for a chimeric Caspase-9 polypeptide. Also, a cell may comprise a nucleic acid comprising the first and third polynucleotides, and the cell may also comprise a nucleic acid comprising a polynucleotide coding for a T cell receptor, a T cell receptor-based chimeric antigen receptor, or a chimeric antigen receptor.

T cell receptors are molecules composed of two different polypeptides that are on the surface of T cells. They recognize antigens bound to major histocompatibility complex molecules; upon recognition with the antigen, the T cell is activated. By "recognize" is meant, for example, that the T cell receptor, or fragment or fragments thereof, such as TCRα polypeptide and TCRβ together, is capable of contacting the antigen and identifying it as a target. TCRs may comprise α and β polypeptides, or chains. The α and β polypeptides include two extracellular domains, the variable and the constant domains. The variable domain of the α and β polypeptides has three complementarity determining regions (CDRs); CDR3 is considered to be the main CDR responsible for recognizing the epitope. The α polypeptide includes the V and J regions, generated by VJ recombination, and the β polypeptide includes the V, D, and J regions, generated by VDJ recombination. The intersection of the VJ regions and VDJ regions corresponds to the CDR3 region. TCRs are often named using the International Immunogenetics (IMGT) TCR nomenclature (IMGT Database, www.IMGT.org; Giudicelli, V., et al., IMGT/LIGM-DB, the IMGT® comprehensive database of immunoglobulin and T cell receptor nucleotide sequences, Nucl. Acids Res., 34, D781-D784 (2006). PMID: 16381979; T cell Receptor Facts book, LeFranc and LeFranc, Academic Press ISBN 0-12-441352-8). T cell receptor-based chimeric antigen receptors, or TCR-like chimeric antigen receptors are chimeric antigen receptors with TCR-like specificity, as discussed in, for example, Zhang, G., et al., Nature Scientific Reports 4, Article 3571 (2014) and Zhang, G., et al., Immunol. Cell. Biol 91(10): 615-24 (2013), which are hereby incorporated by reference herein in their entirety.

The steps of the methods provided may be performed using any suitable method; these methods include, without limitation, methods of transducing, transforming, or otherwise providing nucleic acid to the cell, presented herein. In some embodiments, the truncated MyD88 peptide is encoded by the nucleotide sequence of SEQ ID NO: 5 (with or without DNA linkers or has the amino acid sequence of SEQ ID NO: 6). In some embodiments, the CD40 cytoplasmic polypeptide region is encoded by a polynucleotide sequence in SEQ ID NO: 1.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, β-gal or chloramphenicol acetyltransferase (CAT). In certain embodiments, the marker protein, such as, for example, CD19 is used for selection of the cells for transfusion, such as, for example, in immunomagnetic selection. As discussed herein, a CD19 marker is distinguished from an anti-CD19 antibody, or, for example, an scFv, TCR, or other antigen recognition moiety that binds to CD19.

In certain embodiments, the marker polypeptide is linked to the inducible chimeric stimulating molecule. For example, the marker polypeptide may be linked to the inducible chimeric stimulating molecule via a polypeptide sequence, such as, for example, a cleavable 2A-like sequence. The marker polypeptide may be, for example, CD19, ΔCD19, or may be, for example, a heterologous protein, selected to not affect the activity of the inducible chimeric stimulating molecule.

2A-like sequences, or "peptide bond-skipping" 2A sequences, are derived from, for example, many different viruses, including, for example, from *Thosea asigna*. These sequences are sometimes also known as "peptide skipping sequences." When this type of sequence is placed within a cistron, between two peptides that are intended to be separated, the ribosome appears to skip a peptide bond, in the case of *Thosea asigna* sequence; the bond between the Gly and Pro amino acids at the carboxy terminal "P-G-P" is omitted. This leaves two to three polypeptides, in this case the co-stimulating polypeptide cytoplasmic region and the marker polypeptide. When this sequence is used, the peptide that is encoded 5' of the 2A sequence may end up with additional amino acids at the carboxy terminus, including the Gly residue and any upstream residues in the 2A sequence. The peptide that is encoded 3' of the 2A sequence may end up with additional amino acids at the amino terminus, including the Pro residue and any downstream residues following the 2A sequence.

In some embodiments, a polypeptide may be included in the expression vector to aid in sorting cells. For example, the CD34 minimal epitope may be incorporated into the vector. In some embodiments, the expression vectors used to express the chimeric antigen receptors or chimeric stimulating molecules provided herein further comprise a polynucleotide that encodes the 16 amino acid CD34 minimal epitope. In some embodiments, such as certain embodiments provided in the examples herein, the CD34 minimal epitope is incorporated at the amino terminal position of the CD8 stalk.

Co-Stimulating Polypeptides

Co-stimulating polypeptide molecules are capable of amplifying the cell-mediated immune response through activation of signaling pathways involved in cell survival and proliferation. Co-stimulating proteins that are contemplated include, for example, but are not limited, to the members of tumor necrosis factor receptor (TNFR) family (i.e., CD40, RANK/TRANCE-R, OX40, 4-1BB) and CD28 family members (CD28, ICOS). Co-stimulating proteins may include, for example, CD28, 4-1BB, OX40, and the CD3 chain, or, for example, the cytoplasmic regions thereof. More than one co-stimulating polypeptide or co-stimulating polypeptide cytoplasmic region may be used in the inducible chimeric stimulating molecules discussed herein.

Co-stimulating polypeptides include any molecule or polypeptide that activates the NF-κB pathway, Akt pathway, and/or p38 pathway. The cellular activation system is based upon utilizing a recombinant signaling molecule fused to one or more ligand-binding domains (i.e., a small molecule binding domain) in which the co-stimulating polypeptide is activated and/or regulated with a ligand resulting in oligomerization (i.e., a lipid-permeable, organic, dimerizing drug). Other systems that may be used for crosslinking, or for oligomerization, of co-stimulating polypeptides include antibodies, natural ligands, and/or artificial cross-reacting or synthetic ligands. Yet further, another dimerization systems contemplated include the coumermycin/DNA gyrase B system.

Co-stimulating polypeptides that can be used include those that activate NF-κB and other variable signaling cascades for example the p38 pathway and/or Akt pathway. Such co-stimulating polypeptides include, but are not limited to CD28 family members (e.g. CD28, ICOS), TNF receptors (i.e., CD40, RANK/TRANCE-R, OX40, 4-1BB).

In specific embodiments, the co-stimulating polypeptide molecule is CD40, truncated MyD88, or a chimeric truncated MyD88/CD40 polypeptide.

The CD40 molecule comprises a nucleic acid molecule which: (1) hybridizes under stringent conditions to a nucleic acid having the sequence of a known CD40 gene and (2) codes for a CD40 polypeptide. The CD40 polypeptide may, in certain examples, lack the extracellular domain. Exemplary polynucleotide sequences that encode CD40 polypeptides include, but are not limited to SEQ. ID. NO: 1 and CD40 isoforms from other species. It is contemplated that other normal or mutant variants of CD40 can be used in the present methods and compositions. Thus, a CD40 region can have an amino acid sequence that differs from the native sequence by one or more amino acid substitutions, deletions and/or insertions. For example, one or more TNF receptor associated factor (TRAF) binding regions may be eliminated or effectively eliminated (e.g., a CD40 amino acid sequence is deleted or altered such that a TRAF protein does not bind or binds with lower affinity than it binds to the native CD40 sequence). In particular embodiments, a TRAF 3 binding region is deleted or altered such that it is eliminated or effectively eliminated (e.g., amino acids 250-254 may be altered or deleted; Hauer et al., PNAS 102(8): 2874-2879 (2005)).

In certain embodiments, the present methods involve the manipulation of genetic material to produce expression constructs. Such methods involve the generation of expression constructs containing, for example, a heterologous nucleic acid sequence encoding the chimeric stimulating molecules or chimeric antigen receptors discussed herein, and a means for their expression. The vector can be replicated in an appropriate helper cell, viral particles may be produced therefrom, and cells infected with the recombinant virus particles.

In the context of gene therapy, the gene may be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source.

Co-stimulating polypeptides may comprise, but are not limited to, the amino acid sequences provided herein, and may include functional conservative mutations, including deletions or truncations, and may comprise amino acid sequences that are 70%, 75%, 80%, 85%, 90%, 95% or 100% identical to the amino acid sequences provided herein.

Ligand-Binding Regions

Ligand binding regions may be included in the chimeric polypeptides discussed herein, for example, as part of the inducible caspase polypeptides. The ligand-binding ("dimerization") domain of the expression construct can be any convenient domain that will allow for induction using a natural or unnatural ligand, for example, an unnatural synthetic ligand. The multimerizing region, multimeric ligand binding region, multimerizing region, or ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises an $F_vF_{vls}$ sequence. Sometimes, the $F_vf_{vls}$ sequence further comprises an additional Fv' sequence. Examples include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology: From Small Molecules to Systems Biology and Drug Design (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric, nonimmunogenic, have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen). Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the Caspase-9 polypeptide, the ligand for the ligand-binding domains/receptor domains of the chimeric inducible Caspase-9 polypeptides will usually be multimeric in the sense that it will have at least two binding sites, with each of the binding sites capable of binding to the ligand receptor domain. By "multimeric ligand binding region" is meant a ligand binding region that binds to a multimeric ligand. The term "multimeric ligands" include dimeric ligands. A dimeric ligand will have two binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker domain, or modified receptors, and mutated sequences thereof, and the like, any of a large variety of compounds can be used. A significant characteristic of these ligand units is that each binding site is able to bind the receptor with high affinity and they are able to be dimerized chemically. Also, methods are available to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor. Examples of CIDs include, but are not limited to, AP1903 and AP20187.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. FKBP12 variants having amino acid substitutions and deletions, such as FKBP12v36, that bind to a dimerizer drug, may also be used. In addition, the synthetic ligands are resistant to protease degradation, making them more efficient at activating receptors in vivo than most delivered protein agents.

The ligands used are capable of binding to two or more of the ligand-binding domains. The chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug AP1903 (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by AP1903.

F36V'-FKBP: F36V'-FKBP is a codon-wobbled version of F36V-FKBP. It encodes the identical polypeptide sequence as F36V-FKPB but has only 62% homology at the nucleotide level. F36V'-FKBP was designed to reduce recombination in retroviral vectors (Schellhammer, P. F. et al., J. Urol. 157, 1731-5 (1997)). F36V'-FKBP was constructed by a PCR assembly procedure. The transgene contains one copy of F36V'-FKBP linked directly to one copy of F36V-FKBP.

In some embodiments, the ligand is a small molecule. The appropriate ligand for the selected ligand-binding region may be selected. Often, the ligand is dimeric, sometimes, the ligand is a dimeric FK506 or a dimeric FK506 analog. In certain embodiments, the ligand is AP1903 (CAS Index Name: 2-Piperidinecarboxylic acid, 1-[(2S)-1-oxo-2-(3, 4,5-trimethoxyphenyl)butyl]-, 1,2-ethanediylbis [imino(2-oxo-2,1-ethanediyl)oxy-3,1-phenylene[(1R)-3-(3,4-dimethoxyphenyl)propylidene]] ester, [2S-[1(R*),2R*[S*[S*[1(R*), 2R*]]]]]-(9Cl) CAS Registry Number: 195514-63-7; Molecular Formula: C78H98N4020 Molecular Weight: 1411.65). In certain embodiments, the ligand is AP20187. In certain embodiments, the ligand is an AP20187 analog, such as, for example, AP1510. In some embodiments, certain analogs will be appropriate for the FKBP12, and certain analogs appropriate for the mutant (V36) version of FKBP12. In certain embodiments, one ligand binding region is included in the chimeric protein. In other embodiments, two or more ligand binding regions are included. Where, for example, the ligand binding region is FKBP12, where two of these regions are included, one may, for example, be the wobbled version.

In such methods, the multimeric molecule can be an antibody that binds to an epitope in the CD40 extracellular domain (e.g., humanized anti-CD40 antibody; Tai et al., Cancer Research 64, 2846-2852 (2004)), can be a CD40 ligand (e.g., U.S. Pat. No. 6,497,876 (Maraskovsky et al.)) or may be another co-stimulating molecule (e.g., B7/CD28). It is understood that conservative variations in sequence, that do not affect the function, as assayed herein, are within the scope of the present claims.

Other dimerization systems contemplated include the coumermycin/DNA gyrase B system. Coumermycin-induced dimerization activates a modified Raf protein and stimulates the MAP kinase cascade. See Farrar et al., 1996.

AP1903 API is manufactured by Alphora Research Inc. and AP1903 Drug Product for Injection is made by AAI Pharma Services Corp. It is formulated as a 5 mg/mL solution of AP1903 in a 25% solution of the non-ionic solubilizer Solutol HS 15 (250 mg/mL, BASF). At room temperature, this formulation is a clear solution. Upon refrigeration, this formulation undergoes a reversible phase transition on extended storage, resulting in a milky solution. This phase transition is reversed upon re-warming to room temperature. The fill is 8 mL in a 10 mL glass vial (~40 mg AP1903 for Injection total per vial).

For use, the AP1903 will be warmed to room temperature and diluted prior to administration. For subjects over 50 kg, the AP1903 is administered via i.v. infusion at a dose of 40 mg diluted in 100 mL physiological saline over 2 hours at a rate of 50 mL per hour using a DEHP-free saline bag and solution set. Subjects less than 50 kg receive 0.4 mg/kg AP1903.

All study medication is maintained at a temperature between 2 degrees C. and 8 degrees C., protected from excessive light and heat, and stored in a locked area with restricted access.

Upon determining a need to administer AP1903 and activate Caspase-9 in order to induce apoptosis of the engineered CAR-expressing T cells, patients may be, for example, administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by 0%. The calculated dose is diluted in 100 mL in 0.9% normal saline before infusion.

In a previous Phase I study of AP1903, 24 healthy volunteers were treated with single doses of AP1903 for Injection at dose levels of 0.01, 0.05, 0.1, 0.5 and 1.0 mg/kg infused IV over 2 hours. AP1903 plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 for injection used, for example, may be 0.4 mg/kg intravenously infused over 2 hours. The amount of AP1903 needed in vitro for effective signaling of cells is about 10-100 nM (MW: 1412 Da). This equates to 14-140 µg/L or ~0.014-0.14 mg/kg (1.4-140 µg/kg). The dosage may vary according to the application, and may, in certain examples, be more in the range of 0.1-10 nM, or in the range of 50-150 nM, 10-200 nM, 75-125 nM, 100-500 nM, 100-600 nM, 100-700 nM, 100-800 nM, or 100-900 nM. Doses up to 1 mg/kg were well-tolerated in the Phase I study of AP1903 provided above.

Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S-N-K-S-K-P-K-D-A-S-Q-R-R-R (SEQ ID NO: 283)) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 284), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or C10 isoprenyl moieties, from the C-terminus of G-protein gamma subunits and other proteins (e.g., World Wde Web address ebi.ac.uk/interpro/DisplayIproEntry?ac=1PR001230) also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition discussed above and tested for antimicrobial activity using known methods and those discussed hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association region. Any membrane-targeting sequence can be employed that is functional in the host and may, or may not, be associated with one of the other domains of the chimeric protein. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster J P et al, Biology of the Cell (2007) 99, 1-12, Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3, 4, 5)-P3, PI (3,4)-P2, PI (4,5)-P2) and thus play a key role in recruiting proteins to different membrane or cellular compartments. Often the phosphorylation state of PI lipids is regulated, such as by PI-3 kinase or PTEN, and thus, interaction of membranes with PH domains are not as stable as by acyl lipids.

Where a polypeptide does not include a membrane-targeting region, such as certain chimeric stimulating molecules provided herein, the polypeptide does not include a region that provides for transport of the chimeric protein to a cell membrane. Where a polypeptide comprising a membrane-targeting region may be targeted to a membrane and localized to a 2-dimensional surface of the cell, a polypeptide that does not comprise a membrane-targeting-region or a functional membrane-targeting region will be non-localized in the cytosol. The polypeptide may, for example, not include a sequence that transports the polypeptide to the cell surface membrane, or the polypeptide may, for example, include a dysfunctional membrane-targeting region, that does not transport the polypeptide to the cell surface membrane, for example, a myristoylation region that includes a proline that disrupts the function of the myristoylation-targeting region. (see, for example, Resh, M. D., Biochim. Biophys. Acta. 1451:1-16 (1999)). Polypeptides that are not transported to the membrane are considered to be cytoplasmic polypeptides, such as, for example, the cytoplasmic chimeric stimulating molecules discussed herein. Such cytoplasmic chimeric stimulating molecules may lack a membrane-targeting region, for example, or may lack a functional membrane-targeting region. By "cytoplasmic chimeric stimulating molecule" is meant a polypeptide, such as the MyD88/CD40 polypeptides discussed herein, that does not comprise an amino acid sequence that transports the polypeptide to the cell surface membrane, or includes a dysfunctional membrane-targeting region. A cytoplasmic chimeric stimulating molecule, or a polypeptide that comprises a cytoplasmic chimeric stimulating molecule does not comprise an amino acid sequence, or modified amino acid sequence, that is responsible for directly attaching the polypeptide to a lipid that associates with a lipid membrane; a cytoplasmic chimeric stimulating molecule does not directly interact with lipids of the membrane. Thus, the term "cytoplasmic chimeric stimulating molecule" is not meant to include chimeric stimulating molecules that are part of a CAR polypeptide sequence, or other membrane-bound polypeptide. Following fluorescent or other labeling of a cell comprising a cytoplasmic chimeric stimulating molecule, the cytoplasmic stimulating molecule would be present in the cytoplasm of the cell, and would not stably touch, or directly interact for a prolonged period with, the cytoplasmic hydrophobic lipid portion of the cell membrane.

Transmembrane Regions

A chimeric protein herein may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFβ, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

In some embodiments, the transmembrane domain is fused to the extracellular domain of the CAR. In one embodiment, the transmembrane domain that naturally is associated with one of the domains in the CAR is used. In other embodiments, a transmembrane domain that is not naturally associated with one of the domains in the CAR is used. In some instances, the transmembrane domain can be selected or modified by amino acid substitution (e.g., typically charged to a hydrophobic residue) to avoid binding of such domains to the transmembrane domains of the same or different surface membrane proteins to minimize interactions with other members of the receptor complex.

Transmembrane domains may, for example, be derived from the alpha, beta, or zeta chain of the T cell receptor, CD3-ε, CD3ζ, CD4, CD5, CD8, CD8α, CD9, CD16, CD22, CD28, CD33, CD38, CD64, CD80, CD86, CD134, CD137, or CD154. Or, in some examples, the transmembrane domain may be synthesized de novo, comprising mostly hydrophobic residues, such as, for example, leucine and valine. In certain embodiments a short polypeptide linker may form the linkage between the transmembrane domain and the intracellular domain of the chimeric antigen receptor. The chimeric antigen receptors may further comprise a stalk, that is, an extracellular region of amino acids between the extracellular domain and the transmembrane domain. For example, the stalk may be a sequence of amino acids naturally associated with the selected transmembrane domain. In some embodiments, the chimeric antigen receptor comprises a CD8 transmembrane domain, in certain embodiments, the chimeric antigen receptor comprises a CD8 transmembrane domain, and additional amino acids on the extracellular portion of the transmembrane domain, in certain embodiments, the chimeric antigen receptor comprises a CD8 transmembrane domain and a CD8 stalk. The chimeric antigen receptor may further comprise a region of amino acids between the transmembrane domain and the cytoplasmic domain, which are naturally associated with the polypeptide from which the transmembrane domain is derived.

Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, f3-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Life Technologies (formerly Invitrogen), Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that may be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tetracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity. (Bojak, A., et al., 2002. Vaccine. 20:1975-79; Cazeaux, N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29/CD79b (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262,2345-2351), c-fos, TNF-$\alpha$, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP $\alpha$, IL-1, IL-6 (Poli and Cortese, (1989) Proc. Nat'l Acad. Sci. USA, 86,8202-8206), Complement C3 (Wilson et al., (1990) Mol. Cell. Biol., 6181-6191), IL-8, $\alpha$-1 acid glycoprotein (Prowse and Baumann, (1988) Mol Cell Biol, 8,42-51), $\alpha$-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-$\alpha$, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), $\alpha$-2 macroglobulin and $\alpha$-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole stimulates transcription at a distance and often independent of orientation; this need not be true of a promoter region or its component elements. On the other hand, a promoter has one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers includes locus-control regions (LCRs) that can not only increase transcriptional activity, but (along with insulator elements) can also help to insulate the transcriptional element from adjacent sequences when integrated into the genome. Any promoter/enhancer combination (as per the Eukaryotic Promoter Data Base EPDB) can be used to drive expression of the gene, although many will restrict expression to a particular tissue type or subset of tissues. (Reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Appropriate enhancers may be selected for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. One non-limiting example is the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA. (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. The initiation codon is placed in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been discussed (Pelletier and Sonenberg, 1988), as well an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Sequence Optimization

Protein production may also be increased by optimizing the codons in the transgene. Species specific codon changes may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed. (Kutzler, M. A., and Weiner, D. B., 2008. Nature Rev. Gen. 9:776-88; Yan, J. et al., 2007. Mol. Ther. 15:411-21; Cheung, Y. K., et al., 2004. Vaccine 23:629-38; Narum, D. L., et al., 2001. 69:7250-55; Yadava, A., and Ockenhouse, C. F., 2003. Infect. Immun. 71:4962-69; Smith, J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635). For example, the FBP12 or other multimerizing region polypeptide, the co-stimulating polypeptide cytoplasmic signaling region, and the CD19 sequences may be optimized by changes in the codons.

Leader Sequences

Leader sequences may be added to enhance the stability of mRNA and result in more efficient translation. The leader sequence is usually involved in targeting the mRNA to the endoplasmic reticulum. Examples include the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang, J. S., et al., 2002. Emerg. Infect. Dis. 8:1379-84; Kumar, S., et al., 2006. DNA Cell Biol. 25:383-92; Wang, S., et al, 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression. These methods include, for example, optimizing promoters, delivery methods, and gene sequences, (for example, as presented in Laddy, D. J., et al., 2008. PLoS. ONE 3 e2517; Kutzler, M. A., and Weiner, D. B., 2008. Nature Rev. Gen. 9:776-88).

Nucleic Acids

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, for example, at least 80%, for example, at least 90%, and for example, at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, in certain embodiments, the settings are those that results in the highest sequence similarity.

Nucleic Acid Modification

Any of the modifications discussed below may be applied to a nucleic acid. Examples of modifications include alterations to the RNA or DNA backbone, sugar or base, and various combinations thereof. Any suitable number of backbone linkages, sugars and/or bases in a nucleic acid can be modified (e.g., independently about 5%, 10%, 15%, 20%, 25%, 30%, 35%, 40%, 45%, 50%, 55%, 60%, 65%, 70%, 75%, 80%, 85%, 90%, 95%, up to 100%). An unmodified nucleoside is any one of the bases adenine, cytosine, guanine, thymine, or uracil joined to the 1' carbon of β-D-ribofuranose.

A modified base is a nucleotide base other than adenine, guanine, cytosine and uracil at a 1' position. Non-limiting examples of modified bases include inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e. g., 5-methylcytidine), 5-alkyluridines (e. g., ribothymidine), 5-halouridine (e. g., 5-bromouridine) or 6-azapyrimidines or 6-alkylpyrimidines (e. g. 6-methyluridine), propyne, and the like. Other non-limiting examples of modified bases include nitropyrrolyl (e.g., 3-nitropyrrolyl), nitroindolyl (e.g., 4-, 5-, 6-nitroindolyl), hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, difluorotolyl, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4, 5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl and the like.

In some embodiments, for example, a nucleic acid may comprise modified nucleic acid molecules, with phosphate backbone modifications. Non-limiting examples of backbone modifications include phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl modifications. In certain instances, a ribose sugar moiety that naturally occurs in a nucleoside is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. The hexose may be a D-hexose, glucose, or mannose. In certain instances, the polycyclic heteroalkyl group may be a bicyclic ring containing one oxygen atom in the ring. In certain instances, the polycyclic heteroalkyl group is a bicyclo [2.2.1]heptane, a bicyclo[3.2.1]octane, or a bicyclo[3.3.1] nonane.

Nitropyrrolyl and nitroindolyl nucleobases are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, oligonucleotide duplexes containing 3-nitropyrrolyl nucleobases may be stabilized solely by stacking interactions. The absence of significant hydrogen-bonding interactions with nitropyrrolyl nucleobases obviates the specificity for a specific complementary base. In addition, 4-, 5- and 6-nitroindolyl display very little specificity for the four natural bases. Procedures for the preparation of 1-(2'-O-methyl-43.-D-ribofuranosyl)-5-nitroindole are discussed in Gaubert, G.; Wengel, J. Tetrahedron Letters 2004, 45, 5629. Other universal bases include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof.

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994);

In addition, chemical substituents, for example cross-linking agents, may be used to add further stability or irreversibility to the reaction. Non-limiting examples of cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio] propioimidate.

A nucleotide analog may also include a "locked" nucleic acid. Certain compositions can be used to essentially "anchor" or "lock" an endogenous nucleic acid into a particular structure. Anchoring sequences serve to prevent disassociation of a nucleic acid complex, and thus not only can prevent copying but may also enable labeling, modification, and/or cloning of the endogenous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

Nucleic acid molecules need not be limited to those molecules containing only RNA or DNA, but further encompass chemically modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%).

Nucleic Acid Preparation

In some embodiments, a nucleic acid is provided for use as a control or standard in an assay, or therapeutic, for example. A nucleic acid may be made by any technique known in the art, such as for example, chemical synthesis, enzymatic production or biological production. Nucleic acids may be recovered or isolated from a biological sample. The nucleic acid may be recombinant or it may be natural or endogenous to the cell (produced from the cell's genome). It is contemplated that a biological sample may be treated in a way so as to enhance the recovery of small nucleic acid molecules. Generally, methods may involve lysing cells with a solution having guanidinium and a detergent.

Nucleic acid synthesis may also be performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques or via deoxynucleoside H-phosphonate intermediates. Various different mechanisms of oligonucleotide synthesis have been disclosed elsewhere.

Nucleic acids may be isolated using known techniques. In particular embodiments, methods for isolating small nucleic acid molecules, and/or isolating RNA molecules can be employed. Chromatography is a process used to separate or isolate nucleic acids from protein or from other nucleic acids. Such methods can involve electrophoresis with a gel matrix, filter columns, alcohol precipitation, and/or other chromatography. If a nucleic acid from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column is effective for such isolation procedures.

A nucleic acid isolation processes may sometimes include: a) lysing cells in the sample with a lysing solution comprising guanidinium, where a lysate with a concentration of at least about 1 M guanidinium is produced; b) extracting nucleic acid molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the nucleic acid molecules from the solid support with an ionic solution; and, f) capturing the nucleic acid molecules. The sample may be dried down and resuspended in a liquid and volume appropriate for subsequent manipulation.

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer. A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a T cell, a tumor-infiltrating lymphocyte, a natural killer cell, or a natural killer T cell.

An appropriate host may be determined. Generally this is based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Nucleic acid vaccines may include, for example, non-viral DNA vectors, "naked" DNA and RNA, and viral vectors. Methods of transforming cells with these vaccines, and for optimizing the expression of genes included in these vaccines are known and are also discussed herein.

Examples of Methods of Nucleic Acid or Viral Vector Transfer

Any appropriate method may be used to transfect or transform the cells, for example, the T cells, or to administer the nucleotide sequences or compositions of the present methods. Certain examples are presented herein, and further include methods such as delivery using cationic polymers, lipid like molecules, and certain commercial products such as, for example, IN-VIVO-JET PEI.

1. Ex Vivo Transformation

Various methods are available for transfecting vascular cells and tissues removed from an organism in an ex vivo setting. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism. For example, T cells may be obtained from an animal, the cells transfected or transduced with the expression vector and then administered back to the animal.

2. Injection

In certain embodiments, a cell or a nucleic acid or viral vector may be delivered to an organelle, a cell, a tissue or an organism via one or more injections (i.e., a needle injection), such as, for example, subcutaneous, intradermal, intramuscular, intravenous, intraprotatic, intratumor, intraperitoneal, etc. Methods of injection include, for example, injection of a composition comprising a saline solution. Further embodiments include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair is clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human K-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell Biol., 6,716-718) in this manner.

In vivo electroporation for vaccines, or eVac, is clinically implemented through a simple injection technique. A DNA vector encoding tumor antigen is injected intradermally in a patient. Then electrodes apply electrical pulses to the intradermal space causing the cells localized there, especially resident dermal dendritic cells, to take up the DNA vector and express the encoded tumor antigen. These tumor antigen-expressing dendritic cells activated by local inflammation can then migrate to lymph-nodes, presenting tumor antigens and priming tumor antigen-specific T cells. A nucleic acid is electroporetically administered when it is administered using electroporation, following, for example, but not limited to, injection of the nucleic acid or any other means of administration where the nucleic acid may be delivered to the cells by electroporation Methods of electroporation are discussed in, for example, Sardesai, N.Y., and Weiner, D. B., Current Opinion in Immunotherapy 23:421-9 (2011) and Ferraro, B. et al., Human Vaccines 7:120-127 (2011), which are hereby incorporated by reference herein in their entirety.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52,456-467) using this technique. Also in this manner, mouse L(A9), mouse C127, CHO, CV-1, BHK, NIH3T3 and HeLa cells were transfected with a neomycin marker gene (Chen and Okayama, Mol.

Cell Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7. Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with LIPOFECTAMINE (Gibco BRL) or SUPERFECT (Qiagen).

Receptor-Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been discussed (Wu and Wu, Adv. Drug Delivery Rev., 12:159-167, 1993; incorporated herein by reference). In certain aspects, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149,157-176). It is contemplated that the tissue-specific transforming constructs may be specifically delivered into a target cell in a similar manner.

8. Microprojectile Bombardment

Microprojectile bombardment techniques can be used to introduce a polynucleotide into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods.

In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold, including, for example, nanoparticles. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

Examples of Methods of Viral Vector-Mediated Transfer

Any viral vector suitable for administering nucleotide sequences, or compositions comprising nucleotide sequences, to a cell or to a subject, such that the cell or cells in the subject may express the genes encoded by the nucleotide sequences may be employed in the present methods. In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector may permits replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12,243-249). Later studies showed that a mutant with a deletion in the E1A (194-358 bp) region of the genome grew poorly even in a cell line that complemented the early (E1A) function (Hearing and Shenk, (1983) J. Mol. Biol. 167,809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells, such as, for example, T cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

1. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990). Thus, for example, the present technology includes, for example, cells whereby the polynucleotide used to transduce the cell is integrated into the genome of the cell.

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67,242-248).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may this be desired.

A different approach to targeting of recombinant retroviruses was designed, which used biotinylated antibodies against a retroviral envelope protein and against a specific cell receptor. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

2. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770,79-90; Ferrari et al., (1996) J. Virol., 70,3227-3234; Fisher et al., (1996) J. Virol., 70,520-532; Flotte et al., Proc. Nat'l Acad. Sci. USA, 90,10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70,520-532; Flotte et al., 1993; Kaplitt et al., 1994; 1996; Koeberl et al., 1997; McCown et al., (1996) Brain Res., 713,99-107; Ping et al., (1996) Microcirculation, 3,225-228; Xiao et al., (1996) J. Virol., 70,8098-8108).

3. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Methods for Treating a Disease

The present methods also encompass methods of treatment or prevention of a disease where administration of cells by, for example, infusion, may be beneficial.

Cells, such as, for example, T cells, tumor infiltrating lymphocytes, natural killer cells, natural killer T cells, or progenitor cells, such as, for example, hematopoietic stem cells, mesenchymal stromal cells, stem cells, pluripotent stem cells, and embryonic stem cells may be used for cell therapy. The cells may be from a donor, or may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. Mesenchymal stromal cells have also, for example, been used to provide immunosuppressive activity, and may be used in the treatment of graft versus host disease and autoimmune disorders. The cells provided in the present application contain a safety switch that may be valuable in a situation where following cell therapy, the activity of the therapeutic cells needs to be increased, or decreased. For example, where T cells that express a chimeric antigen receptor are provided to the patient, in some situations there may be an adverse event, such as off-target toxicity. Ceasing the administration of the ligand would return the therapeutic T cells to a non-activated state, remaining at a low, non-toxic, level of expression. Or, for example, the therapeutic cell may work to decrease the tumor cell, or tumor size, and may no longer be needed. In this situation, administration of the ligand may cease, and the therapeutic cells would no longer be activated. If the tumor cells return, or the tumor size increases following the initial therapy, the ligand may be administered again, in order to activate the chimeric antigen receptor-expressing T cells, and re-treat the patient.

By "therapeutic cell" is meant a cell used for cell therapy, that is, a cell administered to a subject to treat or prevent a condition or disease.

The term "unit dose" as it pertains to the inoculum refers to physically discrete units suitable as unitary dosages for mammals, each unit containing a predetermined quantity of pharmaceutical composition calculated to produce the desired immune-stimulating effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition, such as the multimeric ligand presented herein, would be the amount that achieves this selected result of inducing apoptosis in the Caspase-9-expressing cells T cells, such that over 60%, 70%, 80%, 85%, 90%, 95%, or 97%, or that under 80%, 70%, 60%, 50%, 40%, 30%, 20%, or 10% of the therapeutic cells are killed. The term is also synonymous with "sufficient amount." The effective amount where the pharmaceutical composition is the modified T cell may also be the amount that achieves the desired therapeutic response, such as, the reduction of tumor size, the decrease in the level of tumor cells, or the decrease in the level of CD19-expressing leukemic cells, compared to the time before the ligand inducer is administered.

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

Optimized and Personalized Therapeutic Treatment

The dosage and administration schedule of the modified cells may be optimized by determining the level of the disease or condition to be treated. For example, the size of any remaining solid tumor, or the level of targeted cells such as, for example, tumor cells or CD19-expressing B cells, which remain in the patient, may be determined.

For example, determining that a patient has clinically relevant levels of tumor cells, or a solid tumor, after initial therapy, provides an indication to a clinician that it may be necessary to administer the modified T cells. In another example, determining that a patient has a reduced level of tumor cells or reduced tumor size after treatment with the modified cells may indicate to the clinician that no additional dose of the modified cells is needed. Similarly, after treatment with the modified cells, determining that the patient continues to exhibit disease or condition symptoms, or suffers a relapse of symptoms may indicate to the clinician that it may be necessary to administer at least one additional dose of modified cells.

The term "dosage" is meant to include both the amount of the dose and the frequency of administration, such as, for example, the timing of the next dose. The term "dosage level" refers to the amount of the modified cells administered in relation to the body weight of the subject.

In certain embodiments the cells are in an animal, such as human, non-human primate, cow, horse, pig, sheep, goat, dog, cat, or rodent. The subject may be, for example, an animal, such as a mammal, for example, a human, non-human primate, cow, horse, pig, sheep, goat, dog, cat, or rodent. The subject may be, for example, human, for example, a patient suffering from an infectious disease, and/or a subject that is immunocompromised, or is suffering from a hyperproliferative disease.

Thus, for example, in certain embodiments, the methods comprise determining the presence or absence of a tumor size increase and/or increase in the number of tumor cells in a subject relative to the tumor size and/or the number of tumor cells following administration of the modified cells or nucleic acid, and administering an additional dose of the modified cells or nucleic acid to the subject in the event the presence of a tumor size increase and/or increase in the number of tumor cells is determined. The methods also comprise, for example, determining the presence or absence of an increase in CD19-expressing B cells in the subject relative to the level of CD19-expressing B cells following administration of the modified cells or nucleic acid, and administering an additional dose of the modified cells or nucleic acid to the subject in the event the presence of an increase in CD19-expressing B cells in the subject is determined. In these embodiments, for example, the patient is initially treated with the therapeutic cells or nucleic acid according to the methods provided herein. Following the initial treatment, the size of the tumor, the number of tumor cells, or the number of CD19-expressing B cells, for example, may decrease relative to the time prior to the initial treatment. At a certain time after this initial treatment, the patient is again tested, or the patient may be continually monitored for disease symptoms. If it is determined that the size of the tumor, the number of tumor cells, or the number of CD19-expressing B cells, for example, is increased relative to the time just after the initial treatment, then the modified cells or nucleic acid may be administered for an additional dose. This monitoring and treatment schedule may continue while noting that the therapeutic cells that express chimeric antigen receptors or chimeric stimulating molecules remain in the patient.

In other embodiments, following administration of the modified cells or nucleic acid, wherein the modified cells or nucleic acid express the inducible Caspase-9 polypeptide, in the event of a need to reduce the number of modified cells or in vivo modified cells, the multimeric ligand may be administered to the patient. In these embodiments, the methods comprise determining the presence or absence of a negative symptom or condition, such as Graft vs Host Disease, or off target toxicity, and administering a dose of the multimeric ligand. The methods may further comprise monitoring the symptom or condition and administering an additional dose of the multimeric ligand in the event the symptom or condition persists. This monitoring and treatment schedule may continue while the therapeutic cells that express chimeric antigen receptors or chimeric stimulating molecules remain in the patient.

An indication of adjusting or maintaining a subsequent drug dose, such as, for example, a subsequent dose of the modified cells or nucleic acid, and/or the subsequent drug dosage, can be provided in any convenient manner. An indication may be provided in tabular form (e.g., in a physical or electronic medium) in some embodiments. For example, the size of the tumor cell, or the number or level of tumor cells in a sample may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms are provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the activated cell, nucleic acid, or expression construct, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers, or other disease symptoms such as tumor size or tumor antigen expression, to evaluate the effectiveness of treatment and to control toxicity.

In further embodiments, the expression construct and/or expression vector can be utilized as a composition or substance that activates cells. Such a composition that "activates cells" or "enhances the activity of cells" refers to the ability to stimulate one or more activities associated with cells. For example, a composition, such as the expression construct or vector of the present methods, can stimulate upregulation of co-stimulating molecules on cells, induce nuclear translocation of NF-κB in cells, activate toll-like receptors in cells, or other activities involving cytokines or chemokines.

The expression construct, expression vector and/or transduced cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity by eliciting a particular cytokine profile.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In certain embodiments, the cell can be transduced ex vivo or in vivo with a nucleic acid that encodes the chimeric protein. The cell may be sensitized to the antigen at the same time the cell is contacted with the multimeric ligand, or the cell can be pre-sensitized to the antigen before the cell is contacted with the multimerization ligand. In some embodiments, the cell is contacted with the antigen ex vivo.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

In certain embodiments, the cell is transduced with the nucleic acid ex vivo and administered to the subject by intradermal administration, and sometimes the cell is transduced with the nucleic acid ex vivo and administered to the subject by subcutaneous administration. The antigen may be a tumor antigen, and the CTL immune response can be induced by migration of the cell to a draining lymph node. A tumor antigen is any antigen such as, for example, a peptide or polypeptide, that triggers an immune response in a host. The tumor antigen may be a tumor-associated antigen, which is associated with a neoplastic tumor cell.

In some embodiments, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present methods can be utilized to enhance the amount and/or activity of CD4 T helper cells in an immunocompromised subject.

Antigens

Chimeric antigen receptors bind to target antigens. When assaying T cell activation in vitro or ex vivo, target antigens may be obtained or isolated from various sources. The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), Mycobacteria, *Legionella*, Meningiococcus, Group A *Streptococcus, Salmonella, Listeria, Hemophilus influenzae* (U.S. Pat. No. 5,955,596) and the like).

Target antigen may be derived or isolated from, for example, pathogenic yeast including *Aspergillus*, invasive *Candida* (U.S. Pat. No. 5,645,992), *Nocardia*, Histoplasmosis, Cryptosporidia and the like.

Target antigen may be derived or isolated from, for example, a pathogenic protozoan and pathogenic parasites including but not limited to *Pneumocystis carinii*, *Trypanosoma*, *Leishmania* (U.S. Pat. No. 5,965,242), *Plasmodium* (U.S. Pat. No. 5,589,343) and *Toxoplasma gondii*. Target antigen includes an antigen associated with a preneoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750, 395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat. No. 5,840, 839), NY-ESO-1 (Chen et al PNAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

An antigen may be expressed more frequently in cancer cells than in non-cancer cells. The antigen may result from contacting the modified cell with a prostate specific membrane antigen, for example, a prostate specific membrane antigen (PSMA) or fragment thereof.

Prostate antigen (PA001) is a recombinant protein consisting of the extracellular portion of PSMA antigen. PSMA is a ~100 kDa (84 kDa before glycosylation, 180 kDa as dimer) type II membrane protein with neuropeptidase and folate hydrolase activities, but the true function of PSMA is currently unclear. Carter R E, et al., Proc Natl Acad Sci USA. 93: 749-53, 1996; Israeli R S, et al., Cancer Res. 53: 227-30, 1993; Pinto J T, et al., Clin Cancer Res. 2: 1445-51, 1996. Expression is largely, but not exclusively, prostate-specific and is maintained in advanced and hormone refractory disease. Israeli R S, et al., Cancer Res. 54: 1807-11, 1994. Weak non-prostatic detection in normal tissues has also been seen in the salivary gland, brain, small intestines, duodenal mucosa, proximal renal tubules and neuroendocrine cells in colonic crypts. Silver D A, et al., Clin Cancer Res. 3: 81-5, 1997; Troyer J K, et al., Int J Cancer. 62: 552-8, 1995. Moreover, PSMA is up-regulated following androgen deprivation therapy (ADT). Wright G L, Jr., et al., Urology. 48: 326-34, 1996. While most PSMA is expressed as a cytoplasmic protein, the alternatively spliced transmembrane form is the predominate form on the apical surface of neoplastic prostate cells. Su S L, et al., Cancer Res. 55: 1441-3, 1995; Israeli R S, et al., Cancer Res. 54: 6306-10, 1994.

Moreover, PSMA is internalized following cross-linking and has been used to internalize bound antibody or ligand complexed with radionucleotides or viruses and other complex macromolecules. Liu H, et al., Cancer Res. 58: 4055-60, 1998; Freeman L M, et al., Q J Nucl Med. 46: 131-7, 2002; Kraaij R, et al., Prostate. 62: 253-9, 2005. Bander and colleagues demonstrated that pretreatment of tumors with microtubule inhibitors increases aberrant basal surface targeting and antibody-mediated internalization of PSMA. Christiansen J J, et al., Mol Cancer Ther. 4: 704-14, 2005. Tumor targeting may be facilitated by the observation of ectopic expression of PSMA in tumor vascular endothelium of not only prostate, but also renal and other tumors. Liu H, et al., Cancer Res. 57: 3629-34, 1997; Chang S S, et al., Urology. 57: 801-5, 2001; Chang S S, et al., Clin Cancer Res. 5: 2674-81, 1999.

PSMA is not found in the vascular endothelial cells of corresponding benign tissue. De la Taille A, et al., Cancer Detect Prev. 24: 579-88, 2000. Although one early histological study of metastatic prostate disease suggested that only ~50% (8 of 18) of bone metastases (with 7 of 8 lymph node metastases) expressed PSMA, the more sensitive reagent, 177Lu-radiolabeled MoAb J591, targeted to the ectodomain of PSMA, could target all known sites of bone and soft tissue metastasis in 30 of 30 patients, suggesting near universal expression in advanced prostate disease. Bander N H, et al., J Clin Oncol. 23: 4591-601, 2005.

A prostate specific antigen, or PSA, is meant to include any antigen that can induce an immune response, such as, for example, a cytotoxic T lymphocyte response, against a PSA, for example, a PSMA, and may be specifically recognized by any anti-PSA antibody. PSAs used in the present method are capable of being used to load the cell, as assayed using conventional methods. Thus, "prostate specific antigen" or "PSA" may, for example, refer to a protein having the wild type amino acid sequence of a PSA, or a polypeptide that includes a portion of the a PSA protein, A prostate specific membrane antigen, or PSMA, is meant to include any antigen that can induce an immune response, such as, for example, a cytotoxic T lymphocyte response, against PSMA, and may be specifically recognized by an anti-PSMA antibody. PSMAs used in the present method are capable of being used to load the cell, as assayed using conventional methods. Thus, "prostate specific membrane antigen" or "PSMA" may, for example, refer to a protein having the wild type amino acid sequence of PSMA, or a polypeptide that includes a portion of the PSMA protein, such as one encoded by SEQ ID NO: 3, or a portion of the nucleotide sequence of SEQ ID NO: 3, or having the polypeptide of SEQ ID NO: 4, or a portion thereof. The term may also refer to, for example, a peptide having an amino acid sequence of a portion of SEQ ID NO: 4, or any peptide that may induce an immune response against PSMA. Also included are variants of any of the foregoing, including, for example, those having substitutions and deletions. Proteins, polypeptides, and peptides having differential post-translational processing, such as differences in glycosylation, from the wild type PSMA, may also be used in the present methods. Further, various sugar molecules that are capable of inducing an immune response against PSMA, are also contemplated.

A PSA, for example, a PSMA, polypeptide may be used to load the modified cell. In certain embodiments, the modified cell is contacted with a PSMA polypeptide fragment having the amino acid sequence of SEQ ID NO: 4 (e.g., encoded by the nucleotide sequence of SEQ ID NO: 3), or a fragment thereof. In some embodiments, the PSA, for example, PSMA polypeptide fragment does not include the signal peptide sequence. In other embodiments, the modified cell is contacted with a PSA, for example, PSMA polypeptide fragment comprising substitutions or deletions of amino acids in the polypeptide, and the fragment is sufficient to load cells.

A prostate specific protein antigen, or PSPA, also referred to in this specification as a prostate specific antigen, or a PSA, is meant to include any antigen that can induce an immune response, such as, for example, a cytotoxic T lymphocyte response, against a prostate specific protein antigen. This includes, for example, a prostate specific protein antigen or Prostate Specific Antigen. PSPAs used in the present method are capable of being used to load the cell, as assayed using conventional methods. Prostate Specific Antigen, or PSA, may, for example, refer to a protein having the wild type amino acid sequence of a PSA, or a polypeptide that includes a portion of the PSA protein, A prostate specific membrane antigen, or PSMA, is meant to include any antigen that can induce an immune response, such as, for example, a cytotoxic T lymphocyte response, against PSMA, and may be specifically recognized by an anti-PSMA antibody. PSMAs used in the present method are capable of being used to load the cell, as assayed using conventional methods. Thus, "prostate specific membrane antigen" or "PSMA" may, for example, refer to a protein having the wild type amino acid sequence of PSMA, or a polypeptide that includes a portion of the PSMA protein, such as one encoded by SEQ ID NO: 3, or a portion of the nucleotide sequence of SEQ ID NO: 3, or having the polypeptide of SEQ ID NO: 4, or a portion thereof. The term may also refer to, for example, a peptide having an amino acid sequence of a portion of SEQ ID NO: 4, or any peptide that may induce an immune response against PSMA. Also included are variants of any of the foregoing, including, for example, those having substitutions and deletions. Proteins, polypeptides, and peptides having differential post-translational processing, such as differences in glycosylation, from the wild type PSMA, may also be used in the present methods. Further, various sugar molecules that are capable of inducing an immune response against PSMA, are also contemplated.

A PSPA, for example, a PSMA, polypeptide may be used to load the modified cell. In certain embodiments, the modified cell is contacted with a PSMA polypeptide fragment having the amino acid sequence of SEQ ID NO: 4 (e.g., encoded by the nucleotide sequence of SEQ ID NO: 3), or a fragment thereof. In some embodiments, the PSA, for example, PSMA polypeptide fragment does not include the signal peptide sequence. In other embodiments, the modified cell is contacted with a PSPA, for example, PSMA polypeptide fragment comprising substitutions or deletions of amino acids in the polypeptide, and the fragment is sufficient to load cells.

A tumor antigen is any antigen such as, for example, a peptide or polypeptide, that triggers an immune response in a host against a tumor. The tumor antigen may be a tumor-associated antigen, which is associated with a neoplastic tumor cell.

A prostate cancer antigen, or PCA, is any antigen such as, for example, a peptide or polypeptide, that triggers an immune response in a host against a prostate cancer tumor. A prostate cancer antigen may, or may not, be specific to prostate cancer tumors. A prostate cancer antigen may also trigger immune responses against other types of tumors or neoplastic cells. A prostate cancer antigen includes, for example, prostate specific protein antigens, prostate specific antigens, and prostate specific membrane antigens.

The cell may be contacted with tumor antigen, such as PSA, for example, PSMA polypeptide, by various methods, including, for example, pulsing immature DCs with unfractionated tumor lysates, MHC-eluted peptides, tumor-derived heat shock proteins (HSPs), tumor associated antigens (TAAs (peptides or proteins)), or transfecting DCs with bulk tumor mRNA, or mRNA coding for TAAs (reviewed in Gilboa, E. & Vieweg, J., Immunol Rev 199, 251-63 (2004); Gilboa, E, Nat Rev Cancer 4, 401-11 (2004)).

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by routine methods. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified, for example, by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of cells, such as, for example, dendritic cells, with antigens may be achieved, for example, by contacting cells, such as, for example, dendritic cells or progenitor cells with an antigen, for example, by incubating the cells with the antigen. Loading may also be achieved, for example, by incubating DNA (naked or within a plasmid vector) or RNA that code for the antigen; or with antigen-expressing recombinant bacterium or viruses (e.g., vaccinia, fowlpox, adenovirus or lentivirus vectors). Prior to loading, the antigen may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods (see Zitvogel L, et al., J Exp Med 1996. 183:87-97). The cells may be transduced or transfected with the chimeric protein-encoding nucleotide sequence according to the present methods before, after, or at the same time as the cells are loaded with antigen. In particular embodiments, antigen loading is subsequent to transduction or transfection.

In further embodiments, the transduced cell is transfected with tumor cell mRNA. The transduced transfected cell is administered to an animal to effect cytotoxic T lymphocytes and natural killer cell anti-tumor antigen immune response and regulated using dimeric FK506 and dimeric FK506 analogs. The tumor cell mRNA may be, for example, mRNA from a prostate tumor cell.

In some embodiments, the transduced cell may be loaded by pulsing with tumor cell lysates. The pulsed transduced cells are administered to an animal to effect cytotoxic T lymphocytes and natural killer cell anti-tumor antigen immune response and regulated using dimeric FK506 and dimeric FK506 analogs. The tumor cell lysate may be, for example, a prostate tumor cell lysate.

Immune Cells and Cytotoxic T Lymphocyte Response

T-lymphocytes may be activated by contact with the cell that comprises the expression vector discussed herein, where the cell has been challenged, transfected, pulsed, or electrofused with an antigen.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, which are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods discussed herein, for example. For example, CTLs may be assessed in freshly isolated peripheral blood mononuclear cells (PBMC), in a phytohaemaglutinin-stimulated IL-2 expanded cell line established from PBMC (Bernard et al., AIDS, 12(16):2125-2139, 1998) or by T cells isolated from a previously immunized subject and restimulated for 6 days with DC infected with an adenovirus vector containing antigen using standard 4 hour 51Cr release microtoxicity assays. One type of assay uses cloned T-cells. Cloned T-cells have been tested for their ability to mediate both perforin and Fas ligand-dependent killing in redirected cytotoxicity assays (Simpson et al., Gastroenterology, 115(4):849-855, 1998). The cloned cytotoxic T lymphocytes displayed both Fas- and perforin-dependent killing. Recently, an in vitro dehydrogenase release assay has been developed that takes advantage of a new fluorescent amplification system (Page, B., et al., Anticancer Res. 1998 July-August; 18(4A):2313-6). This approach is sensitive, rapid, and reproducible and may be used advantageously for mixed lymphocyte reaction (MLR). It may easily be further automated for large-scale cytotoxicity testing using cell membrane integrity, and is thus considered. In another fluorometric assay developed for detecting cell-mediated cytotoxicity, the fluorophore used is the non-toxic molecule ALAMARBLUE (Nociari et al., J. Immunol. Methods, 213(2): 157-167, 1998). The ALAMARBLUE is fluorescently quenched (i.e., low quantum yield) until mitochondrial reduction occurs, which then results in a dramatic increase in the ALAMARBLUE fluorescence intensity (i.e., increase in the quantum yield). This assay is reported to be extremely sensitive, specific and requires a significantly lower number of effector cells than the standard $^{51}$Cr release assay.

Other immune cells that can be induced by the present methods include natural killer cells (NK). NKs are lymphoid cells that lack antigen-specific receptors and are part of the innate immune system. Typically, infected cells are usually destroyed by T cells alerted by foreign particles bound to the cell surface MHC. However, virus-infected cells signal infection by expressing viral proteins that are recognized by antibodies. These cells can be killed by NKs. In tumor cells, if the tumor cells lose expression of MHC I molecules, then it may be susceptible to NKs.

Formulations and Routes for Administration to Patients

Where clinical applications are contemplated, it will be necessary to prepare pharmaceutical compositions—expression constructs, expression vectors, fused proteins, transduced cells, activated T cells, transduced and loaded T cells—in a form appropriate for the intended application. Generally, this will entail preparing compositions that are essentially free of pyrogens, as well as other impurities that could be harmful to humans or animals.

The multimeric ligand, such as, for example, AP1903, may be delivered, for example at doses of about 0.01 to 1 mg/kg subject weight, of about 0.05 to 0.5 mg/kg subject weight, 0.1 to 2 mg/kg subject weight, of about 0.05 to 1.0 mg/kg subject weight, of about 0.1 to 5 mg/kg subject weight, of about 0.2 to 4 mg/kg subject weight, of about 0.3 to 3 mg/kg subject weight, of about 0.3 to 2 mg/kg subject weight, or about 0.3 to 1 mg/kg subject weight, for example, about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight. In some embodiments, the ligand is provided at 0.4 mg/kg per dose, for example at a concentration of 5 mg/mL. Vials or other containers may be provided containing the ligand at, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

AP1903 for Injection

AP1903 API is manufactured by Alphora Research Inc. and AP1903 Drug Product for Injection is made by Formatech Inc. It is formulated as a 5 mg/mL solution of AP1903 in a 25% solution of the non-ionic solubilizer Solutol HS 15 (250 mg/mL, BASF). At room temperature, this formulation is a clear, slightly yellow solution. Upon refrigeration, this formulation undergoes a reversible phase transition, resulting in a milky solution. This phase transition is reversed upon re-warming to room temperature. The fill is 2.33 mL in a 3 mL glass vial (~10 mg AP1903 for Injection total per vial).

AP1903 is removed from the refrigerator the night before the patient is dosed and stored at a temperature of approximately 21° C. overnight, so that the solution is clear prior to dilution. The solution is prepared within 30 minutes of the start of the infusion in glass or polyethylene bottles or non-DEHP bags and stored at approximately 21° C. prior to dosing.

All study medication is maintained at a temperature between 2 degrees C. and 8 degrees C., protected from excessive light and heat, and stored in a locked area with restricted access.

Administration

In one example, patients are administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by 0%. The calculated dose is diluted in 100 mL in 0.9% normal saline before infusion.

Patients are observed for 15 minutes following the end of the infusion for untoward adverse effects. One may generally desire to employ appropriate salts and buffers to render delivery vectors stable and allow for uptake by target cells. Buffers also may be employed when recombinant cells are introduced into a patient. Aqueous compositions comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route. This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form is sterile and is fluid to the extent that easy syringability exists. It is stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

The administration schedule may be determined as appropriate for the patient and may, for example, comprise a dosing schedule where the nucleic acid is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

The administration schedule may be determined as appropriate for the patient and may, for example, comprise a dosing schedule where the nucleic acid-transduced T cell or other cell is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

Although for administration of transduced T cells, one dose is likely to be sufficient, T cells may be provided more than once, or other cells, such as the non-dendritic cells and non-B cells discussed herein may also be administered multiple times. In addition, nucleic acids targeted to the non-T cell aspects of the present technology may also be administered more than one time for optimum therapeutic efficacy. Therefore, for example, the administration schedule may be determined as appropriate for the patient and may, for example, comprise a dosing schedule where the nucleic acid or nucleic acid-transduced cell is administered at week 0, followed by administration of additional nucleic acid or nucleic acid-transduced cell and inducer at 2 week intervals thereafter for a total of, for example, 2, 4, 6, 8, 10, 12, 14, 16, 18, 20, 22, 24, 26, 28, or 30 weeks.

Administration of a dose of cells may occur in one session, or in more than one session. If needed, the method may further include additional leukaphereses to obtain more cells to be used in treatment.

Methods for Treating a Disease

The present methods also encompass methods of treatment or prevention of a disease caused by pathogenic microorganisms and/or a hyperproliferative disease.

Diseases that may be treated or prevented include diseases caused by viruses, bacteria, yeast, parasites, protozoa, cancer cells and the like. The pharmaceutical composition (transduced T cells, expression vector, expression construct, etc.) may be used as a generalized immune enhancer (T cell activating composition or system) and as such has utility in treating diseases.

Exemplary diseases that can be treated and/or prevented include, but are not limited, to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition (transduced T cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using the T cell and other therapeutic cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, and activated T cells, transduced and loaded T cells) may be for either "prophylactic" or "therapeutic" purpose. When provided prophylactically, the pharmaceutical composition is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the compositions presented herein may be provided either prior to the anticipated exposure to a disease-causing agent or disease state or after the initiation of the infection or disease. Thus provided herein are methods for prophylactic treatment of solid tumors such as those found in cancer, or for example, but not limited to, prostate cancer, using the nucleic acids and cells discussed herein. For example, methods are provided of prophylactically preventing or reducing the size of a tumor in a subject comprising administering a the nucleic acids or cells discussed herein, whereby the nucleic acids or cells are administered in an amount effect to prevent or reduce the size of a tumor in a subject.

Solid tumors from any tissue or organ may be treated using the present methods, including, for example, any tumor expressing PSA, for example, PSMA, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant myeloma.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation. Thus, for example, in one embodiment, the transduced T cells or other cells are administered to a subject in an amount effective to, for example, induce an immune response, or, for example, to reduce the size of a tumor or reduce the amount of tumor vasculature.

In some embodiments, multiple doses of modified cells are administered to the subject, with an escalation of dosage levels among the multiple doses. In some embodiments, the escalation of dosage levels increases the level of CAR-T cell activity, and therefore increases the therapeutic effect, such as, for example, the reduction in the amount or concentration of target cells, such as, for example, tumor cells.

In some embodiments, personalized treatment is provided wherein the stage or level of the disease or condition is determined before administration of the modified cells, before the administration of an additional dose of the modified cells, or in determining method and dosage involved in the administration of the modified cells. These methods may be used in any of the methods of the present application. Where these methods of assessing the patient before administering the modified cells are discussed in the context of, for example, the treatment of a subject with a solid tumor, it is understood that these methods may be similarly applied to the treatment of other conditions and diseases. Thus, for example, in some embodiments of the present application, the method comprises administering the modified cells of the present application to a subject, and further comprises determining the appropriate dose of modified cells to achieve the effective level of reduction of tumor size. The amount of cells may be determined, for example, based on the subject's clinical condition, weight, and/or gender or other relevant physical characteristic. By controlling the amount of modified cells administered to the subject, the likelihood of adverse events such as, for example, a cytokine storm may be reduced.

The term "dosage" is meant to include both the amount of the dose and the frequency of administration, such as, for example, the timing of the next dose. For example, to induce the chimeric Caspase-9 polypeptide, the term "dosage level" refers to the amount of the multimeric ligand administered in relation to the body weight of the subject. Thus increasing the dosage level would mean increasing the amount of the ligand administered relative to the subject's weight. In addition, increasing the concentration of the dose administered, such as, for example, when the multimeric ligand is administered using a continuous infusion pump would mean that the concentration administered (and thus the amount administered) per minute, or second, is increased.

An indication of adjusting or maintaining a subsequent drug dose, such as, for example, a subsequence dose of the multimeric ligand, and/or the subsequent drug dosage, can be provided in any convenient manner. An indication may be provided in tabular form (e.g., in a physical or electronic medium) in some embodiments. For example, the disease or condition symptoms may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms or the stage is provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

A. Genetic Based Therapies

In certain embodiments, a cell is provided with an expression construct capable of providing a co-stimulating polypeptide, such as those discussed herein, and, for example, in a T cell. The lengthy discussion of expression vectors and the genetic elements employed therein is incorporated into this section by reference. In certain examples, the expression vectors may be viral vectors, such as adenovirus, adeno-associated virus, herpes virus, vaccinia virus and retrovirus. In another example, the vector may be a lysosomal-encapsulated expression vector.

Gene delivery may be performed in both in vivo and ex vivo situations. For viral vectors, one generally will prepare a viral vector stock. Examples of viral vector-mediated gene delivery ex vivo and in vivo are presented in the present application. For in vivo delivery, depending on the kind of virus and the titer attainable, one will deliver, for example, about 1, 2, 3, 4, 5, 6, 7, 8, or $9 \times 10^4$, 1, 2, 3, 4, 5, 6, 7, 8, or $9 \times 10^5$, 1, 2, 3, 4, 5, 6, 7, 8, or $9 \times 10^6$, 1, 2, 3, 4, 5, 6, 7, 8, or $9 \times 10^7$, 1, 2, 3, 4, 5, 6, 7, 8, or $9 \times 10^8$, 1, 2, 3, 4, 5, 6, 7, 8, or $9 \times 10^9$, 1, 2, 3, 4, 5, 6, 7, 8, or $9 \times 10^{10}$, 1, 2, 3, 4, 5, 6, 7, 8, or $9 \times 10^{11}$ or 1, 2, 3, 4, 5, 6, 7, 8, or $9 \times 10^{12}$ infectious particles to the patient. Similar figures may be extrapolated for liposomal or other non-viral formulations by comparing relative uptake efficiencies. Formulation as a pharmaceutically acceptable composition is discussed below. The multimeric ligand, such as, for example, AP1903, may be delivered, for example at doses of about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight.

B. Cell based Therapy

Another therapy that is contemplated is the administration of transduced T cells. The T cells may be transduced in vitro. Formulation as a pharmaceutically acceptable composition is discussed herein.

In cell based therapies, the transduced cells may be, for example, transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vectors presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing. The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

In some embodiments, the chemotherapeutic agent may be a lymphodepleting chemotherapeutic. In other examples, the chemotherapeutic agent may be TAXOTERE (docetaxel), or another taxane, such as, for example, cabazitaxel. The chemotherapeutic may be administered before, during, or after treatment with the cells and inducer. For example, the chemotherapeutic may be administered about 1 year, 11, 10, 9, 8, 7, 6, 5, or 4 months, or 18, 17, 16, 15, 14, 13, 12,11, 10, 9, 8, 7, 6, 5, 4, 3, 2, weeks or 1 week prior to administering the first dose of activated nucleic acid. Or, for example, the chemotherapeutic may be administered about 1 week or 2, 3, 4, 5, 6, 7, 8, 9, 10, 11, 12, 13, 14, 15, 16, 17, or 18 weeks or 4, 5, 6, 7, 8, 9, 10, or 11 months or 1 year after administering the first dose of cells or inducer.

Administration of a chemotherapeutic agent may comprise the administration of more than one chemotherapeutic agent. For example, cisplatin may be administered in addition to TAXOTERE or other taxane, such as, for example, cabazitaxel.

Generating an Immune Response Targeted to a Specific Tumor or Disease

Chimeric antigen receptors (CARs) are artificial receptors designed to convey antigen specificity to T cells. They include an antigen-specific component, a transmembrane component, and an intracellular component selected to activate the T cell and provide specific immunity. They may further comprise a stalk polypeptide, along with the transmembrane component. Chimeric antigen receptor-expressing T cells may be used in various therapies, including cancer therapies.

The T cells and other cells transduced with the inducible CD40, inducible MyD88, or the inducible MyD88/CD40 may also be transduced with a nucleic acid coding for a chimeric antigen receptor, or CAR. The chimeric antigen receptor may be selected to target tumor antigens present on the surface of the tumor to be treated, or other antigens associated with disease. Activated T cells expressing the chimeric antigen receptor would then target tumors, or other diseases. Transduced T cells may also include memory T cells, which would maintain the immune defense against the particular tumor or disease. After administration of the modified T cells, modified memory T cells may be present in the subject.

Optimized and Personalized Therapeutic Treatment

Treatment for solid tumor cancers, including, for example, prostate cancer, may be optimized by determining the concentration of IL-6, IL6-sR, or VCAM-1 during the course of treatment. IL-6 refers to interleukin 6. IL-6sR refers to the IL-6 soluble receptor, the levels of which often correlate closely with levels of IL-6. VCAM-1 refers to vascular cell adhesion molecule. Different patients having different stages or types of cancer may react differently to various therapies. The response to treatment may be monitored by following the IL-6, IL-6sR, or VCAM-1 concentrations or levels in various body fluids or tissues. The determination of the concentration, level, or amount of a polypeptide, such as, IL-6, IL-6sR, or VCAM-1, may include detection of the full length polypeptide, or a fragment or variant thereof. The fragment or variant may be sufficient to be detected by, for example, immunological methods, mass spectrometry, nucleic acid hybridization, and the like.

Optimizing treatment for individual patients may help to avoid side effects as a result of overdosing, may help to determine when the treatment is ineffective and to change the course of treatment, or may help to determine when doses may be increased. Technology discussed herein optimizes therapeutic methods for treating solid tumor cancers by allowing a clinician to track a biomarker, such as, for example, IL-6, IL-6sR, or VCAM-1, and determine whether a subsequent dose of a drug or vaccine for administration to a subject may be maintained, reduced or increased, and to determine the timing for the subsequent dose.

Treatment for solid tumor cancers, including, for example, prostate cancer, may also be optimized by determining the concentration of urokinase-type plasminogen activator receptor (uPAR), hepatocyte growth factor (HGF), epidermal growth factor (EGF), or vascular endothelial growth factor (VEGF) during the course of treatment. Different patients having different stages or types of cancer may react differently to various therapies. The levels of uPAR, HGF, EGF, and VEGF over the course of treatment for subject 1003 were measured. Subject 1003 shows systemic perturbation of hypoxic factors in serum, which may indicate a positive response to treatment. Without limiting the interpretation of this observation, this may indicate the secretion of hypoxic factors by tumors in response to treatment. Thus, the response to treatment may be monitored, for example, by following the uPAR, HGF, EGF, or VEGF concentrations or levels in various body fluids or tissues. The determination of the concentration, level, or amount of a polypeptide, such as, uPAR, HGF, EGF, or VEGF may include detection of the full length polypeptide, or a fragment or variant thereof. The fragment or variant may be sufficient to be detected by, for example, immunological methods, mass spectrometry, nucleic acid hybridization, and the like. Optimizing treatment for individual patients may help to avoid side effects as a result of overdosing, may help to determine when the treatment is ineffective and to change the course of treatment, or may help to determine when doses may be increased. Technology discussed herein optimizes therapeutic methods for treating solid tumor cancers by allowing a clinician to track a biomarker, such as, for example, uPAR, HGF, EGF, or VEGF, and determine whether a subsequent dose of a drug or vaccine for administration to a subject may be maintained, reduced or increased, and to determine the timing for the subsequent dose.

For example, it has been determined that amount or concentration of certain biomarkers changes during the course of treatment of solid tumors. Predetermined target levels of such biomarkers, or biomarker thresholds may be identified in normal subject, are provided, which allow a clinician to determine whether a subsequent dose of a drug administered to a subject in need thereof, such as a subject with a solid tumor, such as, for example, a prostate tumor, may be increased, decreased or maintained. A clinician can make such a determination based on whether the presence, absence or amount of a biomarker is below, above or about the same as a biomarker threshold, respectively, in certain embodiments.

For example, determining that an over-represented biomarker level is significantly reduced and/or that an under-represented biomarker level is significantly increased after drug treatment or vaccination provides an indication to a clinician that an administered drug is exerting a therapeutic effect. By "level" is meant the concentration of the biomarker in a fluid or tissue, or the absolute amount in a tissue. Based on such a biomarker determination, a clinician could make a decision to maintain a subsequent dose of the drug or raise or lower the subsequent dose, including modifying the timing of administration. The term "drug" includes traditional pharmaceuticals, such as small molecules, as well as biologics, such as nucleic acids, antibodies, proteins, polypeptides, modified cells and the like. In another example, determining that an over-represented biomarker level is not significantly reduced and/or that an under-represented biomarker level is not significantly increased provides an indication to a clinician that an administered drug is not significantly exerting a therapeutic effect. Based on such a biomarker determination, a clinician could make a decision to increase a subsequent dose of the drug. Given that drugs can be toxic to a subject and exert side effects, methods provided herein optimize therapeutic approaches as they provide the clinician with the ability to "dial in" an efficacious dosage of a drug and minimize side effects. In specific examples, methods provided herein allow a clinician to "dial up" the dose of a drug to a therapeutically efficacious level, where the dialed up dosage is below a toxic threshold level. Accordingly, treatment methods discussed herein enhance efficacy and reduce the likelihood of toxic side effects.

Cytokines are a large and diverse family of polypeptide regulators produced widely throughout the body by cells of diverse origin. Cytokines are small secreted proteins, including peptides and glycoproteins, which mediate and regulate immunity, inflammation, and hematopoiesis. They are produced de novo in response to an immune stimulus. Cytokines generally (although not always) act over short distances and short time spans and at low concentration. They generally act by binding to specific membrane receptors, which then signal the cell via second messengers, often tyrosine kinases, to alter cell behavior (e.g., gene expression). Responses to cytokines include, for example, increasing or decreasing expression of membrane proteins (including cytokine receptors), proliferation, and secretion of effector molecules.

The term "cytokine" is a general description of a large family of proteins and glycoproteins. Other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on cells that secrete them (autocrine action), on nearby cells (paracrine action), or in some instances on distant cells (endocrine action).

Examples of cytokines include, without limitation, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 and the like), interferons (e.g., IFN-β, IFN-γ and the like), tumor necrosis factors (e.g., TNF-α, TNF-β and the like), lymphokines, monokines and chemokines; growth factors (e.g., transforming growth factors (e.g., TGF-α, TGF-β and the like)); colony-stimulating factors (e.g. GM-CSF, granulocyte colony-stimulating factor (G-CSF) etc.); and the like.

A cytokine often acts via a cell-surface receptor counterpart. Subsequent cascades of intracellular signaling then alter cell functions. This signaling may include upregulation and/or downregulation of several genes and their transcription factors, resulting in the production of other cytokines, an increase in the number of surface receptors for other molecules, or the suppression of their own effect by feedback inhibition.

VCAM-1 (vascular cell adhesion molecule-1, also called CD106), contains six or seven immunoglobulin domains and is expressed on both large and small vessels only after the endothelial cells are stimulated by cytokines. Thus, VCAM-1 expression is a marker for cytokine expression.

Cytokines may be detected as full-length (e.g., whole) proteins, polypeptides, metabolites, messenger RNA (mRNA), complementary DNA (cDNA), and various intermediate products and fragments of the foregoing (e.g., cleavage products (e.g., peptides, mRNA fragments)). For example, IL-6 protein may be detected as the complete, full-length molecule or as any fragment large enough to provide varying levels of positive identification. Such a fragment may comprise amino acids numbering less than 10, from 10 to 20, from 20 to 50, from 50 to 100, from 100 to 150, from 150 to 200 and above. Likewise, VCAM-1 protein can be detected as the complete, full-length amino acid molecule or as any fragment large enough to provide varying levels of positive identification. Such a fragment may comprise amino acids numbering less than 10, from 10 to 20, from 20 to 50, from 50 to 100, from 100 to 150 and above.

In certain embodiments, cytokine mRNA may be detected by targeting a complete sequence or any sufficient fragment for specific detection. A mRNA fragment may include fewer than 10 nucleotides or any larger number. A fragment may comprise the 3' end of the mRNA strand with any portion of the strand, the 5' end with any portion of the strand, and any center portion of the strand.

Detection may be performed using any suitable method, including, without limitation, mass spectrometry (e.g., matrix-assisted laser desorption ionization mass spectrometry (MALDI-MS), electrospray mass spectrometry (ES-MS)), electrophoresis (e.g., capillary electrophoresis), high performance liquid chromatography (HPLC), nucleic acid affinity (e.g., hybridization), amplification and detection (e.g., real-time or reverse-transcriptase polymerase chain reaction (RT-PCR)), and antibody assays (e.g., antibody array, enzyme-linked immunosorbant assay (ELISA)). Examples of IL-6 and other cytokine assays include, for example, those provided by Millipore, Inc., (MILLIPLEX Human Cytokine/Chemokine Panel). Examples of IL6-sR assays include, for example, those provided by Invitrogen, Inc. (Soluble IL-6R: (Invitrogen Luminex® Bead-based assay)). Examples of VCAM-1 assays include, for example, those provided by R & D Systems ((CD106) ELISA development Kit, DUOSET from R&D Systems (#DY809)).

Sources of Biomarkers

The presence, absence or amount of a biomarker can be determined within a subject (e.g., in situ) or outside a subject (e.g., ex vivo). In some embodiments, presence, absence or amount of a biomarker can be determined in cells (e.g., differentiated cells, stem cells), and in certain embodiments, presence, absence or amount of a biomarker can be determined in a substantially cell-free medium (e.g., in vitro). The term "identifying the presence, absence or amount of a biomarker in a subject" as used herein refers to any method known in the art for assessing the biomarker and inferring the presence, absence or amount in the subject (e.g., in situ, ex vivo or in vitro methods).

A fluid or tissue sample often is obtained from a subject for determining presence, absence or amount of biomarker ex vivo. Non-limiting parts of the body from which a tissue sample may be obtained include leg, arm, abdomen, upper back, lower back, chest, hand, finger, fingernail, foot, toe, toenail, neck, rectum, nose, throat, mouth, scalp, face, spine, throat, heart, lung, breast, kidney, liver, intestine, colon, pancreas, bladder, cervix, testes, muscle, skin, hair, tumor or area surrounding a tumor, and the like, in some embodiments. A tissue sample can be obtained by any suitable method known in the art, including, without limitation, biopsy (e.g., shave, punch, incisional, excisional, curettage, fine needle aspirate, scoop, scallop, core needle, vacuum assisted, open surgical biopsies) and the like, in certain embodiments. Examples of a fluid that can be obtained from a subject includes, without limitation, blood, cerebrospinal fluid, spinal fluid, lavage fluid (e.g., bronchoalveolar, gastric, peritoneal, ductal, ear, arthroscopic), urine, interstitial fluid, feces, sputum, saliva, nasal mucous, prostate fluid, lavage, semen, lymphatic fluid, bile, tears, sweat, breast milk, breast fluid, fluid from region of inflammation, fluid from region of muscle wasting and the like, in some embodiments.

A sample from a subject may be processed prior to determining presence, absence or amount of a biomarker. For example, a blood sample from a subject may be processed to yield a certain fraction, including without limitation, plasma, serum, buffy coat, red blood cell layer and the like, and biomarker presence, absence or amount can be determined in the fraction. In certain embodiments, a tissue sample (e.g., tumor biopsy sample) can be processed by slicing the tissue sample and observing the sample under a microscope before and/or after the sliced sample is contacted with an agent that visualizes a biomarker (e.g., antibody). In some embodiments, a tissue sample can be exposed to one or more of the following non-limiting conditions: washing, exposure to high salt or low salt solution (e.g., hypertonic, hypotonic, isotonic solution), exposure to shearing conditions (e.g., sonication, press (e.g., French press)), mincing, centrifugation, separation of cells, separation of tissue and the like. In certain embodiments, a biomarker can be separated from tissue and the presence, absence or amount determined in vitro. A sample also may be stored for a period of time prior to determining the presence, absence or amount of a biomarker (e.g., a sample may be frozen, cryopreserved, maintained in a preservation medium (e.g., formaldehyde)).

A sample can be obtained from a subject at any suitable time of collection after a drug is delivered to the subject. For example, a sample may be collected within about one hour after a drug is delivered to a subject (e.g., within about 5, 10, 15, 20, 25, 30, 35, 40, 45, 55 or 60 minutes of delivering a drug), within about one day after a drug is delivered to a subject (e.g., within about 2, 3, 4, 5, 6, 7, 8, 9, 10, 11, 12, 13, 14, 15, 16, 17, 18, 19, 20, 21, 22, 23 or 24 hours of delivering a drug) or within about two weeks after a drug is delivered to a subject (e.g., within about 2, 3, 4, 5, 6, 7, 8, 9, 10, 11, 12, 13 or 14 days of delivering the drug). A collection may be made on a specified schedule including hourly, daily, semi-weekly, weekly, bi-weekly, monthly, bi-monthly, quarterly, and yearly, and the like, for example. If a drug is administered continuously over a time period (e.g., infusion), the delay may be determined from the first moment of drug is introduced to the subject, from the time the drug administration ceases, or a point in-between (e.g., administration time frame midpoint or other point).

Biomarker Detection

The presence, absence or amount of one or more biomarkers may be determined by any suitable method known in the art, and non-limiting determination methods are discussed herein. Determining the presence, absence or amount of a biomarker sometimes comprises use of a biological assay. In a biological assay, one or more signals detected in the assay can be converted to the presence, absence or amount of a biomarker. Converting a signal detected in the assay can comprise, for example, use of a standard curve, one or more standards (e.g., internal, external), a chart, a computer program that converts a signal to a presence, absence or amount of biomarker, and the like, and combinations of the foregoing.

Biomarker detected in an assay can be full-length biomarker, a biomarker fragment, an altered or modified biomarker (e.g., biomarker derivative, biomarker metabolite), or sum of two or more of the foregoing, for example. Modified biomarkers often have substantial sequence identity to a biomarker discussed herein. For example, percent identity between a modified biomarker and a biomarker discussed herein may be in the range of 15-20%, 20-30%, 31-40%, 41-50%, 51-60%, 61-70%, 71-80%, 81-90% and 91-100%, (e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 percent identity). A modified biomarker often has a sequence (e.g., amino acid sequence or nucleotide sequence) that is 90% or more identical to a sequence of a biomarker discussed herein. Percent sequence identity can be determined using alignment methods known in the art.

Detection of biomarkers may be performed using any suitable method known in the art, including, without limitation, mass spectrometry, antibody assay (e.g., ELISA), nucleic acid affinity, microarray hybridization, Northern blot, reverse PCR and RT-PCR. For example, RNA purity and concentration may be determined spectrophotometrically (260/280>1.9) on a Nanodrop 1000. RNA quality may be assessed using methods known in the art (e.g., Agilent 2100 Bioanalyzer; RNA 6000 Nano LabChip® and the like).

Indication for Adjusting or Maintaining Subsequent Drug Dose

An indication for adjusting or maintaining a subsequent drug dose can be based on the presence or absence of a biomarker. For example, when (i) low sensitivity determinations of biomarker levels are available, (ii) biomarker levels shift sharply in response to a drug, (iii) low levels or high levels of biomarker are present, and/or (iv) a drug is not appreciably toxic at levels of administration, presence or absence of a biomarker can be sufficient for generating an indication of adjusting or maintaining a subsequent drug dose.

An indication for adjusting or maintaining a subsequent drug dose often is based on the amount or level of a biomarker. An amount of a biomarker can be a mean, median, nominal, range, interval, maximum, minimum, or relative amount, in some embodiments. An amount of a biomarker can be expressed with or without a measurement error window in certain embodiments. An amount of a biomarker in some embodiments can be expressed as a biomarker concentration, biomarker weight per unit weight, biomarker weight per unit volume, biomarker moles, biomarker moles per unit volume, biomarker moles per unit weight, biomarker weight per unit cells, biomarker volume per unit cells, biomarker moles per unit cells and the like. Weight can be expressed as femtograms, picograms, nanograms, micrograms, milligrams and grams, for example. Volume can be expressed as femtoliters, picoliters, nanoliters, microliters, milliliters and liters, for example. Moles can be expressed in picomoles, nanomoles, micromoles, millimoles and moles, for example. In some embodiments, unit weight can be weight of subject or weight of sample from subject, unit volume can be volume of sample from the subject (e.g., blood sample volume) and unit cells can be per one cell or per a certain number of cells (e.g., micrograms of biomarker per 1000 cells). In some embodiments, an amount of biomarker determined from one tissue or fluid can be correlated to an amount of biomarker in another fluid or tissue, as known in the art.

An indication for adjusting or maintaining a subsequent drug dose often is generated by comparing a determined level of biomarker in a subject to a predetermined level of biomarker. A predetermined level of biomarker sometimes is linked to a therapeutic or efficacious amount of drug in a subject, sometimes is linked to a toxic level of a drug, sometimes is linked to presence of a condition, sometimes is linked to a treatment midpoint and sometimes is linked to a treatment endpoint, in certain embodiments. A predetermined level of a biomarker sometimes includes time as an element, and in some embodiments, a threshold is a time-dependent signature.

For example, an IL-6 or IL6-sR level of about 8-fold more than a normal level, or greater (e.g. about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75-fold more than a normal level) may indicate that the dosage of the drug or the frequency of administration may be increased in a subsequent administration.

The term "dosage" is meant to include both the amount of the dose and the frequency of administration, such as, for example, the timing of the next dose. An IL-6 or IL-6sR level less than about 8-fold more than a normal level (e.g. about 7, 6, 5, 4, 3, 2, or 1-fold more than a normal level, or less than or equal to a normal level) may indicate that the dosage may be maintained or decreased in a subsequent administration. A VCAM-1 level of about 8 fold more than a normal level, or greater (e.g. e.g. about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75-fold more than a normal level) may indicate that the dosage of the drug may be increased in a subsequent administration. A VCAM-1 level less than about 8-fold more than a normal level (e.g. about 7, 6, 5, 4, 3, 2, or 1-fold more than a normal level, or less than or equal to a normal level) may indicate that the dosage may be maintained or decreased in a subsequent administration. A normal level of IL-6, IL-6sR, or VCAM-1 may be assessed in a subject not diagnosed with a solid tumor or the type of solid tumor under treatment in a patient.

Other indications for adjusting or maintaining a drug dose include, for example, a perturbation in the concentration of an individual secreted factor, such as, for example, GM-CSF, MIP-1α, MIP-1β, MCP-1, IFN-γ, RANTES, EGF or HGF, or a perturbation in the mean concentration of a panel of secreted factors, such as two or more of the markers selected from the group consisting of GM-CSF, MIP-1α, MIP-1β, MCP-1, IFN-γ, RANTES, EGF and HGF. This perturbation may, for example, consist of an increase, or decrease, in the concentration of an individual secreted factor by at least 5%, 10%, 20%, 30%, 40%, 50%, 60%, 70%, 80%, 90%, or 100% or an increase or decrease in the mean relative change in serum concentration of a panel of secreted factors by at least 5%, 10%, 20%, 30%, 40%, 50%, 60%, 70%, 80%, 90%, or 100%. This increase may, or may not, be followed by a return to baseline serum concentrations before the next administration. The increase or decrease in the mean relative change in serum concentration may involve, for example, weighting the relative value of each of the factors in the panel. Also, the increase or decrease may involve, for example, weighting the relative value of each of the time points of collected data. The weighted value for each time point or each factor may vary, depending on the state or the extent of the cancer, metastasis, or tumor burden. An indication for adjusting or maintaining the drug dose may include a perturbation in the concentration of an individual secreted factor or the mean concentration of a panel of secreted factors, after 1, 2, 3, 4, 5, 6, 7, 8, 9, or 10 or more administrations. For example, where it is observed that over the course of treatment, for example, 6 administrations of a drug or the vaccines or compositions discussed herein, that the concentration of an individual secreted factor or the mean concentration of a panel of secreted factors is perturbed after at least one administration, then this may be an indication to maintain, decrease, or increase the frequency of administration or the subsequent dosage, or it may be an indication to continue treatment by, for example, preparing additional drug, adenovirus vaccine, or adenovirus transfected or transduced cells.

Some treatment methods comprise (i) administering a drug to a subject in one or more administrations (e.g., 1, 2, 3, 4, 5, 6, 7, 8, 9 or 10 doses), (ii) determining the presence, absence or amount of a biomarker in or from the subject after (i), (iii) providing an indication of increasing, decreasing or maintaining a subsequent dose of the drug for administration to the subject, and (iv) optionally administering the subsequent dose to the subject, where the subsequent dose is increased, decreased or maintained relative to the earlier dose(s) in (i). In some embodiments, presence, absence or amount of a biomarker is determined after each dose of drug has been administered to the subject, and sometimes presence, absence or amount of a biomarker is not determined after each dose of the drug has been administered (e.g., a biomarker is assessed after one or more of the first, second, third, fourth, fifth, sixth, seventh, eighth, ninth or tenth dose, but not assessed every time after each dose is administered).

An indication for adjusting a subsequent drug dose can be considered a need to increase or a need to decrease a subsequent drug dose. An indication for adjusting or maintaining a subsequent drug dose can be considered by a clinician, and the clinician may act on the indication in certain embodiments. In some embodiments, a clinician may opt not to act on an indication.

Thus, a clinician can opt to adjust or not adjust a subsequent drug dose based on the indication provided.

An indication of adjusting or maintaining a subsequent drug dose, and/or the subsequent drug dosage, can be provided in any convenient manner. An indication may be provided in tabular form (e.g., in a physical or electronic medium) in some embodiments. For example, a biomarker threshold may be provided in a table, and a clinician may compare the presence, absence or amount of the biomarker determined for a subject to the threshold. The clinician then can identify from the table an indication for subsequent drug dose. In certain embodiments, an indication can be presented (e.g., displayed) by a computer after the presence, absence or amount of a biomarker is provided to computer (e.g., entered into memory on the computer). For example, presence, absence or amount of a biomarker determined for a subject can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount. A subsequent dose can be determined based on certain factors other than biomarker presence, absence or amount, such as weight of the subject, one or more metabolite levels for the subject (e.g., metabolite levels pertaining to liver function) and the like, for example.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

A subject can be prescreened to determine whether or not the presence, absence or amount of a particular biomarker may be determined. Non-limiting examples of prescreens include identifying the presence or absence of a genetic marker (e.g., polymorphism, particular nucleotide sequence); identifying the presence, absence or amount of a particular metabolite. A prescreen result can be used by a clinician in combination with the presence, absence or amount of a biomarker to determine whether a subsequent drug dose may be adjusted or maintained.

Biomarkers for assessing the effect of the modified T cells and nucleic acids herein may include, for example, IL-2, IL-4, IL-5, IL-6, IL-9, IL-10, IL-13, IL-17, IL-25, IFN-γ, TNF-α, TNFβ, GM-CSF, TGFβ, C-reactive protein and others.

Antibodies and Small Molecules

In some embodiments, an antibody or small molecule is provided for use as a control or standard in an assay, or a therapeutic, for example. In some embodiments, an antibody or other small molecule configured to bind to a cytokine or cytokine receptor, including without limitation IL-6, IL-6sR, and alter the action of the cytokine, or it may be configured to bind to VCAM-1. In certain embodiments an antibody or other small molecule may bind to an mRNA structure encoding for a cytokine or receptor.

The term small molecule as used herein means an organic molecule of approximately 800 or fewer Daltons. In certain embodiments small molecules may diffuse across cell membranes to reach intercellular sites of action. In some embodiments a small molecule binds with high affinity to a biopolymer such as protein, nucleic acid, or polysaccharide and may sometimes alter the activity or function of the biopolymer. In various embodiments small molecules may be natural (such as secondary metabolites) or artificial (such as antiviral drugs); they may have a beneficial effect against a disease (such as drugs) or may be detrimental (such as teratogens and carcinogens). By way of non-limiting example, small molecules may include ribo- or deoxyribonucleotides, amino acids, monosaccharides and small oligomers such as dinucleotides, peptides such as the antioxidant glutathione, and disaccharides such as sucrose.

The term antibody as used herein is to be understood as meaning a gamma globulin protein found in blood or other bodily fluids of vertebrates, and used by the immune system to identify and neutralize foreign objects, such as bacteria and viruses. Antibodies typically include basic structural units of two large heavy chains and two small light chains.

Specific binding to an antibody requires an antibody that is selected for its affinity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with GM-CSF, TNF-α or NF-κ-B modulating protein and not with other proteins. This selection may be achieved by subtracting out antibodies that cross-react with other molecules.

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

An effective amount of the modified cell may be determined by a physician, considering the individual patient. Factors to be considered may include, for example, the extent of the disease or condition, tumor size, extent of infection, metastasis, age, and weight. The dosage and number of administrations may be determined by the physician, or other clinician, by monitoring the patient for disease or condition symptoms, and for responses to previous dosages, for example, by monitoring tumor size, or the level or concentration of tumor antigen. In certain examples, the modified cells may be administered at a dosage of $10^4$ to $10^9$ modified cells/kg body weight, $10^5$ to $10^6$, $10^9$-$10^{11}$, or $10^{16}$-$10^{11}$ modified cells/kg body weight.

EXAMPLES

The examples set forth below illustrate certain embodiments and do not limit the technology. Examples herein that discuss the methods for transforming or transfecting cells in vitro, or ex vivo, provide examples of, but do not limit, the use of nucleic acids that express chimeric polypeptides. Examples of the delivery of the transfected or transduced cells, and ligand inducer, to laboratory animals or human subjects provide examples of, but do not limit, the direct administration of nucleic acids expressing chimeric polypeptides, tumor antigens, and ligand inducer to subjects in need thereof.

Expression of Inducible Chimeric MyD88/CD40 Polypeptides

Examples 1-7 relate to the expression of an inducible form of chimeric stimulating molecules and provide examples of methods that may be used to express the MyD88/CD40 chimeric stimulating molecules discussed herein. These examples may be used as a reference for constructing assaying, and using the chimeric stimulating molecules, and chimeric antigen receptors discussed herein. Examples 8 et seq. relate to the expression and applications of the non-inducible MyD88/CD40 chimeric stimulating molecules and the MyD88/CD40 chimeric antigen receptors discussed herein.

Example 1: Inducible Chimeric Stimulating Molecules

Inducible MyD88/CD40 chimeric costimulatory molecules were expressed in T cells; contacting the T cells with rimiducid (AP1903) resulted in activation of costimulatory activity and activation of T cells, including T cells that co-expressed a chimeric antigen receptor.

The following patents, applications, and patent publications may contain material and methods that may be used in the examples herein, such as, for example, U.S. Pat. No. 7,404,950, issued Jul. 29, 2008, to Spencer, D. et al.; U.S. Pat. No. 8,691,210, issued Apr. 8, 2004 to Spencer, et al.; U.S. patent application Ser. No. 12/532,196 by Spencer et al., filed Sep. 21, 2009; PCT application PCT/US2009/057738 to Spencer et al., published on Apr. 24, 2008 as WO2010/033949; U.S. patent application Ser. No. 13/087,329 by Slawin et al., filed Apr. 14, 2011; PCT application PCT/US2011/032572, published on Oct. 20, 2011 as WO2011/130566; U.S. patent application Ser. No. 14/210,324 by Spencer et al., filed Mar. 13, 2014; PCT application number PCT/US2014/026734 by Spencer et al., published as WO2014/251960 on Feb. 5, 2015; U.S. application Ser. No. 14/622,018, by Foster et al., filed Feb. 13, 2015; PCT application number PCT/US2015/015829 by Foster et al., published as WO2015/123527 on Aug. 20, 2015 are all hereby incorporated by reference herein in their entirety.

Examples of adenoviral vectors used for expression of an inducible MyD88/CD40 chimeric stimulating molecule are provided herein. These vectors may be modified to remove the FKBP regions to obtain adenoviral vectors that express non-inducible chimeric stimulating molecules of the present application.

The following nucleotide sequences were used to construct the Ad5-iMC-P2A-P-FL and Ad5f35-iMC-P2A-P-FL. vectors. The amino acid sequences of the polypeptides coded by the nucleotide sequences are also provided.

```
Ad-iMC-2A-P-FL
                                                                SEQ ID NO: 1
Myr
atggggagtagcaagagcaagcctaaggaccccagccagcgc SEQ ID NO: 2
Myr
MGSSKSKPKDPSQR SEQ ID NO: 3
MyD88
atggctgcaggaggtcccggcgcggggtctgcggccccggtctcctccacatcctcccttccctggctgctctcaacatgcgagtgcggc gccgcctgtctctgttcttgaacgtgcggacacaggtggcggccgactggaccgcgctggcggaggagatggactttgagtacttggagat ccggcaactggagacacaagcggaccccactggcaggctgctggacgcctggcagggacgccctggcgcctctgtaggccgactgct cgatctgcttaccaagctgggccgcgacgacgtgctgctggagctgggacccagcattgaggaggattgccaaaagtatatcttgaagca gcagcaggaggaggctgagaagcctttacaggtggccgctgtagacagcagtgtcccacggacagcagagctggcgggcatcacca cacttgatgacccctggggcatatgcctgagcgtttcgatgccttcatctgctattgccccagcgacatc SEQ ID NO: 4
MyD88
MAAGGPGAGSAAPVSSTSSLPLAALNMRVRRRLSLFLNVRTQVAADWTALAEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI

SEQ ID NO: 5
CD40
aaaaaggtggccaagaagccaaccaataaggcccccacccaagcaggagccccaggagatcaattttcccgacgatcttcctggc tccaacactgctgctccagtgcaggagactttacatggatgccaaccggtcacccaggaggatggcaaagagagtcgcatctcagtgca ggagagacag

SEQ ID NO: 6
CD40
KKVAKKPTNKAPHPKQEPQEINFPDDLPGSNTAAPVQETLHGCQPVTQEDGKESRISVQERQ

SEQ ID NO: 7
Fv'
GGcGTcCAaGTcGAaACcATtagtCCcGGcGAtGGcaGaACaTTtCCtAAaaGgGGaCAaACaTGtGTcG TcCAtTAtACaGGcATGtTgGAgGAcGGcAAaAAgGTgGAcagtagtaGaGAtcGcAAtAAaCCtTTcAAaTT cATGtTgGGaAAaCAaGAaGTcATtaGgGGaTGGGAgGAgGGcGTgGCtCAaATGtccGTcGGcCAacG cGCtAAgCTcACcATcagcCCcGAcTAcGCaTAcGGcGCtACcGGaCAtCCcGGaATtATtCCcCCtCAcG CtACctTgGTgTTtGAcGTcGAaCTgtTgAAgCTc SEQ ID NO: 8:
Fv'
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKL

SEQ ID NO: 9
Fv
ggagtgcaggtggagactatctcccaggagacgggcgcaccttccccaagcgcggccagacctgcgtggtgcactacaccgggatg cttgaagatggaaagaaagttgattcctcccgggacagaaacaagccctttaagtttatgctaggcaagcaggaggtgatccgaggctgg
```

-continued gaagaaggggttgcccagatgagtgtgggtcagagagccaaactgactatatctccagattatgcctatggtgccactgggcacccagg catcatcccaccacatgccactctcgtcttcgatgtggagcttctaaaactggaa SEQ ID NO: 10
Fv
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

SEQ ID NO: 11
P2A
GCTACTAACTTCAGCCTGCTGAAGCAGGCTGGAGACGTGGAGGAGAACCCTGGACCT

SEQ ID NO: 12
P2A
ATNFSLLKQAGDVEENPGP

SEQ ID NO: 13
PSMA
ATGTGGAATCTCCTTCACGAAACCGACTCGGCTGTGGCCACCGCGCGCCGCCCGCGCTGGC

TGTGCGCTGGGGCGCTGGTGCTGGCGGGTGGCTTCTTTCTCCTCGGCTTCCTCTTCGGGTG

GTTTATAAAATCCTCCAATGAAGCTACTAACATTACTCCAAAGCATAATATGAAAGCATTTTGG

ATGAATTGAAAGCTGAGAACATCAAGAAGTTCTTACATAATTTTACACAGATACCACATTTAGC

AGGAACAGAACAAAACTTTCAGCTTGCAAAGCAAATTCAATCCCAGTGGAAAGAATTTGGCCT

GGATTCTGTTGAGCTAGCACATTATGATGTCCTGTTGTCCTACCCAAATAAGACTCATCCCAAC

TACATCTCAATAATTAATGAAGATGGAAATGAGATTTTCAACACATCATTATTTGAACCACCTCC

TCCAGGATATGAAAATGTTTGGGATATTGTACCACCTTTCAGTGCTTTCTCTCCTCAAGGAATG

CCAgAGGGCGATCTAGTGTATGTTaactatgcacgaactgaagacttctttaaattggaacgggacatgaaaatcaattgc tctgggaaaattgtaattgccagatatgggaaagttttcagaggaaataaggttaaaaatgcccagctggcaggggccaaaggagtcatt ctctactccgaccctgctgactactttgctcctggggtgaagtcctatccagatggttggaatcttcctggaggtggtgtccagcgtggaaatat cctaaatctgaatggtgcaggagaccctctcacaccaggttacccagcaaatgaatatgcttataggcgtggaattgcagaggctgttggt cttccaagtattcctgttcatccaattggatactatgatgcacagaagctcctagaaaaaatgggtggctcagcaccaccagatagcagctg gagaggaagtctcaaagtgccctacaatgttggacctggctttactggaaacttttctacacaaaaagtcaagatgcacatccactctacca atgaagtgacaagaatttacaatgtgataggtactctcagaggagcagtggaaccagacagatatgtcattctgggaggtcaccgggact catgggtgtttggtggtattgaccctcagagtggagcagctgttgttcatgaaattgtgaggagctttggaacactgaaaaaggaagggtgg agacctagaagaacaattttgtttgcaagctgggatgcagaagaatttggtcttcttggttctactgagtgggcagaggagaattcaagactc cttcaagagcgtggcgtggcttatattaatgctgactcatctatagaaggaaactacactctgagagttgattgtacaccgctgatgtacagct tggtacacaacctaacaaaagagctgaaaagccctgatgaaggctttgaaggcaaatctctttatgaaagttggactaaaaaaagtccttc cccagagttcagtggcatgcccaggataagcaaattgggatctggaaatgattttgaggtgttcttccaacgacttggaattgcttcaggcag agcacggtatactaaaaattgggaaacaaacaaattcagcggctatccactgtatcacagtgtctatgaaacatatgagttggtggaaaa gttttatgatccaatgtttaaatatcacctcactgtggcccaggttcgaggagggatggtgtttgagctagccaattccatagtgctccccttttg attgtcgagattatgctgtagttttaagaaagtatgctgacaaaatctacagtatttctatgaaacatccacaggaaatgaagacatacagtgta tcatttgattcacttttttctgcagtaaagaattttacagaaattgcttccaagttcagtgagagactccaggactttgacaaaagcaacccaat agtattaagaatgatgaatgatcaactcatgtttctggaaagagcatttattgatccattaggggttaccagacaggccttttttataggcatgtca tctatgctccaagcagccacaacaagtatgcaggggagtcattcccaggaatttatgatgctctgtttgatattgaaagcaaagtggacccttc caaggcctggggagaagtgaagagacagatttatgttgcagccttcacagtgcaggcagctgctgagactttgagtgaagtagcctaa SEQ ID NO: 14
PSMA
MWNLLHETDSAVATARRPRWLCAGALVLAGGFFLLGFLFGWFIKSSNEATNITPKHNMKAFLDEL

KAENIKKFLHNFTQIPHLAGTEQNFQLAKQIQSQWKEFGLDSVELAHYDVLLSYPNKTHPNYISIINE

DGNEIFNTSLFEPPPPGYENVWDIVPPFSAFSPQGMPEGDLVYVNYARTEDFFKLERDMKINCSG

-continued

```
KIVIARYGKVFRGNKVKNAQLAGAKGVILYSDPADYFAPGVKSYPDGWNLPGGGVQRGNILNLNG

AGDPLTPGYPANEYAYRRGIAEAVGLPSIPVHPIGYYDAQKLLEKMGGSAPPDSSWRGSLKVPYN

VGPGFTGNFSTQKVKMHIHSTNEVTRIYNVIGTLRGAVEPDRYVILGGHRDSWVFGGIDPQSGAA

VVHEIVRSFGTLKKEGWRPRRTILFASWDAEEFGLLGSTEWAEENSRLLQERGVAYINADSSIEGN

YTLRVDCTPLMYSLVHNLTKELKSPDEGFEGKSLYESWTKKSPSPEFSGMPRISKLGSGNDFEVF

FQRLGIASGRARYTKNWETNKFSGYPLYHSVYETYELVEKFYDPMFKYHLTVAQVRGGMVFELAN

SIVLPFDCRDYAVVLRKYADKIYSISMKHPQEMKTYSVSFDSLFSAVKNFTEIASKFSERLQDFDKS

NPIVLRMMNDQLMFLERAFIDPLGLPDRPFYRHVIYAPSSHNKYAGESFPGIYDALFDIESKVDPSK

AWGEVKRQIYVAAFTVQAAAETLSEVA
``` pAd1127-02.iMC-P2A-P-FL is the shuttle vector used to make both Ad5-iMC-P2A-P-FL and the serotype 35 pseudotyped Ad5f35-iMC-P2A-P-FL. It contains the inducible MyD88/CD40 and full length PSMA on the same transcript driven by a CMVp and bovine growth hormone poly A site. Annotated Vector Sequence:

```
8931 bp ds-DNA
/note = "MMLV Psi"
/note = "packaging signal of Moloney murine leukemia virus
(MMLV)"
CDS 1226 . . . 3802
/codon_start = 1
/note = "iMC-2A-Delta-CD19"
/translation = "
                                                    SEQ ID NO: 15
MGSSKSKPKDPSQRLEMAAGGPGAGSAAPVSSTSSLPLAALNMRV

RRRLSLFLNVRTQVAADWTALAEEMDFEYLEIRQLETQADPTGRLLDAWQGRPGASVGR

LLDLLTKLGRDDVLLELGPSIEEDCQKYILKQQQEEAEKPLQVAAVDSSVPRTAELAGI

TTLDDPLGHMPERFDAFICYCPSDIKKVAKKPTNKAPHPKQEPQEINFPDDLPGSNTAA

PVQETLHGCQPVTQEDGKESRISVQERQVESGGGSGGVQVETISPGDGRTFPKRGQTCV

VHYTGMLEDGKKVDSSRDRNKPFKFMLGKQEVIRGWEEGVAQMSVGQRAKLTISPDYAY

GATGHPGIIPPHATLVFDVELLKLEVEGVQVETISPGDGRTFPKRGQTCVVHYTGMLED

GKKVDSSRDRNKPFKFMLGKQEVIRGWEEGVAQMSVGQRAKLTISPDYAYGATGHPGII

PPHATLVFDVELLKLESGGGSGVDRAKRGKPIPNPLLGLDSTGSGSATNFSLLKQAGDV

EENPGPTRMPPPRLLFFLLFLTPMEVRPEEPLWKVEEGDNAVLQCLKGTSDGPTQQLT

WSRESPLKPFLKLSLGLPGLGIHMRPLAIWLFIFNVSQQMGGFYLCQPGPPSEKAWQPG

WTVNVEGSGELFRWNVSDLGGLGCGLKNRSSEGPSSPSGKLMSPKLYVWAKDRPEIWEG

EPPCLPPRDSLNQSLSQDLTMAPGSTLWLSCGVPPDSVSRGPLSWTHVHPKGPKSLLSL

ELKDDRPARDMWVMETGLLLPRATAQDAGKYYCHRGNLTMSFHLEITARPVLWHWLLRT

GGWKVSAVTLAYLIFCLCSLVGILHLQRALVLRRKRKRMTDPTRRF"

misc_feature 1226 . . . 1267
/note = "Myr"
misc_feature 1268 . . . 1273
/note = "XhoI"
misc_feature 1274 . . . 1789
/note = "MyD88"
misc_feature 1790 . . . 1975
/note = "Delta-CD40"
misc_feature 1976
/note = "SalI"
misc_feature 1977 . . . 1981
/note = "XhoI"
misc_feature 1982 . . . 1999
/note = "L1"
misc_feature 2000 . . . 2320
/note = "LFv1"
```

-continued

```
misc_feature    2327 . . . 2647
/note = "Fv2L"
misc_feature    2648 . . . 2665
/note = "L1"
misc_feature    2666
/note = "SalI"
misc_feature    2667 . . . 2671
/note = "SalI"
misc_feature    2672 . . . 2683
/note = "Furin"
misc_feature    2684 . . . 2725
/product = "epitope tag from simian virus 5"
/note = "V5 tag"
misc_feature    2726 . . . 2794
/note = "L-2A"
misc_feature    2795 . . . 2800
/note = "MluI"
misc_feature    2801 . . . 3802
/note = "dCD19"
misc_feature    3962 . . . 4551
/note = "LTR"
primer_bind     complement(5250 . . . 5266)
/note = "M13 fwd"
/note = "common sequencing primer, one of multiple similar
variants"
promoter        5741 . . . 5845
/gene = "bla"
/note = "AmpR promoter"
CDS             5846 . . . 6706
/codon_start = 1
/gene = "bla"
/product = "beta-lactamase"
/note = "AmpR"
/note = "confers resistance to ampicillin, carbenicillin, and
related antibiotics"
/translation = "
                                                    SEQ ID NO: 16
MSIQHFRVALIPFFAAFCLPVFAHPETLVKVKDAEDQLGARVGYI

ELDLNSGKILESFRPEERFPMMSTFKVLLCGAVLSRIDAGQEQLGRRIHYSQNDLVEYS

PVTEKHLTDGMTVRELCSAAITMSDNTAANLLLTTIGGPKELTAFLHNMGDHVTRLDRW

EPELNEAIPNDERDTTMPVAMATTLRKLLTGELLTLASRQQLIDWMEADKVAGPLLRSA

LPAGWFIADKSGAGERGSRGIIAALGPDGKPSRIVVIYTTGSQATMDERNRQIAEIGAS

LIKHW"

rep_origin      6877 . . . 7465
/direction = RIGHT
/note = "ori"
/note = "high-copy-number colE1/pMB1/pBR322/pUC origin of
replication"
promoter        7789 . . . 7819
/note = "lac promoter"
/note = "promoter for the E. coli lac operon"
protein_bind    7827 . . . 7843
/bound_moiety = "lac repressor encoded by lacI"
/note = "lac operator"
/note = "The lac repressor binds to the lac operator to
inhibit transcription in E. coli. This inhibition can be
relieved by adding lactose or
isopropyl-β-D-thiogalactopyranoside (IPTG)."
primer_bind     7851 . . . 7867
/note = "M13 rev"
/note = "common sequencing primer, one of multiple similar
variants"
LTR             8276 . . . 8869
/note = "long terminal repeat from Moloney murine leukemia
virus"
                                                    SEQ ID NO: 17
ORIGIN
    1 aagctggcca gcaacttatc tgtgtctgtc cgattgtcta gtgtctatga ctgattttat 61 gcgcctgcgt cggtactagt tagctaacta gctctgtatc tggcggaccc gtggtggaac 121 tgacgagttc ggaacacccg gccgcaaccc tgggagacgt cccagggact cgggggccg 181 tttttgtggc ccgacctgag tcctaaaatc ccgatcgttt aggactcttt ggtgcacccc
```

```
241 ccttagagga gggatatgtg gttctggtag gagacgagaa cctaaaacag ttcccgcctc
301 cgtctgaatt tttgctttcg gtttgggacc gaagccgcgc cgcgcgtctt gtctgctgca
361 gcatcgttct gtgttgtctc tgtctgactg tgtttctgta tttgtctgaa aatatgggcc
421 cgggctagcc tgttaccact cccttaagtt tgaccttagg tcactggaaa gatgtcgagc
481 ggatcgctca caaccagtcg gtagatgtca agaagagacg ttgggttacc ttctgctctg
541 cagaatggcc aacctttaac gtcggatggc cgcgagacgg cacctttaac cgagacctca
601 tcacccaggt taagatcaag gtcttttcac ctggcccgca tggacaccca gaccaggtgg
661 ggtacatcgt gacctgggaa gccttggctt ttgacccccc tccctgggtc aagccctttg
721 tacaccctaa gcctccgcct cctcttcctc catccgcccc gtctctcccc cttgaacctc
781 ctcgttcgac cccgcctcga tcctcccttt atccagccct cactccttct ctaggcgccc
841 ccatatggcc atatgagatc ttatatgggg caccccccgcc ccttgtaaac ttccctgacc
901 ctgacatgac aagagttact aacagcccct ctctccaagc tcacttacag gctctctact
961 tagtccagca cgaagtctgg agacctctgg cggcagccta ccaagaacaa ctggaccgac
1021 cggtggtacc tcacccttac cgagtcggcg acacagtgtg ggtccgccga caccagacta
1081 agaacctaga acctcgctgg aaaggacctt acacagtcct gctgaccacc cccaccgccc
1141 tcaaagtaga cggcatcgca gcttggatac acgccgccca cgtgaaggct gccgaccccg
1201 ggggtggacc atcctctaga ctgccatggg gagtagcaag agcaagccta aggaccccag
1261 ccagcgcctc gagatggccg ctgggggccc aggcgccgga tcagctgctc ccgtatcttc
1321 tacttcttct ttgccgctgg ctgctctgaa catgcgcgtg agaagacgcc tctccctgtt
1381 ccttaacgtt cgcacacaag tcgctgccga ttggaccgcc cttgccgaag aaatggactt
1441 tgaatacctg gaaattagac aacttgaaac acaggccgac cccactggca gactcctgga
1501 cgcatggcag ggaagacctg gtgcaagcgt tggacggctc ctggatctcc tgacaaaact
1561 gggacgcgac gacgtactgc ttgaactcgg acctagcatt gaagaagact gccaaaaata
1621 tatcctgaaa caacaacaag aagaagccga aaaacctctc caagtcgcag cagtggactc
1681 atcagtaccc cgaacagctg agcttgctgg gattactaca ctcgacgacc cactcggaca
1741 tatgcctgaa agattcgacg ctttcatttg ctattgcccc tctgacataa agaaagttgc
1801 aaagaaaccc acaaataaag ccccacaccc taaacaggaa ccccaagaaa tcaatttccc
1861 agatgatctc cctggatcta atactgccgc cccggtccaa gaaaccctgc atggttgcca
1921 gcctgtcacc caagaggacg gaaaagaatc acggattagc gtacaagaga gacaagtcga
1981 gtctggcggt ggatccggag gcgttcaagt agaaacaatc agcccaggag acggaaggac
2041 tttccccaaa cgaggccaaa catgcgtagt tcattatact gggatgctcg aagatggaaa
2101 aaaagtagat agtagtagag accgaaacaa accatttaaa tttatgttgg gaaaacaaga
2161 agtaataagg ggctgggaag aaggtgtagc acaaatgtct gttggccagc gcgcaaaact
2221 cacaatttct cctgattatg cttacggagc taccggccac cccggcatca taccccctca
2281 tgccacactg gtgtttgacg tcgaattgct caaactggaa gtcgagggag tgcaggtgga
2341 gacgattagt cctggggatg ggagaacctt tccaaagcgc ggtcagacct gtgttgtcca
2401 ctacaccggt atgctggagg acgggaagaa ggtggactct tcacgcgatc gcaataagcc
2461 tttcaagttc atgctcggca agcaggaggt gatccggggg tgggaggagg gcgtggctca
2521 gatgtcggtc gggcaacgag cgaagcttac catctcaccc gactacgcgt atggggcaac
2581 ggggcatccg ggaattatcc ctccccacgc tacgctcgta ttcgatgtgg agctcttgaa
```

-continued

```
2641 gcttgagtct ggcggtggat ccggagtcga ccgcgcaaag cgtggaaaac ctatacctaa
2701 tccattgctg ggcttagact caacaggcag cggaagcgca acgaattttt ccctgctgaa
2761 acaggcaggg gacgtagagg aaaatcctgg tcctacgcgt atgcccctc ctagactgct
2821 gttttcctg ctctttctca ccccaatgga agttagacct gaggaaccac tggtcgttaa
2881 agtggaagaa ggtgataatg ctgtcctcca atgccttaaa gggaccagcg acggaccaac
2941 gcagcaactg acttggagcc gggagtcccc tctcaagccg tttctcaagc tgtcacttgg
3001 cctgccaggt cttggtattc acatgcgccc ccttgccatt tggctcttca tattcaatgt
3061 gtctcaacaa atgggtggat ctacccttg ccagcccggc ccccttctg agaaagcttg
3121 gcagcctgga tggaccgtca atgttgaagg ctccggtgag ctgtttagat ggaatgtgag
3181 cgaccttggc ggactcggtt gcggactgaa aataggagc tctgaaggac cctcttctcc
3241 ctccggtaag ttgatgtcac ctaagctgta cgtgtgggcc aaggaccgcc ccgaaatctg
3301 ggagggcgag cctccatgcc tgccgcctcg cgattcactg aaccagtctc tgtcccagga
3361 tctcactatg gcgcccggat ctactctttg gctgtcttgc ggcgttcccc cagatagcgt
3421 gtcaagagga cctctgagct ggacccacgt acaccctaag ggccctaaga gcttgttgag
3481 cctggaactg aaggacgaca gacccgcacg cgatatgtgg gtaatggaga ccggccttct
3541 gctccctcgc gctaccgcac aggatgcagg gaaatactac tgtcatagag ggaatctgac
3601 tatgagcttt catctcgaaa ttacagcacg gcccgttctt tggcattggc tcctccggac
3661 tggaggctgg aaggtgtctg ccgtaacact cgcttacttg atttttgcc tgtgtagcct
3721 ggttgggatc ctgcatcttc agcgagccct tgtattgcgc cgaaaaagaa acgaatgac
3781 tgaccctaca cgacgattct gagcatgcaa cctcgatccg gattagtcca atttgttaaa
3841 gacaggatat cagtggtcca ggctctagtt ttgactcaac aatatcacca gctgaagcct
3901 atagagtacg agccatagat aaaataaaag atttatttta gtctccagaa aaggggga
3961 atgaaagacc ccacctgtag gtttggcaag ctagcttaag taacgccatt ttgcaaggca
4021 tggaaaaata cataactgag aatagagaag ttcagatcaa ggtcaggaac agatggaaca
4081 gctgaatatg ggccaaacag gatatctgtg gtaagcagtt cctgccccgg ctcagggcca
4141 agaacagatg gaacagctga atatgggcca acaggatat ctgtggtaag cagttcctgc
4201 cccggctcag ggccaagaac agatggtccc cagatgcggt ccagcccca gcagtttcta
4261 gagaaccatc agatgtttcc agggtgcccc aaggacctga aatgaccctg tgccttattt
4321 gaactaacca atcagttcgc ttctcgcttc tgttcgcgcg cttctgctcc ccgagctcaa
4381 taaaagagcc cacaaccct cactcggggc gccagtcctc cgattgactg agtcgcccgg
4441 gtacccgtgt atccaataaa ccctcttgca gttgcatccg acttgtggtc tcgctgttcc
4501 ttgggagggt ctcctctgag tgattgacta cccgtcagcg ggggtctttc acacatgcag
4561 catgtatcaa aattaatttg gtttttttc ttaagtattt acattaaatg gccatagtac
4621 ttaaagttac attggcttcc ttgaaataaa catggagtat tcagaatgtg tcataaatat
4681 ttctaatttt aagatagtat ctccattggc tttctacttt tctttatt ttttttgtc
4741 ctctgtcttc catttgttgt tgttgttgtt tgtttgtttg tttgttggtt ggttggttaa
4801 ttttttttta aagatcctac actatagttc aagctagact attagctact ctgtaaccca
4861 gggtgacctt gaagtcatgg gtagcctgct gttttagcct tcccacatct aagattacag
4921 gtatgagcta tcatttttgg tatattgatt gattgattga ttgatgtgtg tgtgtgtgat
4981 tgtgtttgtg tgtgtgactg tgaaaatgtg tgtatgggtg tgtgtgaatg tgtgtatgta
5041 tgtgtgtgtg tgagtgtgtg tgtgtgtgtg tgcatgtgtg tgtgtgtgac tgtgtctatg
```

-continued

```
5101 tgtatgactg tgtgtgtgtg tgtgtgtgtg tgtgtgtgtg tgtgttgtga 5161 aaaaatattc tatggtagtg agagccaacg ctccggctca ggtgtcaggt tggttttga 5221 gacagagtct ttcacttagc ttggaattca ctggccgtcg ttttacaacg tcgtgactgg 5281 gaaaaccctg gcgttaccca acttaatcgc cttgcagcac atccccctt cgccagctgg 5341 cgtaatagcg aagaggcccg caccgatcgc ccttcccaac agttgcgcag cctgaatggc 5401 gaatggcgcc tgatgcggta ttttctcctt acgcatctgt gcggtatttc acaccgcata 5461 tggtgcactc tcagtacaat ctgctctgat gccgcatagt taagccagcc ccgacacccg 5521 ccaacacccg ctgacgcgcc ctgacgggct tgtctgctcc cggcatccgc ttacagacaa 5581 gctgtgaccg tctccgggag ctgcatgtgt cagaggtttt caccgtcatc accgaaacgc 5641 gcgatgacga aagggcctcg tgatacgcct atttttatag gttaatgtca tgataataat 5701 ggtttcttag acgtcaggtg gcacttttcg gggaaatgtg cgcggaaccc ctatttgttt 5761 atttttctaa atacattcaa atatgtatcc gctcatgaga caataaccct gataaatgct 5821 tcaataatat tgaaaaagga agagtatgag tattcaacat ttccgtgtcg cccttattcc 5881 cttttttgcg gcattttgcc ttcctgtttt tgctcaccca gaaacgctgg tgaaagtaaa 5941 agatgctgaa gatcagttgg gtgcacgagt gggttacatc gaactggatc tcaacagcgg 6001 taagatcctt gagagttttc gccccgaaga acgttttcca atgatgagca cttttaaagt 6061 tctgctatgt ggcgcggtat tatcccgtat tgacgccggg caagagcaac tcggtcgccg 6121 catacactat tctcagaatg acttggttga gtactcacca gtcacagaaa agcatcttac 6181 ggatggcatg acagtaagag aattatgcag tgctgccata accatgagtg ataacactgc 6241 ggccaactta cttctgacaa cgatcggagg accgaaggag ctaaccgctt ttttgcacaa 6301 catgggggat catgtaactc gccttgatcg ttgggaaccg gagctgaatg aagccatacc 6361 aaacgacgag cgtgacacca cgatgcctgt agcaatggca acaacgttgc gcaaactatt 6421 aactggcgaa ctacttactc tagcttcccg gcaacaatta atagactgga tggaggcgga 6481 taaagttgca ggaccacttc tgcgctcggc ccttccggct ggctggttta ttgctgataa 6541 atctggagcc ggtgagcgtg ggtctcgcgg tatcattgca gcactgggc cagatggtaa 6601 gccctcccgt atcgtagtta tctacacgac ggggagtcag gcaactatgg atgaacgaaa 6661 tagacagatc gctgagatag gtgcctcact gattaagcat tggtaactgt cagaccaagt 6721 ttactcatat atactttaga ttgatttaaa acttcatttt taatttaaaa ggatctaggt 6781 gaagatcctt tttgataatc tcatgaccaa atcccttaa cgtgagtttt cgttccactg 6841 agcgtcagac cccgtagaaa agatcaaagg atcttcttga gatccttttt ttctgcgcgt 6901 aatctgctgc ttgcaaacaa aaaaaccacc gctaccagcg gtggtttgtt tgccggatca 6961 agagctacca actctttttc cgaaggtaac tggcttcagc agagcgcaga taccaaatac 7021 tgtccttcta gtgtagccgt agttaggcca ccacttcaag aactctgtag caccgcctac 7081 atacctcgct ctgctaatcc tgttaccagt ggctgctgcc agtggcgata agtcgtgtct 7141 taccgggttg gactcaagac gatagttacc ggataaggcg cagcggtcgg gctgaacggg 7201 gggttcgtgc acacagccca gcttggagcg aacgacctac accgaactga gatacctaca 7261 gcgtgagcat tgagaaagcg ccacgcttcc cgaagggaga aaggcggaca ggtatccggt 7321 aagcggcagg gtcggaacag gagagcgcac gagggagctt ccaggggaa acgcctggta 7381 tctttatagt cctgtcgggt ttcgccacct ctgacttgag cgtcgatttt tgtgatgctc 7441 gtcagggggg cggagcctat ggaaaaacgc cagcaacgcg gcctttttac ggttcctggc
```

```
7501 cttttgctgg ccttttgctc acatgttctt tcctgcgtta tccctgatt ctgtggataa 7561 ccgtattacc gcctttgagt gagctgatac cgctcgccgc agccgaacga ccgagcgcag 7621 cgagtcagtg agcgaggaag cggaagagcg cccaatacgc aaaccgcctc tccccgcgcg 7681 ttggccgatt cattaatgca gctggcacga caggtttccc gactggaaag cgggcagtga 7741 gcgcaacgca attaatgtga gttagctcac tcattaggca ccccaggctt tacactttat 7801 gcttccggct cgtatgttgt gtggaattgt gagcggataa caatttcaca caggaaacag 7861 ctatgaccat gattacgcca agctttgctc ttaggagttt cctaatacat cccaaactca 7921 aatatataaa gcatttgact tgttctatgc cctagggggc gggggaagc taagccagct 7981 tttttaaca tttaaaatgt taattccatt ttaaatgcac agatgttttt atttcataag 8041 ggtttcaatg tgcatgaatg ctgcaatatt cctgttacca aagctagtat aaataaaaat 8101 agataaacgt ggaaattact tagagtttct gtcattaacg tttccttcct cagttgacaa 8161 cataaatgcg ctgctgagca agccagtttg catctgtcag gatcaatttc ccattatgcc 8221 agtcatatta attactagtc aattagttga ttttatttt tgacatatac atgtgaatga 8281 aagacccac ctgtaggttt ggcaagctag cttaagtaac gccattttgc aaggcatgga 8341 aaaatacata actgagaata gaaaagttca gatcaaggtc aggaacagat ggaacagctg 8401 aatatgggcc aaacaggata tctgtggtaa gcagttcctg ccccggctca gggccaagaa 8461 cagatggaac agctgaatat gggccaaaca ggatatctgt ggtaagcagt tcctgccccg 8521 gctcagggcc aagaacagat ggtccccaga tgcggtccag ccctcagcag tttctagaga 8581 accatcagat gtttccaggg tgccccaagg acctgaaatg accctgtgcc ttatttgaac 8641 taaccaatca gttcgcttct cgcttctgtt cgcgcgctta tgctcccga gctcaataaa 8701 agagcccaca accctcact cggggcgcca gtcctccgat tgactgagtc gcccgggtac 8761 ccgtgtatcc aataaaccct cttgcagttg catccgactt gtggtctcgc tgttccttgg 8821 gagggtctcc tctgagtgat tgactacccg tcagcggggg tctttcattt ggggctcgt 8881 ccgggatcgg gagacccctg cccagggacc accgacccac caccgggagg t
```

Example 2: Using the Inducible CSM in Human Cells for Therapy

Presented in this example are expression constructs and methods of using the expression constructs in human cells. Although this example refers to the inducible chimeric stimulating molecule, vectors coding for the non-inducible chimeric stimulating molecules, and the MyD88/CD40 chimeric antigen receptors may also be used, including any appropriate modifications.

These methods may be adapted for other cells, such as, for example NK and NKT cells, as well as tumor-infiltrating lymphocytes, and may also be adapted for chimeric stimulating polypeptides that comprise other costimulatory polypeptide cytoplasmic regions as discussed herein.

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at $1 \times 10^6$ cells/ml and stimulated with 0.2 µg/ml αCD3 and 0.5 µg/ml αCD28 soluble antibody. Cells are then cultured at 37° C., 5% $CO_2$ for 4 days. On day four, 1 ml of fresh media containing IL-2 is added. On day 7, cells are harvested and resuspended in Cellgenix DC media for transduction.

Plasmid and Retrovirus

The SFG plasmid consists of inducible CSM linked, via a cleavable 2A-like sequence, to truncated human CD19. The inducible CSM consists of a human FK506-binding protein (FKBP12; GenBank AH002 818) with an F36V mutation, connected via a Ser-Gly-Gly-Gly-Ser linker (SEQ ID NO: 285) to a human CSM. The F36V mutation increases the binding affinity of FKBP12 to the synthetic homodimerizer, AP20187 or AP1903. The 2A-like sequence encodes a 20 amino acid peptide from *Thosea asigna* insect virus, which mediates >95% cleavage between a glycine and terminal proline residue, resulting in 19 extra amino acids in the C terminus of iCSM, and one extra proline residue in the N terminus of CD19. CD19 consists of full-length CD19 (GenBank NM 001770) truncated at amino acid 333 (TDP-TRRF) (SEQ ID NO: 286), which shortens the intracytoplasmic domain from 242 to 19 amino acids, and removes all conserved tyrosine residues that are potential sites for phosphorylation.

A stable PG13-based clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid.

This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

Retro Viral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 □g/ml and anti-CD28 0.2 µg/ml or 10 ml of fibronectin 7 □g/ml at 4° C. overnight. Fluorinated ethylene propylene bags corona-treated for increased cell adherence (2PF-0072AC, American Fluoroseal Corporation, Gaithersburg, Md.) are also used. PBMCs are seeded in anti-CD3, anti-CD28-coated flasks at $1\times10^6$ cells/ml in media supplemented with 100 U/ml IL-2. For retroviral transduction, RETRONECTIN-coated flasks or bags are loaded once with 10 ml of retrovirus-containing supernatant for 2 to 3 hours. Activated T cells are seeded at $1\times10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about $5\times10^5$ cells/ml to $8\times10^5$ cells/ml.

CD19 Immunomagnetic Selection

Immunomagnetic selection for CD19 may, for example, be performed 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CLINIMACS PLUS automated selection device in large scale experiments. CD19-selected cells are expanded for a further 4 days and cryopreserved on day 8 post transduction. These cells are referred to as "gene-modified cells".

Immunophenotyping and Pentamer Analysis

Flow cytometric analysis (FACSCALIBUR and CELL-QUEST software; Becton Dickinson) is performed using the following antibodies: CD3, CD4, CD8, CD19, CD25, CD27, CD28, CD45RA, CD45RO, CD56 and CD62L. CD19-PE (Clone 4G7; Becton Dickinson) is found to give optimum staining and was used in all subsequent analysis. A non-transduced control is used to set the negative gate for CD19. CAR expression is assessed using anti-F(ab')2 (Jackson ImmunoResearch Laboratories, West Grove, Pa.).

Statistical Analysis

Paired, 2-tailed Student's t test is used to determine the statistical significance of differences between samples. All data are represented as mean±1 standard deviation.

Example 3: Treatment of a Leukemia Patient

The present example of the treatment of a leukemia patient having advanced treatment refractory leukemia, using the methods of the present application, may also be applied to other conditions or diseases, such as, for example, other hyperproliferative diseases or solid tumors. The methods may be used essentially as discussed, with the understanding that the single chain variable fragment may vary according to the target antigen.

T cells are transduced with a nucleic acid comprising a polynucleotide coding for a chimeric stimulating molecule of the present application. The T cells are also transduced with a nucleic acid comprising a polynucleotide coding for a chimeric antigen receptor. In other examples, the nucleic acid used to transduce the T cells may include, for example, a polynucleotide coding for the chimeric antigen receptor. The chimeric antigen receptor comprises a single chain variable fragment that recognizes CD19.

The patient undergoes lymphodepletive conditioning, followed by administration of the transduced CD19-targeted T cells. The T cells may be autologous, allogeneic, or non-allogeneic. The dose may be provided, for example, daily, twice a week, or weekly. Because of the concern that an unregulated, too rapid rate of T cell expansion, activation, and tumor cell killing may lead to a more severe cytokine storm that unnecessarily harms the patient, the dosing schedule is designed to achieve a complete recovery at a rate that limits toxicity and does not cause extensive harm to the patient, for example, keeping the patient out of the intensive care unit at a hospital.

Example 4: Measurement of iMC Activity in CAR-Transduced T Cells

This Example discusses the use of an inducible chimeric stimulatory molecule, but methods discussed herein may also applied to a non-inducible chimeric stimulatory molecule.

Aim: To transduce primary T cells with a retroviral vector encoding signaling molecules linked to two FKBPv36 molecules to allow AP1903 activation of the T cells. The experiment is designed to examine whether the inducible costimulatory molecule comprising the truncated MyD88 and CD40 polypeptides, improve killing of the GFP-modified Capan-1 (pancreatic adenocarcinoma) cells by T cells also transduced with a CAR recognizing prostate stem cell antigen (PSCA), which is highly expressed on Capan-1 tumor cells.

Methods:

Design and Cloning of Inducible T Cell Molecules:

1. Transduction of T Cells is Performed with RV-172 (SFG-Myr.MyD88/CD40.Fv.Fv'.2A.ΔCD19) and RV-89 (SFG.PSCAscFv.CH$_2$CH$_3$.CD28.ζ). The scFv targets PSCA using the scFv from the humanized monoclonal antibody, 1G8 (derived from humanized anti-PSCA in US2012077962 A1). This is linked to the CH$_2$CH$_3$ region of human IgG1, which in turn is linked to CD28 which contains both the transmembrane and cytoplasmic portion of the molecule. CD28 is linked to the cytoplasmic portion of CD3ζ.

Production of Retrovirus:

2. Essentially the same as in the previous example.

Generation of GFP-marked Capan-1 (pancreatic adenocarcinoma) cell line:

3. Capan-1 is purchased from ATCC. Subsequently, the cell line is gene-modified by transfection with the pBP0168-pcDNA3.1-EGFPluc which contains the gene for the EGFP/firefly luciferase fusion protein, as well as the neomycin resistance gene allowing stably transfected cells to be selected over time by culturing with G418 antibiotic. Following culture, clones with high GFP expression are selected and subcultured until a cell line with >95% GFP is obtained Co-Culture of iMC-Enabled T Cells with Capan-1 Tumor Cells:

4. Non-transduced or T cells co-transduced with RV-89 (PSCA CAR) and RV-172 (iMC vector) are cultured at a 5:1 ratio of T cells to tumor cells in media supplemented with 50 U/ml IL-2, and either with or without 10 nM AP1903. Co-cultures are then incubated at 37° C. and 5% $CO_2$ for 72 hours. Cultures are subsequently analyzed for the presence of GFP$^+$ tumor cells by fluorescent microscopy and by harvesting the cultures with 0.25% trypsin/EDTA and measuring the frequency of GFP$^+$CD3$^-$ tumor cells in the culture by flow cytometry.

Results:

1. The cultures are examined by fluorescent microscopy to assess an improvement in tumor cell killing in the wells that contain the inducible costimulating molecule- and chimeric antigen receptor-transduced T cells and that received AP1903.

2. Flow cytometry is used to analyze GFP$^+$ cells in the cultures following trypsinization to determine whether AP1903 contributes to a reduction in tumor cell number in this short culture period (72 hours). The time period for the culture may be extended to approximately 5 days. The flow cytometry plots may show the reduction in GFP$^+$ cells in wells, at a 5:1 ratio, that were transduced with both virus and receive AP1903.

3. The remaining viable Capan-1-GFP cells are normalized to the conditions of NT T cells without AP1903 to show the effect of iMC activation on tumor cell killing.

Example 5: Examples of Particular Nucleic Acid and Amino Acid Sequences

The following sequences may be used in the design of expression vectors that encode the chimeric antigen receptors or chimeric stimulating molecules provided herein.

CD28 nt,
SEQ ID NO: 18
TTCTGGGTACTGGTTGTAGTCGGTGGCGTACTTGCTTGTTATTCTCTTCT

TGTTACCGTAGCCTTCATTATATTCTGGGTCCGATCAAAGCGCTCAAGAC

TCCTCCATTCCGATTATATGAACATGACACCTCGCCGACCTGGTCCTACA

CGCAAACATTATCAACCCTACGCACCCCCCCGAGACTTCGCTGCTTATCG

ATCC

CD28 aa,
SEQ ID NO: 19
FWVLVVVGGVLACYSLLVTVAFIIFWVRSKRSRLLHSDYMNMTPRRPGPT

RKHYQPYAPPRDFAAYRS

Linker sequence (between CD28 and 4-1BB) nt,
SEQ ID NO: 20
GGATCC

Linker sequence (between CD28 and 4-1BB) aa,
SEQ ID NO: 21
GS 4-1BB nt,
SEQ ID NO: 22
AGTGTAGTTAAAAGAGGAAGAAAAAAGTTGCTGTATATATTTAAACAACC

ATTTATGAGACCAGTGCAAACCACCCAAGAAGAAGACGGATGTTCATGCA

GATTCCCAGAAGAAGAAGAAGGAGGATGTGAATTG 4-1BB aa,
SEQ ID NO: 23
SVVKRGRKKLLYIFKQPFMRPVQTTQEEDGCSCRFPEEEEGGCEL

Linker sequence (between 4-1BB and CD3 ζ) nt,
SEQ ID NO: 24
ACGCGT

Linker sequence (between 4-1BB and CD3 ζ) aa,
SEQ ID NO: 25
TR

CD3 ζ nt,
SEQ ID NO: 26
CGGGTCAAATTCAGCCGGAGTGCTGACGCCCCAGCATACCAACAGGGACA

AAACCAACTCTACAACGAGCTCAACCTGGGTAGACGCGAGGAGTACGACG

TTCTGGATAAGAGGCGGGGCCGGGACCCAGAGATGGGGGGCAAACCTCAG

CGGCGGAAGAACCCGCAGGAGGGTCTTTATAACGAGCTCCAGAAGGACAA

GATGGCGGAAGCCTATTCAGAAATTGGGATGAAAGGCGAGAGACGCAGGG

GAAAAGGTCACGATGGTCTGTATCAAGGACTGTCAACCGCCACCAAAGAC

ACTTACGATGCGCTCCACATGCAGGCCCTCCCTCCCCGC

CD3 ζ aa,
SEQ ID NO: 27
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

The following is an example of the nucleotide and amino acid sequences for a chimeric antigen receptor (CAR) sequences (in order, without scFv fragments)

Signal peptide nt,
SEQ ID NO: 28
ATGGAGTTTGGGCTGTCATGGCTGTTCCTCGTGGCCATTCTCAAAGGGGT

CCAGTGTTCTCGC

Signal peptide aa,
SEQ ID NO: 29
MGFGLSWLFLVAILKGVQCSR

Flexible linker sequence nt,
SEQ ID NO: 30
GGGGGAGGAGGTTCTGGAGGCGGCGGGAGCGGAGGAGGAGGCAGC Flexible linker sequence aa, -continued Linker sequence (between scFv and CH2CH3) nt, GGGGSGGGGSGGGGS
SEQ ID NO: 31

Linker sequence (between scFv and CH2CH3) nt,
SEQ ID NO: 32
GGATCC

Linker sequence (between scFv and CH2CH3) aa,
SEQ ID NO: 33
GS

IgG1 CH2CH3 nt,
SEQ ID NO: 34
GATCCAGCCGAACCCAAATCCCCCGATAAAACACATACTTGCCCCCCTTG
TCCCGCACCAGAATTGCTTGGCGGACCTTCCGTTTTTCTTTTTCCCCCCA
AACCTAAAGATACCCTGATGATTTCCCGAACCCCTGAAGTTACGTGCGTA
GTCGTAGATGTGTCTCACGAAGATCCAGAAGTAAAATTTAACTGGTACGT
AGATGGAGTCGAAGTTCACAACGCAAAGACGAAGCCCCGAGAAGAACAAT
ATAATTCCACATACCGAGTAGTTAGCGTTCTCACCGTACTGCATCAGGAC
TGGCTTAACGGCAAAGAATATAAATGTAAGGTCTCAAACAAAGCACTCCC
AGCCCCTATCGAAAAGACTATCTCCAAAGCTAAAGGACAACCCCGCGAAC
CCCAGGTCTATACACTTCCCCCCTCACGCGATGAACTCACTAAAAATCAG
GTTTCCCTTACTTGTCTTGTCAAAGGCTTCTACCCTAGCGATATCGCAGT
CGAATGGGAATCCAATGGCCAGCCCGAAAACAACTATAAAACAACCCCAC
CTGTCCTCGATTCAGATGGCTCATTCTTTCTCTATTCCAAACTGACTGTA
GACAAATCCCGATGGCAACAAGGTAACGTGTTCTCTTGCTCAGTCATGCA
TGAAGCGCTTCATAACCATTACACACAAAAATCTCTCTCACTGTCTCCCG
GAAAGAAGGACCCC

IgG1 CH2CH3 aa,
SEQ ID NO: 35
DPAEPKSPDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTV
DKSRWQQGNVFSCSVMHEALHNHYTQKSLSLSPGKKDP

Linker sequence (between scFv and CH2CH3) nt,
SEQ ID NO: 36
CTCGAG

Linker sequence (between scFv and CH2CH3) aa
SEQ ID NO: 37
LE

CD3 ζ transmembrane and cytoplasmic regions nt (transmembrane region is indicated by underline).,
SEQ ID NO: 38
<u>AAACTGTGTTACCTCCTCGATGGCATCCTCTTTATTTATGGCGTGATTCT</u>
<u>GACCGCATTGTTTCTC</u>CGAGTAAAATTCTCTAGATCCGCAGACGCTCCCG
CATATCAGCAAGGACAAAATCAGCTTTATAACGAACTTAACCTCGGCAGA
CGCGAAGAATACGATGTACTGGACAAGAGAAGAGGAAGAGATCCCGAAAT
GGGCGGAAAACCCCAGAGAAGAAAGAATCCCCAAGAAGGTCTTTATAACG
AACTGCAGAAAGATAAAATGGCCGAAGCGTACAGTGAAATTGGTATGAAA
GGAGAAAGAAGACGCGGAAAAGGACATGACGGACTCTACCAAGGACTCTC
AACTGCTACTAAAGATACATACGACGCCCTTCATATGCAAGCCCTCCCCC
CGAGATAA CD3 ζ transmembrane and cytoplasmic regions aa (transmembrane region is indicated by underline).,
SEQ ID NO: 39
<u>KLCYLLDGILFIYGVILTALFLR</u>VKFSRSADAPAYQQGQNQLYNELNLGR
REEYDVLDKRRGRDPEMGGKPQRRKNPQEGLYNELQKDKMAEAYSEIGMK
GERRRGKGHDGLYQGLSTATKDTYDALHMQALPPR Additional Chimeric Stimulating Molecule Sequences OX40 nt,
SEQ ID NO: 40
GTTGCCGCCATCCTGGGCCTGGGCCTGGTGCTGGGGCTGCTGGGCCCCCT
GGCCATCCTGCTGGCCCTGTACCTGCTCCGGGACCAGAGGCTGCCCCCCG
ATGCCCACAAGCCCCCTGGGGGAGGCAGTTTCCGGACCCCCATCCAAGAG
GAGCAGGCCGACGCCCACTCCACCCTGGCCAAGATC OX40 aa,
SEQ ID NO: 41
VAAILGLGLVLGLLGPLAILLALYLLRRDQRLPPDAHKPPGGGSFRTPIQ
EEQADAHSTLAKI SEQ ID NO: 22 nucleotide sequence of 5'LTR sequence,
SEQ ID NO: 42
TGAAAGACCCCACCTGTAGGTTTGGCAAGCTAGCTTAAGTAACGCCATTT
TGCAAGGCATGGAAAATACATAACTGAGAATAGAAAAGTTCAGATCAAG
GTCAGGAACAGATGGAACAGCTGAATATGGGCCAAACAGGATATCTGTGG
TAAGCAGTTCCTGCCCCGGCTCAGGGCCAAGAACAGATGGAACAGCTGAA
TATGGGCCAAACAGGATATCTGTGGTAAGCAGTTCCTGCCCCGGCTCAGG
GCCAAGAACAGATGGTCCCCAGATGCGGTCCAGCCCTCAGCAGTTTCTAG
AGAACCATCAGATGTTTCCAGGGTGCCCCAAGGACCTGAAATGACCCTGT
GCCTTATTTGAACTAACCAATCAGTTCGCTTCTCGCTTCTGTTCGCGCGC
TTATGCTCCCCGAGCTCAATAAAAGAGCCCACAACCCCTCACTCGGGGCG
CCAGTCCTCCGATTGACTGAGTCGCCCGGGTACCCGTGTATCCAATAAAC
CCTCTTGCAGTTGCATCCGACTTGTGGTCTCGCTGTTCCTTGGGAGGGTC
TCCTCTGAGTGATTGACTACCCGTCAGCGGGGGTCTTTCA Additional Sequences Thosea asigna virus-2A from capsid protein precursor nucleotide sequence
SEQ ID NO, 43
GCCGAGGGCAGGGGAAGTCTTCTAACATGCGGGGACGTGGAGGAAA
ATCCCGGGCCC Thosea asigna virus-2A from capsid protein precursor amino acid sequence,
SEQ ID NO: 44
AEGRGSLLTCGDVEENPGP 3'LTR nucleotide sequence,
SEQ ID NO: 45
TGAAAGACCCCACCTGTAGGTTTGGCAAGCTAGCTTAAGTAACGCCATTT
TGCAAGGCATGGAAAATACATAACTGAGAATAGAGAAGTTCAGATCAAG GTCAGGAACAGATGGAACAGCTGAATATGGGCCAAACAGGATATCTGTGG
TAAGCAGTTCCTGCCCCGGCTCAGGGCCAAGAACAGATGGAACAGCTGAA
TATGGGCCAAACAGGATATCTGTGGTAAGCAGTTCCTGCCCCGGCTCAGG
GCCAAGAACAGATGGTCCCCAGATGCGGTCCAGCCCTCAGCAGTTTCTAG
AGAACCATCAGATGTTTCCAGGGTGCCCCAAGGACCTGAAATGACCCTGT
GCCTTATTTGAACTAACCAATCAGTTCGCTTCTCGCTTCTGTTCGCGCGC
TTCTGCTCCCCGAGCTCAATAAAAGAGCCCACAACCCCTCACTCGGGGCG
CCAGTCCTCCGATTGACTGAGTCGCCCGGGTACCCGTGTATCCAATAAAC
CCTCTTGCAGTTGCATCCGACTTGTGGTCTCGCTGTTCCTTGGGAGGGTC
TCCTCTGAGTGATTGACTACCCGTCAGCGGGGGTCTTTCA (nucleotide sequence of linker-F$_v$1-F$_v$2-linker
with XhoI/SalI sites, (wobbled codons lowercase
in F$_v$2')),
SEQ ID NO: 46
CTCGAGTCTGGCGGTGGATCCGGAGGCGTTCAAGTAGAAACAATCAGCCC
AGGAGACGGAAGGACTTTCCCCAAACGAGGCCAAACATGCGTAGTTCATT
ATACTGGGATGCTCGAAGATGGAAAAAAAGTAGATAGTAGTAGAGACCGA
AACAAACCATTTAAATTTATGTTGGGAAAACAAGAAGTAATAAGGGGCTG
GGAAGAAGGTGTAGCACAAATGTCTGTTGGCCAGCGCGCAAAACTCACAA
TTTCTCCTGATTATGCTTACGGAGCTACCGGCCACCCCGGCATCATACCC
CCTCATGCCACACTGGTGTTTGACGTCGAATTGCTCAAACTGGAAGTCGA
GGGaGTgCAgGTgGAgACgATtAGtCCtGGgGAtGGgAGaACcTTtCCaA
AgCGcGGtCAgACcTGtGTtGTcCAcTAcACcGGtATGCTgGAgGAcGGg
AAgAAgGTgGActcTtcacGcGAtCGcAAtAAgCCtTTcAAgTTcATGcT
cGGcAAgCAgGAgGTgATccGGGGgTGGGAgGAgGGcGTgGCtCAgATGT
CgGTcGGgCAaCGaGCgAAgCTtACcATcTCaCCcGAcTAcGCgTAtGGg
GCaACgGGgCATCCgGGaATtATcCCtCCcCAcGCtACgCTcGTaTTcGA
tGTgGAgcTcttgAAgCTtGagTCTGGCGGTGGATCCGGAGTCGAC (F$_V$.F$_{VLS}$ amino acid sequence),
SEQ ID NO: 47
LESGGGSGGVQVETISPGDGRTFPKRGQTCVVHYTGMLEDGKKVDSSRDR
NKPFKFMLGKQEVIRGWEEGVAQMSVGQRAKLTISPDYAYGATGHPGIIP
PHATLVFDVELLKLEVEGVQVETISPGDGRTFPKRGQTCVVHYTGMLEDG
KKVDSSRDRNKPFKFMLGKQEVIRGWEEGVAQMSVGQRAKLTISPDYAYG
ATGHPGIIPPHATLVFDVELLKLESGGGSGVD FKBPv36 (Fv1) nucleotide sequence,
SEQ ID NO: 48
GGCGTTCAAGTAGAAACAATCAGCCCAGGAGACGGAAGGACTTTCCCCAA
ACGAGGCCAAACATGCGTAGTTCATTATACTGGGATGCTCGAAGATGGAA
AAAAAGTAGATAGTAGTAGAGACCGAAACAAACCATTTAAATTTATGTTG
GGAAAACAAGAAGTAATAAGGGGCTGGGAAGAAGGTGTAGCACAAATGTC
TGTTGGCCAGCGCGCAAAACTCACAATTTCTCCTGATTATGCTTACGGAG
CTACCGGCCACCCCGGCATCATACCCCCTCATGCCACACTGGTGTTTGAC
GTCGAATTGCTCAAACTGGAA FKBPv36 (Fv1) amino acid sequence,
SEQ ID NO: 49
GVQVETISPGDGRTFPKRGQTCVVHYTGMLEDGKKVDSSRDRNKPFKFML
GKQEVIRGWEEGVAQMSVGQRAKLTISPDYAYGATGHPGIIPPHATLVFD
VELLKLE FKBPv36 (Fv2) nucleotide sequence,
SEQ ID NO: 50
GGaGTgCAgGTgGAgACgATtAGtCCtGGgGAtGGgAGaACcTTtCCaAA
gCGcGGtCAgACcTGtGTtGTcCAcTAcACcGGtATGCTgGAgGAcGGgA
AgAAgGTgGActcTtcacGcGAtCGcAAtAAgCCtTTcAAgTTcATGcTc
GGcAAgCAgGAgGTgATccGGGGgTGGGAgGAgGGcGTgGCtCAgATGTC
gGTcGGgCAaCGaGCgAAgCTtACcATcTCaCCcGAcTAcGCgTAtGGgG
CaACgGGgCATCCgGGaATtATcCCtCCcCAcGCtACgCTcGTaTTcGAt
GTgGAgcTcttgAAgCTtGag FKBPv36 (Fv2) amino acid sequence,
SEQ ID NO: 51
GVQVETISPGDGRTFPKRGQTCVVHYTGMLEDGKKVDSSRDRNKPFKFML
GKQEVIRGWEEGVAQMSVGQRAKLTISPDYAYGATGHPGIIPPHATLVFD
VELLKLE Myristoylation polypeptide nucleotide sequence,
SEQ ID NO: 52
ATGGGGAGTAGCAAGAGCAAGCCTAAGGACCCCAGCCAGCGC Myristoylation polypeptide amino acid sequence,
SEQ ID NO: 53
MGSSKSKPKDPSQR Linker nucleotide sequence (linker 1),
SEQ ID NO: 54
CTCGAG Linker amino acid sequence (linker 1),
SEQ ID NO: 55
LE Truncated MyD88 polypeptide nucleotide sequence,
SEQ ID NO: 56
ATGGCCGCTGGGGGCCCAGGCGCCGGATCAGCTGCTCCCGTATCTTCTAC
TTCTTCTTTGCCGCTGGCTGCTCTGAACATGCGCGTGAGAAGACGCCTCT
CCCTGTTCCTTAACGTTCGCACACAAGTCGCTGCCGATTGGACCGCCCTT
GCCGAAGAAATGGACTTTGAATACCTGGAAATTAGACAACTTGAAACACA
GGCCGACCCCACTGGCAGACTCCTGGACGCATGGCAGGGAAGACCTGGTG
CAAGCGTTGGACGGCTCCTGGATCTCCTGACAAAACTGGGACGCGACGAC
GTACTGCTTGAACTCGGACCTAGCATTGAAGAAGACTGCCAAAAATATAT
CCTGAAACAACAAGAAGAAGCCGAAAAACCTCTCCAAGTCGCAGCAG
TGGACTCATCAGTACCCCGAACAGCTGAGCTTGCTGGGATTACTACACTC
GACGACCCACTCGGACATATGCCTGAAAGATTCGACGCTTTCATTTGCTA
TTGCCCCTCTGACATA Truncated MyD88 polypeptide amino acid sequence,
SEQ ID NO: 57
MAAGGPGAGSAAPVSSTSSLPLAALNMRVRRRLSLFLNVRTQVAADWTAL
AEEMDFEYLEIRQLETQADPTGRLLDAWQGRPGASVGRLLDLLTKLGRDD

```
VLLELGPSIEEDCQKYILKQQQEEAEKPLQVAAVDSSVPRTAELAGITTL

DDDPLGHMPERFDAFICYCPSDI

ΔCD40 polypeptide nucleotide sequence,
                                         SEQ ID NO: 58
AAGAAAGTTGCAAAGAAACCCACAAATAAAGCCCCACACCCTAAACAGGA

ACCCCAAGAAATCAATTTCCCAGATGATCTCCCTGGATCTAATACTGCCG

CCCCGGTCCAAGAAACCCTGCATGGTTGCCAGCCTGTCACCCAAGAGGAC

GGAAAAGAATCACGGATTAGCGTACAAGAGAGACAA

ΔCD40 polypeptide amino acid sequence,
                                         SEQ ID NO: 59
KKVAKKPTNKAPHPKQEPQEINFPDDLPGSNTAAPVQETLHGCQPVTQED

GKESRISVQERQ

Linker nucleotide sequence (linker 2),
                                         SEQ ID NO: 60
GTCGAGTCTGGCGGTGGATCCGGA Linker amino acid sequence (linker 2),
                                         SEQ ID NO: 61
VESGGGSG FKBPv36 (Fv1) nucleotide sequence,
                                         SEQ ID NO: 62
GGCGTTCAAGTAGAAACAATCAGCCCAGGAGACGGAAGGACTTTCCCCAA

ACGAGGCCAAACATGCGTAGTTCATTATACTGGGATGCTCGAAGATGGAA

AAAAGTAGATAGTAGTAGAGACCGAAACAAACCATTTAAATTTATGTTG

GGAAAACAAGAAGTAATAAGGGGCTGGGAAGAAGGTGTAGCACAAATGTC

TGTTGGCCAGCGCGCAAAACTCACAATTTCTCCTGATTATGCTTACGGAG

CTACCGGCCACCCCGGCATCATACCCCCTCATGCCACACTGGTGTTTGAC

GTCGAATTGCTCAAACTGGAA

FKBPv36 (Fv1) amino acid sequence,
                                         SEQ ID NO: 63
GVQVETISPGDGRTFPKRGQTCVVHYTGMLEDGKKVDSSRDRNKPFKFML
GKQEVIRGWEEGVAQMSVGQRAKLTISPDYAYGATGHPGIIPPHATLVFD
VELLKLE Linker nucleotide sequence (linker 3),
                                         SEQ ID NO: 64
GTCGAG Linker amino acid sequence (linker 3),
                                         SEQ ID NO: 65
VE FKBPv36 (Fv2) nucleotide sequence,
                                         SEQ ID NO: 66
GGaGTgCAgGTgGAgACgATtAGtCCtGGgGAtGGgAGaACcTTtCcAAA gCGcGGtCAgACcTGtGTtGTcCAcTAcACcGGtATGCTgGAgGAcGGgA AgAAgGTgGActcTtcacGcGAtCGcAAtAAgCCtTTcAAgTTcATGCtc GGcAAgCAgGAgGTgATccGGGGgTGGGAgGAgGGcGTgGCtCAgATGTC gGTcGGgCAaCgAGCgAAgCTtACcATcTCaCCcGAcTAcGCgTAtGGgG CaACgGGgCATCCgGGaATtATcCCtCCcCAcGCtACgCTcGTaTTCGAt GTgGAgcTcttgAAgCTtGag FKBPv36 (Fv2) amino acid sequence,
                                         SEQ ID NO: 67
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

Linker nucleotide sequence (linker 4),
                                         SEQ ID NO: 68
TCTGGCGGTGGATCCGGAGTCGAC Linker amino acid sequence (linker 4),
                                         SEQ ID NO: 69
SGGGSGVD Furin protease consensus cleavage site nucleotide
sequence,
                                         SEQ ID NO: 70
CGCGCAAAGCGT Furin protease consensus cleavage site amino acid
sequence,
                                         SEQ ID NO: 71
RAKR V5 epitope nucleotide sequence,
                                         SEQ ID NO: 72
GGAAAACCTATACCTAATCCATTGCTGGGCTTAGACTCAACA V5 epitope nucleotide sequence,
                                         SEQ ID NO: 73
GKPIPNPLLGLDST Linker nucleotide sequence (linker 5),
                                         SEQ ID NO: 74
GGCAGCGGAAGC Linker amino acid sequence (linker 5),
                                         SEQ ID NO: 75
GSGS P2A nucleotide sequence,
                                         SEQ ID NO: 76
GCAACGAATTTTTCCCTGCTGAAACAGGCAGGGGACGTAGAGGAAAATC

CTGGTCCT

P2A amino acid sequence,
                                         SEQ ID NO: 77
ATNFSLLKQAGDVEENPGP Linker nucleotide sequence (linker 6),
                                         SEQ ID NO 78
ACGCGT Linker amino acid sequence (linker 6),
                                         SEQ ID NO: 79
TR ΔCD19 nucleotide sequence,
                                         SEQ ID NO: 80
ATGCCCCCTCCTAGACTGCTGTTTTTCCTGCTCTTTCTCACCCCAATGGA

AGTTAGACCTGAGGAACCACTGGTCGTTAAAGTGGAAGAAGGTGATAATG

CTGTCCTCCAATGCCTTAAAGGGACCAGCGACGGACCAACGCAGCAACTG

ACTTGGAGCCGGGAGTCCCCTCTCAAGCCGTTTCTCAAGCTGTCACTTGG

CCTGCCAGGTCTTGGTATTCACATGGCCCCCTTGCCATTTGGCTCTTCA

TATTCAATGTGTCTCAACAAATGGGTGGATTCTACCTTTGCCAGCCCGGC

CCCCCTTCTGAGAAAGCTTGGCAGCCTGGATGGACCGTCAATGTTGAAGG

CTCCGGTGAGCTGTTTAGATGGAATGTGAGCGACCTTGGCGGACTCGGTT

GCGGACTGAAAAATAGGAGCTCTGAAGGACCCTCTTCTCCCTCCGGTAAG

TTGATGTCACCTAAGCTGTACGTGTGGGCCAAGGACCGCCCCGAAATCTG
```

-continued

```
GGAGGGCGAGCCTCCATGCCTGCCGCCTCGCGATTCACTGAACCAGTCTC

TGTCCCAGGATCTCACTATGGCGCCCGGATCTACTCTTTGGCTGTCTTGC

GGCGTTCCCCCAGATAGCGTGTCAAGAGGACCTCTGAGCTGGACCCACGT

ACACCCTAAGGGCCCTAAGGAGCTTGTTGAGCCTGGAACTGAAGGACGACA

GACCCGCACGCGATATGTGGGTAATGGAGACCGGCCTTCTGCTCCCTCGC

GCTACCGCACAGGATGCAGGGAAATACTACTGTCATAGAGGGAATCTGAC

TATGAGCTTTCATCTCGAAATTACAGCACGGCCCGTTCTTTGGCATTGGC

TCCTCCGGACTGGAGGCTGGAAGGTGTCTGCCGTAACACTCGCTTACTTG

ATTTTTTGCCTGTGTAGCCTGGTTGGGATCCTGCATCTTCAGCGAGCCCT

TGTATTGCGCCGAAAAAGAAAACGAATGACTGACCCTACACGACGATT

CTGA

ΔCD19 amino acid sequence,
                                              SEQ ID NO: 81
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRF*
```

Example 6: Materials and Methods

Methods herein discuss the use of an inducible MyD88/CD40 construct, but may also be used for the non-inducible MyD88/CD40 chimeric stimulating molecules with appropriate modifications.

Cell Lines, Media and Reagents. 293T (HEK 293T/17) and Capan-1, Raji, and Daudi cell lines were obtained from the American Type Culture Collection. Cell lines were maintained in DMEM (Invitrogen, Grand Island, N.Y.) supplemented with 10% fetal calf serum (FCS) and 2 mM GLUTAMAX (Invitrogen) at 37° C. and 5% $CO_2$. T cells generated from peripheral blood mononuclear cells (PBMC) were cultured in 45% RPMI 1640, 45% Click's media (Invitrogen) supplemented with 10% fetal bovine serum (FBS), 2 mM GLUTAMAX (T cell media; TCM) and 100 U/ml IL-2 (Miltenyi Biotec), unless otherwise noted. Clinical grade AP1903 was diluted in ethanol to a 100 mM working solution for in vitro assays, or 0.9% saline for animal studies.

Retroviral and Plasmid Constructs.

Inducible MyD88/CD40 (iMC) comprising the myristoylation targeting sequence (M) (20), the TLR adaptor molecule MyD88, the CD40 cytoplasmic region, and 2 tandem ligand-binding FKBP12v36 domains (Fv'Fv) were cloned in-frame with 2A-ΔCD19 in the SFG retroviral backbone using Gibson assembly (New England Biolabs, Ipswich, Mass.) to generate SFG-M.MyD88/CD40.Fv'Fv-2A-ΔCD19. Similarly, a control vector was generated that contained only the myristoylation sequence and tandem FKBP12v36 binding domains (SFG-M.Fv'Fv-2A-ΔCD19). Additional retroviral vectors were constructed using a synthetic DNA approach (Integrated DNA Technologies, San Diego, Calif.) to generate MyD88 or CD40 only constructs, termed SFG-M.MyD88.Fv'.Fv-2A-ΔCD19 or SFG-M.CD40.Fv'.Fv-2A-ΔCD19, respectively. Two first generation CARs recognizing CD19 or PSCA were synthesized. The CD19 CAR was designed using the anti-CD19 single chin fragment variable (scFv), FMC63, while PSCA recognition was achieved using the murine scFv bm2B3. Both CARs included the IgG1 CH2CH3 spacer region, the CD28 transmembrane domain and CD3ζ cytoplasmic domain (PSCA.ζ) as discussed in Anurathapan et al., 2013 (13). A second generation CAR was constructed by PCR amplification that contained the CD28 transmembrane and cytoplasmic domain (PSCA.28.ζ). To generate a PSCA CAR that contained MC, MyD88/CD40 was synthesized and inserted 5' to CD3ζ (FIG. 3a). For co-culture assays, Capan-1 tumor cells were modified by PIGGYBAC transposase with a plasmid to express GFP (pIRII-GFP-2A-puromycin) and stably selected with 1 μg/ml puromycin.

Retroviral Supernatant.

Retroviral supernatants were produced by transient co-transfection of 293T cells with the SFG vector plasmid, Peg-Pam-e plasmid containing the sequence for MoMLV gag-pol and the RD114 plasmid encoding the RD114 envelope using GENEJUICE (EMD Biosciences, Gibbstown, N.J.) transfection reagent as recommended by the manufacturer as previously discussed (14) Supernatant containing the retrovirus was collected 48 and 72 hours after transfection.

Generation of Activated T Cells.

Using peripheral blood mononuclear cells (PBMC) obtained from the Gulf Coast Blood Bank (Houston, Tex.) anti-CD3/anti-CD28-activated T cells were generated essentially as previously provided (22). Briefly, $5 \times 10^6$ PBMC resuspended in TCM and stimulated on non-tissue culture-treated 24-well plates coated with 0.5 μg/ml each of anti-CD3 and anti-CD28 antibodies (Miltenyi Biotec) in the presence of 100 U/ml IL-2. On day 3, activated T cells were harvested and transduced with retrovirus vectors or expanded in media supplemented with IL-2 as discussed below.

Transduction of T Cells.

Non-tissue culture treated 24 well plates were coated with 7 μg/ml RETRONECTIN (Takara Bio, Otsu, Shiga, Japan) overnight at 4° C. The wells were washed with phosphate-buffered saline then coated with retroviral supernatant. Subsequently, activated T cells were plated at $3 \times 10^6$ cells per well in viral supernatant supplemented with 100 U/ml IL-2. After three days in culture, cells were harvested and expanded in tissue culture treated plates containing TCM plus 100 U/ml IL-2. For two or three-gene transductions, the protocol is identical to above except the wells were coated with equal amounts of each retroviral supernatant and activated T cells were then plated into each well containing equal amounts of viral supernatant supplemented with 100 U/ml IL-2.

Immunophenotyping.

Gene-modified T cells were analyzed for iMC transgene expression 10-14 days post-transduction by using CD3-PerCP.Cy5 and CD19-PE (BioLegend). To detect CAR-transduced cells, T cells were also stained with an Fc-specific monoclonal antibody conjugated to APC (Jackson ImmunoResearch Laboratories, West Grove, Pa.), which recognizes the IgG1 $CH_2CH_3$ component of the receptor. All flow cytometry was performed using an LSRII flow cytometer (Becton Dickenson, East Rutherford, N.J.), and the data analyzed using FLOWJO (Tree star, Ashland, Oreg.).

Cytokine and Chemokine Production.

Production of IFN-γ, IL-2 and IL-6 by T cells modified with iMC, control vectors or CAR-modified T cells were analyzed by ELISA per the manufacturer's protocol (eBioscience, San Diego, Calif.). In this assay, non-transduced T cells and iMC- or control vector-modified T cells were activated with 10 nM AP1903 or vehicle (EtOH), and supernatants collected at 48 hours. For analysis of CAR-modified T cells, T cells were cocultured with Capan-1 tumor cells at 1:1 T cell to tumor cell ratios and supernatants were harvested at 24 and 48 hours.

Cytotoxicity assay. The specific cytotoxicity of CAR T cells against Capan-1 tumor cells was measured in 6 hour and 24 hour lactate dehydrogenase (LDH) assays per the manufacturer's recommendations (Clontech Laboratories, Mountain View, Calif.) using effector to target (E:T) ratios ranging from 10:1 to 0.5:1 and using Capan-1 as target cells.

Coculture Experiment.

To test the cytotoxicity, activation, proliferation and cytokine production following PSCA.ζ CAR activation, co-culture assays were performed co-culture assays with Capan-1-GFP tumor cells at E:T ratios of 10:1, 5:1, 1:1, 1:5 and 1:10 in TCM in the absence of exogenous IL-2. After 7 days, all residual cells were collected by trypsinization, counted and stained with CD3 and Fc-specific antibodies and analyzed by flow cytometry. In addition, similar co-culture experiments were performed using CD19 CAR with and without MC costimulation. CAR-modified T cells were cultured for 7 days with CD19+ Raji or Daudi cell lines and subsequently analyzed by flow cytometry for $CD3^+$ and $CD19^+$ cells.

Statistics.

Data are represented as mean±SEM. Data were analyzed using unpaired Student's t test to calculate 2-tailed or 1-tailed P values to determine statistical significance in differences when comparing 2 treatment groups in all assays. Data were analyzed using GraphPad Prism version 5.0 software (GraphPad).

Example 7: Activation of Primary T Cells with Inducible MyD88, CD40, or MyD88/CD40

Methods herein discuss the use of an inducible MyD88/CD40 construct, and the synergy obtained when both MyD88 and CD40 polypeptides are combined into one chimeric stimulating molecule. These methods may also be used for the non-inducible MyD88/CD40 chimeric stimulating molecules with appropriate modifications.

In a parallel study, it was observed that a novel costimulating molecule, iMC, can provide controlled costimulation to T cells. To examine whether MyD88, CD40 or both molecules should be included as endodomains in potential CAR constructs, four distinct vectors were designed containing the AP1903-binding domains only (Fv'Fv), or genetically fused with MyD88 (iMyD88), CD40 (iCD40) or with both MyD88 and CD40 (iMC) (FIG. 3a). CD3/CD28-activated T cells were transduced, and the transduction efficiency of each of the vectors was measured by flow cytometric detection of CD19 on the surface of CD3 T cells ($CD3^+CD19^+$), showing that each of the retroviruses were sufficiently expressed in primary T cells (57%-95%) compared to non-transduced T cells (FIG. 3b). The ability of iMyD88, iCD40 or iMC to activate T cells following exposure to AP1903 by measuring IFN-γ and IL-6 production by ELISA was then assayed. It was observed that only iMC-transduced T cells produced significant quantities of both IFN-γ and IL-6 following AP1903 activation, whereas neither NT, iMyD88, nor iCD40 showed cytokine production (FIGS. 3c and d). These data suggest that MyD88 and CD40 synergize as activation signaling molecules in human T cells, and that a CAR molecule should benefit from inclusion of the composite MC signaling domain.

Expression of MyD88/CD40 Chimeric Antigen Receptors and Chimeric Stimulating Molecules The following examples discuss the compositions and methods relating to MyD88/CD40 chimeric antigen receptors and chimeric stimulating molecules, as provided in this application. Also included are compositions and methods related to a Caspase-9-based safety switch, and its use in cells that express the MyD88/CD40 chimeric antigen receptors or chimeric stimulating molecules.

Example 8: Design and Activity of MyD88/CD40 Chimeric Antigen Receptors

Design of MC-CAR Constructs

Based on the activation data from the inducible MyD88/CD40 experiments discussed herein, the potential of MC signaling in a CAR molecule in place of conventional endodomains (e.g., CD28 and 4-1BB) was examined. MC (without AP1903-binding FKBPv36 regions) was subcloned into the PSCA.ζ to emulate the position of the CD28 endodomain (FIG. 4a). Retrovirus was generated for each of the three constructs, transduced human T cells and subsequently measured transduction efficiency demonstrating that PSCA.MC.ζ could be expressed (FIGS. 4b and 4c). To confirm that T cells bearing each of these CAR constructs retained their ability to recognize $PSCA^+$ tumor cells, 6-hour cytotoxicity assays were performed, which showed lysis of Capan-1 target cells (FIG. 4d). Therefore, the addition of MC into the cytoplasmic region of a CAR molecule does not affect CAR expression or the recognition of antigen on target cells.

MC costimulation enhances T cell killing, proliferation and survival in CAR-modified T cells As demonstrated in short-term cytotoxicity assays, each of the three CAR designs showed the capacity to recognize and lyse Capan-1 tumor cells. Cytolytic effector function in effector T cells is mediated by the release of pre-formed granzymes and perforin following tumor recognition, and activation through CD3ζ is sufficient to induce this process without the need for costimulation. First generation CAR T cells (e.g., CARs constructed with only the CD3ζ cytoplasmic region) can lyse tumor cells; however, survival and proliferation is impaired due to lack of costimulation. Hence, the addition of CD28 or 4-1BB co-stimulating domains constructs has significantly improved the survival and proliferative capacity of CAR T cells.

To examine whether MC can similarly provide costimulating signals affecting survival and proliferation, coculture assays were performed with $PSCA^+$ Capan-1 tumor cells under high tumor:T cell ratios (1:1, 1:5, 1:10 T cell to tumor cell). When T cell and tumor cell numbers were equal (1:1), there was efficient killing of Capan-1-GFP cells from all three constructs compared to non-transduced control T cells (FIGS. 4a and b). However, when the CAR T cells were challenged with high numbers of tumor cells (1:10), there was a significant reduction of Capan-1-GFP tumor cells only when the CAR molecule contained either MC or CD28 (FIG. 4c).

To further examine the mechanism of costimulation by these two CARs cell viability and proliferation was assayed. PSCA CARs containing MC or CD28 showed improved survival compared to non-transduced T cells and the CD3ζ only CAR, and T cell proliferation by PSCA.MC.ζ and PSCA.28.ζ was significantly enhanced (FIGS. 4a and b). As other groups have shown that CARs that contain co-stimulating signaling regions produce IL-2, a key survival and growth molecule for T cells (4), ELISAs were performed on supernatants from CAR T cells challenged with Capan-1 tumor cells. Although PSCA.28.ζ produced high levels of IL-2, PSCA.MC.ζ signaling also produced significant levels of IL-2, which likely contributes to the observed T cell survival and expansion in these assays (FIG. 6c). Additionally, IL-6 production by CAR-modified T cells was examined, as IL-6 has been implicated as a key cytokine in the potency and efficacy of CAR-modified T cells (15). In contrast to IL-2, PSCA.MC.ζ produced higher levels of IL-6 compared to PSCA.28.ζ, consistent with the observations that iMC activation in primary T cells induces IL-6 (FIG. 6d.). Together, these data suggest that co-stimulation through MC produces similar effects to that of CD28, whereby following tumor cell recognition, CAR-modified T cells produce IL-2 and IL-6, which enhance T cell survival and expansion.

Immunotherapy using CAR-modified T cells holds great promise for the treatment of a variety of malignancies. While CARs were first designed with a single signaling domain (e.g., CD3ζ), (16-19) clinical trials evaluating the feasibility of CAR immunotherapy showed limited clinical benefit.(1,2,20,21) This has been primarily attributed to the incomplete activation of T cells following tumor recognition, which leads to limited persistence and expansion in vivo.(22) To address this deficiency, CARs have been engineered to include another stimulating domain, often derived from the cytoplasmic portion of T cell costimulating molecules including CD28, 4-1BB, OX40, ICOS and DAP10, (4,23-30) which allow CAR T cells to receive appropriate costimulation upon engagement of the target antigen. Indeed, clinical trials conducted with anti-CD19 CARs bearing CD28 or 4-1BB signaling domains for the treatment of refractory acute lymphoblastic leukemia (ALL) have demonstrated impressive T cell persistence, expansion and serial tumor killing following adoptive transfer. (6-8)

CD28 costimulation provides a clear clinical advantage for the treatment of CD19$^+$ lymphomas. Savoldo and colleagues conducted a CAR-T cell clinical trial comparing first (CD19.ζ) and second generation CARs (CD19.28.ζ) and found that CD28 enhanced T cell persistence and expansion following adoptive transfer.31 One of the principal functions of second generation CARs is the ability to produce IL-2 that supports T cell survival and growth through activation of the NFAT transcription factor by CD3ζ (signal 1), and NF-κB (signal 2) by CD28 or 4-1BB.32 This suggested other molecules that similarly activated NF-κB might be paired with the CD3ζ chain within a CAR molecule. Our approach has employed a T cell costimulating molecule that was originally developed as an adjuvant for a dendritic cell (DC) vaccine.(12,33) For full activation or licensing of DCs, TLR signaling is usually involved in the upregulation of the TNF family member, CD40, which interacts with CD40L on antigen-primed CD4$^+$ T cells. Because iMC was a potent activator of NF-κB in DCs, transduction of T cells with CARs that incorporated MyD88 and CD40 might provide the required costimulation (signal 2) to T cells, and enhance their survival and proliferation.

A set of experiments was performed to examine whether MyD88, CD40 or both components were required for optimum T cell stimulation using the iMC molecule. Remarkably, it was found that neither MyD88 nor CD40 could sufficiently induce T cell activation, as measured by cytokine production (IL-2 and IL-6), but when combined as a single fusion protein, could induce potent T cell activation (FIG. 3). A PSCA CAR incorporating MC was constructed and subsequently compared its function against a first (PSCA.) and second generation (PSCA.28.ζ) CAR. Here it was found that MC enhanced survival and proliferation of CAR T cells to a comparable level as the CD28 endodomain, suggesting that costimulation was sufficient (FIG. 4). While PSCA.MC.ζ CAR-transduced T cells produced lower levels of IL-2 than PSCA.28.ζ, the secreted levels were significantly higher than non-transduced T cells and T cells transduced with the PSCA.ζ CAR (FIG. 6). On the other hand, PSCA.MC.ζ CAR-transduced T cells secreted significantly higher levels of IL-6, an important cytokine associated with T cell activation, than PSCA.28.ζ transduced T cells, indicating that MC conferred unique properties to CAR function that may translate to improved tumor cell killing in vivo. While molecular analyses of the relevant signaling pathways still needs to be performed, these experiments indicate that MC can activate NF-κB (signal 2) following antigen recognition by the extracellular CAR domain.

FIG. 3. Design of inducible costimulating molecules and effect on T cell activation. A) Four vectors were designed incorporating FKBPv36 AP1903-binding domains (Fv'.Fv) alone, or with MyD88, CD40 or the MyD88/CD40 fusion protein. B) Transduction efficiency of primary activated T cells using CD3$^+$CD19$^+$ flow cytometric analysis. C) Analysis of IFN-γ production of modified T cells following activation with and without 10 nM AP1903. D) Analysis of IL-6 production of modified T cells following activation with and without 10 nM AP1903. * denotes a p value of <0.05.

FIG. 4. Design and functional validation of MC-CAR. A) Three PSCA CAR constructs were designed incorporating only CD3ζ, or with CD28 or MC endodomains. B) Transduction efficiency (percentage) was measured by anti-CAR-APC (recognizing the IgG1 $CH_2CH_3$ domain). C) Flow cytometry analysis demonstrating high transduction efficiency of T cells with PSCA.MC.ζ CAR. D) Analysis of specific lysis of PSCA$^+$ Capan-1 tumor cells by CAR-modified T cells in a 6 hour LDH release assay at a ratio of 1:1 T cells to tumor cells. * denotes a p value of <0.05.

FIG. 4. MC-CAR modified T cells kill Capan-1 tumor cells in long-term coculture assays. A) Flow cytometric analysis of CAR-modified and non-transduced T cells cultured with Capan-1-GFP tumor cells after 7 days in culture at a 1:1 ratio. Quantitation of viable GFP$^+$ cells by flow cytometry in coculture assays at a 1:1 (B) and 1:10 (C) T cell to tumor cell ratio. * denotes a p value of <0.05.

FIG. 6. MC and CD28 costimulation enhance T cell survival, proliferation and cytokine production. T cells isolated from 1:10 T cell to tumor cell coculture assays were assayed for cell viability (A) and cell number (B) to assess survival and proliferation in response to tumor cell exposure. Supernatants from coculture assays were subsequently measured for IL-2 (C) and IL-6 (D) production by ELISA. * denotes a p value of <0.05.

Apart from survival and growth advantages, MC-induced costimulation may also provide additional functions to CAR-modified T cells. Medzhitov and colleagues recently demonstrated that MyD88 signaling was critical for both Th1 and Th17 responses and that it acted via IL-1 to render CD4$^+$ T cells refractory to regulatory T cell (Treg)-driven inhibition.(34) Experiments with iMC show that IL-1α and β are secreted following AP1903 activation (data not shown). In addition, Martin et al demonstrated that CD40 signaling in CD8$^+$ T cells via Ras, PI3K and protein kinase C, result in NF-κB-dependent induction of cytotoxic mediators granzyme and perforin that lyse CD4+CD25+ Treg cells (35). Thus, MyD88 and CD40 co-activation may render CAR-T cells resistant to the immunosuppressive effects of Treg cells, a function that could be critically important in the treatment of solid tumors and other types of cancers.

In summary, MC can be incorporated into a CAR molecule and primary T cells transduced with retrovirus can express PSCA.MC.ζ without overt toxicity or CAR stability issues. Further, MC appears to provide similar costimulation to that of CD28, where transduced T cells show improved survival, proliferation and tumor killing compared to T cells transduced with a first generation CAR. Additional experiments to determine whether MC adds additional benefits to CARs, such as resistance to the inhibitory effects of Treg cells may be considered.

FIG. 10 provides an example of a plasmid map for a MyD88/CD40 chimeric antigen receptor.

Example 9: Chimeric Stimulating Molecules Co-Expressed in T Cells with CARS

A MyD88/CD40 chimeric stimulating molecule may also be expressed in a cell along with a CAR, which may, for example, comprise the scFv polypeptide, and the CD3-ζ chain. In this method, the CSM molecule is used in combination with a CAR, thereby segregating CAR signaling into two separate functions. This second function, provided by the CAR, provides antigen-specific cytotoxicity to the engineered T cells. For example, a CAR with specificity against PSMA may be expressed in T cells along with a MyD88/CD40 chimeric stimulating molecule. Also, the MyD88/CD40 CSM and the CAR portions may be transfected or transduced into the cells either on the same vector, in cis, or on separate vectors, in trans. Thus, the two polypeptides may be expressed using two nucleic acids, such as, for example, two plasmids or two viruses, and the T cells may be, for example, transfected twice, or in particular embodiments, the two nucleic acids may be co-transfected. In other embodiments, the two polypeptides may be expressed in one nucleic acid, such as, for example, in the same plasmid or virus. The nucleic acid may express the two polypeptides using two separate promoters, one for the CAR and one for the CSM. Or, in other embodiments, the two polypeptides may be expressed using the same promoter. In this embodiment, the two polypeptides may be separated by a cleavable polypeptide, such as, for example, a 2A sequence. The engineered T may, for example, be administered to a subject to generate a specific immune response, for example one directed against a prostate cancer tumor.

In some embodiments, the chimeric stimulating molecule does not comprise CD40. It is understood that the methods, constructs, polypeptide, and cells provided for the MyD88/CD40 chimeric stimulating molecules may be modified as necessary for expression and use of the MyD88 chimeric stimulating molecules.

MyD88/CD40 basal activity was found to be sufficient to stimulate a T cell which expresses a CD19-binding chimeric antigen receptor. The MyD88/CD40 vector used in the assay expressed a chimeric inducible MyD88/CD40 polypeptide, and was designed to be inducible by AP1903. In the absence of AP1903, there was sufficient basal activity to provide co-stimulation to the CD19-CAR following encounter with tumor cells.

Example of a MyD88/CD40 costimulating polypeptide co-expressed on the same vector as a chimeric antigen receptor SFG-Myr.MC.2A.CD19scFv.CD34e.CD8stm.zeta sequence
Myristoylation
SEQ ID NO: 82
atggggagtagcaagagcaagcctaaggaccccagccagcgc Myristoylation
SEQ ID NO: 83
MGSSKSKPKDPSQR Linker
SEQ ID: 84
ctcgac Linker
SEQ ID NO: 85
LD Truncated MyD88 lacking the TIR domain
SEQ ID NO: 86
atggctgcaggaggtcccggcgcggggtctgcggccccggtctcctccac atcctcccttccctggctgctctcaacatgcgagtgcggcgccgcctgt ctctgttcttgaacgtgcggacacaggtggcggccgactggaccgcgctg gcggaggagatggactttgagtacttggagatccggcaactggagacaca agcggacccactggcaggctgctggacgcctggcagggacgccctggcg cctctgtaggccgactgctcgatctgcttaccaagctgggccgcgacgac gtgctgctggagctgggacccagcattgaggaggattgccaaaagtatat cttgaagcagcagcaggaggaggctgagaagcctttacaggtggccgctg tagacagcagtgtcccacggacagcagagctggcgggcatcaccacactt gatgacccctggggcatatgcctgagcgtttcgatgccttcatctgcta ttgccccagcgacatc Truncated MyD88 lacking the TIR domain
SEQ ID NO: 87
MAAGGPGAGSAAPVSSTSSLPLAALNMRVRRRLSLFLNVRTQVAADWTAL

AEEMDFEYLEIRQLETQADPTGRLLDAWQGRPGASVGRLLDLLTKLGRDD

VLLELGPSIEEDCQKYILKQQQEEAEKPLQVAAVDSSVPRTAELAGITTL

DDPLGHMPERFDAFICYCPSDI

Linker
SEQ ID NO: 88
gtcgag

Linker
SEQ ID NO: 89
VE

CD40 without extracellular region
SEQ ID NO: 90
aaaaaggtggccaagaagccaaccaataaggccccccaccccaagcagga gccccaggagatcaattttcccgacgatcttcctggctccaacactgctg ctccagtgcaggagactttacatggatgccaaccggtcacccaggaggat ggcaaagagagtcgcatctcagtgcaggagacag CD40 without extracellular region -continued

KKVAKKPTNKAPHPKQEPQEINFPDDLPGSNTAAPVQETLHGCQPVTQED
GKESRISVQERQ

Linker
SEQ ID NO: 92
CCGCGG

Linker
SEQ ID NO: 93
PR

T2A sequence
SEQ ID NO: 94
GAAGGCCGAGGGAGCCTGCTGACATGTGGCGATGTGGAGGAAAACC
CAGGACCA T2A sequence
SEQ ID NO: 95
EGRGSLLTCGDVEENPGP Signal peptide
SEQ ID NO: 96
ATGGAGTTTGGACTTTCTTGGTTGTTTTTGGTGGCAATTCTGAAGGGTGT
CCAGTGTAGCAGG Signal peptide
SEQ ID NO: 97
MEFGLSWLFLVAILKGVQCSR FMC63 variable light chain
SEQ ID NO: 98
GACATCCAGATGACACAGACTACATCCTCCCTGTCTGCCTCTCTGGGAGA
CAGAGTCACCATCAGTTGCAGGGCAAGTCAGGACATTAGTAAATATTTAA
ATTGGTATCAGCAGAAACCAGATGGAACTGTTAAACTCCTGATCTACCAT
ACATCAAGATTACACTCAGGAGTCCCATCAAGGTTCAGTGGCAGTGGGTC
TGGAACAGATTATTCTCTCACCATTAGCAACCTGGAGCAAGAAGATATTG
CCACTTACTTTTGCCAACAGGGTAATACGCTTCCGTACACGTTCGGAGGG
GGGACTAAGTTGGAAATAACA FMC63 variable light chain
SEQ ID NO: 99
DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEIT Flexible linker
SEQ ID NO: 100
GGCGGAGGAAGCGGAGGTGGGGGC Flexible linker
SEQ ID NO: 101
GGGSGGGG FMC63 variable heavy chain
SEQ ID NO: 102
GAGGTGAAACTGCAGGAGTCAGGACCTGGCCTGGTGGCGCCCTCACAGAG
CCTGTCCGTCACATGCACTGTCTCAGGGGTCTCATTACCCGACTATGGTG
TAAGCTGGATTCGCCAGCCTCCACGAAAGGGTCTGGAGTGGCTGGGAGTA
ATATGGGGTAGTGAAACCACATACTATAATTCAGCTCTCAAATCCAGACT
GACCATCATCAAGGACAACTCCAAGAGCCAAGTTTTCTTAAAAATGAACA
GTCTGCAAACTGATGACACAGCCATTTACTACTGTGCCAAACATTATTAC
TACGGTGGTAGCTATGCTATGGACTACTGGGGTCAAGGAACCTCAGTCAC
CGTCTCCTCA FMC83 variable heavy chain:
SEQ ID NO: 103
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSS Linker
SEQ ID NO: 104
GGATCC Linker
SEQ ID NO: 105
GS CD34 minimal epitope
SEQ ID NO: 106
GAACTTCCTACTCAGGGGACTTTCTCAAACGTTAGCACAAACGTAAGT CD34 minimal epitope
SEQ ID NO: 107
ELPTQGTFSNVSTNVS CD8 α stalk domain
SEQ ID NO: 108
CCCGCCCCAAGACCCCCCACACCTGCGCCGACCATTGCTTCTCAACCCCT
GAGTTTGAGACCCGAGGCCTGCCGGCCAGCTGCCGGCGGGGCCGTGCATA
CAAGAGGACTCGATTTCGCTTGCGAC CD8 α stalk domain
SEQ ID NO: 109
PAPRPPTPAPTIASQPLSLRPEACRPAAGGAVHTRGLDFACD CD8 α transmembrane domain
SEQ ID NO: 110
ATCTATATCTGGGCACCTCTCGCTGGCACCTGTGGAGTCCTTCTGCTCAG
CCTGGTTATTACTCTGTACTGTAATCACCGGAATCGCCGCCGCGTTTGTA
AGTGTCCCAGG CD8 α transmembrane domain
SEQ ID NO: 111
IYIWAPLAGTCGVLLLSLVITLYCNHRNRRRVCKCPR Linker
SEQ ID NO: 112
GTCGAC Linker
SEQ ID NO: 113
VD CD3 zeta
SEQ ID NO: 114
AGAGTGAAGTTCAGCAGGAGCGCAGACGCCCCCGCGTACCAGCAGGGCCA
GAACCAGCTCTATAACGAGCTCAATCTAGGACGAAGAGAGGAGTACGATG
TTTTGGACAAGAGACGTGGCCGGGACCCTGAGATGGGGGGAAAGCCGAGA
AGGAAGAACCCTCAGGAAGGCCTGTACAATGAACTGCAGAAAGATAAGAT
GGCGGAGGCCTACAGTGAGATTGGGATGAAAGGCGAGCGCCGGAGGGGCA
AGGGGCACGATGGCCTTTACCAGGGTCTCAGTACAGCCACCAAGGACACC
TACGACGCCCTTCACATGCAGGCCCTGCCCCCTCGC CD3 zeta -continued

SEQ ID NO: 115
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

Example 10: References

The following references are cited in, or provide additional information that may be relevant.
1. Till B G, Jensen M C, Wang J, et al: CD20-specific adoptive immunotherapy for lymphoma using a chimeric antigen receptor with both CD28 and 4-1BB domains: pilot clinical trial results. Blood 119:3940-50, 2012.
2. Pule M A, Savoldo B, Myers G D, et al: Virus-specific T cells engineered to coexpress tumor-specific receptors: persistence and antitumor activity in individuals with neuroblastoma. Nat Med 14:1264-70, 2008.
3. Kershaw M H, Westwood J A, Parker L L, et al: A phase I study on adoptive immunotherapy using gene-modified T cells for ovarian cancer. Clin Cancer Res 12:6106-15, 2006.
4. Carpenito C, Milone M C, Hassan R, et al: Control of large, established tumor xenografts with genetically retargeted human T cells containing CD28 and CD137 domains. Proc Natl Acad Sci USA 106:3360-5, 2009.
5. Song D G, Ye Q, Poussin M, et al: CD27 costimulation augments the survival and antitumor activity of redirected human T cells in vivo. Blood 119:696-706, 2012.
6. Kalos M, Levine B L, Porter D L, et al: T cells with chimeric antigen receptors have potent antitumor effects and can establish memory in patients with advanced leukemia. Sci Transl Med 3:95ra73, 2011.
7. Porter D L, Levine B L, Kalos M, et al: Chimeric antigen receptor-modified T cells in chronic lymphoid leukemia. N Engl J Med 365:725-33, 2011.
8. Brentjens R J, Davila M L, Riviere I, et al: CD19-targeted T cells rapidly induce molecular remissions in adults with chemotherapy-refractory acute lymphoblastic leukemia. Sci Transl Med 5:177ra38, 2013.
9. Pule M A, Straathof K C, Dotti G, et al: A chimeric T cell antigen receptor that augments cytokine release and supports clonal expansion of primary human T cells. Mol Ther 12:933-41, 2005.
10. Finney H M, Akbar A N, Lawson A D: Activation of resting human primary T cells with chimeric receptors: costimulation from CD28, inducible costimulator, CD134, and CD137 in series with signals from the TCR zeta chain. J Immunol 172:104-13, 2004.
11. Guedan S, Chen X, Madar A, et al: ICOS-based chimeric antigen receptors program bipolar TH17/TH1 cells. Blood, 2014.
12. Narayanan P, Lapteva N, Seethammagari M, et al: A composite MyD88/CD40 switch synergistically activates mouse and human dendritic cells for enhanced antitumor efficacy. J Clin Invest 121:1524-34, 2011.
13. Anurathapan U, Chan R C, Hindi H F, et al: Kinetics of tumor destruction by chimeric antigen receptor-modified T cells. Mol Ther 22:623-33, 2014.
14. Craddock J A, Lu A, Bear A, et al: Enhanced tumor trafficking of GD2 chimeric antigen receptor T cells by expression of the chemokine receptor CCR2b. J Immunother 33:780-8, 2010.
15. Lee D W, Gardner R, Porter D L, et al: Current concepts in the diagnosis and management of cytokine release syndrome. Blood 124:188-95, 2014.
16. Becker M L, Near R, Mudgett-Hunter M, et al: Expression of a hybrid immunoglobulin-T cell receptor protein in transgenic mice. Cell 58:911-21, 1989.
17. Goverman J, Gomez S M, Segesman K D, et al: Chimeric immunoglobulin-T cell receptor proteins form functional receptors: implications for T cell receptor complex formation and activation. Cell 60:929-39, 1990.
18. Gross G, Waks T, Eshhar Z: Expression of immunoglobulin-T-cell receptor chimeric molecules as functional receptors with antibody-type specificity. Proc Natl Acad Sci USA 86:10024-8, 1989.
19. Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
20. Jensen M C, Popplewell L, Cooper L J, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
21. Park J R, Digiusto D L, Slovak M, et al: Adoptive transfer of chimeric antigen receptor re-directed cytolytic T lymphocyte clones in patients with neuroblastoma. Mol Ther 15:825-33, 2007.
22. Ramos C A, Dotti G: Chimeric antigen receptor (CAR)-engineered lymphocytes for cancer therapy. Expert Opin Biol Ther 11:855-73, 2011.
23. Finney H M, Lawson A D, Bebbington C R, et al: Chimeric receptors providing both primary and costimulatory signaling in T cells from a single gene product. J Immunol 161:2791-7, 1998.
24. Hombach A, Weczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
25. Maher J, Brentjens R J, Gunset G, et al: Human T-lymphocyte cytotoxicity and proliferation directed by a single chimeric TCRzeta/CD28 receptor. Nat Biotechnol 20:70-5, 2002.
26. Imai C, Mihara K, Andreansky M, et al: Chimeric receptors with 4-1BB signaling capacity provoke potent cytotoxicity against acute lymphoblastic leukemia. Leukemia 18:676-84, 2004.
27. Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
28. Zhao Y, Wang Q J, Yang S, et al: A herceptin-based chimeric antigen receptor with modified signaling domains leads to enhanced survival of transduced T lymphocytes and antitumor activity. J Immunol 183:5563-74, 2009.
29. Milone M C, Fish J D, Carpenito C, et al: Chimeric receptors containing CD137 signal transduction domains mediate enhanced survival of T cells and increased anti-leukemic efficacy in vivo. Mol Ther 17:1453-64, 2009.
30. Yvon E, Del Vecchio M, Savoldo B, et al: Immunotherapy of metastatic melanoma using genetically engineered GD2-specific T cells. Clin Cancer Res 15:5852-60, 2009.

31. Savoldo B, Ramos C A, Liu E, et al: CD28 costimulation improves expansion and persistence of chimeric antigen receptor-modified T cells in lymphoma patients. J Clin Invest 121:1822-6, 2011.
32. Kalinski P, Hilkens C M, Wierenga E A, et al: T-cell priming by type-1 and type-2 polarized dendritic cells: the concept of a third signal. Immunol Today 20:561-7, 1999.
33. Kemnade J O, Seethammagari M, Narayanan P, et al: Off-the-shelf Adenoviral-mediated Immunotherapy via Bicistronic Expression of Tumor Antigen and iMyD88/CD40 Adjuvant. Mol Ther, 2012.
34. Schenten D, Nish S A, Yu S, et al: Signaling through the adaptor molecule MyD88 in CD4+ T cells is required to overcome suppression by regulatory T cells. Immunity 40:78-90, 2014.
35. Martin S, Pahari S, Sudan R, et al: CD40 signaling in CD8+CD40+ T cells turns on contra-T regulatory cell functions. J Immunol 184:5510-8, 2010.

Example 11: Expression of MyD88/CD40 Costimulating Molecules in T Cell-Receptor-Expressing Cells and Tumor Infiltrating Lymphocytes The modified cells that express the MyD88/CD40 costimulating molecules provided herein may also express a T cell receptor. In these examples, the T cell receptor may be endogenous to the cell, or may be provided to the cell through transfection or transformation with a nucleic acid comprising a polynucleotide encoding a T cell receptor. In certain examples, the T cell receptor may be expressed on the same nucleic acid vector as the MyD88/CD40 costimulating molecule. In further examples, the T cell receptor may be expressed on the same nucleic acid vector as a chimeric inducible Caspase-9 molecule. Methods provided herein for constructing vectors which co-express, or separately express a chimeric antigen receptor, MyD88/CD40 costimulating molecule, or inducible Caspase-9 molecule, may be modified as appropriate for co-expression or separate expression of the T cell receptor, MyD88/CD40 costimulating molecule, or inducible Caspase-9 molecule. In some examples, the modified cells are tumor infiltrating lymphocytes.

Example 12: Selective Apoptosis of the Modified Cells

The modified cells may be provided with a mechanism to remove some, or all of the cells if the patient experiences negative effects, and there is a need to reduce, or stop treatment. These cells may be used for all CSM- or CAR-expressing modified T cells, or the cells may be provided with this ability where the CAR is directed against antigens that have previously caused, or are at risk to cause, lethal on-target, off-organ toxicity, where there is a need for an option to rapidly terminate therapy.

An example of a chimeric polypeptide that may be expressed in the modified cells is provided in FIG. 7. In this example, a single polypeptide is encoded by the nucleic acid vector. The inducible Caspase-9 polypeptide is separated from the CAR polypeptide during translation, due to skipping of a peptide bond. (Donnelly, M L 2001, J. Gen. Virol. 82:1013-25).

Vector Construction and Confirmation of Expression

A safety switch that can be stably and efficiently expressed in human T cells is presented herein. Expression vectors suitable for use as a therapeutic agent were constructed that included a modified human Caspase-9 activity fused to a human FK506 binding protein (FKBP), such as, for example, FKBP12v36. The Caspase-9/FKBP12 hybrid activity can be dimerized using a small molecule pharmaceutical. Full length, truncated, and modified versions of the Caspase-9 activity were fused to the ligand binding domain, multimerizing, dimerizing, dimerization, or multimerization region, and inserted into the retroviral vector MSCV.IRES-.GRP, which also allows expression of the fluorescent marker, GFP.

The full-length inducible Caspase-9 molecule (F'-F-C-Casp9) includes 2, 3, or more FK506 binding proteins (FKBPs—for example, FKBP12v36 variants) linked with a Ser-Gly-Gly-Gly-Ser-Gly linker (SEQ ID NO: 119) to the small and large subunit of the caspase molecule. Full-length inducible Caspase-9 (F'F—C-Casp9.I.GFP) has a full-length Caspase-9, also includes a caspase recruitment domain (CARD; GenBank NM001 229) linked to 2 12-kDa human FK506 binding proteins (FKBP12; GenBank AH002 818) that contain an F36V mutation. The amino acid sequence of one or more of the FKBPs (F') was codon-wobbled (e.g., the 3rd nucleotide of each amino acid codon was altered by a silent mutation that maintained the originally encoded amino acid) to prevent homologous recombination when expressed in a retrovirus. F'F—C-Casp9C3S includes a cysteine to serine mutation at position 287 that disrupts its activation site. In constructs F'F-Casp9, F—C—Casp9, and F'-Casp9, either the caspase activation domain (CARD), one FKBP, or both, were deleted, respectively. All constructs were cloned into MSCV.IRES.GFP as EcoRI-XhoI fragments. Coexpression of the inducible Caspase-9 constructs of the expected size with the marker gene GFP in transfected 293T cells was demonstrated by Western blot using a Caspase-9 antibody specific for amino acid residues 299-318, present both in the full-length and truncated caspase molecules as well as a GFP-specific antibody.

An initial screen indicated that the full length iCasp9 could not be maintained stably at high levels in T cells, possibly due to transduced cells being eliminated by the basal activity of the transgene. The CARD domain is involved in physiologic dimerization of Caspase-9 molecules, by a cytochrome C and adenosine triphosphate (ATP)-driven interaction with apoptotic protease-activating factor 1 (Apaf-1). Because of the use of a CID to induce dimerization and activation of the suicide switch, the function of the CARD domain is superfluous in this context and removal of the CARD domain was investigated as a method of reducing basal activity.

Using the iCasp9 Suicide Gene to Improve the Safety of Allodepleted T Cells after Haploidentical Stem Cell Transplantation Presented in this example are expression constructs and methods of using the expression constructs to improve the safety of allodepleted T cells after haploidentical stem cell transplantation. Similar methods may be used to express the Caspase-9 expression constructs in non allodepleted cells. A retroviral vector encoding iCasp9 and a selectable marker (truncated CD19) was generated as a safety switch for donor T cells. Even after allodepletion (using anti-CD25 immunotoxin), donor T cells could be efficiently transduced, expanded, and subsequently enriched by CD19 immunomagnetic selection to >90% purity. The engineered cells retained anti-viral specificity and functionality, and contained a subset with regulatory phenotype and function. Activating iCasp9 with a small-molecule dimerizer rapidly produced >90% apoptosis. Although transgene expression was downregulated in quiescent T cells, iCasp9 remained an efficient suicide gene, as expression was rapidly upregulated in activated (alloreactive) T cells.

Materials and Methods

Generation of Allodepleted T Cells

Allodepleted cells were generated from healthy volunteers as previously presented. Briefly, peripheral blood mononuclear cells (PBMCs) from healthy donors were co-cultured with 30 Gy-irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that expressed CD25 were depleted from the co-culture by overnight incubation in RFTS-SMPT-dgA immunotoxin. Allodepletion was considered adequate if the residual $CD3^+CD25^+$ population was <1% and residual proliferation by 3H-thymidine incorporation was <10%.

Plasmid and Retrovirus

SFG.iCasp9.2A.CD19 consists of inducible Caspase-9 (iCasp9) linked, via a cleavable 2A-like sequence, to truncated human CD19. iCasp9 consists of a human FK506-binding protein (FKBP12; GenBank AH002 818) with an F36V mutation, connected via a Ser-Gly-Gly-Gly-Ser-Gly linker (SEQ ID NO: 119) to human Caspase-9 (CASP9; GenBank NM 001229). The F36V mutation increases the binding affinity of FKBP12 to the synthetic homodimerizer, AP20187 or AP1903. The caspase recruitment domain (CARD) has been deleted from the human Caspase-9 sequence because its physiological function has been replaced by FKBP12, and its removal increases transgene expression and function. The 2A-like sequence encodes an 20 amino acid peptide from *Thosea asigna* insect virus, which mediates >99% cleavage between a glycine and terminal proline residue, resulting in 19 extra amino acids in the C terminus of iCasp9, and one extra proline residue in the N terminus of CD19. CD19 consists of full-length CD19 (GenBank NM 001770) truncated at amino acid 333 (TDP-TRRF) (SEQ ID NO: 286), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus was made by transiently transfecting Phoenix Eco cell line (ATCC product #SD3444; ATCC, Manassas, Va.) with SFG.iCasp9.2A.CD19. This produced Eco-pseudotyped retrovirus. The PG13 packaging cell line (ATCC) was transduced three times with Eco-pseudotyped or retrovirus to generate a producer line that contained multiple SFG.iCasp9.2A.CD19 proviral integrants per cell. Single cell cloning was performed, and the PG13 clone that produced the highest titer was expanded and used for vector production.

Retroviral Transduction

Culture medium for T cell activation and expansion consisted of 45% RPMI 1640 (Hyclone, Logan, Utah), 45% Clicks (Irvine Scientific, Santa Ana, Calif.) and 10% fetal bovine serum (FBS; Hyclone). Allodepleted cells were activated by immobilized anti-CD3 (OKT3; Ortho Biotech, Bridgewater, N.J.) for 48 hours before transduction with retroviral vector Selective allodepletion was performed by co-culturing donor PBMC with recipient EBV-LCL to activate alloreactive cells: activated cells expressed CD25 and were subsequently eliminated by anti-CD25 immunotoxin. The allodepleted cells were activated by OKT3 and transduced with the retroviral vector 48 hours later. Immunomagnetic selection was performed on day 4 of transduction; the positive fraction was expanded for a further 4 days and cryopreserved.

In small-scale experiments, non-tissue culture-treated 24-well plates (Becton Dickinson, San Jose, Calif.) were coated with OKT3 1 g/ml for 2 to 4 hours at 37° C. Allodepleted cells were added at $1 \times 10^6$ cells per well. At 24 hours, 100 U/ml of recombinant human interleukin-2 (IL-2) (PROLEUKIN; Chiron, Emeryville, Calif.) was added. Retroviral transduction was performed 48 hours after activation. Non-tissue culture-treated 24-well plates were coated with 3.5 µg/cm2 recombinant fibronectin fragment (CH-296; RETRONECTIN; Takara Mirus Bio, Madison, Wis.) and the wells loaded twice with retroviral vector-containing supernatant at 0.5 ml per well for 30 minutes at 37° C., following which OKT3-activated cells were plated at $5 \times 10^5$ cells per well in fresh retroviral vector-containing supernatant and T cell culture medium at a ratio of 3:1, supplemented with 100 U/ml IL-2. Cells were harvested after 2 to 3 days and expanded in the presence of 50 U/ml IL-2.

Scaling-Up Production of Gene-Modified Allodepleted Cells

Scale-up of the transduction process for clinical application used non-tissue culture-treated T75 flasks (Nunc, Rochester, N.Y.), which were coated with 10 ml of OKT3 1 µg/ml or 10 ml of fibronectin 7 µg/ml at 4° C. overnight. Fluorinated ethylene propylene bags corona-treated for increased cell adherence (2PF-0072AC, American Fluoroseal Corporation, Gaithersburg, Md.) were also used. Allodepleted cells were seeded in OKT3-coated flasks at $1 \times 10^6$ cells/ml. 100 U/ml IL-2 was added the next day. For retroviral transduction, RETRONECTIN-coated flasks or bags were loaded once with 10 ml of retrovirus-containing supernatant for 2 to 3 hours. OKT3-activated T cells were seeded at $1 \times 10^6$ cells/ml in fresh retroviral vector-containing medium and T cell culture medium at a ratio of 3:1, supplemented with 100 U/ml IL-2. Cells were harvested the following morning and expanded in tissue-culture treated T75 or T175 flasks in culture medium supplemented with between about 50 to 100 U/ml IL-2 at a seeding density of between about $5 \times 10^5$ cells/ml to $8 \times 10^5$ cells/ml.

CD19 Immunomagnetic Selection

Immunomagnetic selection for CD19 was performed 4 days after transduction. Cells were labeled with paramagnetic microbeads conjugated to monoclonal mouse anti-human CD19 antibodies (Miltenyi Biotech, Auburn, Calif.) and selected on MS or LS columns in small scale experiments and on a CLINIMACS-PLUS automated selection device in large scale experiments. CD19-selected cells were expanded for a further 4 days and cryopreserved on day 8 post transduction. These cells were referred to as "gene-modified allodepleted cells".

Immunophenotyping and Pentamer Analysis

Flow cytometric analysis (FACSCALIBUR and CELLQUEST software; Becton Dickinson) was performed using the following antibodies: CD3, CD4, CD8, CD19, CD25, CD27, CD28, CD45RA, CD45RO, CD56 and CD62L. CD19-PE (Clone 4G7; Becton Dickinson) was found to give optimum staining and was used in all subsequent analysis. A Non-transduced control was used to set the negative gate for CD19. An HLA-pentamer, HLA-B8-RAKFKQLL ("RAKFKQLL" disclosed as SEQ ID NO: 287) (Proimmune, Springfield, Va.) was used to detect T cells recognizing an epitope from EBV lytic antigen (BZLF1). HLA-A2-NLVPMVATV pentamer ("NLVPMVATV" disclosed as SEQ ID NO: 288) was used to detect T cells recognizing an epitope from CMV-pp65 antigen.

Induction of Apoptosis with Chemical Inducer of Dimerization, AP20187

Suicide gene functionality was assessed by adding a small molecule synthetic homodimerizer, AP20187 (Ariad Pharmaceuticals; Cambridge, Mass.), at 10 nM final concentration the day following CD19 immunomagnetic selection. AP1903 may also be used. Cells were stained with annexin V and 7-amino actinomycin (7-AAD) (BD Pharmingen) at 24 hours and analyzed by flow cytometry. Cells negative for both annexin V and 7-AAD were considered viable, cells that were annexin V positive were apoptotic, and cells that were both annexin V and 7-AAD positive were necrotic. The percentage killing induced by dimerization was corrected for baseline viability as follows: Percentage killing=100%−(% Viability in AP20187-treated cells÷% Viability in non-treated cells).

Assessment of Transgene Expression Following Extended Culture and Reactivation

Cells were maintained in T cell medium containing 50 U/ml IL-2 until 22 days after transduction. A portion of cells was reactivated on 24-well plates coated with 1 g/ml OKT3 and 1 µg/ml anti-CD28 (Clone CD28.2, BD Pharmingen, San Jose, Calif.) for 48 to 72 hours. CD19 expression and suicide gene function in both reactivated and non-reactivated cells were measured on day 24 or 25 post transduction.

In some experiments, cells also were cultured for 3 weeks post transduction and stimulated with 30G☐ irradiated allogeneic PBMC at a responder: stimulator ratio of 1:1. After 4 days of co-culture, a portion of cells was treated with 10 nM AP20187. Killing was measured by annexin V/7-AAD staining at 24 hours, and the effect of dimerizer on bystander virus-specific T cells was assessed by pentamer analysis on AP20187-treated and untreated cells.

Optimal culture conditions for maintaining the immunological competence of suicide gene-modified T cells must be determined and defined for each combination of safety switch, selectable marker and cell type, since phenotype, repertoire and functionality can all be affected by the stimulation used for polyclonal T cell activation, the method for selection of transduced cells, and duration of culture.

Phase I Clinical Trial of Allodepleted T Cells Transduced with Inducible Caspase-9 Suicide Gene after Haploidentical Stem Cell Transplantation This example presents results of a phase 1 clinical trial using an alternative suicide gene strategy. Briefly, donor peripheral blood mononuclear cells were co-cultured with recipient irradiated EBV-transformed lymphoblastoid cells (40:1) for 72 hrs., allodepleted with a CD25 immunotoxin and then transduced with a retroviral supernatant carrying the iCasp9 suicide gene and a selection marker (ΔCD19); ΔCD19 allowed enrichment to >90% purity via immunomagnetic selection.

An Example of a Protocol for Generation of a Cell Therapy Product is Provided Herein.

Source Material

Up to 240 ml (in 2 collections) of peripheral blood was obtained from the transplant donor according to established protocols. In some cases, dependent on the size of donor and recipient, a leukopheresis was performed to isolate sufficient T cells. 10-30 cc of blood also was drawn from the recipient and was used to generate the Epstein Barr virus (EBV)-transformed lymphoblastoid cell line used as stimulator cells. In some cases, dependent on the medical history and/or indication of a low B cell count, the LCLs were generated using appropriate 1st degree relative (e.g., parent, sibling, or offspring) peripheral blood mononuclear cells.

Generation of Allodepleted Cells

Allodepleted cells were generated from the transplant donors as presented herein. Peripheral blood mononuclear cells (PBMCs) from healthy donors were co-cultured with irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that express CD25 were depleted from the co-culture by overnight incubation in RFTS-SMPT-dgA immunotoxin. Allodepletion is considered adequate if the residual $CD3^+$ $CD25^+$ population was <1% and residual proliferation by 3H-thymidine incorporation was <10%.

Retroviral Production

A retroviral producer line clone was generated for the iCasp9-ΔCD19 construct. A master cell-bank of the producer also was generated. Testing of the master-cell bank was performed to exclude generation of replication competent retrovirus and infection by *Mycoplasma*, HIV, HBV, HCV and the like. The producer line was grown to confluency, supernatant harvested, filtered, aliquoted and rapidly frozen and stored at −80° C. Additional testing was performed on all batches of retroviral supernatant to exclude Replication Competent Retrovirus (RCR) and issued with a certificate of analysis, as per protocol.

Transduction of Allodepleted Cells

Allodepleted T-lymphocytes were transduced using Fibronectin. Plates or bags were coated with recombinant Fibronectin fragment CH-296 (RETRONECTIN, Takara Shuzo, Otsu, Japan). Virus was attached to RETRONECTIN by incubating producer supernatant in coated plates or bags. Cells were then transferred to virus coated plates or bags. After transduction allodepleted T cells were expanded, feeding them with IL-2 twice a week to reach the sufficient number of cells as per protocol.

CD19 Immunomagnetic Selection

Immunomagnetic selection for CD19 was performed 4 days after transduction. Cells are labeled with paramagnetic microbeads conjugated to monoclonal mouse anti-human CD19 antibodies (Miltenyi Biotech, Auburn, Calif.) and selected on a CLINIMACS PLUS automated selection device. Depending upon the number of cells required for clinical infusion cells were either cryopreserved after the CLINIMACS selection or further expanded with IL-2 and cryopreserved on day 6 or day 8 post transduction.

Freezing

Aliquots of cells were removed for testing of transduction efficiency, identity, phenotype and microbiological culture as required for final release testing by the FDA. The cells were cryopreserved prior to administration according to protocol.

Study Drugs

RFTS-SMPT-dgA

RFTS-SMPT-dgA is a murine IgG1 anti-CD25 (IL-2 receptor α chain) conjugated via a heterobifunctional crosslinker [N-succinimidyloxycarbonyl-α-methyl-d-(2-pyridylthio) toluene] (SMPT) to chemically deglycosylated ricin A chain (dgA). RFT5-SMPT-dgA is formulated as a sterile solution at 0.5 mg/ml.

Synthetic homodimerizer, AP1903

Mechanism of Action: AP1903-inducible cell death is achieved by expressing a chimeric protein comprising the pro-domain-deleted portion of human (Caspase-9) protein receptor, which signals apoptotic cell death, fused to a drug-binding domain derived from human FK506-binding protein (FKBP). This chimeric protein remains quiescent inside cells until administration of AP1903, which crosslinks the FKBP domains, initiating caspase signaling and apoptosis.

Toxicology: AP1903 has been evaluated as an Investigational New Drug (IND) by the FDA and has successfully completed a phase I clinical safety study. No significant adverse effects were noted when AP1903 was administered over a 0.01 mg/kg to 1.0 mg/kg dose range.

Pharmacology/Pharmacokinetics: Patients received 0.4 mg/kg of AP1903 as a 2 h infusion—based on published PK data which show plasma concentrations of 10 ng/mL-1275 ng/mL over the 0.01 mg/kg to 1.0 mg/kg dose range with plasma levels falling to 18% and 7% of maximum at 0.5 and 2 hrs post dose.

Side Effect Profile in Humans: No serious adverse events occurred during the Phase 1 study in volunteers. The incidence of adverse events was very low following each treatment, with all adverse events being mild in severity. Only one adverse event was considered possibly related to AP1903. This was an episode of vasodilatation, presented as "facial flushing" for 1 volunteer at the 1.0 mg/kg AP1903 dosage. This event occurred at 3 minutes after the start of infusion and resolved after 32 minutes duration. All other adverse events reported during the study were considered by the investigator to be unrelated or to have improbable relationship to the study drug. These events included chest pain, flu syndrome, halitosis, headache, injection site pain, vasodilatation, increased cough, rhinitis, rash, gum hemorrhage, and ecchymosis.

Patients developing grade 1 GvHD were treated with 0.4 mglkg AP1903 as a 2-hour infusion. Protocols for administration of AP1903 to patients grade 1 GvHD were established as follows. Patients developing GvHD after infusion of allodepleted T cells are biopsied to confirm the diagnosis and receive 0.4 mg/kg of AP1903 as a 2 h infusion. Patients with Grade I GvHD received no other therapy initially, however if they showed progression of GvHD conventional GvHD therapy was administered as per institutional guidelines. Patients developing grades 2-4 GvHD were administered standard systemic immunosuppressive therapy per institutional guidelines, in addition to the AP1903 dimerizer drug.

Instructions for preparation and infusion: AP1903 for injection is obtained as a concentrated solution of 2.33 ml in a 3 ml vial, at a concentration of 5 mg/mi, (i.e., 10.66 mg per vial). Prior to administration, the calculated dose was diluted to 100 ml in 0.9% normal saline for infusion. AP1903 for injection (0.4 mg/kg) in a volume of 100 ml was administered via IV infusion over 2 hours, using a non-DEHP, non-ethylene oxide sterilized infusion set and infusion pump.

The iCasp9 suicide gene expression construct (e.g., SFG.iCasp9.2A.ΔCD19) consists of inducible Caspase-9 (iCasp9) linked, via a cleavable 2A-like sequence, to truncated human CD19 (ΔCD19). iCasp9 includes a human FK506-binding protein (FKBP12; GenBank AH002 818) with an F36V mutation, connected via a Ser-Gly-Gly-Gly linker (SEQ ID NO: 289) to human Caspase-9 (CASP9; GenBank NM 001229). The F36V mutation may increase the binding affinity of FKBP12 to the synthetic homodimerizer, AP20187 or API903. The caspase recruitment domain (CARD) has been deleted from the human Caspase-9 sequence and its physiological function has been replaced by FKBP12. The replacement of CARD with FKBP12 increases transgene expression and function. The 2A-like sequence encodes an 18 amino acid peptide from *Thosea Asigna* insect virus, which mediates >99% cleavage between a glycine and terminal proline residue, resulting in 17 extra amino acids in the C terminus of iCasp9, and one extra proline residue in the N terminus of CD19. ΔCD19 consists of full length CD19 (GenBank NM 001770) truncated at amino acid 333 (TDPTRRF) (SEQ ID NO: 286), which shortens the intracytoplasmic domain from 242 to 19 amino acids, and removes all conserved tyrosine residues that are potential sites for phosphorylation.

In Vivo Studies

Three patients received iCasp9$^+$ T cells after haplo-CD34$^+$ stem cell transplantation (SCT), at dose levels between about $1\times10^6$ to about $3\times10^6$ cells/kg.

Infused T cells were detected in vivo by flow cytometry (CD3$^+$ ΔCD19$^+$) or qPCR as early as day 7 after infusion, with a maximum fold expansion of 170±5 (day 29±9 after infusion. Two patients developed grade I/II aGvHD and AP1903 administration caused >90% ablation of CD3$^+$ ΔCD19$^+$ cells, within 30 minutes of infusion, with a further log reduction within 24 hours, and resolution of skin and liver aGvHD within 24 hrs, showing that iCasp9 transgene was functional in vivo.

Ex vivo experiments confirmed this data. Furthermore, the residual allodepleted T cells were able to expand and were reactive to viruses (CMV) and fungi (*Aspergillus fumigatus*) (IFN-γ production). These in vivo studies found that a single dose of dimerizer drug can reduce or eliminate the subpopulation of T cells causing GvHD, but can spare virus specific CTLs, which can then re-expand.

Immune Reconstitution

Depending on availability of patient cells and reagents, immune reconstitution studies (Immunophenotyping, T and B cell function) may be obtained at serial intervals after transplant. Several parameters measuring immune reconstitution resulting from icaspase transduced allodepleted T cells will be analyzed. The analysis includes repeated measurements of total lymphocyte counts, T and CD19 B cell numbers, and FACS analysis of T cell subsets (CD3, CD4, CD8, CD16, CD19, CD27, CD28, CD44, CD62L, CCR7, CD56, CD45RA, CD45RO, alpha/beta and gamma/delta T cell receptors). Depending on the availability of a patients T cells T regulatory cell markers such as CD41CD251FoxP3 also are analyzed. Approximately 10-60 ml of patient blood is taken, when possible, 4 hours after infusion, weekly for 1 month, monthly×9 months, and then at 1 and 2 years. The amount of blood taken is dependent on the size of the recipient and does not exceed 1-2 cc/kg in total (allowing for blood taken for clinical care and study evaluation) at any one blood draw.

Modified Caspase-9 Polypeptides with Lower Basal Activity and Minimal Loss of Ligand IC50

Basal signaling, signaling in the absence of agonist or activating agent, is prevalent in a multitude of biomolecules. For example, it has been observed in more than 60 wild-type G protein coupled receptors (GPCRs) from multiple subfamilies [1], kinases, such as ERK and abl [2], surface immunoglobulins [3], and proteases. Basal signaling has been hypothesized to contribute to a vast variety of biological events, from maintenance of embryonic stem cell pluripotency, B cell development and differentiation [4-6], T cell differentiation [2, 7], thymocyte development [8], endocytosis and drug tolerance [9], autoimmunity [10], to plant growth and development [11]. While its biological significance is not always fully understood or apparent, defective basal signaling can lead to serious consequences. Defective basal G$_s$ protein signaling has led to diseases, such as retinitis pigmentosa, color blindness, nephrogenic diabetes insipidus, familial ACTH resistance, and familial hypocalciuric hypercalcemia [12, 13].

Even though homo-dimerization of wild-type initiator Caspase-9 is energetically unfavorable, making them mostly monomers in solution [14-16], the low-level inherent basal activity of unprocessed Caspase-9 [15, 17] is enhanced in the presence of the Apaf-1-based "apoptosome", its natural allosteric regulator [6]. Moreover, supra-physiological expression levels and/or co-localization could lead to proximity-driven dimerization, further enhancing basal activation. The modified cells of the present application may comprise nucleic acids coding for a chimeric Caspase-9 polypeptide having lower basal signaling activity. Examples of Caspase-9 mutants with lower basal signaling are provided in the table below. Polynucleotides comprising Caspase-9 mutants with lower basal signaling may be expressed in the modified cells used for cell therapy herein. In these examples, the modified cells may include a safety switch, comprising a polynucleotide encoding a lower basal signaling chimeric Caspase-9 polypeptide. In the event of an adverse event following administration of the modified cells comprising the chimeric stimulating molecules or chimeric antigen receptors herein, Caspase-9 activity may be induced by administering the dimerizer to the patient, thus inducing apoptosis and clearance of some, or all of the modified cells. In some examples, the amount of dimerizer administered may be determined as an amount designed to remove the highest amount, at least 80% or 90% of the modified cells. In other examples, the amount of dimerizer administered may be determined as an amount designed to remove only a portion of the modified cells, in order to alleviate negative symptoms or conditions, while leaving a sufficient amount of therapeutic modified cells in the patient, in order to continue therapy. Methods for using chimeric Caspase-9 polypeptides to induce apoptosis are discussed in PCT Application Number PCT/US2011/037381 by Malcolm K. Brenner et al., titled Methods for Inducing Selective Apoptosis, filed May 20, 2011, and in U.S. patent application Ser. No. 13/112,739 by Malcolm K. Brenner et al., titled Methods for Inducing Selective Apoptosis, filed May 20, 2011, issued Jul. 28, 2015 as U.S. Pat. No. 9,089,520. Chimeric caspase polypeptides having modified basal activity are discussed in PCT Application Serial Number PCT/US2014/022004 by David Spencer et al., titled Modified Caspase Polypeptides and Uses Thereof, filed Mar. 7, 2014, published Oct. 9, 2014 as WO2014/164348, and in U.S. patent application Ser. No. 13/792,135 by David Spencer et al., titled Modified Caspase Polypeptides and Uses Thereof, filed Mar. 7, 2014; and in U.S. patent application Ser. No. 14/640,553 by Spencer et al., filed Mar. 6, 2015. Methods for inducing partial apoptosis of the therapeutic modified cells are discussed in PCT Application Number PCT/US14/040964 by Kevin Slawin et al., titled Methods for Inducing Partial Apoptosis Using Caspase Polypeptides, filed Jun. 4, 2014, published Dec. 11, 2014 as WO2014/197638, and in U.S. patent application Ser. No. 14/296,404 by Kevin Slawin et al., titled Methods for Inducing Partial Apoptosis Using Caspase Polypeptides, filed Jun. 4, 2014. These patent applications and publications are all incorporated by reference herein in their entireties.

FIG. 10 provides a plasmid map for a MyD88/CD40 chimeric antigen receptor co-expressed with a Caspase-9 polypeptide. FIG. 11 provides a plasmid map of a chimeric antigen receptor co-expressed with a Caspase-9 polypeptide.

TABLE 1

Caspase Mutant Classes and Basal Activity

| Basal Activity | Homodimerization domain | Cleavage sites & XIAP Interaction | Phosphorylation | Double mutants, Misc. | Total mutants |
|---|---|---|---|---|---|
| Decreased basal and similar $IC_{50}$ |  |  | S144A S144D |  | 80 *, predicted |
|  |  | T317S | S196D |  |  |
| Decreased basal but higher $IC_{50}$ | N405Q | D330A | S183A | D330A-N405Q | Bold, Tested in T cells |
|  | $^{402}$GCFNF$^{406}$ISAQT (Casp-10) | D330E | S195A | D330A-S144A |  |
|  | F404Y | D330G | S196A | D330A-S144D |  |
|  | F406A | D330N |  | D330A-S183A |  |
|  | F406W | D330S |  | D330A-S196A |  |
|  | F406Y | D330V |  | N405Q-S144A |  |
|  | N405Qco | L329E |  | N405Q-S144D |  |
|  |  | T317A |  | N405Q-S196D |  |
|  |  |  |  | N405Q-T317S |  |
|  |  |  |  | *N405Q-S144Aco |  |
|  |  |  |  | *N405Q-T317Sco |  |
| Decreased basal but much higher $IC_{50}$ | F404T F404W N405F F406T | D315A A316G F319W | Y153A Y153F S307A |  |  |
| Similar basal and $IC_{50}$ | C403A | $^{316}$ATPF$^{319}$AVPI (SMAC/Diablo) |  |  |  |
|  | C403S | T317C |  |  |  |
|  | C403T | P318A |  |  |  |
|  | N405A | F319A |  |  |  |
| Increased basal | N405T | T317E F326K D327G D327K D327R Q328K Q328R |  | D330A-N405T |  |

TABLE 1-continued

Caspase Mutant Classes and Basal Activity

| Basal Activity | Homodimerization domain | Cleavage sites & XIAP Interaction | Phosphorylation | Double mutants, Misc. | Total mutants |
|---|---|---|---|---|---|
| Catalytically dead | $^{402}$GCFNF$^{406}$AAAAA<br>$^{402}$GCFNF$^{406}$YCSTL (Casp-2)<br>$^{402}$GCFNF$^{406}$CIVSM (Casp-3)<br>$^{402}$GCFNF$^{406}$QPTFT (Casp-8)<br>G402A<br>G402I<br>G402Q<br>G402Y<br>C403P<br>F404A<br>F404S<br>F406L | L329G<br>L329K<br>A331K | | C285A<br>D315A-D330A<br>D330A-Y153A<br>D330A-Y153F<br>D330A-T317E | |

Literature References Cited or Providing Additional Support to the Present Example 1. Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
2. Roose, J. P., et al., T cell receptor-independent basal signaling via Erk and Abl kinases suppresses RAG gene expression. PLoS Biol, 2003. 1(2): p. E53.
3. Tze, L. E., et al., Basal immunoglobulin signaling actively maintains developmental stage in immature B cells. PLoS Biol, 2005. 3(3): p. e82.
4. Schram, B. R., et al., B cell receptor basal signaling regulates antigen-induced Ig light chain rearrangements. J Immunol, 2008. 180(7): p. 4728-41.
5. Randall, K. L., et al., Dock8 mutations cripple B cell immunological synapses, germinal centers and long-lived antibody production. Nat Immunol, 2009. 10(12): p. 1283-91.
6. Kouskoff, V., et al., B cell receptor expression level determines the fate of developing B lymphocytes: receptor editing versus selection. Proc Natl Acad Sci USA, 2000. 97(13): p. 7435-9.
7. Hong, T., et al., A simple theoretical framework for understanding heterogeneous differentiation of CD4+ T cells. BMC Syst Biol, 2012. 6: p. 66.
8. Rudd, M. L., A. Tua-Smith, and D. B. Straus, Lck SH3 domain function is required for T-cell receptor signals regulating thymocyte development. Mol Cell Biol, 2006. 26(21): p. 7892-900.
9. Sorkin, A. and M. von Zastrow, Endocytosis and signaling: intertwining molecular networks. Nat Rev Mol Cell Biol, 2009. 10(9): p. 609-22.
10. Luning Prak, E. T., M. Monestier, and R. A. Eisenberg, B cell receptor editing in tolerance and autoimmunity. Ann N Y Acad Sci, 2011. 1217: p. 96-121.
11. Boss, W. F., et al., Basal signaling regulates plant growth and development. Plant Physiol, 2010. 154(2): p. 439-43.
12. Tao, Y. X., Constitutive activation of G protein-coupled receptors and diseases: insights into mechanisms of activation and therapeutics. Pharmacol Ther, 2008. 120(2): p. 129-48.
13. Spiegel, A. M., Defects in G protein-coupled signal transduction in human disease. Annu Rev Physiol, 1996. 58: p. 143-70.
14. Shiozaki, E. N., et al., Mechanism of XIAP-mediated inhibition of Caspase-9. Mol Cell, 2003. 11(2): p. 519-27.
15. Renatus, M., et al., Dimer formation drives the activation of the cell death protease Caspase-9. Proc Natl Acad Sci USA, 2001. 98(25): p. 14250-5.
16. Shi, Y., Mechanisms of Caspase activation and inhibition during apoptosis. Mol Cell, 2002. 9(3): p. 459-70.
17. Shiozaki, E. N., J. Chai, and Y. Shi, Oligomerization and activation of Caspase-9, induced by Apaf-1 CARD. Proc Natl Acad Sci USA, 2002. 99(7): p. 4197-202.
18. Straathof, K. C., et al., An inducible Caspase-9 safety switch for T-cell therapy. Blood, 2005. 105(11): p. 4247-54.
19. MacCorkle, R. A., K. W. Freeman, and D. M. Spencer, Synthetic activation of Caspases: artificial death switches. Proc Natl Acad Sci USA, 1998. 95(7): p. 3655-60.
20. Di Stasi, A., et al., Inducible apoptosis as a safety switch for adoptive cell therapy. N Engl J Med, 2011. 365(18): p. 1673-83.
21. Chang, W. C., et al., Modifying ligand-induced and constitutive signaling of the human 5-HT4 receptor. PLoS One, 2007. 2(12): p. e1317.
22. Bloom, J. D. and F. H. Arnold, In the light of directed evolution: pathways of adaptive protein evolution. Proc Natl Acad Sci USA, 2009. 106 Suppl 1: p. 9995-10000.
23. Boatright, K. M. and G. S. Salvesen, Mechanisms of Caspase activation. Curr Opin Cell Biol, 2003. 15(6): p. 725-31.
24. Boatright, K. M., et al., A unified model for apical Caspase activation. Mol Cell, 2003. 11(2): p. 529-41.
25. Chao, Y., et al., Engineering a dimeric Caspase-9: a re-evaluation of the induced proximity model for Caspase activation. PLoS Biol, 2005. 3(6): p. e183.
26. Stennicke, H. R., et al., Caspase-9 can be activated without proteolytic processing. J Biol Chem, 1999. 274(13): p. 8359-62.
27. Brady, S. C., L. A. Allan, and P. R. Clarke, Regulation of Caspase-9 through phosphorylation by protein kinase C zeta in response to hyperosmotic stress. Mol Cell Biol, 2005. 25(23): p. 10543-55.
28. Martin, M. C., et al., Protein kinase A regulates Caspase-9 activation by Apaf-1 downstream of cytochrome c. J Biol Chem, 2005. 280(15): p. 15449-55.
29. Cardone, M. H., et al., Regulation of cell death protease Caspase-9 by phosphorylation. Science, 1998. 282(5392): p. 1318-21.

30. Raina, D., et al., c-Abl tyrosine kinase regulates Caspase-9 autocleavage in the apoptotic response to DNA damage. J Biol Chem, 2005. 280(12): p. 11147-51.

31. Papworth, C., Bauer, J. C., Braman, J. and Wright, D. A., Site-directed mutagenesis in one day with >80% efficiency. Strategies, 1996. 9(3): p. 3-4.

32. Spencer, D. M., et al., Functional analysis of Fas signaling in vivo using synthetic inducers of dimerization. Curr Biol, 1996. 6(7): p. 839-47.

33. Hsiao, E. C., et al., Constitutive Gs activation using a single-construct tetracycline-inducible expression system in embryonic stem cells and mice. Stem Cell Res Ther, 2011. 2(2): p. 11.

34. Waldner, C., et al., Double conditional human embryonic kidney cell line based on FLP and PhiC31 mediated transgene integration. BMC Res Notes, 2011. 4: p. 420.

Example 13: MC Costimulation Enhances Function and Proliferation of CD19 CARs FIGS. 34 and 40 show the results of experiments similar to those discussed herein, using an antigen recognition moiety that recognizes the CD19 antigen. It is understood that the vectors provided herein may be modified to construct a MyD88/CD40 CAR construct that targets CD19+ tumor cells, which also incorporates an inducible Caspase-9 safety switch.

To examine whether MC costimulation functioned in CARs targeting other antigens, T cells were modified with either CD19.ζ or with CD19.MC.ζ. The cytotoxicity, activation and survival against CD19+ Burkitt's lymphoma cell lines (Raji and Daudi) of the modified cells were assayed. In coculture assays, T cells transduced with either CAR showed killing of CD19+ Raji cells at an effector to target ratio as low as 1:1 (FIGS. 21a and b). However, analysis of cytokine production from co-culture assays showed that CD19.MC.ζ transduced T cells produced higher levels of IL-2 and IL-6 compared to CD19. (FIGS. 21c and d), which is consistent with the costimulatory effects observed with iMC and PSCA CARs containing the MC signaling domain. Further, T cells transduced with CD19.MC.ζ showed enhanced proliferation following activation by Raji tumor cells (FIG. 21e). These data support earlier experiments demonstrating that MC signaling in CAR molecules improves T cell activation, survival and proliferation following ligation to a target antigen expressed on tumor cells.

pBP0526-SFG.iCasp9 wt.2A.CD19scFv.CD34e.CD8stm.MC.zeta (FIG. 22)

FKBPv36
SEQ ID NO: 116
ATGCTGGAGGGAGTGCAGGTGGAGACTATTAGCCCCGGAGATGGCAGAAC

ATTCCCCAAAAGAGGACAGACTTGCGTCGTGCATTATACTGGAATGCTGG

AAGACGGCAAGAAGGTGGACAGCAGCCGGGACCGAAACAAGCCCTTCAAG

TTCATGCTGGGGAAGCAGGAAGTGATCCGGGCTGGGAGGAAGGAGTCGC

ACAGATGTCAGTGGGACAGAGGGCCAAACTGACTATTAGCCCAGACTACG

CTTATGGAGCAACCGGCCACCCCGGGATCATTCCCCCTCATGCTACACTG

GTCTTCGATGTGGAGCTGCTGAAGCTGGAA

FKBPv36
SEQ ID NO: 117
MLEGVQVETISPGDGRTFPKRGQTCVVHYTGMLEDGKKVDSSRDRNKPFK

FMLGKQEVIRGWEEGVAQMSVGQRAKLTISPDYAYGATGHPGIIPPHATL

VFDVELLKLE

Linker
SEQ ID NO: 118
AGCGGAGGAGGATCCGGA

Linker
SEQ ID NO: 119
SGGGSG

Caspase-9
SEQ ID NO: 120
GTGGACGGGTTTGGAGATGTGGGAGCCCTGGAATCCCTGCGGGGCAATGC

CGATCTGGCTTACATCCTGTCTATGGAGCCTTGCGGCCACTGTCTGATCA

TTAACAATGTGAACTTCTGCAGAGAGAGCGGGCTGCGGACCAGAACAGGA

TCCAATATTGACTGTGAAAAGCTGCGGAGAAGGTTCTCTAGTCTGCACTT

TATGGTCGAGGTGAAAGGCGATCTGACCGCTAAGAAAATGGTGCTGGCCC

TGCTGGAACTGGCTCGGCAGGACCATGGGGCACTGGATTGCTGCGTGGTC

GTGATCCTGAGTCACGGCTGCCAGGCTTCACATCTGCAGTTCCCTGGGGC

AGTCTATGGAACTGACGGCTGTCCAGTCAGCGTGGAGAAGATCGTGAACA

TCTTCAACGGCACCTCTTGCCCAAGTCTGGGCGGAAGCCCAAACTGTTC

TTTATTCAGGCCTGTGGAGGCGAGCAGAAAGATCACGGCTTCGAAGTGGC

TAGCACCTCCCCCGAGGACGAATCACCTGGAAGCAACCCTGAGCCAGATG

CAACCCCCTTCCAGGAAGGCCTGAGGACATTTGACCAGCTGGATGCCATC

TCAAGCCTGCCCACACCTTCTGACATTTTCGTCTCTTACAGTACTTTCCC

TGGATTTGTGAGCTGGCGCGATCCAAAGTCAGGCAGCTGGTACGTGGAGA

CACTGGACGATATCTTTGAGCAGTGGGCCCATTCTGAAGACCTGCAGAGT

CTGCTGCTGCGAGTGGCCAATGCTGTCTCTGTGAAGGGGATCTACAAACA

GATGCCAGGATGCTTCAACTTTCTGAGAAAGAAACTGTTCTTTAAGACCT

CCGCATCTAGGGCC

Caspase-9
SEQ ID NO: 121
VDGFGDVGALESLRGNADLAYILSMEPCGHCLIINNVNFCRESGLRTRTG

SNIDCEKLRRRFSSLHFMVEVKGDLTAKKMVLALLELARQDHGALDCCVV

VILSHGCQASHLQFPGAVYGTDGCPVSVEKIVNIFNGTSCPSLGGKPKLF

FIQACGGEQKDHGFEVASTSPEDESPGSNPEPDATPFQEGLRTFDQLDAI

SSLPTPSDIFVSYSTFPGFVSWRDPKSGSWYVETLDDIFEQWAHSEDLQS

LLLRVANAVSVKGIYKQMPGCFNFLRKKLFFKTSASRA

Linker
SEQ ID NO: 122
CCGCGG

Linker
SEQ ID NO: 123
PR

-continued

T2A
SEQ ID NO: 124
GAAGGCCGAGGGAGCCTGCTGACATGTGGCGATGTGGAGGAAAACC

CAGGACCA

T2A
SEQ ID NO: 125
EGRGSLLTCGDVEENPGP

Linker
SEQ ID NO: 126
CCATGG

Linker
SEQ ID NO: 127
PW

Signal peptide
SEQ ID NO: 128
ATGGAGTTTGGACTTTCTTGGTTGTTTTTGGTGGCAATTCTGAAGGGTGT

CCAGTGTAGCAGG

Signal peptide
SEQ ID NO: 129
MEFGLSWLFLVAILKGVQCSR

FMC63 variable light chain (anti-CD19)
SEQ ID NO: 130
GACATCCAGATGACACAGACTACATCCTCCCTGTCTGCCTCTCTGGGAGA

CAGAGTCACCATCAGTTGCAGGGCAAGTCAGGACATTAGTAAATATTTAA

ATTGGTATCAGCAGAAACCAGATGGAACTGTTAAACTCCTGATCTACCAT

ACATCAAGATTACACTCAGGAGTCCCATCAAGGTTCAGTGGCAGTGGGTC

TGGAACAGATTATTCTCTCACCATTAGCAACCTGGAGCAAGAAGATATTG

CCACTTACTTTTGCCAACAGGGTAATACGCTTCCGTACACGTTCGGAGGG

GGGACTAAGTTGGAAATAACA

FMC63 variable light chain (anti CD19)
SEQ ID NO: 131
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

Flexible linker
SEQ ID NO: 132
GGCGGAGGAAGCGGAGGTGGGGGC

Flexible linker
SEQ ID NO: 133
GGGSGGGG

FMC63 variable heavy chain (anti-CD19)
SEQ ID NO: 134
GAGGTGAAACTGCAGGAGTCAGGACCTGGCCTGGTGGCGCCCTCACAGAG

CCTGTCCGTCACATGCACTGTCTCAGGGGTCTCATTACCCGACTATGGTG

TAAGCTGGATTCGCCAGCCTCCACGAAAGGGTCTGGAGTGGCTGGGAGTA

ATATGGGGTAGTGAAACCACATACTATAATTCAGCTCTCAAATCCAGACT

GACCATCATCAAGGACAACTCCAAGAGCCAAGTTTTCTTAAAAATGAACA

GTCTGCAAACTGATGACACAGCCATTTACTACTGTGCCAAACATTATTAC

TACGGTGGTAGCTATGCTATGGACTACTGGGGTCAAGGAACCCTCAGTCAC

CGTCTCCTCA

FMC63 variable heavy chain (anti CD19)
SEQ ID NO: 135
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

Linker
SEQ ID NO: 136
GGATCC

Linker
SEQ ID NO: 137
GS

CD34 minimal epitope
SEQ ID NO: 138
GAACTTCCTACTCAGGGGACTTTCTCAAACGTTAGCACAAACGTAAGT CD34 minimal epitope
SEQ ID NO: 139
ELPTQGTFSNVSTNVS CD8 α stalk domain
SEQ ID NO: 140
CCCGCCCCAAGACCCCCCACACCTGCGCCGACCATTGCTTCTCAACCCCT

GAGTTTGAGACCCGAGGCCTGCCGGCCAGCTGCCGGCGGGGCCGTGCATA

CAAGAGGACTCGATTTCGCTTGCGAC

CD8 α stalk domain
SEQ ID NO: 141
PAPRPPTPAPTIASQPLSLRPEACRPAAGGAVHTRGLDFACD

CD8 α transmembrane domain
SEQ ID NO: 142
ATCTATATCTGGGCACCTCTCGCTGGCACCTGTGGAGTCCTTCTGCTCAG

CCTGGTTATTACTCTGTACTGTAATCACCGGAATCGCCGCCGCGTTTGTA

AGTGTCCCAGG

CD8 α transmembrane domain
SEQ ID NO: 143
IYIWAPLAGTCGVLLLSLVITLYCNHRNRRRVCKCPR

Linker
SEQ ID NO: 144
GTCGAC

Linker
SEQ ID NO: 145
VD

Truncated MyD88 lacking the TIR domain
SEQ ID NO: 146
ATGGCCGCTGGGGGCCCAGGCGCCGGATCAGCTGCTCCCGTATCTTCTAC

TTCTTCTTTGCCGCTGGCTGCTCTGAACATGCGCGTGAGAAGACGCCTCT

CCCTGTTCCTTAACGTTCGCACACAAGTCGCTGCCGATTGGACCGCCCTT

GCCGAAGAAATGGACTTTGAATACCTGGAAATTAGACAACTTGAAACACA

GGCCGACCCCACTGGCAGACTCCTGGACGCATGGCAGGGAAGACCTGGTG

CAAGCGTTGGACGGCTCCTGGATCTCCTGACAAAACTGGGACGCGACGAC

GTACTGCTTGAACTCGGACCTAGCATTGAAGAAGACTGCCAAAAATATAT

CCTGAAACAACAACAAGAAGAAGCCGAAAAACCTCTCCAAGTCGCAGCAG

TGGACTCATCAGTACCCCGAACAGCTGAGCTTGCTGGGATTACTACACTC

GACGACCCACTCGGACATATGCCTGAAAGATTCGACGCTTTCATTTGCTA

TTGCCCCTCTGACATA

Truncated MyD88 lacking the TIR domain

SEQ ID NO: 147
MAAGGPGAGSAAPVSSTSSLPLAALNMRVRRRLSLFLNVRTQVAADWTAL

AEEMDFEYLEIRQLETQADPTGRLLDAWQGRPGASVGRLLDLLTKLGRDD

VLLELGPSIEEDCQKYILKQQQEEAEKPLQVAAVDSSVPRTAELAGITTL

DDPLGHMPERFDAFICYCPSDI

CD40 without the extracellular domain
SEQ ID NO: 148
AAGAAAGTTGCAAAGAAACCCACAAATAAAGCCCCACACCCTAAACAGGA

ACCCCAAGAAATCAATTTCCCAGATGATCTCCCTGGATCTAATACTGCCG

CCCCGGTCCAAGAAACCCTGCATGGTTGCCAGCCTGTCACCCAAGAGGAC

GGAAAAGAATCACGGATTAGCGTACAAGAGAGACAA

CD40 without the extracellular domain
SEQ ID NO: 149
KKVAKKPTNKAPHPKQEPQEINFPDDLPGSNTAAPVQETLHGCQPVTQED

GKESRISVQERQ

CD3 zeta
SEQ ID NO: 150
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta
SEQ ID NO: 151
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

Casp 9 (truncated) nucleotide sequence
SEQ ID NO: 152
GGATTTGGTGATGTCGGTGCTCTTGAGAGTTTGAGGGGAAATGCAGATTT

GGCTTACATCCTGAGCATGGAGCCCTGTGGCCACTGCCTCATTATCAACA

ATGTGAACTTCTGCCGTGAGTCCGGGCTCCGCACCCGCACTGGCTCCAAC

ATCGACTGTGAGAAGTTGCGGCGTCGCTTCTCCTCGCTGCATTTCATGGT

GGAGGTGAAGGGCGACCTGACTGCCAAGAAAATGGTGCTGGCTTTGCTGG

AGCTGGCGCAGCAGGACCACGGTGCTCTGGACTGCTGCGTGGTGGTCATT

CTCTCTCACGGCTGTCAGGCCAGCCACCTGCAGTTCCCAGGGGCTGTCTA

CGGCACAGATGGATGCCCTGTGTCGGTCGAGAAGATTGTGAACATCTTCA

ATGGGACCAGCTGCCCCAGCCTGGGAGGGAAGCCCAAGCTCTTTTTCATC

CAGGCCTGTGGTGGGGAGCAGAAAGACCATGGGTTTGAGGTGGCCTCCAC

TTCCCCTGAAGACGAGTCCCCTGGCAGTAACCCCGAGCCAGATGCCACCC

CGTTCCAGGAAGGTTTGAGGACCTTCGACCAGCTGGACGCCATATCTAGT

TTGCCCACACCCAGTGACATCTTTGTGTCCTACTCTACTTTCCCAGGTTT

TGTTTCCTGGAGGGACCCCAAGAGTGGCTCCTGGTACGTTGAGACCCTGG

ACGACATCTTTGAGCAGTGGGCTCACTCTGAAGACCTGCAGTCCCTCCTG

CTTAGGGTCGCTAATGCTGTTTCGGTGAAAGGGATTTATAAACAGATGCC

TGGTTGCTTTAATTTCCTCCGGAAAAAACTTTTCTTTAAAACATCA

Caspase-9 (truncated) amino acid
sequence - CARD domain deleted
SEQ ID NO: 153
G F G D V G A L E S L R G N A D L A Y I L S M E P

C G H C L I I N N V N F C R E S G L R T R T G S N

I D C E K L R R R F S S L H F M V E V K G D L T A

K K M V L A L L E L A Q Q D H G A L D C C V V V I

L S H G C Q A S H L Q F P G A V Y G T D G C P V S

V E K I V N I F N G T S C P S L G G K P K L F F I

Q A C G G E Q K D H G F E V A S T S P E D E S P G

S N P E P D A T P F Q E G L R T F D Q L D A I S S

L P T P S D I F V S Y S T F P G F V S W R D P K S

G S W Y V E T L D D I F E Q W A H S E D L Q S L L

L R V A N A V S V K G I Y K Q M P G C F N F L R K

K L F F K T S

Example 14: Cytokine Production of T Cells Co-Expressing a MyD88/CD40 Chimeric Antigen Receptor and Inducible Caspase-9 Polypeptide Various chimeric antigen receptor constructs were created to compare cytokine production of transduced T cells after exposure to antigen. The chimeric antigen receptor constructs all had an antigen recognition region that bound to CD19. FIG. 30 provides schematics of the various retroviral constructs used in the assays. FIG. 12 compares transduction efficiency and chimeric antigen receptor expression. FIG. 13 compares IL-2 and IL-6 secretion after the transduced T cells are exposed to Daudi Burkitt's lymphoma cells. FIG. 14 provides the results of another assay comparing IL-2 and IL-6 secretion after the transduced T cells are exposed to Raji Burkitt's lymphoma cells. FIG. 15 shows the elimination of CD19+ Daudi and Raji tumor cells following a co-culture with CAR-modified T cells.

Example 15: An Example of a MyD88/CD40 CAR Construct for Targeting Her2+ Tumor Cells FIGS. 18 and 19 show the results of experiments similar to those discussed herein, using an antigen recognition moiety that recognizes the Her2/Neu antigen. It is understood that the vectors provided herein may be modified to construct a MyD88/CD40 CAR construct that targets Her2$^+$ tumor cells, which also incorporates an inducible Caspase-9 safety switch.

SFG-Her2scFv.CD34e.CD8stm.MC.zeta Sequence

Signal peptide
SEQ ID NO: 152
ATGGAGTTTGGACTTTCTTGGTTGTTTTTGGTGGCAATTCTGAAGGGTG

TCCAGTGTAGCAGG

Signal peptide
SEQ ID NO: 153
MEFGLSWLFLVAILKGVQCSR

FRP5 variable light chain (anti-Her2)
SEQ ID NO: 154
GACATCCAATTGACACAATCACACAAATTTCTCTCAACTTCTGTAGGAGA
CAGAGTGAGCATAACCTGCAAAGCATCCCAGGACGTGTACAATGCTGTGG
CTTGGTACCAACAGAAGCCTGGACAATCCCCAAAATTGCTGATTTATTCT
GCCTCTAGTAGGTACACTGGGGTACCTTCTCGGTTTACGGGCTCTGGGTC
CGGACCAGATTTCACGTTCACAATCAGTTCCGTTCAAGCTGAAGACCTCG
CTGTTTATTTTTGCCAGCAGCACTTCCGAACCCCTTTTACTTTTGGCTCA
GGCACTAAGTTGGAAATCAAGGCTTTG FRP5 variable light chain (anti-Her2)
SEQ ID NO: 155
DIQLTQSHKFLSTSVGDRVSITCKASQDVYNAVAVVYQQKPGQSPKLLIY
SASSRYTGVPSRFTGSGSGPDFTFTISSVQAEDLAVYFCQQHFRTPFTFG
SGTKLEIKAL Flexible linker
SEQ ID NO: 156
GGCGGAGGAAGCGGAGGTGGGGGC Flexible linker
SEQ ID NO: 157
GGGSGGGG FRP5 variable heavy chain (anti-Her2/Neu)
SEQ ID NO: 158
GAAGTCCAATTGCAACAGTCAGGCCCCGAATTGAAAAAGCCCGGCGAAAC
AGTGAAGATATCTTGTAAAGCCTCCGGTTACCCTTTTACGAACTATGGAA
TGAACTGGGTCAAACAAGCCCCTGGACAGGGATTGAAGTGGATGGGATGG
ATCAATACATCAACAGGCGAGTCTACCTTCGCAGATGATTTCAAAGGTCG
CTTTGACTTCTCACTGGAGACCAGTGCAAATACCGCCTACCTTCAGATTA
ACAATCTTAAAAGCGAGGATATGGCAACCTACTTTTGCGCAAGATGGGAA
GTTTATCACGGGTACGTGCCATACTGGGGACAAGGAACGACAGTGACAGT
TAGTAGC FRP5 variable heavy chain (anti-Her2/Neu)
SEQ ID NO: 159
EVQLQQSGPELKKPGETVKISCKASGYPFTNYGMNWVKQAPGQGLKWMG
WINTSTGESTFADDFKGRFDFSLETSANTAYLQINNLKSEDMATYFCARW
EVYHGYVPYWGQGTTVTVSS Linker
SEQ ID NO: 160
GGATCC Linker
SEQ ID NO: 161
GS CD34 minimal epitope
SEQ ID NO: 162
GAACTTCCTACTCAGGGGACTTTCTCAAACGTTAGCACAAACGTAAGT CD34 minimal epitope
SEQ ID NO: 163
ELPTQGTFSNVSTNVS CD8 alpha stalk
SEQ ID NO: 164
CCCGCCCCAAGACCCCCCACACCTGCGCCGACCATTGCTTCTCAACCCCT
GAGTTTGAGACCCGAGGCCTGCCGGCCAGCTGCCGGCGGGGCCGTGCATA
CAAGAGGACTCGATTTCGCTTGCGAC CD8 alpha stalk
SEQ ID NO: 165
PAPRPPTPAPTIASQPLSLRPEACRPAAGGAVHTRGLDFACD CD8 alpha transmembrane region
SEQ ID NO: 166
ATCTATATCTGGGCACCTCTCGCTGGCACCTGTGGAGTCCTTCTGCTCAG
CCTGGTTATTACTCTGTACTGTAATCACCGGAATCGCCGCCGCGTTTGTA
AGTGTCCCAGG CD8 alpha transmembrane region
SEQ ID NO: 167
IYIWAPLAGTCGVLLLSLVITLYCNHRNRRRVCKCPR Linker
SEQ ID NO: 168
Ctcgag Linker
SEQ ID NO: 169
LE Truncated MyD88
SEQ ID NO: 170
ATGGCCGCTGGGGGCCCAGGCGCCGGATCAGCTGCTCCCGTATCTTCTAC
TTCTTCTTTGCCGCTGGCTGCTCTGAACATGCGCGTGAGAAGACGCCTCT
CCCTGTTCCTTAACGTTCGCACACAAGTCGCTGCCGATTGGACCGCCCTT
GCCGAAGAAATGGACTTTGAATACCTGGAAATTAGACAACTTGAAACACA
GGCCGACCCCACTGGCAGACTCCTGGACGCATGGCAGGGAAGACCTGGTG
CAAGCGTTGGACGGCTCCTGGATCTCCTGACAAAACTGGGACGCGACGAC
GTACTGCTTGAACTCGGACCTAGCATTGAAGAAGACTGCCAAAAATATAT
CCTGAAACAACAACAAGAAGAAGCCGAAAAACCTCTCCAAGTCGCAGCAG
TGGACTCATCAGTACCCCGAACAGCTGAGCTTGCTGGGATTACTACACTC
GACGACCCACTCGGACATATGCCTGAAAGATTCGACGCTTTCATTTGCTA
TTGCCCCTCTGACATA Truncated MyD88
SEQ ID NO: 171
MAAGGPGAGSAAPVSSTSSLPLAALNMRVRRRLSLFLNVRTQVAADWTAL
AEEMDFEYLEIRQLETQADPTGRLLDAWQGRPGASVGRLLDLLTKLGRDD
VLLELGPSIEEDCQKYILKQQQEEAEKPLQVAAVDSSVPRTAELAGITTL
DDPLGHMPERFDAFICYCPSDI CD40 cytoplasmic domain
SEQ ID NO: 172
AAGAAAGTTGCAAAGAAACCCACAAATAAAGCCCCACACCCTAAACAGGA
ACCCCAAGAAATCAATTTCCCAGATGATCTCCCTGGATCTAATACTGCCG
CCCCCGGTCCAAGAAACCCTGCATGGTTGCCAGCCTGTCACCCAAGAGGAC
GGAAAAGAATCACGGATTAGCGTACAAGAGAGACAA CD40 cytoplasmic domain

```
                                                    -continued
                                                SEQ ID NO: 173
KKVAKKPTNKAPHPKQEPQEINFPDDLPGSNTAAPVQETLHGCQPVTQED

GKESRISVQERQ

Linker
                                                SEQ ID NO: 174
gcggccgcagtcgag Linker
                                                SEQ ID NO: 175
AAAVE CD3 zeta cytoplasmic domain
                                                SEQ ID NO: 176
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG
```

```
TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta cytoplasmic domain
                                                SEQ ID NO: 177
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Example 16: Additional Sequences

```
ΔCasp9 (res. 135-416),
                                                SEQ ID NO: 178
G F G D V G A L E S L R G N A D L A Y I L S M E P C G H C L I I N N V N

F C R E S G L R T R T G S N I D C E K L R R R F S S L H F M V E V K G D

L T A K K M V L A L L E L A R Q D H G A L D C C V V V I L S H G C Q A S

H L Q F P G A V Y G T D G C P V S V E K I V N I F N G T S C P S L G G K

P K L F F I Q A C G G E Q K D H G F E V A S T S P E D E S P G S N P E P

D A T P F Q E G L R T F D Q L D A I S S L P T P S D I F V S Y S T F P G F

V S W R D P K S G S W Y V E T L D D I F E Q W A H S E D L Q S L L L R

V A N A V S V K G I Y K Q M P G C F N F L R K K L F F K T S

ΔCasp9 (res. 135-416) D330A, nucleotide sequence,
                                                SEQ ID NO: 179
GGATTTGGTGATGTCGGTGCTCTTGAGAGTTTGAGGGGAAATGCAGATTTGGCTTACATCCTG

AGCATGGAGCCCTGTGGCCACTGCCTCATTATCAACAATGTGAACTTCTGCCGTGAGTCCGG

GCTCCGCACCCGCACTGGCTCCAACATCGACTGTGAGAAGTTGCGGCGTCGCTTCTCCTCGC

TGCATTTCATGGTGGAGGTGAAGGGCGACCTGACTGCCAAGAAAATGGTGCTGGCTTTGCTG

GAGCTGGCGCGgCAGGACCACGGTGCTCTGGACTGCTGCGTGGTGGTCATTCTCTCTCACG

GCTGTCAGGCCAGCCACCTGCAGTTCCCAGGGGCTGTCTACGGCACAGATGGATGCCCTGT

GTCGGTCGAGAAGATTGTGAACATCTTCAATGGGACCAGCTGCCCCAGCCTGGGAGGGAAG

CCCAAGCTCTTTTTCATCCAGGCCTGTGGTGGGGAGCAGAAAGACCATGGGTTTGAGGTGGC

CTCCACTTCCCCTGAAGACGAGTCCCCTGGCAGTAACCCCGAGCCAGATGCCACCCCGTTCC

AGGAAGGTTTGAGGACCTTCGACCAGCTGGCCGCCATATCTAGTTTGCCCACACCCAGTGAC

ATCTTTGTGTCCTACTCTACTTTCCCAGGTTTTGTTTCCTGGAGGGACCCCAAGAGTGGCTCC

TGGTACGTTGAGACCCTGGACGACATCTTTGAGCAGTGGGCTCACTCTGAAGACCTGCAGTC

CCTCCTGCTTAGGGTCGCTAATGCTGTTTCGGTGAAAGGGATTTATAAACAGATGCCTGGTTG

CTTTAATTTCCTCCGGAAAAAACTTTTCTTTAAAACATCA

ΔCasp9 (res. 135-416) D330A, amino acid sequence,
                                                SEQ ID NO: 180
G F G D V G A L E S L R G N A D L A Y I L S M E P C G H C L I I N N V N

F C R E S G L R T R T G S N I D C E K L R R R F S S L H F M V E V K G D

L T A K K M V L A L L E L A R Q D H G A L D C C V V V I L S H G C Q A S

H L Q F P G A V Y G T D G C P V S V E K I V N I F N G T S C P S L G G K
```

```
P K L F F I Q A C G G E Q K D H G F E V A S T S P E D E S P G S N P E P

D A T P F Q E G L R T F D Q L A A I S S L P T P S D I F V S Y S T F P G F

V S W R D P K S G S W Y V E T L D D I F E Q W A H S E D L Q S L L L R

V A N A V S V K G I Y K Q M P G C F N F L R K K L F F K T S
```

ΔCasp9 (res. 135-416) N405Q nucleotide sequence,
SEQ ID NO: 181

```
GGATTTGGTGATGTCGGTGCTCTTGAGAGTTTGAGGGGAAATGCAGATTTGGCTTACATCCTG
AGCATGGAGCCCTGTGGCCACTGCCTCATTATCAACAATGTGAACTTCTGCCGTGAGTCCGG
GCTCCGCACCCGCACTGGCTCCAACATCGACTGTGAGAAGTTGCGGCGTCGCTTCTCCTCGC
TGCATTTCATGGTGGAGGTGAAGGGCGACCTGACTGCCAAGAAAATGGTGCTGGCTTTGCTG
GAGCTGGCGCgGCAGGACCACGGTGCTCTGGACTGCTGCGTGGTGGTCATTCTCTCTCACG
GCTGTCAGGCCAGCCACCTGCAGTTCCCAGGGGCTGTCTACGGCACAGATGGATGCCCTGT
GTCGGTCGAGAAGATTGTGAACATCTTCAATGGGACCAGCTGCCCCAGCCTGGGAGGGAAG
CCCAAGCTCTTTTTCATCCAGGCCTGTGGTGGGGAGCAGAAAGACCATGGGTTTGAGGTGGC
CTCCACTTCCCCTGAAGACGAGTCCCCTGGCAGTAACCCCGAGCCAGATGCCACCCCGTTCC
AGGAAGGTTTGAGGACCTTCGACCAGCTGGACGCCATATCTAGTTTGCCCACACCCAGTGAC
ATCTTTGTGTCCTACTCTACTTTCCCAGGTTTTGTTTCCTGGAGGGACCCCAAGAGTGGCTCC
TGGTACGTTGAGACCCTGGACGACATCTTTGAGCAGTGGGCTCACTCTGAAGACCTGCAGTC
CCTCCTGCTTAGGGTCGCTAATGCTGTTTCGGTGAAAGGGATTTATAAACAGATGCCTGGTTG
CTTTCAGTTCCTCCGGAAAAAACTTTTCTTTAAAACATCA
```

ΔCasp9 (res. 135-416) N405Q amino acid sequence,
SEQ ID NO: 182

```
G F G D V G A L E S L R G N A D L A Y I L S M E P C G H C L I I N N V N

F C R E S G L R T R T G S N I D C E K L R R R F S S L H F M V E V K G D

L T A K K M V L A L L E L A R Q D H G A L D C C V V V I L S H G C Q A S

H L Q F P G A V Y G T D G C P V S V E K I V N I F N G T S C P S L G G K

P K L F F I Q A C G G E Q K D H G F E V A S T S P E D E S P G S N P E P

D A T P F Q E G L R T F D Q L D A I S S L P T P S D I F V S Y S T F P G F

V S W R D P K S G S W Y V E T L D D I F E Q W A H S E D L Q S L L L R

V A N A V S V K G I Y K Q M P G C F Q F L R K K L F F K T S
```

ΔCasp9 (res. 135-416) D330A N405Q nucleotide sequence,
SEQ ID NO: 183

```
GGATTTGGTGATGTCGGTGCTCTTGAGAGTTTGAGGGGAAATGCAGATTTGGCTTACATCCTG
AGCATGGAGCCCTGTGGCCACTGCCTCATTATCAACAATGTGAACTTCTGCCGTGAGTCCGG
GCTCCGCACCCGCACTGGCTCCAACATCGACTGTGAGAAGTTGCGGCGTCGCTTCTCCTCGC
TGCATTTCATGGTGGAGGTGAAGGGCGACCTGACTGCCAAGAAAATGGTGCTGGCTTTGCTG
GAGCTGGCGCgGCAGGACCACGGTGCTCTGGACTGCTGCGTGGTGGTCATTCTCTCTCACG
GCTGTCAGGCCAGCCACCTGCAGTTCCCAGGGGCTGTCTACGGCACAGATGGATGCCCTGT
GTCGGTCGAGAAGATTGTGAACATCTTCAATGGGACCAGCTGCCCCAGCCTGGGAGGGAAG
CCCAAGCTCTTTTTCATCCAGGCCTGTGGTGGGGAGCAGAAAGACCATGGGTTTGAGGTGGC
CTCCACTTCCCCTGAAGACGAGTCCCCTGGCAGTAACCCCGAGCCAGATGCCACCCCGTTCC
AGGAAGGTTTGAGGACCTTCGACCAGCTGGCCGCCATATCTAGTTTGCCCACACCCAGTGAC
ATCTTTGTGTCCTACTCTACTTTCCCAGGTTTTGTTTCCTGGAGGGACCCCAAGAGTGGCTCC
```

```
TGGTACGTTGAGACCCTGGACGACATCTTTGAGCAGTGGGCTCACTCTGAAGACCTGCAGTC

CCTCCTGCTTAGGGTCGCTAATGCTGTTTCGGTGAAAGGGATTTATAAACAGATGCCTGGTTG

CTTTCAGTTCCTCCGGAAAAAACTTTTCTTTAAAACATCA
```

ΔCasp9 (res. 135-416) D330A N405Q amino acid sequence,
SEQ ID NO: 184
```
G F G D V G A L E S L R G N A D L A Y I L S M E P C G H C L I I N N V N

F C R E S G L R T R T G S N I D C E K L R R R F S S L H F M V E V K G D

L T A K K M V L A L L E L A R Q D H G A L D C C V V V I L S H G C Q A S

H L Q F P G A V Y G T D G C P V S V E K I V N I F N G T S C P S L G G K

P K L F F I Q A C G G E Q K D H G F E V A S T S P E D E S P G S N P E P

D A T P F Q E G L R T F D Q L A A I S S L P T P S D I F V S Y S T F P G F

V S W R D P K S G S W Y V E T L D D I F E Q W A H S E D L Q S L L L R

V A N A V S V K G I Y K Q M P G C F Q F L R K K L F F K T S
```

Caspase-9.co nucleotide sequence,
SEQ ID NO: 185
```
GTGGACGGGTTTGGAGATGTGGGAGCCCTGGAATCCCTGCGGGGCAATGCCGATCTGGCTT

ACATCCTGTCTATGGAGCCTTGCGGCCACTGTCTGATCATTAACAATGTGAACTTCTGCAGAG

AGAGCGGGCTGCGGACCAGAACAGGATCCAATATTGACTGTGAAAAGCTGCGGAGAAGGTTC

TCTAGTCTGCACTTTATGGTCGAGGTGAAAGGCGATCTGACCGCTAAGAAAATGGTGCTGGC

CCTGCTGGAACTGGCTCGGCAGGACCATGGGGCACTGGATTGCTGCGTGGTCGTGATCCTG

AGTCACGGCTGCCAGGCTTCACATCTGCAGTTCCCTGGGGCAGTCTATGGAACTGACGGCTG

TCCAGTCAGCGTGGAGAAGATCGTGAACATCTTCAACGGCACCTCTTGCCCAAGTCTGGGCG

GGAAGCCCAAACTGTTCTTTATTCAGGCCTGTGGAGGCGAGCAGAAAGATCACGGCTTCGAA

GTGGCTAGCACCTCCCCCGAGGACGAATCACCTGGAAGCAACCCTGAGCCAGATGCAACCC

CCTTCCAGGAAGGCCTGAGGACATTTGACCAGCTGGATGCCATCTCAAGCCTGCCCACACCT

TCTGACATTTTCGTCTCTTACAGTACTTTCCCTGGATTTGTGAGCTGGCGCGATCCAAAGTCA

GGCAGCTGGTACGTGGAGACACTGGACGATATCTTTGAGCAGTGGGCCCATTCTGAAGACCT

GCAGAGTCTGCTGCTGCGAGTGGCCAATGCTGTCTCTGTGAAGGGGATCTACAAACAGATGC

CAGGATGCTTCCAGTTTCTGAGAAAGAAACTGTTCTTTAAGACCTCCGCATCTAGGGCC
```

Caspase-9.co amino acid sequence,
SEQ ID NO: 186
```
VDGFGDVGALESLRGNADLAYILSMEPCGHCLIINNVNFCRESGLRTRTGSNIDCEKLRRRFSSLH

FMVEVKGDLTAKKMVLALLELARQDHGALDCCVVVILSHGCQASHLQFPGAVYGTDGCPVSVEKI

VNIFNGTSCPSLGGKPKLFFIQACGGEQKDHGFEVASTSPEDESPGSNPEPDATPFQEGLRTFDQ

LDAISSLPTPSDIFVSYSTFPGFVSWRDPKSGSWYVETLDDIFEQWAHSEDLQSLLLRVANAVSVK

GIYKQMPGCFQFLRKKLFFKTSASRA
```

Caspase9 D330E nucleotide sequence:
SEQ ID NO: 187
```
GTCGACGGATTTGGTGATGTCGGTGCTCTTGAGAGTTTGAGGGGAAATGCAGATTTGGCTTA

CATCCTGAGCATGGAGCCCTGTGGCCACTGCCTCATTATCAACAATGTGAACTTCTGCCGTGA

GTCCGGGCTCCGCACCCGCACTGGCTCCAACATCGACTGTGAGAAGTTGCGGCGTCGCTTCT

CCTCGCTGCATTTCATGGTGGAGGTGAAGGGCGACCTGACTGCCAAGAAAATGGTGCTGGCT

TTGCTGGAGCTGGCGCGGCAGGACCACGGTGCTCTGGACTGCTGCGTGGTGGTCATTCTCT

CTCACGGCTGTCAGGCCAGCCACCTGCAGTTCCCAGGGGCTGTCTACGGCACAGATGGATG

CCCTGTGTCGGTCGAGAAGATTGTGAACATCTTCAATGGGACCAGCTGCCCCAGCCTGGGAG
```

```
GGAAGCCCAAGCTCTTTTTCATCCAGGCCTGTGGTGGGGAGCAGAAAGACCATGGGTTTGAG

GTGGCCTCCACTTCCCCTGAAGACGAGTCCCCTGGCAGTAACCCCGAGCCAGATGCCACCC

CGTTCCAGGAAGGTTTGAGGACCTTCGACCAGCTGGcCGCCATATCTAGTTTGCCCACACCCA

GTGACATCTTTGTGTCCTACTCTACTTTCCCAGGTTTTGTTTCCTGGAGGGACCCCAAGAGTG

GCTCCTGGTACGTTGAGACCCTGGACGACATCTTTGAGCAGTGGGCTCACTCTGAAGACCTG

CAGTCCCTCCTGCTTAGGGTCGCTAATGCTGTTTCGGTGAAAGGGATTTATAAACAGATGCCT

GGTTGCTTTAATTTCCTCCGGAAAAAACTTTTCTTTAAAACATCAGCTAGCAGAGCC

Caspase9 D330E amino acid sequence:
                                                   SEQ ID NO: 188
VDGFGDVGALESLRGNADLAYILSMEPCGHCLIINNVNFCRESGLRTRTGSNIDCEKLRRRFSS

LHFMVEVKGDLTAKKMVLALLELARQDHGALDCCVWILSHGCQASHLQFPGAVYGTDGC

PVSVEKIVNIFNGTSCPSLGGKPKLFFIQACGGEQKDHGFEVASTSPEDESPGSNPEPDA

TPFQEGLRTFDQLeAISSLPTPSDIFVSYSTFPGFVSWRDPKSGSWYVETLDDIFEQWAH

SEDLQSLLLRVANAVSVKGIYKQMPGCFNFLRKKLFFKTSASRA

Sequences for pBPO509 (represented in FIG. 23)
   pBP0509-SFG-
PSCAscFv.CH2CH3.CD28tm.zeta.MyD88/CD40 Sequence Signal peptide
                                                   SEQ ID NO: 189
ATGGAGTTTGGACTTTCTTGGTTGTTTTTGGTGGCAATTCTGAAGGGTGTCCAGTGTAGCAGG Signal peptide
                                                   SEQ ID NO: 190
MEFGLSWLFLVAILKGVQCSR bm2B3 variable light chain
                                                   SEQ ID NO: 191
GACATCCAGCTGACACAAAGTCCCAGTAGCCTGTCAGCCAGTGTCGGCGATAGGGTGACAAT

TACATGCTCCGCAAGTAGTAGCGTCAGATTCATACACTGGTACCAGCAGAAGCCTGGGAAGG

CCCCAAAGAGGCTTATCTACGATACCAGTAAACTCGCCTCTGGAGTTCCTAGCCGGTTTTCTG

GATCTGGCAGCGGAACTAGCTACACCCTCACAATCTCCAGTCTGCAACCAGAGGACTTTGCA

ACCTACTACTGCCAGCAATGGAGCAGCTCCCCTTTCACCTTTGGGCAGGGTACTAAGGTGGA

GATCAAG bm2B3 variable light chain
                                                   SEQ ID NO: 192
DIQLTQSPSSLSASVGDRVTITCSASSSVRFIHWYQQKPGKAPKRLIYDTSKLASGVPSRFSGSGS

GTSYTLTISSLQPEDFATYYCQQWSSSPFTFGQGTKVEIK

Flexible linker
                                                   SEQ ID NO: 193
GGCGGAGGAAGCGGAGGTGGGGGC Flexible linker
                                                   SEQ ID NO: 194
GGGSGGGG bm2B3 variable heavy chain
                                                   SEQ ID NO: 195
GAGGTGCAGCTTGTAGAGAGCGGGGGAGGCCTCGTACAGCCAGGGGGCTCTCTGCGCCTGT

CATGTGCAGCTTCAGGATTCAATATAAAGGACTATTACATTCACTGGGTACGGCAAGCTCCCG

GTAAGGGCCTGGAATGGATCGGTTGGATCGACCCTGAAAACGGAGATACAGAATTTGTGCCC

AAGTTCCAGGGAAAGGCTACCATGTCTGCCGATACTTCTAAGAATACAGCATACCTTCAGATG

AATTCTCTCCGCGCCGAGGACACAGCCGTGTATTATTGTAAAACGGGAGGGTTCTGGGGTCA
```

GGGTACCCTTGTGACTGTGTCTTCC bm2B3 variable heavy chain
SEQ ID NO: 196
EVQLVESGGGLVQPGGSLRLSCAASGFNIKDYYIHWVRQAPGKGLEWIGWIDPENGDTEFVPKF

QGKATMSADTSKNTAYLQMNSLRAEDTAVYYCKTGGFWGQGTLVTVSS

Linker
SEQ ID NO: 197
GGGGATCCCGCC

Linker
SEQ ID NO: 198
GDPA

IgG1 hinge region
SEQ ID NO: 199
GAGCCCAAATCTCCTGACAAAACTCACACATGCCCA

IgG1 hinge region
SEQ ID NO: 200
EPKSPDKTHTCP

IgG1 CH2 region
SEQ ID NO: 201
CCGTGCCCAGCACCTGAACTCCTGGGGGGACCGTCAGTCTTCCTCTTCCCCCCAAAACCCAA

AGACACCCTCATGATCTCCCGGACCCCTGAGGTCACATGCGTGGTGGTGGACGTGAGCCAC

GAAGACCCTGAGGTCAAGTTCAACTGGTATGTGGACGGCGTGGAGGTGCATAATGCAAAGAC

AAAGCCGCGGGAGGAGCAGTACAACAGCACGTACCGTGTGGTCAGCGTCCTCACCGTCCTG

CACCAGGACTGGCTGAATGGCAAGGAGTACAAGTGCAAGGTCTCCAACAAAGCCCTCCCAGC

CCCCATCGAGAAAACCATCTCCAAAGCCAAA

IgG1 CH2 region
SEQ ID NO: 202
PCPAPELLGGPSVFLFPPKPKDTLMISRTPEVTCVWDVSHEDPEVKFNWYVDGVEVHNAKTKPR

EEQYNSTYRWSVLTVLHQDWLNGKEYKCKVSNKALPAPIEKTISKAK

IgG1 CH3 region
SEQ ID NO: 203
GGGCAGCCCCGAGAACCACAGGTGTACACCCTGCCCCCATCCCGGGATGAGCTGACCAAGA

ACCAGGTCAGCCTGACCTGCCTGGTCAAAGGCTTCTATCCCAGCGACATCGCCGTGGAGTGG

GAGAGCAATGGGCAACCGGAGAACAACTACAAGACCACGCCTCCCGTGCTGGACTCCGACG

GCTCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCT

GTCTCCGGGTAAA

IgG1 CH3 region
SEQ ID NO: 204
GQPREPQVYTLPPSRDELTKNQVSLTCLVKGFYPSDIAVEWESNGQPENNYKTTPPVLDSDGSFF

LYSKLTVDKSRWQQGNVFSCSVMHEALHNHYTQKSLSLSPGK

Linker
SEQ ID NO: 205
AAAGATCCCAAA

Linker
SEQ ID NO: 206
KDPK

CD28 transmembrane region
SEQ ID NO: 207
TTTTGGGTGCTGGTGGTGGTTGGTGGAGTCCTGGCTTGCTATAGCTTGCTAGTAACAGTGGC

CTTTATTATT

-continued

CD28 transmembrane region

SEQ ID NO: 208

FWVLVWGGVLACYSLLVTVAFII

Linker

SEQ ID NO: 209 gccggc

Linker

SEQ ID NO: 210

AG

CD3 zeta

SEQ ID NO: 211

AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAGGCCCTGCCCCCTCGC

CD3 zeta

SEQ ID NO: 212

RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

MyD88

SEQ ID NO: 213

GCCGCTGGGGGCCCAGGCGCCGGATCAGCTGCTCCCGTATCTTCTACTTCTTCTTTGCCGCT

GGCTGCTCTGAACATGCGCGTGAGAAGACGCCTCTCCCTGTTCCTTAACGTTCGCACACAAG

TCGCTGCCGATTGGACCGCCCTTGCCGAAGAAATGGACTTTGAATACCTGGAAATTAGACAAC

TTGAAACACAGGCCGACCCCACTGGCAGACTCCTGGACGCATGGCAGGGAAGACCTGGTGC

AAGCGTTGGACGGCTCCTGGATCTCCTGACAAAACTGGGACGCGACGACGTACTGCTTGAAC

TCGGACCTAGCATTGAAGAAGACTGCCAAAAATATATCCTGAAACAACAACAAGAAGAAGCCG

AAAAACCTCTCCAAGTCGCAGCAGTGGACTCATCAGTACCCCGAACAGCTGAGCTTGCTGGG

ATTACTACACTCGACGACCCACTCGGACATATGCCTGAAAGATTCGACGCTTTCATTTGCTATT

GCCCCTCTGACATA

213 MyD88

SEQ ID NO: 214

AAGGPGAGSAAPVSSTSSLPLAALNMRVRRRLSLFLNVRTQVAADWTALAEEMDFEYLEIRQLET

QADPTGRLLDAWQGRPGASVGRLLDLLTKLGRDDVLLELGPSIEEDCQKYILKQQQEEAEKPLQV

AAVDSSVPRTAELAGITTLDDPLGHMPERFDAFICYCPSDI

CD40

SEQ ID NO: 215

AAGAAAGTTGCAAAGAAACCCACAAATAAAGCCCCACACCCTAAACAGGAACCCCAAGAAATC

AATTTCCCAGATGATCTCCCTGGATCTAATACTGCCGCCCCGGTCCAAGAAACCCTGCATGGT

TGCCAGCCTGTCACCCAAGAGGACGGAAAAGAATCACGGATTAGCGTACAAGAGAGACAATAG

CD40

SEQ ID NO: 216

KKVAKKPTNKAPHPKQEPQEINFPDDLPGSNTAAPVQETLHGCQPVTQEDGKESRISVQERQ*

Sequences for pBPO425 (Represented in FIG. 24)
pBP0521-SFG-CD19scFv.CH2CH3.CD28tm.MyD88/
CD40.zeta sequence

```
Signal peptide
                                            SEQ ID NO: 217
ATGGAGTTTGGACTTTCTTGGTTGTTTTTGGTGGCAATTCTGAAGGGTGTCCAGTGTAGCAGG Signal peptide
                                            SEQ ID NO: 218
MEFGLSWLFLVAILKGVQCSR FMC63 variable light chain
                                            SEQ ID NO: 219
GACATCCAGAT
```

GACACAGACTACATCCTCCCTGTCTGCCTCTCTGGGAGACAGAGTCACCATCAGTTGCAGGG

CAAGTCAGGACATTAGTAAATATTTAAATTGGTATCAGCAGAAACCAGATGGAACTGTTAAACT

CCTGATCTACCATACATCAAGATTACACTCAGGAGTCCCATCAAGGTTCAGTGGCAGTGGGTC

TGGAACAGATTATTCTCTCACCATTAGCAACCTGGAGCAAGAAGATATTGCCACTTACTTTTGC

CAACAGGGTAATACGCTTCCGTACACGTTCGGAGGGGGGACTAAGTTGGAAATAACA

```
FMC63 variable light chain
                                            SEQ ID NO: 220
DIQMTQTTSSLSASLGDRVTISCRASQDISKYLNWYQQKPDGTVKLLIYHTSRLHSGVPSRFSGSG

SGTDYSLTISNLEQEDIATYFCQQGNTLPYTFGGGTKLEIT

Flexible linker
                                            SEQ ID NO: 221
GGCGGAGGAAGCGGAGGTGGGGGC Flexible linker
                                            SEQ ID NO: 222
GGGSGGGG FMC63 variable heavy chain
                                            SEQ ID NO: 223
GAGGTGAAACTGCAGGAGTCAGGACCTGGCCTGGTGGCGCCCTCACAGAGCCTGTCCGTCA

CATGCACTGTCTCAGGGGTCTCATTACCCGACTATGGTGTAAGCTGGATTCGCCAGCCTCCA

CGAAAGGGTCTGGAGTGGCTGGGAGTAATATGGGGTAGTGAAACCACATACTATAATTCAGC

TCTCAAATCCAGACTGACCATCATCAAGGACAACTCCAAGAGCCAAGTTTTCTTAAAAATGAAC

AGTCTGCAAACTGATGACACAGCCATTTACTACTGTGCCAAACATTATTACTACGGTGGTAGCT

ATGCTATGGACTACTGGGGTCAAGGAACCTCAGTCACCGTCTCCTCA

FMC63 variable heavy chain
                                            SEQ ID NO: 224
EVKLQESGPGLVAPSQSLSVTCTVSGVSLPDYGVSWIRQPPRKGLEWLGVIWGSETTYYNSALKS

RLTIIKDNSKSQVFLKMNSLQTDDTAIYYCAKHYYYGGSYAMDYWGQGTSVTVSS

Linker
                                            SEQ ID NO: 225
GGGGATCCCGCC

Linker
                                            SEQ ID NO: 226
GDPA

IgG1 hinge
                                            SEQ ID NO: 227
GAGCCCAAATCTCCTGACAAAACTCACACATGCCCA IgG1 hinge
                                            SEQ ID NO: 228
EPKSPDKTHTCP
```

-continued

IgG1 CH2 region
SEQ ID NO: 229
CCGTGCCCAGCACCTGAACTCCTGGGGGACCGTCAGTCTTCCTCTTCCCCCCAAAACCCAA

AGACACCCTCATGATCTCCCGGACCCCTGAGGTCACATGCGTGGTGGTGGACGTGAGCCAC

GAAGACCCTGAGGTCAAGTTCAACTGGTATGTGGACGGCGTGGAGGTGCATAATGCAAAGAC

AAAGCCGCGGGAGGAGCAGTACAACAGCACGTACCGTGTGGTCAGCGTCCTCACCGTCCTG

CACCAGGACTGGCTGAATGGCAAGGAGTACAAGTGCAAGGTCTCCAACAAAGCCCTCCCAGC

CCCCATCGAGAAAACCATCTCCAAAGCCAAA

IgG1 CH2 region
SEQ ID NO: 230
PCPAPELLGGPSVFLFPPKPKDTLMISRTPEVTCVWDVSHEDPEVKFNWYVDGVEVHNAKTKPR

EEQYNSTYRWSVLTVLHQDWLNGKEYKCKVSNKALPAPIEKTISKAK

IgG1 CH3 region
SEQ ID NO: 231
GGGCAGCCCCGAGAACCACAGGTGTACACCCTGCCCCCATCCCGGGATGAGCTGACCAAGA

ACCAGGTCAGCCTGACCTGCCTGGTCAAAGGCTTCTATCCCAGCGACATCGCCGTGGAGTGG

GAGAGCAATGGGCAACCGGAGAACAACTACAAGACCACGCCTCCCGTGCTGGACTCCGACG

GCTCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCT

GTCTCCGGGTAAA

IgG1 CH3 region
SEQ ID NO: 232
GQPREPQVYTLPPSRDELTKNQVSLTCLVKGFYPSDIAVEWESNGQPENNYKTTPPVLDSDGSFF

LYSKLTVDKSRWQQGNVFSCSVMHEALHNHYTQKSLSLSPGK

Linker
SEQ ID NO: 233
AAAGATCCCAAA

Linker
SEQ ID NO: 234
KDPK

CD28 transmembrane region
SEQ ID NO: 235
TTTTGGGTGCTGGTGGTGGTTGGTGGAGTCCTGGCTTGCTATAGCTTGCTAGTAACAGTGGC

CTTTATTATT

CD28 transmembrane region
SEQ ID NO: 236
FWVLVWGGVLACYSLLVTVAFII

Linker
SEQ ID NO: 237
Ctcgag

Linker
SEQ ID NO: 238
LE

MyD88
SEQ ID NO: 239
ATGGCCGCTGGGGGCCCAGGCGCCGGATCAGCTGCTCCCGTATCTTCTACTTCTTCTTTGCC

GCTGGCTGCTCTGAACATGCGCGTGAGAAGACGCCTCTCCCTGTTCCTTAACGTTCGCACAC

AAGTCGCTGCCGATTGGACCGCCCTTGCCGAAGAAATGGACTTTGAATACCTGGAAATTAGAC

AACTTGAAACACAGGCCGACCCCACTGGCAGACTCCTGGACGCATGGCAGGGAAGACCTGG

TGCAAGCGTTGGACGGCTCCTGGATCTCCTGACAAAACTGGGACGCGACGACGTACTGCTTG

AACTCGGACCTAGCATTGAAGAAGACTGCCAAAAATATATCCTGAAACAACAACAAGAAGAAG

CCGAAAAACCTCTCCAAGTCGCAGCAGTGGACTCATCAGTACCCCGAACAGCTGAGCTTGCT

```
GGGATTACTACACTCGACGACCCACTCGGACATATGCCTGAAAGATTCGACGCTTTCATTTGC

TATTGCCCCTCTGACATA
```

MyD88
SEQ ID NO: 240
```
MAAGGPGAGSAAPVSSTSSLPLAALNMRVRRRLSLFLNVRTQVAADWTALAEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI
```

CD40
SEQ ID NO: 241
```
AAGAAAGTTGCAAAGAAACCCACAAATAAAGCCCCACACCCTAAACAGGAACCCCAAGAAATC

AATTTCCCAGATGATCTCCCTGGATCTAATACTGCCGCCCCGGTCCAAGAAACCCTGCATGGT

TGCCAGCCTGTCACCCAAGAGGACGGAAAAGAATCACGGATTAGCGTACAAGAGAGACAA
```

CD40
SEQ ID NO: 242
```
KKVAKKPTNKAPHPKQEPQEINFPDDLPGSNTAAPVQETLHGCQPVTQEDGKESRISVQERQ
```

Linker
SEQ ID NO: 243
```
gcggccgcagTCGAG
```

Linker
SEQ ID NO: 244
```
AAAVE
```

CD3 zeta chain
SEQ ID NO: 245
```
AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAGGCCCTGCCCCCTCGCTAA
```

CD3 zeta chain
SEQ ID NO: 246
```
RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR*
```

Sequences for SFG-Myr.MC-2A-CD19.scfv.CD34e.- CD8stm.zeta (FIG. 25)
SFG-Myr.MC.2A.CD19scFv.CD34e.CD8stm.zeta Sequence Myristolation
SEQ ID NO: 247
```
atggggagtagcaagagcaagcctaaggaccccagccagcgc
```

Myristolation
SEQ ID NO: 248
```
MGSSKSKPKDPSQR
```

Linker
SEQ ID NO: 249
```
ctcgac
```

Linker
SEQ ID NO: 250
```
LD
```

MyD88
SEQ ID NO: 251 atggctgcaggaggtcccggcgcggggtctgcggccccggtctcctccacatcctcccttcccctggctgctctcaacatgcgagtgcggc gccgcctgtctctgttcttgaacgtgcggacacaggtggcggccgactggaccgcgctggcggaggagatggactttgagtacttggagat ccggcaactggagacacaagcggaccccactggcaggctgctggacgcctggcagggacgccctggcgcctctgtaggccgactgct cgatctgcttaccaagctgggccgcgacgacgtgctgctggagctgggacccagcattgaggaggattgccaaaagtatatcttgaagca gcagcaggaggaggctgagaagccttttacaggtggccgctgtagacagcagtgtcccacggacagcagagctggcgggcatcacca cacttgatgacccctggggcatatgcctgagcgtttcgatgccttcatctgctattgccccagcgacatc MyD88
SEQ ID NO: 252

MAAGGPGAGSAAPVSSTSSLPLAALNMRVRRRLSLFLNVRTQVAADWTALAEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI

Linker
SEQ ID NO: 253 gtcgag

Linker
SEQ ID NO: 254

VE

CD40
SEQ ID NO: 255 aaaaaggtggccaagaagccaaccaataaggccccccaccccaagcaggagccccaggagatcaatttccccgacgatcttcctggc tccaacactgctgctccagtgcaggagactttacatggatgccaaccggtcacccaggaggatggcaaagagagtcgcatctcagtgca ggagagacag

CD40
SEQ ID NO: 256

KKVAKKPTNKAPHPKQEPQEINFPDDLPGSNTAAPVQETLHGCQPVTQEDGKESRISVQERQ

Linker
SEQ ID NO: 257

CCGCGG

Linker
SEQ ID NO: 258

PR

T2A sequence
SEQ ID NO: 259

GAAGGCCGAGGGAGCCTGCTGACATGTGGCGATGTGGAGGAAAACCCAGGACCA

T2A sequence
SEQ ID NO: 260

EGRGSLLTCGDVEENPGP

Signal peptide
SEQ ID NO: 261

ATGGAGTTTGGACTTTCTTGGTTGTTTTTGGTGGCAATTCTGAAGGGTGTCCAGTGTAGCAGG

Signal peptide
SEQ ID NO: 262

MEFGLSWLFLVAILKGVQCSR

FMC63 variable light chain
SEQ ID NO: 263

GACATCCAGATGACACAGACTACATCCTCCCTGTCTGCCTCTCTGGGAGACAGAGTCACCATC

AGTTGCAGGGCAAGTCAGGACATTAGTAAATATTTAAATTGGTATCAGCAGAAACCAGATGGA

ACTGTTAAACTCCTGATCTACCATACATCAAGATTACACTCAGGAGTCCCATCAAGGTTCAGTG

GCAGTGGGTCTGGAACAGATTATTCTCTCACCATTAGCAACCTGGAGCAAGAAGATATTGCCA

CTTACTTTTGCCAACAGGGTAATACGCTTCCGTACACGTTCGGAGGGGGGACTAAGTTGGAAA

TAACA

| | |
|---|---|
| FMC63 variable light chain | SEQ ID NO: 264 |
| DIQMTQTTSSLSASLGDRVTISCRASQDISKYLNWYQQKPDGTVKLLIYHTSRLHSGVPSRFSGSG | |
| SGTDYSLTISNLEQEDIATYFCQQGNTLPYTFGGGTKLEIT | |
| Flexible linker | SEQ ID NO: 265 |
| GGCGGAGGAAGCGGAGGTGGGGGC | |
| Flexible linker | SEQ ID NO: 266 |
| GGGSGGGG | |
| FMC63 variable heavy chain | SEQ ID NO: 267 |
| GAGGTGAAACTGCAGGAGTCAGGACCTGGCCTGGTGGCGCCCTCACAGAGCCTGTCCGTCA | |
| CATGCACTGTCTCAGGGGTCTCATTACCCGACTATGGTGTAAGCTGGATTCGCCAGCCTCCA | |
| CGAAAGGGTCTGGAGTGGCTGGGAGTAATATGGGGTAGTGAAACCACATACTATAATTCAGC | |
| TCTCAAATCCAGACTGACCATCATCAAGGACAACTCCAAGAGCCAAGTTTTCTTAAAAATGAAC | |
| AGTCTGCAAACTGATGACACAGCCATTTACTACTGTGCCAAACATTATTACTACGGTGGTAGCT | |
| ATGCTATGGACTACTGGGGTCAAGGAACCTCAGTCACCGTCTCCTCA | |
| FMC63 variable heavy chain | SEQ ID NO: 268 |
| EVKLQESGPGLVAPSQSLSVTCTVSGVSLPDYGVSWIRQPPRKGLEWLGVIWGSETTYYNSALKS | |
| RLTIIKDNSKSQVFLKMNSLQTDDTAIYYCAKHYYYGGSYAMDYWGQGTSVTVSS | |
| Linker | SEQ ID NO: 269 |
| GGATCC | |
| Linker | SEQ ID NO: 270 |
| GS | |
| CD34 minimal epitope | SEQ ID NO: 271 |
| GAACTTCCTACTCAGGGGACTTTCTCAAACGTTAGCACAAACGTAAGT | |
| CD34 minimal epitope | SEQ ID NO: 272 |
| ELPTQGTFSNVSTNVS | |
| CD8 alpha stalk domain | SEQ ID NO: 273 |
| CCCGCCCCAAGACCCCCCACACCTGCGCCGACCATTGCTTCTCAACCCCTGAGTTTGAGACC | |
| CGAGGCCTGCCGGCCAGCTGCCGGCGGGGCCGTGCATACAAGAGGACTCGATTTCGCTTGC | |
| GAC | |
| CD8 alpha stalk domain | SEQ ID NO: 274 |
| PAPRPPTPAPTIASQPLSLRPEACRPAAGGAVHTRGLDFACD | |
| CD8 alpha transmembrane domain | SEQ ID NO: 275 |
| ATCTATATCTGGGCACCTCTCGCTGGCACCTGTGGAGTCCTTCTGCTCAGCCTGGTTATTACT | |
| CTGTACTGTAATACCGGAATCGCCGCCGCGTTTGTAAGTGTCCCAGG | |
| CD8 alpha transmembrane domain | SEQ ID NO: 276 |
| IYIWAPLAGTCGVLLLSLVITLYCNHRNRRRVCKCPR | |
| Linker | SEQ ID NO: 277 |
| GTCGAC | |
| Linker | SEQ ID NO: 278 |
| VD | |
| CD3 zeta | |

-continued

AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAGGCCCTGCCCCCTCGC

CD3 zeta

SEQ ID NO: 280

RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR (MyD88 nucleotide sequence)

SEQ ID NO: 281 atggctgcaggaggtcccggcgcggggtctgcggcccggtctcctccacatcctcccttccccttggctgctctcaacatgcgagtgcggc gccgcctgtctctgttcttgaacgtgcggacacaggtggcggccgactggaccgcgctggcggaggagatggactttgagtacttggagat ccggcaactggagacacaagcggacccactggcaggctgctggacgcctggcagggacgccctggcgcctctgtaggccgactgct cgagctgcttaccaagctgggccgcgacgacgtgctgctggagctgggacccagcattgaggaggattgccaaaagtatatcttgaagc agcagcaggaggaggctgagaagcctttacaggtggccgctgtagacagcagtgtcccacggacagcagagctggcgggcatcacc acacttgatgacccctggggcatatgcctgagcgtttcgatgccttcatctgctattgccccagcgacatccagtttgtgcaggagatgatcc ggcaactggaacagacaaactatcgactgaagttgtgtgtgtctgaccgcgatgtcctgcctggcacctgtgtctggtctattgctagtgagct catcgaaaagaggtgccgccggatggtggtggttgtctctgatgattacctgcagagcaaggaatgtgacttccagaccaaatttgcactc agcctctctccaggtgcccatcagaagcgactgatccccatcaagtacaaggcaatgaagaaagagttccccagcatcctgaggttcatc actgtctgcgactacaccaaccctgcaccaaatcttggttctggactcgccttgccaaggccttgtccctgccc (MyD88 amino acid sequence)

SEQ ID NO: 282

M A A G G P G A G S A A P V S S T S S L P L A A L N M R V R R R L S L F L N V R T Q V A A D

W T A L A E E M D F E Y L E I R Q L E T Q A D P T G R L L D A W Q G R P G A S V G R L L E L

L T K L G R D D V L L E L G P S I E E D C Q K Y I L K Q Q Q E E A E K P L Q V A A V D S S V P

R T A E L A G I T T L D D P L G H M P E R F D A F I C Y C P S D I Q F V Q E M I R Q L E Q T N

Y R L K L C V S D R D V L P G T C V W S I A S E L I E K R C R R M V V V V S D D Y L Q S K E

C D F Q T K F A L S L S P G A H Q K R L I P I K Y K A M K K E F P S I L R F I T V C D Y T N P C

T K S W F W T R L A K A L S L P

Example 17: Modification of the Position of the MyD88/CD40 Costimulatory Domain in CAR-Modified T Cells and Costimulatory Activity of a Cytoplasmic Chimeric Stimulating Molecule Examples presented herein evaluating the utility of MyD88/CD40 (MC) costimulation in CAR-T cells focused on including the MyD88/CD40 polypeptide within the CAR, in the conventional location for costimulatory domains such as CD28 or OX40, for example. In the present example, the polynucleotide encoding the MyD88/CD40 polypeptide was placed between the CD8 transmembrane region and CD3ζ (FIG. 26). This CAR design (designated MC.) demonstrated significantly higher cytokine production (e.g. IL-2 and IL-6), enhanced T cell survival and proliferation, and superior tumor killing during in vitro coculture assays. However, the in vivo mouse studies showed that although antitumor activity was enhanced compared to CARs lacking costimulation, long term tumor control against CD19+ or Her2+ tumors was not achieved.

Following retroviral transduction, CAR expression (mean fluorescent intensity; MFI) is decreased with CARs containing the MyD88/CD40 signaling domain. To assess whether basal activity from the MyD88/CD40 domain or protein instability may be the cause of lower MFI in transduced T cells, T cells were transduced with vectors that encoded the MyD88/CD40 signaling domain and CD3zeta (FIG. 27). Whether lower CAR molecule expression in transduced T cells adversely affects the function and antitumor properties of the CAR, possibly contributing the suboptimal tumor control in our animal studies, was also assessed.

In these experiments, a cytoplasmic chimeric stimulating molecule, MyD88/CD40, expressed constitutively, but separate from the CAR molecule, was tested to determine whether it could retain the costimulatory properties while increasing CAR expression and stability. An additional vector was designed, SFG-iCasp9.2A.CAR.ζ.2A.MC that produces MyD88/CD40 constitutively using a P2A self-cleavage element. The MyD88/CD40 polypeptide is constitutively expressed, and constitutively active, that is, it does not have a multimeric ligand binding region and it stimulates immune activity without the need for an inducer. Construct designations in this example that include "MC" refer to a polynucleotide sequence coding for a MyD88/CD40 polypeptide that also includes a myristoylation sequence—the functionality of this myristoylation sequence, however, is destroyed due to the addition of a proline. (Resh, M. D., Biochim. Biophys. Acta. 1451: 1-16 (1999)). Initially, experiments evaluating the function of this design was performed with the CD19 scFv (FMC63), and then subsequently with a Her2 scFv (FRP5). Following transduction, although all T cells were efficiently transduced (>75%), T cells expressing the 2A form of MyD88/CD40 demonstrated increased CAR MFI compared to the MC.ζ format (FIG. 27). This indicated that removing MC from the CAR domain restored CAR stability or mitigated CAR-dependent MyD88/CD40 toxicity.

To examine whether constitutive expression of MyD88/CD40 could provide costimulation following CAR engagement to tumor cells bearing the cognate antigen, coculture experiments were performed using CD19-targeted CARs with CD19+ Raji lymphoma cells. Here, MyD88/CD40, whether it was expressed within the CAR molecule itself, or as a constitutive protein, enabled T cells to secrete IL-2 and IL-6 which require costimulation in addition to CD3ζ signaling (FIG. 28). Further analysis of these coculture assays using flow cytometry revealed that while all CD19-specific CAR constructs efficiently killed Raji tumor cells (FIG. 29), only MC.ζ and 2A.MC CAR formats allowed T cell proliferation in response to antigenic stimulation (FIG. 30). These data suggest that constitutive costimulation with MyD88/CD40 can preserve high CAR expression levels while simultaneously providing signaling for T cell proliferation and survival.

In addition to CD19-targeted CARs, similar experiments were performed examining whether Her2-specific CARs with the alternative MyD88/CD40 format would function as with the CD19-specific CARs. As with the CD19 CARs, constitutively expressing MyD88/CD40 by a 2A element improved CAR MFI compared to Her2.MC.ζ (FIGS. 31 and 32), and enhanced cytokine production (FIG. 33). Next, coculture assays were conducted against the Her2+ SK-BR-3 breast cancer cell line, and both Her2.MC.ζ as well as 2A.MC demonstrated enhanced tumor control and corresponding T cell proliferation, consistent with potent costimulation (FIGS. 34 and 35).

To evaluate the antitumor potency of the 2A format, tumor xenograft animal studies were performed. Immune deficient NSG mice were engrafted with SK-BR-3-EGFPluciferase tumor cells and after 7 days, treated with 2 doses of 1×10$^7$T cells that were either non-transduced (NT), or transduced with Her2., Her2.28.ζ, Her2.MC.ζ or Her2.ζ.2A.MC via intratumoral injection. Mice treated with Her2.ζ.2A.MC-modified T cells showed complete tumor regression by day 14 post-T cell injection (FIG. 36). Importantly, T cell toxicity as characterized by weight loss was not observed. These data further support that MyD88/CD40 can be constitutively co-expressed with a CAR to support T cell growth and antitumor activity.

In summary, MyD88/CD40 can both be incorporated into a CAR molecule (scFv.MC.ζ), or as a constitutively expressed accessory protein, which when introduced into primary T cells with a first generation CAR (scFv.ζ.2A.MC), enhances cytokine production, proliferation and antitumor activity both in vitro and in vivo.

Example 18: Nucleotide and amino acid sequence of pBP0813-SFG-iCasp9.2A.CD19.zeta.2A.MC Plasmid pBP0813-SFG-iCasp9.2A.CD19.zeta.2A.MC comprises a polynucleotide encoding an example of a chimeric antigen receptor of the present technology; this polynucleotide does not include a membrane-targeting region. The polynucleotide also encodes a chimeric inducible Caspase-9 polypeptide.

```
FKBP12v36
                                                                    (SEQ ID NO: 298)
ATGGGAGTGCAGGTGGAGACTATTAGCCCCGGAGATGGCAGAACATTCCCCAAAAGAGGACA

GACTTGCGTCGTGCATTATACTGGAATGCTGGAAGACGGCAAGAAGGTGGACAGCAGCCGG

GACCGAAACAAGCCCTTCAAGTTCATGCTGGGGAAGCAGGAAGTGATCCGGGGCTGGGAGG

AAGGAGTCGCACAGATGTCAGTGGGACAGAGGGCCAAACTGACTATTAGCCCAGACTACGCT

TATGGAGCAACCGGCCACCCCGGGATCATTCCCCCTCATGCTACACTGGTCTTCGATGTGGA

GCTGCTGAAGCTGGAA
                                                                    (SEQ ID NO: 299)
MGVQVETISPGDGRTFPKRGQTCVVHYTGMLEDGKKVDSSRDRNKPFKFMLGKQEVIRGWEEG

VAQMSVGQRAKLTISPDYAYGATGHPGIIPPHATLVFDVELLKLE

Linker
                                                                    (SEQ ID NO: 300)
AGCGGAGGAGGATCCGGA (SEQ ID NO: 301)
SGGGSG (SEQ ID NO: 302)
Caspase-9
GTGGACGGGTTTGGAGATGTGGGAGCCCTGGAATCCCTGCGGGGCAATGCCGATCTGGCTT

ACATCCTGTCTATGGAGCCTTGCGGCCACTGTCTGATCATTAACAATGTGAACTTCTGCAGAG

AGAGCGGGCTGCGGACCAGAACAGGATCCAATATTGACTGTGAAAAGCTGCGGAGAAGGTTC
```

-continued

TCTAGTCTGCACTTTATGGTCGAGGTGAAAGGCGATCTGACCGCTAAGAAAATGGTGCTGGC

CCTGCTGGAACTGGCTCGGCAGGACCATGGGGCACTGGATTGCTGCGTGGTCGTGATCCTG

AGTCACGGCTGCCAGGCTTCACATCTGCAGTTCCCTGGGGCAGTCTATGGAACTGACGGCTG

TCCAGTCAGCGTGGAGAAGATCGTGAACATCTTCAACGGCACCTCTTGCCCAAGTCTGGGCG

GGAAGCCCAAACTGTTCTTTATTCAGGCCTGTGGAGGCGAGCAGAAAGATCACGGCTTCGAA

GTGGCTAGCACCTCCCCCGAGGACGAATCACCTGGAAGCAACCCTGAGCCAGATGCAACCC

CCTTCCAGGAAGGCCTGAGGACATTTGACCAGCTGGATGCCATCTCAAGCCTGCCCACACCT

TCTGACATTTTCGTCTCTTACAGTACTTTCCCTGGATTTGTGAGCTGGCGCGATCCAAAGTCA

GGCAGCTGGTACGTGGAGACACTGGACGATATCTTTGAGCAGTGGGCCCATTCTGAAGACCT

GCAGAGTCTGCTGCTGCGAGTGGCCAATGCTGTCTCTGTGAAGGGGATCTACAAACAGATGC

CAGGATGCTTCAACTTTCTGAGAAAGAAACTGTTCTTTAAGACCTCCGCATCTAGGGCC (SEQ ID NO: 303)

VDGFGDVGALESLRGNADLAYILSMEPCGHCLIINNVNFCRESGLRTRTGSNIDCEKLRRRFSSLH

FMVEVKGDLTAKKMVLALLELARQDHGALDCCVVVILSHGCQASHLQFPGAVYGTDGCPVSVEKI

VNIFNGTSCPSLGGKPKLFFIQACGGEQKDHGFEVASTSPEDESPGSNPEPDATPFQEGLRTFDQ

LDAISSLPTPSDIFVSYSTFPGFVSWRDPKSGSWYVETLDDIFEQWAHSEDLQSLLLRVANAVSVK

GIYKQMPGCFNFLRKKLFFKTSASRA

Linker (SEQ ID NO: 304)

CCGCGG (SEQ ID NO: 305)

PR

T2A (SEQ ID NO: 306)

GAAGGCCGAGGGAGCCTGCTGACATGTGGCGATGTGGAGGAAAACCCAGGACCA (SEQ ID NO: 307)

EGRGSLLTCGDVEENPGP

Linker (SEQ ID NO: 308)

CCATGG (SEQ ID NO: 309)

PW

Signal peptide (SEQ ID NO: 310)

ATGGAGTTTGGACTTTCTTGGTTGTTTTTGGTGGCAATTCTGAAGGGTGTCCAGTGTAGCAGG (SEQ ID NO: 311)

MEFGLSWLFLVAILKGVQCSR

FMC63 scFv V$_L$ (SEQ ID NO: 312)

GACATCCAGATGACACAGACTACATCCTCCCTGTCTGCCTCTCTGGGAGACAGAGTCACCATC

AGTTGCAGGGCAAGTCAGGACATTAGTAAATATTTAAATTGGTATCAGCAGAAACCAGATGGA

ACTGTTAAACTCCTGATCTACCATACATCAAGATTACACTCAGGAGTCCCATCAAGGTTCAGTG

GCAGTGGGTCTGGAACAGATTATTCTCTCACCATTAGCAACCTGGAGCAAGAAGATATTGCCA

CTTACTTTTGCCAACAGGGTAATACGCTTCCGTACACGTTCGGAGGGGGGACTAAGTTGGAAA

TAACA (SEQ ID NO: 313)

DIQMTQTTSSLSASLGDRVTISCRASQDISKYLNWYQQKPDGTVKLLIYHTSRLHSGVPSRFSGSG

SGTDYSLTISNLEQEDIATYFCQQGNTLPYTFGGGTKLEIT

```
Linker                                                                              (SEQ ID NO: 314)
GGCGGAGGAAGCGGAGGTGGGGGC (SEQ ID NO: 315)
GGGSGGGG FMC63 scFv V_H                                                                      (SEQ ID NO: 316)
GAGGTGAAACTGCAGGAGTCAGGACCTGGCCTGGTGGCGCCCTCACAGAGCCTGTCCGTCA

CATGCACTGTCTCAGGGGTCTCATTACCCGACTATGGTGTAAGCTGGATTCGCCAGCCTCCA

CGAAAGGGTCTGGAGTGGCTGGGAGTAATATGGGGTAGTGAAACCACATACTATAATTCAGC

TCTCAAATCCAGACTGACCATCATCAAGGACAACTCCAAGAGCCAAGTTTTCTTAAAAATGAAC

AGTCTGCAAACTGATGACACAGCCATTTACTACTGTGCCAAACATTATTACTACGGTGGTAGCT

ATGCTATGGACTACTGGGGTCAAGGAACCTCAGTCACCGTCTCCTCA (SEQ ID NO: 317)
EVKLQESGPGLVAPSQSLSVTCTVSGVSLPDYGVSWIRQPPRKGLEWLGVIWGSETTYYNSALKS
RLTIIKDNSKSQVFLKMNSLQTDDTAIYYCAKHYYYGGSYAMDYWGQGTSVTVSS

Linker                                                                              (SEQ ID NO: 318)
GGATCC (SEQ ID NO: 319)
GS CD34 QBEND-10 epitope                                                               (SEQ ID NO: 320)
GAACTTCCTACTCAGGGGACTTTCTCAAACGTTAGCACAAACGTAAGT (SEQ ID NO: 321)
ELPTQGTFSNVSTNVS CD8 alpha stalk                                                                     (SEQ ID NO: 322)
CCCGCCCCAAGACCCCCCACACCTGCGCCGACCATTGCTTCTCAACCCCTGAGTTTGAGACC

CGAGGCCTGCCGGCCAGCTGCCGGCGGGGCCGTGCATACAAGAGGACTCGATTTCGCTTGC

GAC (SEQ ID NO: 323)
PAPRPPTPAPTIASQPLSLRPEACRPAAGGAVHTRGLDFACD

CD8 alpha transmembrane                                                             (SEQ ID NO: 324)
ATCTATATCTGGGCACCTCTCGCTGGCACCTGTGGAGTCCTTCTGCTCAGCCTGGTTATTACT

CTGTACTGTAATCACCGGAATCGCCGCCGCGTTTGTAAGTGTCCCAGG (SEQ ID NO: 325)
IYIWAPLAGTCGVLLLSLVITLYCNHRNRRRVCKCPR

Linker                                                                              (SEQ ID NO: 326)
GTCGAC (SEQ ID NO: 327)
VD CD3 zeta                                                                            (SEQ ID NO: 328)
AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAAGCTCTTCCACCTCGT
```

```
                                                                    (SEQ ID NO: 329)
RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

P2A
                                                                    (SEQ ID NO: 330)
GCAACGAATTTTTCCCTGCTGAAACAGGCAGGGGACGTAGAGGAAAATCCTGGTCCT (SEQ ID NO: 331)
ATNFSLLKQAGDVEENPGP

Myristoylation sequence
                                                                    (SEQ ID NO: 332)
atggggagtagcaagagcaagcctaaggaccccagccagcgc (SEQ ID NO: 333)
MGSSKSKPKDPSQR Linker
                                                                    (SEQ ID NO: 334)
ctcgac (SEQ ID NO: 335)
LD MyD88
                                                                    (SEQ ID NO: 336)
atggctgcaggaggtcccggcgcggggtctgcggccccggtctcctccacatcctcccttcccctggctgctctcaacatgcgagtgcggc gccgcctgtctctgttcttgaacgtgcggacacaggtggcggccgactggaccgcgctggcggaggagatggactttgagtacttggagat ccggcaactggagacacaagcggaccccactggcaggctgctggacgcctggcagggacgccctggcgcctctgtaggccgactgct cgatctgcttaccaagctgggccgcgacgacgtgctgctggagctgggacccagcattgaggaggattgccaaaagtatatcttgaagca gcagcaggaggaggctgagaagcctttacaggtggccgctgtagacagcagtgtcccacggacagcagagctggcgggcatcacca cacttgatgacccctggggcatatgcctgagcgtttcgatgccttcatctgctattgccccagcgacatc (SEQ ID NO: 337)
MAAGGPGAGSAAPVSSTSSLPLAALNMRVRRRLSLFLNVRTQVAADWTALAEEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI

Linker
                                                                    (SEQ ID NO: 338)
gtcgag (SEQ ID NO: 339)
VE CD40
                                                                    (SEQ ID NO: 340)
aaaaaggtggccaagaagccaaccaataaggccccccaccccaagcaggagccccaggagatcaattttcccgacgatcttcctggc tccaacactgctgctccagtgcaggagactttacatggatgccaaccggtcacccaggaggatggcaaagagagtcgcatctcagtgca ggagagacag (SEQ ID NO: 341)
KKVAKKPTNKAPHPKQEPQEINFPDDLPGSNTAAPVQETLHGCQPVTQEDGKESRISVQERQ
```

Example 19: MyD88/CD40-Based Costimulation to Enhance Survival and Proliferation of Chimeric Antigen Receptor (CAR)-Modified T Cells The efficacy of therapy with chimeric antigen receptor (CAR) T cells is associated with T cell expansion, persistence, and elaboration of multiple cytokines, in response to antigen exposure following in vivo adoptive transfer. Chimeric stimulating molecules including MyD88, CD40, or MyD88/CD40 polypeptides were assayed for their ability to costimulate CAR T cell activity. Cells that also co-expressed an inducible chimeric Caspase-9 polypeptide were assayed for their effectiveness as a safety switch; administration of the inducing ligand resulted in normalization of cytokine levels without loss of tumor control in in vivo tumor models.

Chimeric antigen receptor molecules that contain costimulatory domains such as CD28 and CD137 (4-1BB) exhibit varying degrees of persistence and proliferation, but have uniformly shown limited anti-tumor effects when used to treat solid tumors. Rather than including a CD28 or 4-1BB costimulatory domain as part of the CAR molecule, a chimeric costimulating molecule fusion costimulatory molecule comprised of MyD88 and CD40 (MyD88/CD40; "MC") activates broad costimulatory pathways (e.g., NF-κB, MAPK, Akt, JNK) in human T cells that can drive proliferation and survival when expressed in CAR-T cells.

To ensure the safety of highly potent MC-enabled CARs, an iCaspase-9 safety switch (iC9) was been incorporated to allow either complete or partial elimination of CAR T cells through titration of the small molecule dimerizing agent, rimiducid (AP1903) This safety switch rapidly clears T cells and reduces cytokine levels following rimiducid infusion. Titrating rimiducid, allowed for partial T cell elimination that still preserved CAR-T cell function.

Retrovirus and Transduction

CAR molecules containing single chain variable fragments (scFv) specific for CD19 (FMC63) and Her2 (FRP5) containing the anti-CD34 QBEnd-10 minimal epitope, CD8 stalk and transmembrane region and the CD3ζ cytoplasmic domain were cloned in-frame with the inducible chimeric Caspase-9-encoding polynucleotide. Additional constructs were made that included the CD28 costimulatory domain, or MyD88, CD40 or MyD88/CD40 (FIG. 37). T cells were transduced with EGFPluciferase (enhanced green fluorescent protein luciferase) to monitor in vivo expansion. PBMCs were activated with αCD3 and αCD28 antibodies and transduced with retrovirus. After 10 days, transduction was measured using CD3, CD19 and CD34 antibodies.

Coculture Assays:

T cells transduced with CAR vectors were cocultured together with GFP-expressing CD19$^+$ Raji lymphoma or Her2$^+$ SK-BR-3 breast cancer cell lines in the absence of exogenous IL-2. Cytokine production was assessed at 48 hours using ELISAs. Tumor and T cell number was measured using flow cytometry and cell counting on day 10.

Animal Models:

CD19:

5×10$^5$ Raji tumor cells were injected i.v. into NSG mice. On day 3, CD19 CAR-modified T cells were injected i.v. and bioluminescence (BLI) was measured for either tumor or T cells on a weekly basis by IVIS imaging. Mice losing >20% body weight were treated i.p. with 5 mg/kg rimiducid.

Ic9 Titration:

NSG mice were engrafted with Raji tumors, as above, then administered i.v. 5×10$^6$ CAR-modified T cells. After 15% body weight loss, mice were treated with rimiducid i.p. using a log-dose titration (0.0005-5 mg/kg).

Her2:

1×10$^6$ SK-BR-3 tumor cells were injected s.c. into NSG mice. After 7 days, mice were treated with i.t. injection of CAR-modified T cells. Tumor growth was measured by calipers (2-3 days) and BLI (weekly). T cell expansion BLI was measured by IVIS.

MyD88/CD40 (MC) Costimulation in CAR-T Cells

FIG. 38 provides results of assays of MC costimulation in Her2 CAR-T cells. A) Transduction and detection of primary T cells with iCasp9-Her2.ζ-MC CAR construct. B) IL-2 production from a coculture experiment mixing CAR-T cells with Her2$^+$ SK-BR-3-GFP tumor cells (1:1 ratio) after 48 hours (n=4). C and D) T cell and SK-BR-3-GFP tumor cell number from coculture experiment with different CAR constructs following 10 days of culture. E) Efficacy of tumor cell elimination comparing CAR-T cell costimulation with CD40 only, MyD88 only or with MC in a coculture assay against SK-BR-3-GFP after 10 days in culture. F) IL-2 production from coculture assay using constructs with the indicated costimulatory domains. *P-value=<0.01.

MC Enhances Her2 CAR-T Cell Efficacy In Vivo

FIG. 39 provides results of mouse in vivo efficacy assays using the various Her-2-specific CAR constructs. A) T cells were transduced with Her2., Her2.28.ζ or Her2.ζ-MC CARs and injected directly into luciferase-expressing s.c. Her2+ SK-BR-3 tumors engrafted into NSG mice (n=5). Bioluminescence (BLI) of tumor cells was measured by IVIS. Tumor size (B) was measured by calipers and survival (C) was calculated over 75 days. D) T cells were subsequently co-transduced with CAR and luciferase and injected directly into s.c. Her2$^+$ SK-BR-3 tumors engrafted into NSG mice (n=5). E) CAR-T cell expansion was calculated by region-of-interest ROI using IVIS imaging. F) Tumor size was calculated by caliper measurements and shows individual mice in each treatment group. *P-value=<0.05.

MC Enhances CD19 CAR-T Cell Efficacy In Vivo

FIG. 40 provides the results of mouse in vivo efficacy assays using the various CD19-specific CAR constructs. A) NSG mice (n=5 per group) were engrafted with Raji-luciferase tumor cells and then treated with non-transduced (NT) or iC9-CD19.ζ-MC CAR-modified T cells on day 3. Tumor growth was measured by IVIS imaging and calculated by whole-body BLI (B). C) Kaplan-Meier analysis from (A). At objective evidence of sCRS, rimiducid was administered (red boxes, panel A), leading to normalization of cytokines within 24 hrs and complete resolution of clinical sCRS without compromising tumor control (not shown).

Titration of Inducible Chimeric Caspase-9 Safety Switch Enabled CARs with Rimiducid FIG. 41 provides the results of mouse in vivo assays including CD19-specific CAR constructs and the Caspase-9 safety switch. A and B) NSG mice (n=5 per group) were engrafted with CD19$^+$ Raji lymphoma cells and treated with 5×10$^6$ iC9-CD19.ζ-MC/luciferase-transduced T cells at day 3. After 6 days, mice were treated i.p. with log dilutions of rimiducid (0.00005-5 mg/kg). BLI of CAR-T cells was assessed prior to rimiducid treatment and at 24 and 48 hours post-injection. C) Serum cytokine levels were measured from each group before (black line) and 24 hours post-administration (orange line) of rimiducid. *P-value=<0.01.

Summary

In these assays, it was found that MyD88 and CD40 ("MC") synergize to provide potent costimulation in CAR-modified T cells targeting both CD19+ "liquid" and Her2+ "solid" tumors. The MC costimulation resulted in increased T cell proliferation, cytokine production and antitumor efficacy in vivo compared to control CARs that included standard costimulatory molecules (e.g., CD28). The constructs that also expressed the inducible chimeric Caspase-9 polypeptide allowed for cessation of therapy at high levels, and also combined a versatile, titratable, cell therapy safety switch with the MC-driven CAR T cells, permitting rimiducid-dependent normalization of cytokine levels without loss of tumor control in in vivo tumor models.

Example 20: MyD88/CD40 Chimeric Stimulating Molecule Activity in T Cells Transduced with Composite Retroviral Vectors The signaling activity and physical expression of the chimeric stimulating molecule MyD88/CD40 (MC) either in cytoplasmic for (MC) or membrane-targeted form (myr-MC, for example was compared, and also compared to the inducible MyD88/CD40 molecule that includes a multimerizing ligand binding FKBP12 region. High level expression of MC was sufficient to generate a substantial basal activity whether 5' or 3' to DNA sequences encoding a Chimeric Antigen Receptor (CAR). Membrane localization strongly induced signaling activity but may reduce steady-state MC protein expression. The FKBP12 fusion on the 3' side of MC attenuated basal MC activity, and dimerization with the FKBP ligand strongly induced signaling activity without increasing iMC expression.

Methods

Summary of DNA Constructs:

The recombinant DNA vectors used to generate retroviruses capable of transducing genes encoding a CAR and/or MC and/or inducible Caspase-9 (iC9) as an operon are outlined schematically in FIGS. 48 and 49. Each construct used the pSFG retroviral vector backbone:

pBP0844—pSFG-iCasp9-T2A-CD19-ζ-P2A-MC:

This construct encodes human Caspase-9 fused with an SGGGSG linker (SEQ ID NO: 119) 3' to an F36V mutants of human FKBP12 with a short 5' MLEMLE linker (SEQ ID NO: 342). A T2A cotranslational cleavage sequence derived from *Thosea asigna* virus separates a sequence coding for an inducible chimeric caspase polypeptide (iC9) from a chimeric antigen receptor (CAR) containing a single chain variable fragment (scFv) targeting CD19, fused with a hinge and transmembrane domain, further fused on its cytoplasmic domain with the ζ chain of the T cell receptor CD3 complex. A P2A cotranslational cleavage sequence derived from porcine teschovirus-1 virus separates the CAR from the human MyD88/CD40 (MC) fusion protein.

pBP0414—pSFG-iCasp9-T2A-CD19-ζ is identical to pBP0844 but does not include the P2A and MC sequences 3' to the CAR.

pBP1099—pSFG-CD19-ζ encodes the CD19 CAR with its 5' translational initiation site modified to match that of the plasmids discussed below. It served as a negative control for MC function.

pBP1151—pSFG-MC-T2A-CD19-ζ-P2A encodes MC (human MyD88-CD40 fusion) 5' to the CAR construct with the two polypeptides separated by the T2A cotranslational cleavage site.

pBP1152—pSFG-MyrMC-T2A-CD19-ζ-P2A encodes MC with a 5' myristoylation-targeting sequence derived from human c-Src. N-terminal myristoylation of MC is predicted to lead to the accumulation of the signaling molecule at the plasma membrane of transduced cells. The CAR sequences are identical to pBP1151.

pBP0774—pSFG-iMC-T2A-CD19-ζ-P2A encodes MC as the soluble version of MC as a carboxy-terminal fusion with two tandem copies of human FKBP12v36, rendering MC rimiducid-inducible (iMC).

Costimulatory Activity Generated by MC Expression Constructs

HEK-293T cells were transduced with the SFG-based recombinant retroviral constructs outlined above, with helper plasmids pBP0049 and pBP0175 encoding the gag-pol and env genes necessary to package the recombinant RNAs as retroviruses. These retroviruses were transduced into CD3/CD28-activated donor-derived primary T cells. Cytokine production from transduced T cells was then used to assess the degree of costimulatory signaling activity conferred by the MC allele (if present) in the construct.

Three days following transduction, T cells were split and one population treated with 2 nM rimiducid. 24 or 48 hours after drug treatment, an aliquot of media supernatant was harvested and the T cell-derived cytokines, IL-2 and IL-6, were quantitated by enzyme linked immunosorbent assay (ELISA). IL-2 production typically requires both signal transduction from the antigen receptor (signal 1) via the NF-AT pathway and from costimulatory signals most simply assessed by NF-κB activation. In this experiment, signal 1 was provided by the initial activation of the T cells. It was found that T cells transduced with constructs pBP1099 or pBP0414 supported little IL-2 production nor did T cells that were not transduced at all (but were initially activated) (FIG. 50). In contrast, cells carrying pBP0844 had measurable IL-2 production 24 hours after media from T cells was changed. Rimiducid treatment only slightly reduced IL-2 production from these cells at 24 hours. By 48 hours, IL-2 production was substantial at above 2 ng/mL from $1 \times 10^6$ cells/mL. This 'basal' activity was dramatically lowered by rimiducid-mediated activation of apoptosis with iCaspase-9 at 48 hours.

Transduction with BP1151 (MC-CAR), encoding a comparable MC molecule but expressed at the 5' end of the bicistronic message, also had significant basal IL-2 production at 24 and 48 hours. Rimiducid treatment did not affect production significantly, as iC9 was not contained in this construct. BP1152 (MyrMC-CAR) transduction supported very robust IL-2 production, markedly elevated over BP1151 (MC-CAR), again without respect to rimiducid treatment. This construct contained a myristoylated- and hence membrane-localized MC, which likely elevated its signaling potential.

Markedly different basal activity was observed when cells were transduced with iMC-encoding BP774. 'Basal activity' (IL-2 secretion without rimiducid) was minimal but rimiducid-mediated MC aggregation revealed robust signaling as seen by high-level IL-2 production.

The inflammatory cytokine, IL-6, requires persistent costimulatory signaling (signal 2) but had a reduced requirement for antigen receptor-mediated NF-AT activity. IL-6 production is an independent assessment of MC activity in transduced cells. Overall, MC expression had a similar effect on IL-6 production, as it did with IL-2 levels in transduced human T cells. IL-6 secretion was negligible in the absence of MC transduction (FIG. 51, untransduced cells or transduced with BP1099 or BP0414). Substantial 'basal' production was observed at 24 or 48 hours from cells transduced with BP0844, which was silenced dramatically when iCaspase9 (iC9) was activated by rimiducid. Although substantial IL-6 production was induced by the non-targeted MC construct encoded by BP1151 (MC-CAR), IL-6 was highly elevated above these levels when MC contained the myristoylation-targeting domain (BP1152) (MyrMC-CAR). In both MC versions, which lack FKBPs, IL-6 production was rimiducid-independent, as expected. A low, but detectable basal costimulatory activity (~110 pg/ml from $10^6$/mL T cells), consistent with basal MC function, was observed with BP0774 transduction. Dimerization with 2 nM rimiducid robustly activated MC activity and IL-6 secretion to a level similar to that driven by the inducible chimeric Caspase-9 construct BP844.

Summary

This example provides data demonstrating that MC chimeric costimulating molecules support significant cytokine production. The high cytokine release from T cells transduced with BP1152 (MyrMC-CAR) did not correlate with high-level steady-state protein expression. Localization to the membrane via myristate tagging is likely to greatly enhance MC signaling. It is possible that full Myr-MC expression may not be observed due to incomplete solubilization of membrane proteins during extract preparation. Because MyD88 and CD40 are naturally situated at the plasma membrane, factors controlling their degradation may also localize to the membrane leading to reduced Myr-MC expression. The reduced observed expression of Myr-MC may also be due to high MC activity being selected against in individual cells within a transduced population. pBP1152 (MyrMC-CAR) had a reduced observed transduction efficiency and overall cell viability. Cells that were transduced expressed less of the same CAR than cells transduced with BP1151 (MC-CAR) possibly indicating selection for lower recombinant gene expression in BP1152 (MyrMC-CAR). The source of the proposed selection against high expression may be activation induced cell death (AICD) of T cells. High-level MC signaling may possibly feedback and negatively regulate MC protein expression. Myr-MC has high activity and low protein expression. Furthermore, T cells transduced with iMC encoded by BP0774 had reduced expression of soluble iMC with rimiducid treatment despite far greater MC activity. The reduction of 'basal' MC activity in non-localized iMC versus MC appeared to be greater than the more modest reduction of protein expression observed when comparing BP1151 (MC-CAR) and BP0774-transduced cells. FKBP12 fusion appeared to negatively affect spontaneous MC activity.

Example 21: Representative Embodiments

Provided hereafter are examples of certain embodiments of the technology.

A1. A nucleic acid comprising a polynucleotide encoding a chimeric antigen receptor, wherein the chimeric antigen receptor comprises (i) a transmembrane region; (ii) a MyD88 polypeptide or a truncated MyD88 polypeptide lacking a TIR domain; (iii) a CD40 cytoplasmic polypeptide region lacking a CD40 extracellular domain; (iv) a T cell activation molecule; and (v) an antigen recognition moiety.

A1.1. The nucleic acid of embodiment A1, wherein the chimeric antigen receptor further comprises a stalk polypeptide.

A2. The nucleic acid of any of embodiments A1-A1.1, wherein the chimeric antigen receptor is a polypeptide which comprises regions (i)-(v) in order from the amino to the carboxyl terminal of the polypeptide of (v), (i), (ii), (iii), (iv).

A3. The nucleic acid of any of embodiments A1-A1.1, wherein the chimeric antigen receptor is a polypeptide which comprises regions (i)-(v) in order from the amino to the carboxyl terminal of the polypeptide of (v), (i), (iii), (ii), (iv).

A4. Reserved.

A5. Reserved.

A6. The nucleic acid of any one of embodiments A1-A3, wherein the T cell activation molecule is an ITAM-containing, Signal 1 conferring molecule.

A7. The nucleic acid of any one of embodiments A1-A6, wherein the T cell activation molecule is a CD3ζ polypeptide.

A8. The nucleic acid of any one of embodiments A1-A6, wherein the T cell activation molecule is an Fc epsilon receptor gamma (FcεR1γ) subunit polypeptide.

A9. The nucleic acid of any one of embodiments A1-A8, wherein the antigen recognition moiety binds to an antigen on a tumor cell.

A10. The nucleic acid of any one of embodiments A1-A9, wherein the antigen recognition moiety binds to an antigen on a cell involved in a hyperproliferative disease.

A11. The nucleic acid of any one of embodiments A1-A10, wherein the antigen recognition moiety binds to an antigen selected from the group consisting of PSMA, PSCA, MUC1, CD19, ROR1, Mesothelin, GD2, CD123, MUC16, and Her2/Neu.

A12. The nucleic acid of any one of embodiments A1-A11, wherein the antigen recognition moiety binds to PSCA.

A13. The nucleic acid of any one of embodiments A1-A11, wherein the antigen recognition moiety binds to CD19.

A14. The nucleic acid of any one of embodiments A1-A11, wherein the antigen recognition moiety binds to a viral or bacterial antigen.

A15. The nucleic acid of any one of embodiments A1-A14, wherein the antigen recognition moiety is a single chain variable fragment.

A16. The nucleic acid of any one of embodiments A1-A16, wherein the transmembrane region is a CD8 transmembrane region.

A17. The nucleic acid of any one of embodiments A1-A17, wherein the MyD88 polypeptide has the amino acid sequence of SEQ ID NO: 282, or a functional fragment thereof.

A18. The nucleic acid of any one of embodiments A1-A17, wherein the truncated MyD88 polypeptide has the amino acid sequence of SEQ ID NO: 147, or a functional fragment thereof.

A19. The nucleic acid of any one of embodiments A1-A18, wherein the cytoplasmic CD40 polypeptide has the amino acid sequence of SEQ ID NO: 149, or a functional fragment thereof.

A20. The nucleic acid of any one of embodiments A1-A19, wherein the antigen recognition moiety is a single chain variable fragment that binds to CD19.

A20.1. The nucleic acid of any one of embodiments A1-A19, wherein the antigen recognition moiety is a single chain variable fragment that binds to Her2/Neu.

A21. The nucleic acid of any one of embodiments A1-A20.1, wherein the CD3 polypeptide has comprises an amino acid sequence of SEQ ID NO:151, or a functional fragment thereof.

A22. The nucleic acid of any one of embodiments A1-A21, wherein the transmembrane region polypeptide comprises an amino acid sequence of SEQ ID NO: 143, or a functional fragment thereof.

A23. Reserved.

A24. Reserved.

A25. The nucleic acid of any one of embodiments A1-A24, wherein the nucleic acid comprises a promoter sequence operably linked to the polynucleotide.

A26. The nucleic acid of any one of embodiments A1-A25, wherein the nucleic acid is contained within a viral vector.

A27. The nucleic acid of embodiment A26, wherein the viral vector is a retroviral vector.

A28. The nucleic acid of embodiment A27, wherein the retroviral vector is a murine leukemia virus vector.

A29. The nucleic acid of embodiment A28, wherein the retroviral vector is an SFG vector.

A30. The nucleic acid of embodiment A26, wherein the viral vector is an adenoviral vector.

A31. The nucleic acid of embodiment A26, wherein the viral vector is a lentiviral vector.

A31.1. The nucleic acid of embodiment A26, wherein the viral vector is selected from the group consisting of adeno-associated virus (AAV), Herpes virus, and Vaccinia virus.

A31.2. The nucleic acid of any one of embodiments A1-A25, wherein the nucleic acid is prepared or in a vector designed for electroporation, sonoporation, or biolistics, or is attached to or incorporated in chemical lipids, polymers, inorganic nanoparticles, or polyplexes.

A32. The nucleic acid of any one of embodiments A1-A25, wherein the nucleic acid is contained within a plasmid.

A32.1. The nucleic acid of any one of embodiments A1-A32, comprising a nucleotide sequence of Example 18, or encoding a chimeric antigen receptor polypeptide of Example 18.

A33. A chimeric antigen receptor polypeptide encoded by the nucleic acid of any one of embodiments A1-A32.1

A34. A modified cell transfected or transduced with a nucleic acid of any one of embodiments A1-A32.1.

A34.1. The modified cell of embodiment A34, wherein the chimeric antigen receptor does not contain a T cell activation molecule, further comprising a nucleic acid comprising a polynucleotide encoding a T cell activation molecule.

A34.2. The modified cell of embodiment A34.1, wherein the T cell activation molecule is a CD3ζ polypeptide.

A35. The modified cell of any one of embodiments A34-A34.2, wherein the modified cell is a T cell, tumor infiltrating lymphocyte, NK-T cell, or NK cell.

A36. The modified cell of any one of embodiments A34-A34.2, wherein the cell is a T cell.

A37. The modified cell of any one of embodiments A34-A36, wherein the cell is obtained or prepared from bone marrow.

A38. The modified cell of any one of embodiments A34-A36, wherein the cell is obtained or prepared from umbilical cord blood.

A39. The modified cell of any one of embodiments A34-A36, wherein the cell is obtained or prepared from peripheral blood.

A40. The modified cell of any one of embodiments A34-A36, wherein the cell is obtained or prepared from peripheral blood mononuclear cells.

A42. The modified cell of any one of embodiments A34-A40, wherein the cell is a human cell.

A42.1. The modified cell of any one of embodiments A34-A42, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

A43. A method for stimulating a cell mediated immune response to a target cell population or tissue in a subject, comprising administering a modified cell of any one of embodiments A34-A42.1 to the subject, wherein the antigen recognition moiety binds to an antigen on the target cell.

A44. The method of embodiment A43, wherein the target cell is a tumor cell.

A45. The method of any one of embodiments A43 or A44, wherein the number or concentration of target cells in the subject is reduced following administration of the modified cell.

A46. The method of any one of embodiments A43-A45, comprising measuring the number or concentration of target cells in a first sample obtained from the subject before administering the modified cell, measuring the number concentration of target cells in a second sample obtained from the subject after administration of the modified cell, and determining an increase or decrease of the number or concentration of target cells in the second sample compared to the number or concentration of target cells in the first sample.

A47. The method of embodiment A46, wherein the concentration of target cells in the second sample is decreased compared to the concentration of target cells in the first sample.

A48. The method of embodiment A46, wherein the concentration of target cells in the second sample is increased compared to the concentration target cells in the first sample.

A49. The method of any one of embodiments A43-A48, wherein an additional dose of modified cells is administered to the subject.

A50. A method for providing anti-tumor immunity to a subject, comprising administering to the subject an effective amount of a modified cell of any one of embodiments A34-A42.1.

A51. A method for treating a subject having a disease or condition associated with an elevated expression of a target antigen, comprising administering to the subject an effective amount of a modified cell of any one of embodiments A34-A42.1.

A52. The method of embodiment A51, wherein the target antigen is a tumor antigen.

A53. The method of any one of embodiments A43-A52, wherein the modified cells are autologous T cells.

A54. The method of any one of embodiments A43-A52, wherein the modified cells are allogeneic T cells.

A55. A method for reducing the size of a tumor in a subject, comprising administering a modified cell of any one of embodiments A34-A42.1 to the subject, wherein the antigen recognition moiety binds to an antigen on the tumor.

A56. The method of any one of embodiments A43-A55, wherein the subject has been diagnosed as having a tumor.

A57. The method of any one of embodiments A43-A56, wherein the subject has cancer.

A58. The method of any one of embodiments A43-A57, wherein the subject has a solid tumor.

A59. The method of any one of embodiments A43-A58, wherein the modified cell is a tumor infiltrating lymphocyte or a T cell.

A60. The method of any one of embodiments A43-A59, wherein the modified cell is delivered to a tumor bed.

A61. The method of embodiment A57, wherein the cancer is present in the blood or bone marrow of the subject.

A62. The method of any one of embodiments A43-A55, wherein the subject has a blood or bone marrow disease.

A63. The method of any one of embodiments A43-A55, wherein the subject has been diagnosed with any condition or condition that can be alleviated by stem cell transplantation.

A64. The method of any one of embodiments A43-A55, wherein the subject has been diagnosed with sickle cell anemia or metachromatic leukodystrophy.

A65. The method of any one of embodiments A43-A55, wherein the patient has been diagnosed with a condition selected from the group consisting of a primary immune deficiency condition, hemophagocytosis lymphohistiocytosis (HLH) or other hemophagocytic condition, an inherited marrow failure condition, a hemoglobinopathy, a metabolic condition, and an osteoclast condition.

A66. The method of any one of embodiments A43-A65, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

A67. The method of any one of embodiments A43-A66, further comprising determining whether an additional dose of the modified cell should be administered to the subject.

A68. The method of any one of embodiments A44-A67, further comprising administering an additional dose of the modified cell to the subject, wherein the disease or condition symptoms remain or are detected following a reduction in symptoms.

A69. The method of any one of embodiments A44-A67, further comprising identifying the presence, absence or stage of a condition or disease in a subject; and transmitting an indication to administer modified cell of any one of embodiments 28-35, maintain a subsequent dosage of the modified cell, or adjust a subsequent dosage of the modified cell administered to the patient based on the presence, absence or stage of the condition or disease identified in the subject.

A70. The method of any one of embodiments A44-A69, wherein the condition is leukemia.

A71. The method of any one of embodiments A44-A70, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

A72. The method of any one of embodiments A44-A71, wherein the modified cell is transfected or transduced in vivo.

A73. The modified cell of any one of embodiments A34-A42, wherein the modified cell is transfected or transduced in vivo.

A74. A method for expressing a chimeric antigen receptor in a cell, comprising contacting a nucleic acid of any one of embodiments A1 to A33 with a cell under conditions in which the nucleic acid is incorporated into the cell, whereby the cell expresses the chimeric antigen receptor from the incorporated nucleic acid.

A75. The method of embodiment A74, wherein the nucleic acid is contacted with the cell ex vivo.

A76. The method of embodiment A74, wherein the nucleic acid is contacted with the cell in vivo.

A77. The modified cell of any one of embodiments A34-A42, wherein the modified cell further comprises a polynucleotide encoding a chimeric Caspase-9 polypeptide comprising a multimeric ligand binding region and a Caspase-9 polypeptide.

A77.1. A nucleic acid comprising
a first polynucleotide encoding a chimeric antigen receptor, wherein the chimeric antigen receptor comprises (i) a transmembrane region; (ii) a MyD88 polypeptide or a truncated MyD88 polypeptide lacking a TIR domain; (iii) a CD40 cytoplasmic polypeptide region lacking a CD40 extracellular domain; (iv) a T cell activation molecule; and (v) an antigen recognition moiety; and
a second polynucleotide encoding a chimeric Caspase-9 polypeptide comprising a multimeric ligand binding region and a Caspase-9 polypeptide.

A77.2. The nucleic acid of embodiment A77.1, further comprising at least one promoter.

A77.3. The nucleic acid of embodiment A77.1, further comprising at least two promoters.

A77.4. The nucleic acid of embodiment A77.1, wherein one promoter is operably linked to both the first and second polynucleotide.

A77.5. The nucleic acid of embodiment A77.1, further comprising a third polynucleotide encoding a linker polypeptide between the first and second polynucleotide, wherein the linker polypeptide separates the translation products of the first and second polynucleotides during or after translation.

A77.6. The nucleic acid of embodiment A77.5, wherein the linker polypeptide is a 2A polypeptide.

A77.7. The nucleic acid of embodiment A77.5, wherein the nucleic acid encodes a polypeptide comprising a chimeric antigen receptor, a 2A polypeptide, and a Caspase-9 polypeptide.

A77.8. The nucleic acid of embodiment A77.3, therein the first polynucleotide is operably linked to a first promoter, and the second polynucleotide is operably linked to a second promoter.

A77.9. The nucleic acid of embodiment A77.2, wherein two RNA transcripts are produced complementary to the two polynucleotides.

A77.10. A modified cell transfected or transduced with a nucleic acid of any one of embodiments A77.1-A77.9.

A78. The modified cell of any one of embodiments A77 or A77.10, wherein the multimeric ligand binding region is an FKB12v36 region.

A79. The modified cell of any one of embodiments 77-78, wherein the multimeric ligand is AP1903, or AP20187.

A80. The modified cell of any one of embodiments 77-79, wherein the Caspase-9 polypeptide is a modified Caspase-9 polypeptide comprising an amino acid substitution selected from the group consisting of the caspase variants in Table 1.

A81. The method of any one of embodiments A44-A71, wherein the modified cell further comprises a polynucleotide encoding a chimeric caspase polypeptide comprising a multimeric ligand binding region and a Caspase-9 polypeptide.

A82. The method of embodiment A81, wherein the multimeric ligand binding region is an FKB12v36 region.

A83. The method of any one of embodiments A81-A82, wherein the multimeric ligand is AP1903 or AP20187.

A84. The method of any one of embodiments A81-A83, wherein the Caspase-9 polypeptide is a modified Caspase-9 polypeptide comprising an amino acid substitution selected from the group consisting of the caspase variants in Table 1.

A85. The method of any one of embodiments A81-A84, further comprising administering the multimeric ligand to the subject following administration of the modified cells to the subject.

A86. The method of embodiment A85, wherein after administration of the multimeric ligand, the number of modified cells comprising the chimeric Caspase-9 polypeptide is reduced.

A87. The method of embodiment A86, wherein the number of modified cells comprising the chimeric Caspase-9 polypeptide is reduced by 90%.

A88. The method of any one of embodiments A81-A87, comprising determining that the subject is experiencing a negative symptom following administration of the modified cells to the subject, and administering the ligand to reduce or alleviate the negative symptom.

B1. A nucleic acid comprising a polynucleotide encoding a chimeric stimulating molecule, wherein the chimeric stimulating molecule comprises (i) a membrane targeting region; (ii) a MyD88 polypeptide or a truncated MyD88 polypeptide lacking the TIR domain; and (iii) a CD40 cytoplasmic polypeptide region lacking the CD40 extracellular domain.

B1.1. A nucleic acid comprising a polynucleotide encoding a chimeric stimulating molecule, wherein the chimeric stimulating molecule comprises (i) a membrane targeting region; and (ii) a MyD88 polypeptide or a truncated MyD88 polypeptide lacking the TIR domain.

B1.2. A nucleic acid comprising a polynucleotide encoding a chimeric stimulating molecule, wherein the chimeric stimulating molecule comprises (i) a membrane targeting region; and (ii) a CD40 cytoplasmic polypeptide region lacking the CD40 extracellular domain.

B2. The nucleic acid of any one of embodiments B1-B1.2, wherein the chimeric stimulating molecule is a polypeptide which comprises regions (i)-(iii) in order from the amino to the carboxyl terminal of the polypeptide of (i), (ii), (iii).

B3. The nucleic acid of any one of embodiments B1-B1.2, wherein the chimeric antigen receptor is a polypeptide which comprises regions (i)-(iii) in order from the amino to the carboxyl terminal of the polypeptide of (i), (iii), (ii).

B4. The nucleic acid of any one of embodiments B1-B3, wherein the chimeric stimulating molecule further comprises a T cell activation molecule.

B5. The nucleic acid of embodiment B4, wherein the T cell activation molecule is an ITAM-containing signal 1 conferring molecule.

B6. The nucleic acid of embodiment B4, wherein the T cell activation molecule is a CD3ζ polypeptide.

B6.1. The nucleic acid of embodiment B4, wherein the T cell activation molecule is an Fc epsilon receptor gamma (FcεR1γ) subunit polypeptide.

B7. The nucleic acid of any one of embodiments B1-B6, wherein the truncated MyD88 polypeptide has the amino acid sequence of SEQ ID NO: 147, or a functional fragment thereof.

B7.1. The nucleic acid of any one of embodiments A1-A17, wherein the MyD88 polypeptide has the amino acid sequence of SEQ ID NO: 282, or a functional fragment thereof.

B8. The nucleic acid of any one of embodiments B1, or B2-B7, wherein the cytoplasmic CD40 polypeptide has the amino acid sequence of SEQ ID NO: 149, or a functional fragment thereof.

B9. The nucleic acid of any one of embodiments B6-B8, wherein the CD3ζ polypeptide comprises an amino acid sequence of SEQ ID NO: 151, or a functional fragment thereof.

B10. The nucleic acid of any one of embodiments B1-B9, wherein the membrane targeting region is selected from the group consisting of a myristoylation region, palmitoylation region, prenylation region, and transmembrane sequences of receptors.

B11. The nucleic acid of any one of embodiments B1-B10, wherein the membrane targeting region is a myristoylation region.

B11.1. The nucleic acid of any one of embodiments B1-B10, wherein the polynucleotide encoding the chimeric stimulating molecule does not include a dimerization or multimerization molecule binding region.

B12. The nucleic acid of any one of embodiments B1-B11.1, wherein the nucleic acid comprises a promoter sequence operably linked to the polynucleotide.

B13. The nucleic acid of any one of embodiments B1-B12, wherein the nucleic acid is contained within a viral vector.

B14. The nucleic acid of embodiment B13, wherein the viral vector is a retroviral vector.

B15. The nucleic acid of embodiment B14, wherein the retroviral vector is a murine leukemia virus vector.

B16. The nucleic acid of embodiment B14, wherein the retroviral vector is an SFG vector.

B17. The nucleic acid of embodiment B13, wherein the viral vector is an adenoviral vector.

B18. The nucleic acid of embodiment B13, wherein the viral vector is a lentiviral vector.

B18.1. The nucleic acid of embodiment B13, wherein the viral vector is selected from the group consisting of adeno-associated virus (AAV), Herpes virus, and Vaccinia virus.

B19. The nucleic acid of any one of embodiments B1-B12, wherein the nucleic acid is contained within a plasmid.

B20. A chimeric stimulating molecule polypeptide encoded by the nucleic acid of any one of embodiments B1-B19.

B21. A modified cell transfected or transduced with a nucleic acid of any one of embodiments B1-B19.

B22. The modified cell of embodiment B21, wherein the modified cell is a T cell, tumor infiltrating lymphocyte, NK-T cell, TCR-expressing cell, or NK cell.

B23. The modified cell of embodiment B21, wherein the cell is a T cell.

B24. The modified cell of any one of embodiments B21-B23, wherein the cell is obtained or prepared from bone marrow.

B25. The modified cell of any one of embodiments B21-B23, wherein the cell is obtained or prepared from umbilical cord blood.

B26. The modified cell of any one of embodiments B21-B25, wherein the cell is obtained or prepared from peripheral blood.

B27. The modified cell of any one of embodiments B21-B25, wherein the cell is obtained or prepared from peripheral blood mononuclear cells.

B27.1 A modified cell comprising
a) a nucleic acid, wherein the nucleic acid comprises a polynucleotide encoding a chimeric stimulating molecule, wherein the chimeric stimulating molecule comprises (i) a membrane targeting region; (ii) a MyD88 polypeptide or a truncated MyD88 polypeptide lacking the TIR domain; and (iii) a CD40 cytoplasmic polypeptide region lacking the CD40 extracellular domain; and
b) a chimeric antigen receptor.

B27.2. A modified cell comprising
a) a nucleic acid, wherein the nucleic acid comprises a polynucleotide encoding a chimeric stimulating molecule, wherein the chimeric stimulating molecule comprises (i) a membrane targeting region; and (ii) a MyD88 polypeptide or a truncated MyD88 polypeptide lacking the TIR domain; and
b) a chimeric antigen receptor.

B27.3. A modified cell comprising
a) a nucleic acid, wherein the nucleic acid comprises a polynucleotide encoding a chimeric stimulating molecule, wherein the chimeric stimulating molecule comprises (i) a membrane targeting region; and (ii) a CD40 cytoplasmic polypeptide region lacking the CD40 extracellular domain; and
b) a chimeric antigen receptor.

B28. The modified cell of any one of embodiments B21-B27.3, wherein the cell is a human cell.

B29. The modified cell of any one of embodiments B21-B28, wherein the modified cell further comprises a polynucleotide encoding a chimeric antigen receptor.

B30. The modified cell of embodiment B29, wherein the chimeric antigen receptor comprises an antigen-recognition moiety.

B30.1. The modified cell of any one of embodiments B21-B30, wherein the cell is a T cell.

B30.2. The modified cell of any one of embodiments B21-B28, wherein the modified cell further comprises a polynucleotide encoding a T cell receptor.

B30.3. The modified cell of any one of embodiments B21-28, wherein the modified cell further comprises a polynucleotide encoding a T cell receptor-based CAR.

B30.4. The modified cell of any one of embodiments B30.2 or B30.3, wherein modified cell is transfected or transduced with a nucleic acid comprising a polynucleotide encoding the T cell receptor or T cell receptor-based CAR.

B31. The modified cell of any one of embodiments B27.1 or B30, wherein the antigen-recognition moiety is a single chain variable fragment.

B31.1. The modified cell of any one of embodiments B29-B31, wherein the chimeric antigen receptor or T cell receptor binds to an antigen on a tumor cell.

B32. The modified cell of any one of embodiments B29-B31.1, wherein the chimeric antigen receptor or T cell receptor binds to an antigen on a cell involved in a hyperproliferative disease.

B33. The modified cell of any one of embodiments B29-B31.1, wherein the chimeric antigen receptor or T cell receptor binds to an antigen selected from the group consisting of PSMA, PSCA, MUC1, CD19, ROR1, Mesothelin, GD2, CD123, MUC16, and Her2/Neu.

B34 The modified cell of any one of embodiments B29-B33, wherein the chimeric antigen receptor or T cell receptor binds to CD19.

B35. The modified cell of any one of embodiments B29-B33, wherein the chimeric antigen receptor or T cell receptor binds to Her2/Neu.

B36. The modified cell of any one of embodiments B29-B33, wherein the antigen recognition moiety binds to a viral or bacterial antigen.

B36.1. The modified cell of any one of embodiments B29-B36, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

B37. A method for stimulating a T cell-mediated immune response in a subject, comprising administering a modified cell of any one of embodiments B21-B36.1 to the subject.

B37.1. The method of embodiment B37, wherein the modified cell comprises a chimeric antigen receptor or T cell receptor that binds to an antigen on a target cell.

B38. The method of embodiment B37.1, wherein the target cell is a tumor cell.

B39. The method of any one of embodiments B37-B38, wherein the number or concentration of target cells in the subject is reduced following administration of the modified cell.

B40. The method of any one of embodiments B37-B39, comprising measuring the number or concentration of target cells in a first sample obtained from the subject before administering the modified cell, measuring the number concentration of target cells in a second sample obtained from the subject after administration of the modified cell, and determining an increase or decrease of the number or concentration of target cells in the second sample compared to the number or concentration of target cells in the first sample.

B41. The method of embodiment B40, wherein the concentration of target cells in the second sample is decreased compared to the concentration of target cells in the first sample.

B42. The method of embodiment B40, wherein the concentration of target cells in the second sample is increased compared to the concentration target cells in the first sample.

B43. The method of any one of embodiments B40-B42, wherein an additional dose of modified cells is administered to the subject.

B44. A method for providing anti-tumor immunity to a subject, comprising administering to the subject an effective amount of a modified cell of any one of embodiments B21-B36.1.

B45. A method for treating a subject having a disease or condition associated with an elevated expression of a target antigen, comprising administering to the subject an effective amount of a modified cell of any one of embodiments B21-B36.1.

B46. The method of embodiment B45, wherein the target antigen is a tumor antigen.

B47. The method of any one of embodiments B37-B46, wherein the modified cells are autologous T cells.

B48. The method of any one of embodiments B37-B46, wherein the modified cells are allogeneic T cells.

B50. A method for reducing the size of a tumor in a subject, comprising administering a modified cell of any one of embodiments B29-B36.1 to the subject, wherein the antigen recognition moiety binds to an antigen on the tumor.

B51. The method of any one of embodiments B37-B50, wherein the subject has been diagnosed as having a tumor.

B52. The method of any one of embodiments B37-B51, wherein the subject has cancer.

B53. The method of any one of embodiments B37-B51, wherein the subject has a solid tumor.

B54. The method of any one of embodiments B37-B53, wherein the modified cell is a tumor infiltrating lymphocyte or a T cell.

B55. The method of any one of embodiments B37-B54, wherein the modified cell is delivered to a tumor bed.

B56. The method of embodiment B52, wherein the cancer is present in the blood or bone marrow of the subject.

B57. The method of any one of embodiments B37-B51, wherein the subject has a blood or bone marrow disease.

B58. The method of any one of embodiments B37-B51, wherein the subject has been diagnosed with any condition or condition that can be alleviated by stem cell transplantation.

B59. The method of any one of embodiments B37-B51, wherein the subject has been diagnosed with sickle cell anemia or metachromatic leukodystrophy.

B60. The method of any one of embodiments B37-B51, wherein the patient has been diagnosed with a condition selected from the group consisting of a primary immune deficiency condition, hemophagocytosis lymphohistiocytosis (HLH) or other hemophagocytic condition, an inherited marrow failure condition, a hemoglobinopathy, a metabolic condition, and an osteoclast condition.

B61. The method of any one of embodiments B37-B51, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

B62. The method of any one of embodiments B37-B61, further comprising determining whether an additional dose of the modified cell should be administered to the subject.

B63. The method of any one of embodiments B37-B62, further comprising administering an additional dose of the modified cell to the subject, wherein the disease or condition symptoms remain or are detected following a reduction in symptoms.

B64. The method of any one of embodiments B37-B63, further comprising identifying the presence, absence or stage of a condition or disease in a subject; and transmitting an indication to administer modified cell of any one of embodiments B31-B36, maintain a subsequent dosage of the modified cell, or adjust a subsequent dosage of the modified cell administered to the patient based on the presence, absence or stage of the condition or disease identified in the subject.

B65. The method of any one of embodiments B37-B64, wherein the condition is leukemia.

B66. Reserved.

B67. The method of any one of embodiments B37-B64, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

B68. The method of any one of embodiments B37-B67, wherein the modified cell is transfected or transduced in vivo.

B69. The modified cell of any one of embodiments B21-B67, wherein the modified cell is transfected or transduced in vivo.

B70. A method for expressing a chimeric stimulating molecule in a cell, comprising contacting a nucleic acid of any one of embodiments B1 to B20 with a cell under conditions in which the nucleic acid is incorporated into the cell, whereby the cell expresses the chimeric antigen receptor from the incorporated nucleic acid.

B71. The method of embodiment B70, wherein the nucleic acid is contacted with the cell ex vivo.

B72. The method of embodiment B70, wherein the nucleic acid is contacted with the cell in vivo.

B73. The modified cell of any one of embodiments B1-B36.1, wherein the modified cell further comprises a polynucleotide encoding a chimeric Caspase-9 polypeptide comprising a multimeric ligand binding region and a Caspase-9 polypeptide.

B73.1. A nucleic acid comprising
a first polynucleotide encoding a chimeric stimulating molecule, wherein the chimeric stimulating molecule comprises (i) a membrane targeting region; (ii) a MyD88 polypeptide or a truncated MyD88 polypeptide lacking the TIR domain; and (iii) a CD40 cytoplasmic polypeptide region lacking the CD40 extracellular domain; and
a second polynucleotide encoding a chimeric Caspase-9 polypeptide comprising a multimeric ligand binding region and a Caspase-9 polypeptide.

B73.2. The nucleic acid of embodiment B73.1, further comprising at least one promoter.

B73.3. The nucleic acid of embodiment B73.1, further comprising at least two promoters.

B73.4. The nucleic acid of embodiment B73.1, wherein one promoter is operably linked to both the first and second polynucleotide.

B73.5. The nucleic acid of embodiment B73.1, further comprising a third polynucleotide encoding a linker polypeptide between the first and second polynucleotide, wherein the linker polypeptide separates the translation products of the first and second polynucleotides during or after translation.

B73.6. The nucleic acid of embodiment B73.5, wherein the linker polypeptide is a 2A polypeptide.

B73.7. The nucleic acid of embodiment B73.5, wherein the nucleic acid encodes a polypeptide comprising a chimeric stimulating molecule, a 2A polypeptide, and a Caspase-9 polypeptide.

B73.8. The nucleic acid of embodiment B73.3, therein the first polynucleotide is operably linked to a first promoter, and the second polynucleotide is operably linked to a second promoter.

B73.9. The nucleic acid of embodiment B73.2, wherein two RNA transcripts are produced complementary to the two polynucleotides.

B73.10. A modified cell transfected or transduced with a nucleic acid of any one of embodiments B73.1-B73.9.

B74. The modified cell of any one of embodiments B73 or B73.10, wherein the multimeric ligand binding region is an FKB12v36 region.

B75. The modified cell of any one of embodiments B73, B73.10, or B74, wherein the multimeric ligand is AP1903 or AP20187.

B76. The modified cell of any one of embodiments B73-B75, wherein the Caspase-9 polypeptide is a modified Caspase-9 polypeptide comprising an amino acid substitution selected from the group consisting of the caspase variants in Table 1.

B77. The method of any one of embodiments B37-B72, wherein the modified cell further comprises a polynucleotide encoding a chimeric caspase polypeptide comprising a multimeric ligand binding region and a Caspase-9 polypeptide.

B78. The method of embodiment B77, wherein the multimeric ligand binding region is an FKB12v36 region.

B79. The method of any one of embodiments B77-B78, wherein the multimeric ligand is AP1903, or AP20187.

B80. The method of any one of embodiments B77-B79, wherein the Caspase-9 polypeptide is a modified Caspase-9 polypeptide comprising an amino acid substitution selected from the group consisting of the caspase variants in Table 1.

B81. The method of any one of embodiments B77-B80, further comprising administering the multimeric ligand to the subject following administration of the modified cells to the subject.

B82. The method of embodiment B81, wherein after administration of the multimeric ligand, the number of modified cells comprising the chimeric Caspase-9 polypeptide is reduced.

B83. The method of embodiment B82, wherein the number of modified cells comprising the chimeric Caspase-9 polypeptide is reduced by 90%.

B84. The method of any one of embodiments B77-B83, comprising determining that the subject is experiencing a negative symptom following administration of the modified cells to the subject, and administering the ligand to reduce or alleviate the negative symptom.

C1. A nucleic acid comprising a promoter operably linked to a polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain.

C2. A nucleic acid comprising a promoter operably linked to a polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, with the proviso that the chimeric stimulating molecule does not include a membrane targeting region.

C3. A nucleic acid comprising
  a) a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and
  b) a second polynucleotide encoding a chimeric Caspase-9 polypeptide comprising a multimeric ligand binding region and a Caspase-9 polypeptide.

C4. A nucleic acid comprising
  a) a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, with the proviso that the chimeric stimulating molecule does not include a membrane targeting region; and
  b) a second polynucleotide encoding a chimeric Caspase-9 polypeptide comprising a multimeric ligand binding region and a Caspase-9 polypeptide.

C5. A nucleic acid comprising
  a) a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and
  b) a second polynucleotide encoding a chimeric antigen receptor.

C6. A nucleic acid comprising
  a) a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, with the proviso that the chimeric stimulating molecule does not include a membrane targeting region; and
  b) a second polynucleotide encoding a chimeric antigen receptor.

C7. A nucleic acid comprising
  a) a promoter operably linked to a first polynucleotide encoding a cytoplasmic chimeric stimulating molecule, wherein the cytoplasmic chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain; and
  b) a second polynucleotide encoding a T cell receptor or a T cell receptor-based chimeric antigen receptor.

C8. A nucleic acid comprising
  a) a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, with the proviso that the chimeric stimulating molecule does not include a membrane targeting region; and
  b) a second polynucleotide encoding a T cell receptor or a T cell receptor-based chimeric antigen receptor.

C9. A nucleic acid comprising
  a) a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, with the proviso that the chimeric stimulating molecule does not include a membrane targeting region; and
  b) a second polynucleotide encoding a T cell receptor, a T cell receptor-based chimeric antigen receptor, or a chimeric antigen receptor; and
  c) a third polynucleotide encoding a chimeric Caspase-9 polypeptide comprising a multimeric ligand binding region and a Caspase-9 polypeptide.

C10. The nucleic acid of any one of embodiments C5-C6 or C8-C9, wherein the chimeric antigen receptor comprises (i) a transmembrane region; (ii) a T cell activation molecule; and (iii) an antigen recognition moiety.

C11. The nucleic acid of embodiment 010, wherein the chimeric antigen receptor further comprises a co-stimulatory molecule.

C12. The nucleic acid of embodiment C11, wherein the co-stimulatory molecule is selected from the group consisting of CD28, OX40, and 4-1BB.

C13. The nucleic acid of any one of embodiments C1-C12, comprising a second promoter operably linked to the second polynucleotide.

C14. The nucleic acid of embodiment C9, comprising a second promoter operably linked to the second polynucleotide and a third promoter operably linked to the third polynucleotide.

C15. The nucleic acid of any one of embodiments C1-C8, or C10-C14, wherein one promoter is operably linked to both the first and second polynucleotides.

C16. The nucleic acid of any one of embodiments C9, or C13-C14, wherein one promoter is operably linked to the first, second, and third polynucleotides.

C17. The nucleic acid of embodiment C15, further comprising a third polynucleotide encoding a linker polypeptide between the first and second polynucleotides, wherein the linker polypeptide separates the translation products of the first and second polynucleotides during or after translation.

C18. The nucleic acid of embodiment C16, further comprising polynucleotides encoding linker polypeptides between the three polynucleotides, wherein the three polynucleotides comprise the first, second, and third polynucleotides, wherein the linker polypeptides separate the translation products of the three polynucleotides during or after translation, C19. The nucleic acid of any one of embodiments C17 or C18, wherein the linker polypeptide is a 2A polypeptide.

C20. The nucleic acid of any one of embodiments 010-C19, wherein the T cell activation molecule is an ITAM-containing, Signal 1 conferring molecule.

C21. The nucleic acid of any one of embodiments 010-C19, wherein the T cell activation molecule is a CD3ζ polypeptide.

C22. The nucleic acid of any one of embodiments 010-C19, wherein the T cell activation molecule is an Fc epsilon receptor gamma (FcεR1γ) subunit polypeptide.

C23. The nucleic acid of any one of embodiments 010-C22, wherein the antigen recognition moiety binds to an antigen on a tumor cell.

C24. The nucleic acid of any one of embodiments 010-C22, wherein the antigen recognition moiety binds to an antigen on a cell involved in a hyperproliferative disease.

C25. The nucleic acid of any one of embodiments 010-C22, wherein the antigen recognition moiety binds to an antigen selected from the group consisting of PSMA, PSCA, MUC1, CD19, ROR1, Mesothelin, GD2, CD123, MUC16, and Her2/Neu.

C26. The nucleic acid of any one of embodiments 010-C22, wherein the antigen recognition moiety binds to PSCA.

C27. The nucleic acid of any one of embodiments 010-C22, wherein the antigen recognition moiety binds to CD19.

C28. The nucleic acid of any one of embodiments 010-C22, wherein the antigen recognition moiety binds to Her2/Neu.

C29. The nucleic acid of any one of embodiments 010-C22, wherein the antigen recognition moiety binds to a viral or bacterial antigen.

C30. The nucleic acid of any one of embodiments 010-C29, wherein the antigen recognition moiety is a single chain variable fragment.

C31. The nucleic acid of any one of embodiments 010-C30, wherein the transmembrane region is a CD28 transmembrane region.

C32. The nucleic acid of any one of embodiments 010-C30, wherein the transmembrane region is a CD8 transmembrane region.

C33. The nucleic acid of any one of embodiments C31-C32, wherein the chimeric antigen receptor further comprises a CD8 stalk region.

C33.1. The nucleic acid of any one of embodiments C1-C33, with the proviso that the cytoplasmic chimeric stimulating molecule does not include a multimeric ligand binding region.

C34. The nucleic acid of any one of embodiments C1-C33.1, wherein the truncated MyD88 polypeptide has the amino acid sequence of SEQ ID NO: 147, or a functional fragment thereof.

C35. The nucleic acid of any one of embodiments C1-C33.1, wherein the MyD88 polypeptide has the amino acid sequence of SEQ ID NO: 282, or a functional fragment thereof.

C36. The nucleic acid of any one of embodiments C1-C35, wherein the cytoplasmic CD40 polypeptide has the amino acid sequence of SEQ ID NO: 149, or a functional fragment thereof.

C37. The nucleic acid of any one of embodiments C21-C36, wherein the CD3ζ polypeptide comprises an amino acid sequence of SEQ ID NO: 151, or a functional fragment thereof.

C38. The nucleic acid of any one of embodiments C3-C4, or C9-C37, wherein the multimeric ligand binding region is a ligand binding region selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

C39. The nucleic acid of embodiment C38, wherein the ligand binding region is an FKBP12 region.

C40. The nucleic acid of embodiment C39, wherein the FKBP12 region is an FKBP12v36 region. C41. The nucleic acid of embodiment C38, wherein the FKBP region is Fv'Fvls.

C42. The nucleic acid of any one of embodiments C3-C4 or C9-C37, wherein the ligand is an FK506 dimer or a dimeric FK506 analog ligand.

C43. The nucleic acid of any one of embodiments C38-C42, wherein the ligand is AP1903 or AP20187.

C44. The nucleic acid of any one of embodiments C1-C43, wherein the nucleic acid is contained within a viral vector.

C45. The nucleic acid of embodiment C44, wherein the viral vector is a retroviral vector.

C46. The nucleic acid of embodiment C45, wherein the retroviral vector is a murine leukemia virus vector.

C47. The nucleic acid of embodiment C45, wherein the retroviral vector is an SFG vector.

C48. The nucleic acid of embodiment C44, wherein the viral vector is an adenoviral vector.

C48. The nucleic acid of embodiment C44, wherein the viral vector is a lentiviral vector.

C50. The nucleic acid of embodiment C44, wherein the viral vector is selected from the group consisting of adeno-associated virus (AAV), Herpes virus, and Vaccinia virus.

C51. The nucleic acid of any one of embodiments C1-C43, wherein the nucleic acid is contained within a plasmid.

C52. A chimeric stimulating molecule polypeptide encoded by the nucleic acid of any one of embodiments C1-C2, or C34-C36.

D1. A modified cell transfected or transduced with a nucleic acid of any one of embodiments C1-C51.

D2. A modified cell transfected or transduced with a nucleic acid of any one of embodiments C1-C2, or C10-C51.

D3. A modified cell transfected or transduced with a nucleic acid of any one of embodiments C1-C2, or C10-C51, with the proviso that the nucleic acid does not comprise a polynucleotide encoding a chimeric antigen receptor and does not comprise a polynucleotide encoding a chimeric Caspase-9 polypeptide.

D4. A modified cell transfected or transduced with a nucleic acid of any one of embodiments C1-C4, or C10-C51.

D5. A modified cell transfected or transduced with a nucleic acid of any one of embodiments C1-C4, or C10-C51, with the proviso that the nucleic acid does not comprise a polynucleotide encoding a chimeric antigen receptor.

D5.1. The modified cell of any one of embodiments D1-D5, wherein the cytoplasmic chimeric stimulating molecule is constitutively expressed.

D5.2. The modified cell of any one of embodiments D1-D5.2, wherein the cytoplasmic chimeric stimulating molecule is constitutively active.

D6. The modified cell of embodiments D1-D5.2, wherein the modified cell further comprises a nucleic acid comprising a polynucleotide encoding a chimeric antigen receptor.

D7. The modified cell of embodiments D1-D3, wherein the modified cell further comprises a nucleic acid comprising a polynucleotide encoding a chimeric Caspase-9 polypeptide, wherein the chimeric Caspase-9 polypeptide comprises a multimeric ligand binding region and a Caspase-9 polypeptide.

D8. The modified cell of embodiment D6, wherein the chimeric antigen receptor comprises (i) a transmembrane region; (ii) a T cell activation molecule; and (iii) an antigen recognition moiety.

D9. The modified cell of embodiment D8, wherein the chimeric antigen receptor further comprises a co-stimulatory molecule.

D10. The modified cell of embodiment D9, wherein the co-stimulatory molecule is selected from the group consisting of CD28, OX40, and 4-1BB.

D11. The modified cell of any one of embodiments D8-D10, wherein the T cell activation molecule is an ITAM-containing, Signal 1 conferring molecule.

D12. The modified cell of any one of embodiments D8-D10, wherein the T cell activation molecule is a CD3ζ polypeptide.

D13. The modified cell of any one of embodiments D8-D10, wherein the T cell activation molecule is an Fc epsilon receptor gamma (FcεR1γ) subunit polypeptide.

D14. The modified cell of any one of embodiments D8-D13, wherein the antigen recognition moiety binds to an antigen on a tumor cell.

D15. The modified cell of any one of embodiments D8-D13, wherein the antigen recognition moiety binds to an antigen on a cell involved in a hyperproliferative disease.

D16. The modified cell of any one of embodiments D8-D13, wherein the antigen recognition moiety binds to an antigen selected from the group consisting of PSMA, PSCA, MUC1, CD19, ROR1, Mesothelin, GD2, CD123, MUC16, and Her2/Neu.

D17. The modified cell of any one of embodiments D8-D13, wherein the antigen recognition moiety binds to PSCA.

D18. The modified cell of any one of embodiments D8-D13, wherein the antigen recognition moiety binds to CD19.

D19. The modified cell of any one of embodiments D8-D13, wherein the antigen recognition moiety binds to Her2/Neu.

D20. The modified cell of any one of embodiments D8-D13, wherein the antigen recognition moiety binds to a viral or bacterial antigen.

D21. The modified cell of any one of embodiments D8-D20, wherein the antigen recognition moiety is a single chain variable fragment.

D22. The modified cell of any one of embodiments D8-D21, wherein the transmembrane region is a CD28 transmembrane region.

D23. The modified cell of any one of embodiments D8-D21, wherein the transmembrane region is a CD8 transmembrane region.

D24. The modified cell of any one of embodiments D22-D23, wherein the chimeric antigen receptor further comprises a CD8 stalk region.

D25. The modified cell of embodiment D7, wherein the multimeric ligand binding region is a ligand binding region selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

D26. The modified cell of embodiment D25, wherein the ligand binding region is an FKBP12 region.

D27. The modified cell of embodiment D26, wherein the FKBP12 region is an FKBP12v36 region.

D28. The modified cell of embodiment D25, wherein the FKBP region is Fv'Fvls.

D29. The modified cell of any one of embodiments D25-D28, wherein the ligand is an FK506 dimer or a dimeric FK506 analog ligand.

D30. The modified cell of any one of embodiments D25-D28, wherein the ligand is AP1903 or AP20187.

D31. The modified cell of any one of embodiments D1-D30, wherein the modified cell is a T cell, tumor infiltrating lymphocyte, NK-T cell, TCR-expressing cell, or NK cell.

D32. The modified cell of any one of embodiments D1-D30, wherein the cell is a T cell.

D33. The modified cell of any one of embodiments D1-D30, wherein the cell is obtained or prepared from bone marrow.

D34. The modified cell of any one of embodiments D1-D30, wherein the cell is obtained or prepared from umbilical cord blood.

D35. The modified cell of any one of embodiments D1-D30, wherein the cell is obtained or prepared from peripheral blood.

D36. The modified cell of any one of embodiments D1-D30, wherein the cell is obtained or prepared from peripheral blood mononuclear cells.

D37. The modified cell of any one of embodiments D1-D30, wherein the cell is a human cell.

D38. The modified cell of any one of embodiments D1-D30, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

E1. A method for stimulating a T cell-mediated immune response in a subject, comprising administering an effective amount of modified cells of any one of embodiments D1-D38 to the subject.

E2. The method of embodiment E1, wherein the modified cell comprises a chimeric antigen receptor or T cell receptor that binds to an antigen on a target cell.

E3. The method of embodiment E1, wherein the target cell is a tumor cell.

E4. The method of any one of embodiments E2-E3, wherein the number or concentration of target cells in the subject is reduced following administration of the modified cell.

E5. The method of any one of embodiments E2-E4, comprising measuring the number or concentration of target cells in a first sample obtained from the subject before administering the modified cell, measuring the number concentration of target cells in a second sample obtained from the subject after administration of the modified cell, and determining an increase or decrease of the number or concentration of target cells in the second sample compared to the number or concentration of target cells in the first sample.

E6. The method of embodiment E5, wherein the concentration of target cells in the second sample is decreased compared to the concentration of target cells in the first sample.

E7. The method of embodiment E5, wherein the concentration of target cells in the second sample is increased compared to the concentration target cells in the first sample.

E8. The method of any one of embodiments E1-E7, wherein an additional dose of modified cells is administered to the subject.

E9. A method for providing anti-tumor immunity to a subject, comprising administering to the subject an effective amount of a modified cell of any one of embodiments E1-E9.

E10. A method for treating a subject having a disease or condition associated with an elevated expression of a target antigen, comprising administering to the subject an effective amount of a modified cell of any one of embodiments D1-D38.

E11. The method of embodiment E10, wherein the target antigen is a tumor antigen.

E12. A method for reducing the size of a tumor in a subject, comprising administering a modified cell of any one of embodiments D1-D38 to the subject, wherein the cell comprises a chimeric antigen receptor or T cell receptor comprising an antigen recognition moiety binds to an antigen on the tumor.

E13. The method of any one of embodiments E1-E12, wherein the subject has been diagnosed as having a tumor.

E14. The method of any one of embodiments E1-E12, wherein the subject has cancer.

E15. The method of any one of embodiments E1-E12, wherein the subject has a solid tumor. E16. The method of any one of embodiments E1-E12, wherein the modified cell is a tumor infiltrating lymphocyte or a T cell.

E17. The method of any one of embodiments E1-E16, wherein the modified cell is delivered to a tumor bed.

E18. The method of embodiment E14, wherein the cancer is present in the blood or bone marrow of the subject.

E19. The method of any one of embodiments E10-E18, wherein the subject has a blood or bone marrow disease.

E20. The method of any one of embodiments E10-E18, wherein the subject has been diagnosed with any condition or condition that can be alleviated by stem cell transplantation.

E21. The method of any one of embodiments E10-E18, wherein the subject has been diagnosed with sickle cell anemia or metachromatic leukodystrophy.

E22. The method of any one of embodiments E10-E18, wherein the subject has been diagnosed with a condition selected from the group consisting of a primary immune deficiency condition, hemophagocytosis lymphohistiocytosis (HLH) or other hemophagocytic condition, an inherited marrow failure condition, a hemoglobinopathy, a metabolic condition, and an osteoclast condition.

E23. The method of any one of embodiments E10-E18, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

E24. The method of any one of embodiments E1-E23, further comprising determining whether an additional dose of the modified cell should be administered to the subject.

E25. The method of any one of embodiments E1-E24, further comprising administering an additional dose of the modified cell to the subject, wherein the disease or condition symptoms remain or are detected following a reduction in symptoms.

E26. The method of any one of embodiments E1-E25 further comprising identifying the presence, absence or stage of a condition or disease in a subject; and transmitting an indication to administer modified cell of any one of embodiments D1-D38, maintain a subsequent dosage of the modified cell, or adjust a subsequent dosage of the modified cell administered to the patient based on the presence, absence or stage of the condition or disease identified in the subject.

E27. The method of any one of embodiments E10-E26, wherein the condition is leukemia.

E28. The method of any one of embodiments E10-E26, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

E29. The method of any one of embodiments E1-E28, wherein the modified cell comprises a chimeric Caspase-9 polypeptide comprising a multimeric ligand binding region and a Caspase-9 polypeptide.

E30. The method of embodiment E29, further comprising administering a multimeric ligand that binds to the multimeric ligand binding region to the subject following administration of the modified cells to the subject.

E31. The method of embodiment E30, wherein after administration of the multimeric ligand, the number of modified cells comprising the chimeric Caspase-9 polypeptide is reduced.

E32. The method of embodiment E31, wherein the number of modified cells comprising the chimeric Caspase-9 polypeptide is reduced by 50%.

E33. The method of embodiment E31, wherein the number of modified cells comprising the chimeric Caspase-9 polypeptide is reduced by 75%.

E34. The method of embodiment E31, wherein the number of modified cells comprising the chimeric Caspase-9 polypeptide is reduced by 90%.

E35. The method of any one of embodiments E29-E32, comprising determining that the subject is experiencing a negative symptom following administration of the modified cells to the subject, and administering the ligand to reduce or alleviate the negative symptom.

E36. The method of any one of embodiments E29-E35, wherein the ligand is AP1903 or AP20187.

E37. The method of any one of embodiments E1-E36, wherein the modified cells are autologous T cells.

E38. The method of any one of embodiments E1-E36, wherein the modified cells are allogeneic T cells.

E39. The method of any one of embodiments E1-E38, wherein the modified cells are transfected or transduced in vivo.

E40. The modified cell of any one of embodiments E1-E38, wherein the modified cells are transfected or transduced ex vivo.

E41. A method for expressing a chimeric stimulating molecule in a cell, comprising contacting a nucleic acid of any one of embodiments C1-C52 with a cell under conditions in which the nucleic acid is incorporated into the cell, whereby the cell expresses the chimeric antigen receptor from the incorporated nucleic acid.

E42. The method of embodiment E41, wherein the nucleic acid is contacted with the cell ex vivo.

E43. The method of embodiment E41, wherein the nucleic acid is contacted with the cell in vivo.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A nucleic acid comprising a polynucleotide, in order from 5' to 3', encoding
   (a) a chimeric antigen receptor, comprising, in order from the amino terminus of the receptor, (i) an scFv antigen recognition moiety; (ii) a transmembrane region; and (iii) a CD3 zeta polypeptide;
   (b) linker polypeptide, wherein the linker polypeptide is a cleavable 2A polypeptide that links the chimeric antigen receptor to the chimeric stimulating molecule; and
   (c) a chimeric stimulating molecule, wherein:
   the chimeric stimulating molecule comprises (i) a truncated MyD88 polypeptide lacking the TIR domain, and (ii) a CD40 cytoplasmic polypeptide region lacking the CD40 extracellular domain;
   the chimeric stimulating molecule is constitutively active;
   the chimeric stimulating molecule does not include a dimerization or multimerization molecule binding region; and
   the polynucleotide is operably linked to a promoter.

2. The nucleic acid of claim 1, wherein the chimeric stimulating molecule does not include a membrane-targeting region.

3. The nucleic acid of claim 1, wherein the transmembrane region is a CD8 transmembrane region.

4. The nucleic acid of claim 3, wherein the chimeric antigen receptor comprises a CD8 stalk region between the scFv antigen recognition moiety and the CD8 transmembrane region.

5. The nucleic acid of claim 1, wherein the antigen recognition moiety binds to an antigen selected from the group consisting of PSMA, PSCA, MUC1, CD19, ROR1, Mesothelin, GD2, CD123, MUC16, Her2/Neu, CD20, CD30, PRAME, NY-ESO-1, and EGFRvIII.

6. The nucleic acid of claim 1, wherein the antigen recognition moiety binds to an antigen selected from the group consisting of PSCA, CD19, and Her2/Neu.

7. The nucleic acid of claim 1, wherein the antigen recognition moiety binds to Her2/Neu.

8. The nucleic acid of claim 7, wherein the antigen recognition moiety comprises the amino acid sequence of SEQ ID NO: 155 and the amino acid sequence of SEQ ID NO: 159.

9. The nucleic acid of claim 1, wherein the antigen recognition moiety binds to CD19.

10. The nucleic acid of claim 9, wherein the antigen recognition moiety comprises the amino acid sequence of SEQ ID NO: 131 and the amino acid sequence of SEQ ID NO: 135.

11. A modified T cell comprising the nucleic acid of claim 1.

12. A modified T cell comprising the nucleic acid of claim 2.

13. A modified T cell comprising the nucleic acid of claim 5.

14. A modified cell comprising the nucleic acid of claim 9.

15. The modified cell of claim 14, wherein the modified cell is a T cell, tumor infiltrating lymphocyte, NK-T cell, TCR-expressing cell, or NK cell.

16. The modified cell of claim 14, wherein the modified cell is a T cell.

* * * * *

SEQUENCE LISTING

```
<160> NUMBER OF SEQ ID NOS: 344

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atggggagta gcaagagcaa gcctaaggac cccagccagc gc                         42

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Gly Ser Ser Lys Ser Lys Pro Lys Asp Pro Ser Gln Arg
1               5                   10

<210> SEQ ID NO 3
<211> LENGTH: 516
<212> TYPE: DNA
<213> ORGANISM: Artificial Sequence
<220> FEATURE:
<223> OTHER INFORMATION: Description of Artificial Sequence: Synthetic
```

<400> SEQUENCE: 3

```
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca agcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatc                              516
```

<210> SEQ ID NO 4
<211> LENGTH: 172
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170
```

<210> SEQ ID NO 5
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5

```
aaaaaggtgg ccaagaagcc aaccaataag gccccccacc ccaagcagga gccccaggag      60
```

```
atcaattttc cgacgatct tcctggctcc aacactgctg ctccagtgca ggagacttta      120
catggatgcc aaccggtcac ccaggaggat ggcaaagaga gtcgcatctc agtgcaggag      180
agacag                                                                 186
```

<210> SEQ ID NO 6
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60
```

<210> SEQ ID NO 7
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ggcgtccaag tcgaaaccat tagtcccggc gatggcagaa catttcctaa aaggggacaa      60
acatgtgtcg tccattatac aggcatgttg gaggacggca aaaggtgga cagtagtaga       120 gatcgcaata aacctttcaa attcatgttg gaaaacaag aagtcattag gggatgggag       180
gagggcgtgg ctcaaatgtc cgtcggccaa cgcgctaagc tcaccatcag ccccgactac      240
gcatacggcg ctaccggaca tcccggaatt attccccctc acgctacctt ggtgtttgac      300
gtcgaactgt tgaagctc                                                    318
```

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
```

Leu Val Phe Asp Val Glu Leu Leu Lys Leu
            100                 105

<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggagtgcagg tggagactat ctccccagga cgggcgca ccttcccaa gcgcggccag     60 acctgcgtgg tgcactacac cgggatgctt gaagatggaa agaaagttga ttcctcccgg    120
gacagaaaca agccctttaa gtttatgcta ggcaagcagg aggtgatccg aggctgggaa    180
gaaggggttg cccagatgag tgtgggtcag agagccaaac tgactatatc tccagattat    240
gcctatggtg ccactgggca cccaggcatc atcccaccac atgccactct cgtcttcgat    300
gtggagcttc taaaactgga a                                              321

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gctactaact tcagcctgct gaagcaggct ggagacgtgg aggagaaccc tggacct      57

<210> SEQ ID NO 12
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 12

Ala Thr Asn Phe Ser Leu Leu Lys Gln Ala Gly Asp Val Glu Glu Asn
1               5                   10                  15

Pro Gly Pro

<210> SEQ ID NO 13
<211> LENGTH: 2253
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgtggaatc tccttcacga aaccgactcg gctgtggcca ccgcgcgccg cccgcgctgg      60
ctgtgcgctg gggcgctggt gctggcgggt ggcttctttc cctcggctt cctcttcggg     120 tggtttataa atcctccaa tgaagctact aacattactc caaagcataa tatgaaagca     180
tttttggatt aattgaaagc tgagaacatc aagaagttct acataatttt tacacagata     240
ccacatttag caggaacaga acaaaacttt cagcttgcaa agcaaattca atcccagtgg     300
aaagaatttg gcctggattc tgttgagcta gcacattatg atgtcctgtt gtcctaccca     360
aataagactc atcccaacta catctcaata attaatgaag atggaaatga gattttcaac     420
acatcattat ttgaaccacc tcctccagga tatgaaaatg tttgggatat tgtaccacct     480
ttcagtgctt tctctcctca aggaatgcca gagggcgatc tagtgtatgt taactatgca     540
cgaactgaag acttctttaa attggaacgg gacatgaaaa tcaattgctc tgggaaaatt     600
gtaattgcca gatatgggaa agtttttcaga ggaaataagg ttaaaaatgc ccagctggca     660
ggggccaaag gagtcattct ctactccgac cctgctgact actttgctcc tggggtgaag     720
tcctatccag atggttggaa tcttcctgga ggtggtgtcc agcgtggaaa tatcctaaat     780
ctgaatggtg caggagaccc tctcacacca ggttacccag caaatgaata tgcttatagg     840
cgtggaattg cagaggctgt tggtcttcca agtattcctg ttcatccaat tggatactat     900
gatgcacaga gctcctaga aaaaatgggt ggctcagcac caccagatag cagctggaga     960
ggaagtctca aagtgcccta caatgttgga cctggcttta ctggaaactt ttctacacaa    1020
aaagtcaaga tgcacatcca ctctaccaat gaagtgacaa gaatttacaa tgtgataggt    1080
actctcagag gagcagtgga accagacaga tatgtcattc tggaggtca ccgggactca    1140 tgggtgtttg gtggtattga ccctcagagt ggagcagctg ttgttcatga aattgtgagg    1200
agctttggaa cactgaaaaa ggaagggtgg agacctagaa gaacaatttt gtttgcaagc    1260
tgggatgcag aagaatttgg tcttcttggt tctactgagt gggcagagga gaattcaaga    1320
ctccttcaag agcgtggcgt ggcttatatt aatgctgact catctataga aggaaactac    1380
actctgagag ttgattgtac accgctgatg tacagcttgg tacacaacct aacaaaagag    1440
ctgaaaagcc ctgatgaagg ctttgaaggc aaatctcttt atgaaagttg gactaaaaaa    1500
agtccttccc cagagttcag tggcatgccc aggataagca aattgggatc tggaaatgat    1560
tttgaggtgt tcttccaacg acttggaatt gcttcaggca gagcacggta tactaaaaat    1620
tgggaaacaa acaaattcag cggctatcca ctgtatcaca gtgtctatga acatatgag    1680 ttggtggaaa agttttatga tccaatgttt aaatatcacc tcactgtggc ccaggttcga    1740
```

-continued

```
ggagggatgg tgtttgagct agccaattcc atagtgctcc cttttgattg tcgagattat    1800
gctgtagttt taagaaagta tgctgacaaa atctacagta tttctatgaa acatccacag    1860
gaaatgaaga catacagtgt atcatttgat tcactttttt ctgcagtaaa gaattttaca    1920
gaaattgctt ccaagttcag tgagagactc caggactttg acaaaagcaa cccaatagta    1980
ttaagaatga tgaatgatca actcatgttt ctggaaagag catttattga tccattaggg    2040
ttaccagaca ggccttttta taggcatgtc atctatgctc caagcagcca acaagtat     2100 gcagggagt cattcccagg aatttatgat gctctgtttg atattgaaag caaagtggac     2160
ccttccaagg cctggggaga agtgaagaga cagatttatg ttgcagcctt cacagtgcag    2220
gcagctgctg agactttgag tgaagtagcc taa                                 2253
```

<210> SEQ ID NO 14
<211> LENGTH: 750
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Trp Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270
```

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
                450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

```
His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 15
<211> LENGTH: 858
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ser Ser Lys Ser Lys Pro Lys Asp Pro Ser Gln Arg Leu Glu
1               5                   10                  15

Met Ala Ala Gly Gly Pro Gly Ala Gly Ser Ala Ala Pro Val Ser Ser
            20                  25                  30

Thr Ser Ser Leu Pro Leu Ala Ala Leu Asn Met Arg Val Arg Arg Arg
        35                  40                  45

Leu Ser Leu Phe Leu Asn Val Arg Thr Gln Val Ala Ala Asp Trp Thr
50                  55                  60

Ala Leu Ala Glu Glu Met Asp Phe Glu Tyr Leu Glu Ile Arg Gln Leu
65                  70                  75                  80

Glu Thr Gln Ala Asp Pro Thr Gly Arg Leu Leu Asp Ala Trp Gln Gly
                85                  90                  95

Arg Pro Gly Ala Ser Val Gly Arg Leu Leu Asp Leu Leu Thr Lys Leu
            100                 105                 110

Gly Arg Asp Asp Val Leu Leu Glu Leu Gly Pro Ser Ile Glu Glu Asp
        115                 120                 125

Cys Gln Lys Tyr Ile Leu Lys Gln Gln Gln Glu Glu Ala Glu Lys Pro
130                 135                 140

Leu Gln Val Ala Ala Val Asp Ser Ser Val Pro Arg Thr Ala Glu Leu
145                 150                 155                 160

Ala Gly Ile Thr Thr Leu Asp Asp Pro Leu Gly His Met Pro Glu Arg
                165                 170                 175

Phe Asp Ala Phe Ile Cys Tyr Cys Pro Ser Asp Ile Lys Lys Val Ala
            180                 185                 190

Lys Lys Pro Thr Asn Lys Ala Pro His Pro Lys Gln Glu Pro Gln Glu
        195                 200                 205

Ile Asn Phe Pro Asp Asp Leu Pro Gly Ser Asn Thr Ala Ala Pro Val
210                 215                 220

Gln Glu Thr Leu His Gly Cys Gln Pro Val Thr Gln Glu Asp Gly Lys
225                 230                 235                 240

Glu Ser Arg Ile Ser Val Gln Glu Arg Gln Val Glu Ser Gly Gly Gly
                245                 250                 255

Ser Gly Gly Val Gln Val Glu Thr Ile Ser Pro Gly Asp Gly Arg Thr
            260                 265                 270

Phe Pro Lys Arg Gly Gln Thr Cys Val Val His Tyr Thr Gly Met Leu
        275                 280                 285

Glu Asp Gly Lys Lys Val Asp Ser Ser Arg Asp Arg Asn Lys Pro Phe
290                 295                 300
```

```
Lys Phe Met Leu Gly Lys Gln Glu Val Ile Arg Gly Trp Glu Glu Gly
305                 310                 315                 320

Val Ala Gln Met Ser Val Gly Gln Arg Ala Lys Leu Thr Ile Ser Pro
            325                 330                 335

Asp Tyr Ala Tyr Gly Ala Thr Gly His Pro Gly Ile Ile Pro Pro His
                340                 345                 350

Ala Thr Leu Val Phe Asp Val Glu Leu Leu Lys Leu Glu Val Glu Gly
                355                 360                 365

Val Gln Val Glu Thr Ile Ser Pro Gly Asp Gly Arg Thr Phe Pro Lys
370                 375                 380

Arg Gly Gln Thr Cys Val Val His Tyr Thr Gly Met Leu Glu Asp Gly
385                 390                 395                 400

Lys Lys Val Asp Ser Ser Arg Asp Arg Asn Lys Pro Phe Lys Phe Met
                405                 410                 415

Leu Gly Lys Gln Glu Val Ile Arg Gly Trp Glu Glu Gly Val Ala Gln
                420                 425                 430

Met Ser Val Gly Gln Arg Ala Lys Leu Thr Ile Ser Pro Asp Tyr Ala
            435                 440                 445

Tyr Gly Ala Thr Gly His Pro Gly Ile Ile Pro Pro His Ala Thr Leu
450                 455                 460

Val Phe Asp Val Glu Leu Leu Lys Leu Glu Ser Gly Gly Ser Gly
465                 470                 475                 480

Val Asp Arg Ala Lys Arg Gly Lys Pro Ile Pro Asn Pro Leu Leu Gly
            485                 490                 495

Leu Asp Ser Thr Gly Ser Gly Ser Ala Thr Asn Phe Ser Leu Leu Lys
                500                 505                 510

Gln Ala Gly Asp Val Glu Glu Asn Pro Gly Pro Thr Arg Met Pro Pro
            515                 520                 525

Pro Arg Leu Leu Phe Phe Leu Leu Phe Leu Thr Pro Met Glu Val Arg
            530                 535                 540

Pro Glu Glu Pro Leu Val Val Lys Val Glu Glu Gly Asp Asn Ala Val
545                 550                 555                 560

Leu Gln Cys Leu Lys Gly Thr Ser Asp Gly Pro Thr Gln Gln Leu Thr
                565                 570                 575

Trp Ser Arg Glu Ser Pro Leu Lys Pro Phe Leu Lys Leu Ser Leu Gly
            580                 585                 590

Leu Pro Gly Leu Gly Ile His Met Arg Pro Leu Ala Ile Trp Leu Phe
            595                 600                 605

Ile Phe Asn Val Ser Gln Gln Met Gly Gly Phe Tyr Leu Cys Gln Pro
            610                 615                 620

Gly Pro Pro Ser Glu Lys Ala Trp Gln Pro Gly Trp Thr Val Asn Val
625                 630                 635                 640

Glu Gly Ser Gly Glu Leu Phe Arg Trp Asn Val Ser Asp Leu Gly Gly
                645                 650                 655

Leu Gly Cys Gly Leu Lys Asn Arg Ser Ser Glu Gly Pro Ser Ser Pro
                660                 665                 670

Ser Gly Lys Leu Met Ser Pro Lys Leu Tyr Val Trp Ala Lys Asp Arg
            675                 680                 685

Pro Glu Ile Trp Glu Gly Glu Pro Pro Cys Leu Pro Pro Arg Asp Ser
            690                 695                 700

Leu Asn Gln Ser Leu Ser Gln Asp Leu Thr Met Ala Pro Gly Ser Thr
705                 710                 715                 720
```

Leu Trp Leu Ser Cys Gly Val Pro Pro Asp Ser Val Ser Arg Gly Pro
                725                 730                 735

Leu Ser Trp Thr His Val His Pro Lys Gly Pro Lys Ser Leu Leu Ser
            740                 745                 750

Leu Glu Leu Lys Asp Asp Arg Pro Ala Arg Asp Met Trp Val Met Glu
        755                 760                 765

Thr Gly Leu Leu Leu Pro Arg Ala Thr Ala Gln Asp Ala Gly Lys Tyr
    770                 775                 780

Tyr Cys His Arg Gly Asn Leu Thr Met Ser Phe His Leu Glu Ile Thr
785                 790                 795                 800

Ala Arg Pro Val Leu Trp His Trp Leu Leu Arg Thr Gly Gly Trp Lys
                805                 810                 815

Val Ser Ala Val Thr Leu Ala Tyr Leu Ile Phe Cys Leu Cys Ser Leu
            820                 825                 830

Val Gly Ile Leu His Leu Gln Arg Ala Leu Val Leu Arg Arg Lys Arg
        835                 840                 845

Lys Arg Met Thr Asp Pro Thr Arg Arg Phe
    850                 855

<210> SEQ ID NO 16
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

```
Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
            245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
        275                 280                 285
```

<210> SEQ ID NO 17
<211> LENGTH: 8931
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

| | | | | | |
|---|---|---|---|---|---|
| aagctggcca | gcaacttatc | tgtgtctgtc | cgattgtcta | gtgtctatga | ctgattttat | 60 |
| gcgcctgcgt | cggtactagt | tagctaacta | gctctgtatc | tggcggaccc | gtggtggaac | 120 |
| tgacgagttc | ggaacacccg | gccgcaaccc | tgggagacgt | cccagggact | tcggggggccg | 180 |
| ttttttgtggc | ccgacctgag | tcctaaaatc | ccgatcgttt | aggactcttt | ggtgcacccc | 240 |
| ccttagagga | gggatatgtg | gttctggtag | gagacgagaa | cctaaaacag | ttcccgcctc | 300 |
| cgtctgaatt | tttgctttcg | gtttgggacc | gaagccgcgc | cgcgcgtctt | gtctgctgca | 360 |
| gcatcgttct | gtgttgtctc | tgtctgactg | tgtttctgta | tttgtctgaa | aatatgggcc | 420 |
| cgggctagcc | tgttaccact | cccttaagtt | tgaccttagg | tcactggaaa | gatgtcgagc | 480 |
| ggatcgctca | caaccagtcg | gtagatgtca | agaagagacg | ttgggttacc | ttctgctctg | 540 |
| cagaatggcc | aacctttaac | gtcggatggc | cgcgagacgg | cacctttaac | cgagacctca | 600 |
| tcacccaggt | taagatcaag | gtcttttcac | ctggcccgca | tggacaccca | gaccaggtgg | 660 |
| ggtacatcgt | gacctgggaa | gccttggctt | ttgaccccc | tccctgggtc | aagccctttg | 720 |
| tacaccctaa | gcctccgcct | cctcttcctc | catccgcccc | gtctctcccc | cttgaacctc | 780 |
| ctcgttcgac | cccgcctcga | tcctcccttt | atccagccct | cactccttct | ctaggcgccc | 840 |
| ccatatggcc | atatgagatc | ttatatgggg | caccccgcc | ccttgtaaac | ttccctgacc | 900 |
| ctgacatgac | aagagttact | aacagcccct | ctctccaagc | tcacttacag | gctctctact | 960 |
| tagtccagca | cgaagtctgg | agacctctgg | cggcagccta | ccaagaacaa | ctggaccgac | 1020 |
| cggtggtacc | tcacccttac | cgagtcggcg | acacagtgtg | ggtccgccga | caccagacta | 1080 |
| agaacctaga | acctcgctgg | aaaggaccttt | acacagtcct | gctgaccacc | cccaccgccc | 1140 |
| tcaaagtaga | cggcatcgca | gcttggatac | acgccgccca | cgtgaaggct | gccgaccccg | 1200 |
| ggggtggacc | atcctctaga | ctgccatggg | gagtagcaag | agcaagccta | aggaccccag | 1260 |
| ccagcgcctc | gagatggccg | ctgggggccc | aggcgccgga | tcagctgctc | ccgtatcttc | 1320 |
| tacttcttct | ttgccgctgg | ctgctctgaa | catgcgcgtg | agaagacgcc | tctccctgtt | 1380 |
| ccttaacgtt | cgcacacaag | tcgctgccga | ttggaccgcc | cttgccgaag | aaatggactt | 1440 |
| tgaatacctg | gaaattagac | aacttgaaac | acaggccgac | cccactggca | gactcctgga | 1500 |
| cgcatggcag | ggaagacctg | gtgcaagcgt | tggacggctc | ctggatctcc | tgacaaaact | 1560 |
| gggacgcgac | gacgtactgc | ttgaactcgg | acctagcatt | gaagaagact | gccaaaaata | 1620 |
| tatcctgaaa | caacaacaag | aagaagccga | aaaacctctc | caagtcgcag | cagtggactc | 1680 |

```
atcagtaccc cgaacagctg agcttgctgg gattactaca ctcgacgacc cactcggaca   1740
tatgcctgaa agattcgacg ctttcatttg ctattgcccc tctgacataa agaaagttgc   1800
aaagaaaccc acaaataaag ccccacaccc taaacaggaa ccccaagaaa tcaatttccc   1860
agatgatctc cctggatcta atactgccgc cccggtccaa gaaaccctgc atggttgcca   1920
gcctgtcacc caagaggacg aaaagaatc acggattagc gtacaagaga gacaagtcga    1980
gtctggcggt ggatccggag gcgttcaagt agaaacaatc agcccaggag acggaaggac   2040
tttccccaaa cgaggccaaa catgcgtagt tcattatact gggatgctcg aagatggaaa   2100
aaaagtagat agtagtagag accgaaacaa accatttaaa tttatgttgg gaaaacaaga   2160
agtaataagg ggctgggaag aaggtgtagc acaaatgtct gttggccagc gcgcaaaact   2220
cacaatttct cctgattatg cttacggagc taccggccac cccggcatca taccccctca   2280
tgccacactg gtgtttgacg tcgaattgct caaactggaa gtcgagggag tgcaggtgga   2340
gacgattagt cctggggatg ggagaacctt ccaaagcgc ggtcagacct gtgttgtcca    2400
ctacaccggt atgctggagg acgggaagaa ggtggactct tcacgcgatc gcaataagcc   2460
tttcaagttc atgctcggca agcaggaggt gatccggggg tgggaggagg cgtggctca    2520
gatgtcggtc gggcaacgag cgaagcttac catctcaccc gactacgcgt atggggcaac   2580
ggggcatccg ggaattatcc ctccccacgc tacgctcgta ttcgatgtgg agctcttgaa   2640
gcttgagtct ggcggtggat ccggagtcga ccgcgcaaag cgtggaaaac ctatacctaa   2700
tccattgctg ggcttagact caacaggcag cggaagcgca acgaattttt ccctgctgaa   2760
acaggcaggg gacgtagagg aaaatcctgg tcctacgcgt atgccccctc ctagactgct   2820
gttttttcctg ctctttctca ccccaatgga agttagacct gaggaaccac tggtcgttaa   2880
agtggaagaa ggtgataatg ctgtcctcca atgccttaaa gggaccagcg acggaccaac   2940
gcagcaactg acttggagcc gggagtcccc tctcaagccg tttctcaagc tgtcacttgg   3000
cctgccaggt cttggtattc acatgcgccc ccttgccatt tggctcttca tattcaatgt   3060
gtctcaacaa atgggtggat tctacctttg ccagcccggc ccccttctg agaaagcttg    3120
gcagcctgga tggaccgtca atgttgaagg ctccggtgag ctgtttagat ggaatgtgag   3180
cgaccttggc ggactcggtt gcggactgaa aaataggagc tctgaaggac cctcttctcc   3240
ctccggtaag ttgatgtcac ctaagctgta cgtgtgggcc aaggaccgcc ccgaaatctg   3300
ggagggcgag cctccatgcc tgccgcctcg cgattcactg aaccagtctc tgtcccagga   3360
tctcactatg gcgcccggat ctactctttg gctgtcttgc ggcgttcccc cagatagcgt   3420
gtcaagagga cctctgagct ggacccacgt acaccctaag ggccctaaga gcttgttgag   3480
cctgaaactg aaggacgaca gacccgcacg cgatatgtgg gtaatggaga ccggccttct   3540
gctccctcgc gctaccgcac aggatgcagg gaaatactac tgtcatagag ggaatctgac   3600
tatgagcttt catctcgaaa ttacagcacg gcccgttctt tggcattggc tcctccggac   3660
tggaggctgg aaggtgtctg ccgtaacact cgcttacttg attttttgcc tgtgtagcct   3720
ggttgggatc ctgcatcttc agcgagccct tgtattgcgc cgaaaaagaa acgaatgac    3780
tgaccctaca cgacgattct gagcatgcaa cctcgatccg gattagtcca atttgttaaa   3840
gacaggatat cagtggtcca ggctctagtt ttgactcaac aatatcacca gctgaagcct   3900
atagagtacg agccatagat aaaataaaag atttttattta gtctccagaa aaagggggga   3960
atgaaagacc ccacctgtag gtttggcaag ctagcttaag taacgccatt ttgcaaggca   4020
```

```
tggaaaaata cataactgag aatagagaag ttcagatcaa ggtcaggaac agatggaaca    4080
gctgaatatg ggccaaacag gatatctgtg gtaagcagtt cctgcccgg  ctcagggcca    4140 agaacagatg gaacagctga atatgggcca acaggatat  ctgtggtaag cagttcctgc    4200
cccggctcag ggccaagaac agatggtccc cagatgcggt ccagccctca gcagtttcta    4260
gagaaccatc agatgtttcc agggtgcccc aaggacctga atgaccctg  tgccttattt    4320 gaactaacca atcagttcgc ttctcgcttc tgttcgcgcg cttctgctcc ccgagctcaa    4380
taaaagagcc cacaacccct cactcggggc gccagtcctc cgattgactg agtcgcccgg    4440
gtacccgtgt atccaataaa ccctcttgca gttgcatccg acttgtggtc tcgctgttcc    4500
ttgggagggt ctcctctgag tgattgacta cccgtcagcg ggggtctttc acacatgcag    4560
catgtatcaa aattaatttg gttttttttc ttaagtattt acattaaatg gccatagtac    4620
ttaaagttac attggcttcc ttgaaataaa catggagtat tcagaatgtg tcataaatat    4680
ttctaatttt aagatagtat ctccattggc tttctacttt tcttttatt  tttttttgtc    4740 ctctgtcttc catttgttgt tgttgttgtt tgtttgtttg tttgttggtt ggttggttaa    4800 tttttttta  aagatcctac actatagttc aagctagact attagctact ctgtaaccca    4860
gggtgacctt gaagtcatgg gtagcctgct gttttagcct tcccacatct aagattacag    4920
gtatgagcta tcattttgg  tatattgatt gattgattga ttgatgtgtg tgtgtgtgat    4980
tgtgtttgtg tgtgtgactg tgaaaatgtg tgtatgggtg tgtgtgaatg tgtgtatgta    5040
tgtgtgtgtg tgagtgtgtg tgtgtgtgtg tgcatgtgtg tgtgtgtgac tgtgtctatg    5100
tgtatgactg tgtgtgtgtg tgtgtgtgtg tgtgtgtgtg tgtgtgtgtg tgtgttgtga    5160
aaaaatattc tatggtagtg agagccaacg ctccggctca ggtgtcaggt tggttttga    5220 gacagagtct ttcacttagc ttggaattca ctggccgtcg ttttacaacg tcgtgactgg    5280
gaaaaccctg gcgttaccca acttaatcgc cttgcagcac atccccctt  cgccagctgg    5340 cgtaatagcg aagaggcccg caccgatcgc ccttcccaac agttgcgcag cctgaatggc    5400
gaatggcgcc tgatgcggta ttttctcctt acgcatctgt gcggtatttc acaccgcata    5460
tggtgcactc tcagtacaat ctgctctgat gccgcatagt taagccagcc ccgacacccg    5520
ccaacacccg ctgacgcgcc ctgacgggct tgtctgctcc cggcatccgc ttacagacaa    5580
gctgtgaccg tctccgggag ctgcatgtgt cagaggtttt caccgtcatc accgaaacgc    5640
gcgatgacga agggcctcg  tgatacgcct atttttatag gttaatgtca tgataataat    5700
ggtttcttag acgtcaggtg gcacttttcg gggaaatgtg cgcggaaccc ctatttgttt    5760 attttctaa  atacattcaa atatgtatcc gctcatgaga caataaccct gataaatgct    5820
tcaataatat tgaaaagga  agagtatgag tattcaacat ttccgtgtcg cccttattcc    5880
cttttttgcg gcattttgcc ttcctgtttt tgctcaccca gaaacgctgg tgaaagtaaa    5940
agatgctgaa gatcagttgg gtgcacgagt gggttacatc gaactggatc tcaacagcgg    6000
taagatcctt gagagttttc gccccgaaga acgttttcca atgatgagca cttttaaagt    6060
tctgctatgt ggcgcggtat tatcccgtat tgacgccggg caagagcaac tcggtcgccg    6120
catacactat tctcagaatg acttggttga gtactcacca gtcacagaaa agcatcttac    6180
ggatggcatg acagtaagag aattatgcag tgctgccata accatgagtg ataacactgc    6240
ggccaactta cttctgacaa cgatcggagg accgaaggag ctaaccgctt ttttgcacaa    6300 catggggat  catgtaactc gccttgatcg ttgggaaccg gagctgaatg aagccatacc    6360
aaacgacgag cgtgacacca cgatgcctgt agcaatggca acaacgttgc gcaaactatt    6420
```

```
aactggcgaa ctacttactc tagcttcccg gcaacaatta atagactgga tggaggcgga    6480
taaagttgca ggaccacttc tgcgctcggc ccttccggct ggctggttta ttgctgataa    6540
atctggagcc ggtgagcgtg ggtctcgcgg tatcattgca gcactggggc cagatggtaa    6600
gccctcccgt atcgtagtta tctacacgac ggggagtcag gcaactatgg atgaacgaaa    6660
tagacagatc gctgagatag gtgcctcact gattaagcat tggtaactgt cagaccaagt    6720
ttactcatat atactttaga ttgatttaaa acttcatttt taatttaaaa ggatctaggt    6780
gaagatcctt tttgataatc tcatgaccaa atcccttaa cgtgagtttt cgttccactg    6840
agcgtcagac cccgtagaaa agatcaaagg atcttcttga tccttttt ttctgcgcgt    6900 aatctgctgc ttgcaaacaa aaaaaccacc gctaccagcg gtggtttgtt tgccggatca    6960
agagctacca actctttttc cgaaggtaac tggcttcagc agagcgcaga taccaaatac    7020
tgtccttcta gtgtagccgt agttaggcca ccacttcaag aactctgtag caccgcctac    7080
atacctcgct ctgctaatcc tgttaccagt ggctgctgcc agtggcgata agtcgtgtct    7140 taccggggttg gactcaagac gatagttacc ggataaggcg cagcggtcgg gctgaacggg    7200
gggttcgtgc acacagccca gcttggagcg aacgacctac accgaactga gatacctaca    7260
gcgtgagcat tgagaaagcg ccacgcttcc cgaagggaga aaggcggaca ggtatccggt    7320
aagcggcagg gtcggaacag gagagcgcac gagggagctt ccaggggaa acgcctggta    7380 tctttatagt cctgtcgggt ttcgccacct ctgacttgag cgtcgatttt tgtgatgctc    7440 gtcaggggg cggagcctat ggaaaaacgc cagcaacgcg gcctttttac ggttcctggc    7500
cttttgctgg ccttttgctc acatgttctt tcctgcgtta tcccctgatt ctgtggataa    7560
ccgtattacc gcctttgagt gagctgatac cgctcgccgc agccgaacga ccgagcgcag    7620
cgagtcagtg agcgaggaag cggaagagcg cccaatacgc aaaccgcctc tccccgcgcg    7680
ttggccgatt cattaatgca gctggcacga caggtttccc gactggaaag cgggcagtga    7740
gcgcaacgca attaatgtga gttagctcac tcattaggca ccccaggctt tacactttat    7800
gcttccggct cgtatgttgt gtggaattgt gagcggataa caatttcaca caggaaacag    7860
ctatgaccat gattacgcca agctttgctc ttaggagttt cctaatacat cccaaactca    7920
aatatataaa gcatttgact tgttctatgc cctaggggc gggggaagc taagccagct    7980 ttttttaaca tttaaaatgt taattccatt ttaaatgcac agatgttttt atttcataag    8040
ggtttcaatg tgcatgaatg ctgcaatatt cctgttacca aagctagtat aaataaaaat    8100
agataaacgt ggaaattact tagagtttct gtcattaacg tttccttcct cagttgacaa    8160
cataaatgcg ctgctgagca agccagtttg catctgtcag gatcaatttc ccattatgcc    8220
agtcatatta attactagtc aattagttga ttttttatttt tgacatatac atgtgaatga    8280
aagaccccac ctgtaggttt ggcaagctag cttaagtaac gccattttgc aaggcatgga    8340
aaaatacata actgagaata gaaaagttca gatcaaggtc aggaacagat ggaacagctg    8400
aatatgggcc aaacaggata tctgtggtaa gcagttcctg ccccggctca gggccaagaa    8460
cagatggaac agctgaatat gggccaaaca ggatatctgt ggtaagcagt tcctgccccg    8520
gctcagggcc aagaacagat ggtccccaga tgcggtccag ccctcagcag tttctagaga    8580
accatcagat gtttccaggg tgccccaagg acctgaaatg accctgtgcc ttatttgaac    8640
taaccaatca gttcgcttct cgcttctgtt cgcgcgctta tgctccccga gctcaataaa    8700
agagcccaca cccctcact cggggcgcca gtcctccgat tgactgagtc gcccgggtac    8760
```

```
ccgtgtatcc aataaaccct cttgcagttg catccgactt gtggtctcgc tgttccttgg     8820
gagggtctcc tctgagtgat tgactacccg tcagcggggg tctttcattt gggggctcgt     8880
ccgggatcgg gagacccctg cccagggacc accgacccac caccgggagg t             8931

<210> SEQ ID NO 18
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ttctgggtac tggttgtagt cggtggcgta cttgcttgtt attctcttct tgttaccgta       60
gccttcatta tattctgggt ccgatcaaag cgctcaagac tcctccattc cgattatatg      120
aacatgacac ctcgccgacc tggtcctaca cgcaaacatt atcaaccctg cgcacccccc      180
cgagacttcg ctgcttatcg atcc                                             204

<210> SEQ ID NO 19
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Ala Asp Phe Ala
    50                  55                  60

Ala Tyr Arg Ser
65

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 ggatcc                                                                    6

<210> SEQ ID NO 21
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser
1
```

<210> SEQ ID NO 22
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
agtgtagtta aaagaggaag aaaaaagttg ctgtatatat ttaaacaacc atttatgaga      60
ccagtgcaaa ccacccaaga agaagacgga tgttcatgca gattcccaga agaagaagaa    120
ggaggatgtg aattg                                                     135

<210> SEQ ID NO 23
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Val Val Lys Arg Gly Arg Lys Lys Leu Leu Tyr Ile Phe Lys Gln
1               5                   10                  15

Pro Phe Met Arg Pro Val Gln Thr Thr Gln Glu Glu Asp Gly Cys Ser
            20                  25                  30

Cys Arg Phe Pro Glu Glu Glu Gly Gly Cys Glu Leu
        35                  40                  45

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 acgcgt                                                                 6

<210> SEQ ID NO 25
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Arg
1

<210> SEQ ID NO 26
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
cgggtcaaat tcagccggag tgctgacgcc ccagcatacc aacagggaca aaaccaactc      60
tacaacgagc tcaacctggg tagacgcgag gagtacgacg ttctggataa gaggcggggc    120
cgggacccag agatgggggg caaacctcag cggcggaaga acccgcagga gggtctttat    180

-continued

```
aacgagctcc agaaggacaa gatggcggaa gcctattcag aaattgggat gaaaggcgag      240
agacgcaggg gaaaaggtca cgatggtctg tatcaaggac tgtcaaccgc caccaaagac      300
acttacgatg cgctccacat gcaggccctc cctccccgc                            339
```

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 28
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28

```
atggagtttg gctgtcatg gctgttcctc gtggccattc tcaaagggt ccagtgttct       60 cgc                                                                   63
```

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

```
Met Gly Phe Gly Leu Ser Trp Leu Phe Leu Val Ala Ile Leu Lys Gly
1               5                   10                  15

Val Gln Cys Ser Arg
            20
```

<210> SEQ ID NO 30
<211> LENGTH: 45
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 30
gggggaggag gttctggagg cggcgggagc ggaggaggag gcagc                45

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 ggatcc                                                           6

<210> SEQ ID NO 33
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser
1

<210> SEQ ID NO 34
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatccagccg aacccaaatc ccccgataaa acacatactt gcccccttg tcccgcacca    60 gaattgcttg gcggaccttc cgttttctt tttccccccca aacctaaaga tacctgatg   120 atttcccgaa cccctgaagt tacgtgcgta gtcgtagatg tgtctcacga agatccagaa  180
gtaaaattta actggtacgt agatggagtc gaagttcaca acgcaaagac gaagccccga  240
gaagaacaat ataattccac ataccgagta gttagcgttc tcaccgtact gcatcaggac  300
tggcttaacg gcaaagaata taatgtaag gtctcaaaca aagcactccc agccccctatc  360 gaaaagacta tctccaaagc taaaggacaa ccccgcgaac cccaggtcta tacacttccc  420 cccctcacgcg atgaactcac taaaaatcag gtttccctta cttgtcttgt caaaggcttc  480 tacccctagcg atatcgcagt cgaatgggaa tccaatggcc agcccgaaaa caactataaa  540 acaacccccac ctgtcctcga ttcagatggc tcattctttc tctattccaa actgactgta  600
```

```
                   gacaaatccc gatggcaaca aggtaacgtg ttctcttgct cagtcatgca tgaagcgctt    660
cataaccatt acacacaaaa atctctctca ctgtctcccg gaaagaagga cccc           714
```

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Asp Pro Ala Glu Pro Lys Ser Pro Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys Lys Asp Pro
225                 230                 235
```

<210> SEQ ID NO 36
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
ctcgag                                                                      6
```

<210> SEQ ID NO 37
<211> LENGTH: 2
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 37

Leu Glu
1

<210> SEQ ID NO 38
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
aaactgtgtt acctcctcga tggcatcctc tttatttatg gcgtgattct gaccgcattg    60
tttctccgag taaaattctc tagatccgca gacgctcccg catatcagca aggacaaaat   120
cagctttata cgaacttaa cctcggcaga cgcgaagaat acgatgtact ggacaagaga    180
agaggaagag atcccgaaat gggcggaaaa ccccagagaa gaaagaatcc caagaaggt    240 ctttataacg aactgcagaa agataaaatg gccgaagcgt acagtgaaat tggtatgaaa   300
ggagaaagaa gacgcggaaa aggacatgac ggactctacc aaggactctc aactgctact   360
aaagatacat acgacgccct tcatatgcaa gccctccccc cgagataa               408

<210> SEQ ID NO 39
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Leu Cys Tyr Leu Leu Asp Gly Ile Leu Phe Ile Tyr Gly Val Ile
1               5                   10                  15

Leu Thr Ala Leu Phe Leu Arg Val Lys Phe Ser Arg Ser Ala Asp Ala
            20                  25                  30

Pro Ala Tyr Gln Gln Gly Gln Asn Gln Leu Tyr Asn Glu Leu Asn Leu
        35                  40                  45

Gly Arg Arg Glu Glu Tyr Asp Val Leu Asp Lys Arg Gly Arg Asp
    50                  55                  60

Pro Glu Met Gly Gly Lys Pro Gln Arg Arg Lys Asn Pro Gln Glu Gly
65                  70                  75                  80

Leu Tyr Asn Glu Leu Gln Lys Asp Lys Met Ala Glu Ala Tyr Ser Glu
                85                  90                  95

Ile Gly Met Lys Gly Glu Arg Arg Arg Gly Lys Gly His Asp Gly Leu
            100                 105                 110

Tyr Gln Gly Leu Ser Thr Ala Thr Lys Asp Thr Tyr Asp Ala Leu His
        115                 120                 125

Met Gln Ala Leu Pro Pro Arg
    130                 135

<210> SEQ ID NO 40
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
gttgccgcca tcctgggcct gggcctggtg ctggggctgc tgggcccccct ggccatcctg      60
ctggccctgt acctgctccg ggaccagagg ctgccccccg atgcccacaa gcccctggg      120
ggaggcagtt tccggacccc catccaagag gagcaggccg acgcccactc caccctggcc    180
aagatc                                                                   186
```

<210> SEQ ID NO 41
<211> LENGTH: 63
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Val Ala Ala Ile Leu Gly Leu Gly Leu Val Leu Gly Leu Leu Gly Pro
 1               5                  10                  15

Leu Ala Ile Leu Leu Ala Leu Tyr Leu Leu Arg Arg Asp Gln Arg Leu
            20                  25                  30

Pro Pro Asp Ala His Lys Pro Pro Gly Gly Gly Ser Phe Arg Thr Pro
        35                  40                  45

Ile Gln Glu Glu Gln Ala Asp Ala His Ser Thr Leu Ala Lys Ile
    50                  55                  60
```

<210> SEQ ID NO 42
<211> LENGTH: 590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
tgaaagaccc cacctgtagg tttggcaagc tagcttaagt aacgccattt tgcaaggcat      60
ggaaaatac ataactgaga atagaaaagt tcagatcaag gtcaggaaca gatggaacag      120
ctgaatatgg gccaaacagg atatctgtgg taagcagttc ctgccccggc tcagggccaa    180
gaacagatgg aacagctgaa tatgggccaa acaggatatc tgtggtaagc agttcctgcc    240
ccggctcagg gccaagaaca gatggtcccc agatgcggtc cagccctcag cagtttctag    300
agaaccatca gatgtttcca gggtgcccca aggacctgaa atgaccctgt gccttatttg    360
aactaaccaa tcagttcgct tctcgcttct gttcgcgcgc ttatgctccc cgagctcaat    420
aaaagagccc acaacccctc actcgggggcg ccagtcctcc gattgactga gtcgcccggg    480
tacccgtgta tccaataaac cctcttgcag ttgcatccga cttgtggtct cgctgttcct    540
tgggagggtc tcctctgagt gattgactac ccgtcagcgg gggtctttca                 590
```

<210> SEQ ID NO 43
<211> LENGTH: 57
<212> TYPE: DNA
<213> ORGANISM: Thosea asigna virus

<400> SEQUENCE: 43

```
gccgagggca gggaagtct tctaacatgc ggggacgtgg aggaaaatcc cgggccc          57
```

<210> SEQ ID NO 44
<211> LENGTH: 19
<212> TYPE: PRT

-continued

<213> ORGANISM: Thosea asigna virus

<400> SEQUENCE: 44

Ala Glu Gly Arg Gly Ser Leu Leu Thr Cys Gly Asp Val Glu Glu Asn
1               5                   10                  15

Pro Gly Pro

<210> SEQ ID NO 45
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
tgaaagaccc cacctgtagg tttggcaagc tagcttaagt aacgccattt tgcaaggcat     60
ggaaaaatac ataactgaga atagagaagt tcagatcaag gtcaggaaca gatggaacag    120
ctgaatatgg gccaaacagg atatctgtgg taagcagttc ctgccccggc tcagggccaa    180
gaacagatgg aacagctgaa tatgggccaa acaggatatc tgtggtaagc agttcctgcc    240
ccggctcagg gccaagaaca gatggtcccc agatgcggtc cagccctcag cagtttctag    300
agaaccatca gatgtttcca gggtgcccca aggacctgaa atgaccctgt gccttatttg    360
aactaaccaa tcagttcgct tctcgcttct gttcgcgcgc ttctgctccc cgagctcaat    420
aaaagagccc acaaccccctc actcggggcg ccagtcctcc gattgactga gtcgcccggg    480
tacccgtgta tccaataaac cctcttgcag ttgcatccga cttgtggtct cgctgttcct    540
tgggagggtc tcctctgagt gattgactac ccgtcagcgg gggtctttca    590

<210> SEQ ID NO 46
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ctcgagtctg gcggtggatc cggaggcgtt caagtagaaa caatcagccc aggagacgga     60
aggactttcc ccaaacgagg ccaaacatgc gtagttcatt atactgggat gctcgaagat    120
ggaaaaaaag tagatagtag tagagaccga acaaaccat ttaaatttat gttgggaaaa    180
caagaagtaa taaggggctg gaagaaggt gtagcacaaa tgtctgttgg ccagcgcgca    240
aaactcacaa tttctcctga ttatgcttac ggagctaccg gccaccccgg catcataccc    300
cctcatgcca cactggtgtt tgacgtcgaa ttgctcaaac tggaagtcga gggagtgcag    360
gtggagacga ttagtcctgg ggatgggaga acctttccaa agcgcggtca gacctgtgtt    420
gtccactaca ccggtatgct ggaggacggg aagaaggtgg actcttcacg cgatcgcaat    480
aagcctttca agttcatgct cggcaagcag gaggtgatcc ggggggtggga ggagggcgtg    540 gctcagatgt cggtcgggca acgagcgaag cttaccatct cacccgacta cgcgtatggg    600
gcaacggggc atccgggaat tatccctccc cacgctacgc tcgtattcga gtgtggagctc    660 ttgaagcttg agtctggcgg tggatccgga gtcgac    696

<210> SEQ ID NO 47
<211> LENGTH: 232
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 47

Leu Glu Ser Gly Gly Ser Gly Gly Val Gln Val Glu Thr Ile Ser
1               5                   10                  15

Pro Gly Asp Gly Arg Thr Phe Pro Lys Arg Gly Gln Thr Cys Val Val
                20                  25                  30

His Tyr Thr Gly Met Leu Glu Asp Gly Lys Lys Val Asp Ser Ser Arg
                35                  40                  45

Asp Arg Asn Lys Pro Phe Lys Phe Met Leu Gly Lys Gln Glu Val Ile
            50                  55                  60

Arg Gly Trp Glu Glu Gly Val Ala Gln Met Ser Val Gly Gln Arg Ala
65                  70                  75                  80

Lys Leu Thr Ile Ser Pro Asp Tyr Ala Tyr Gly Ala Thr Gly His Pro
                85                  90                  95

Gly Ile Ile Pro Pro His Ala Thr Leu Val Phe Asp Val Glu Leu Leu
                100                 105                 110

Lys Leu Glu Val Glu Gly Val Gln Val Glu Thr Ile Ser Pro Gly Asp
            115                 120                 125

Gly Arg Thr Phe Pro Lys Arg Gly Gln Thr Cys Val Val His Tyr Thr
130                 135                 140

Gly Met Leu Glu Asp Gly Lys Lys Val Asp Ser Ser Arg Asp Arg Asn
145                 150                 155                 160

Lys Pro Phe Lys Phe Met Leu Gly Lys Gln Glu Val Ile Arg Gly Trp
                165                 170                 175

Glu Glu Gly Val Ala Gln Met Ser Val Gly Gln Arg Ala Lys Leu Thr
            180                 185                 190

Ile Ser Pro Asp Tyr Ala Tyr Gly Ala Thr Gly His Pro Gly Ile Ile
        195                 200                 205

Pro Pro His Ala Thr Leu Val Phe Asp Val Glu Leu Leu Lys Leu Glu
    210                 215                 220

Ser Gly Gly Gly Ser Gly Val Asp
225                 230

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ggcgttcaag tagaaacaat cagcccagga gacggaagga ctttccccaa acgaggccaa      60
acatgcgtag ttcattatac tgggatgctc gaagatggaa aaaagtagta gtagtagaga     120
gaccgaaaca aaccatttaa atttatgttg gaaaacaag aagtaataag gggctgggaa     180
gaaggtgtag cacaaatgtc tgttggccag cgcgcaaaac tcacaatttc tcctgattat     240
gcttacggag ctaccggcca ccccggcatc atacccctc atgccacact ggtgtttgac     300
gtcgaattgc tcaaactgga a                                                321

<210> SEQ ID NO 49
<211> LENGTH: 107
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 49

```
Gly Val Gln Val Glu Thr Ile Ser Pro Gly Asp Gly Arg Thr Phe Pro
1               5                   10                  15
Lys Arg Gly Gln Thr Cys Val Val His Tyr Thr Gly Met Leu Glu Asp
            20                  25                  30
Gly Lys Lys Val Asp Ser Ser Arg Asp Arg Asn Lys Pro Phe Lys Phe
        35                  40                  45
Met Leu Gly Lys Gln Glu Val Ile Arg Gly Trp Glu Glu Gly Val Ala
    50                  55                  60
Gln Met Ser Val Gly Gln Arg Ala Lys Leu Thr Ile Ser Pro Asp Tyr
65                  70                  75                  80
Ala Tyr Gly Ala Thr Gly His Pro Gly Ile Ile Pro Pro His Ala Thr
                85                  90                  95
Leu Val Phe Asp Val Glu Leu Leu Lys Leu Glu
            100                 105
```

<210> SEQ ID NO 50
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agccttttca agttcatgct ggcaagcagg aggtgatccg ggggtgggag     180
gagggcgtgg ctcagatgtc ggtcgggcaa cgagcgaagc ttaccatctc acccgactac     240
gcgtatgggg caacggggca tccgggaatt atccctcccc acgctacgct cgtattcgat     300
gtggagctct tgaagcttga g                                               321
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gly Val Gln Val Glu Thr Ile Ser Pro Gly Asp Gly Arg Thr Phe Pro
1               5                   10                  15
Lys Arg Gly Gln Thr Cys Val Val His Tyr Thr Gly Met Leu Glu Asp
            20                  25                  30
Gly Lys Lys Val Asp Ser Ser Arg Asp Arg Asn Lys Pro Phe Lys Phe
        35                  40                  45
Met Leu Gly Lys Gln Glu Val Ile Arg Gly Trp Glu Glu Gly Val Ala
    50                  55                  60
Gln Met Ser Val Gly Gln Arg Ala Lys Leu Thr Ile Ser Pro Asp Tyr
65                  70                  75                  80
Ala Tyr Gly Ala Thr Gly His Pro Gly Ile Ile Pro Pro His Ala Thr
                85                  90                  95
```

Leu Val Phe Asp Val Glu Leu Leu Lys Leu Glu
            100                 105

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atggggagta gcaagagcaa gcctaaggac cccagccagc gc                         42

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Gly Ser Ser Lys Ser Lys Pro Lys Asp Pro Ser Gln Arg
1               5                   10

<210> SEQ ID NO 54
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 ctcgag                                                                  6

<210> SEQ ID NO 55
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Glu
1

<210> SEQ ID NO 56
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggccgctg ggggcccagg cgccggatca gctgctcccg tatcttctac ttcttctttg      60
ccgctggctg ctctgaacat gcgcgtgaga agacgcctct ccctgttcct taacgttcgc     120
acacaagtcg ctgccgattg accgcccttt gccgaagaaa tggactttga atacctggaa     180
attagacaac ttgaaacaca ggccgacccc actggcagac tcctggacgc atggcaggga     240
agacctggtg caagcgttgg acggctcctg gatctcctga caaaactggg acgcgacgac     300

```
gtactgcttg aactcggacc tagcattgaa gaagactgcc aaaaatatat cctgaaacaa      360
caacaagaag aagccgaaaa acctctccaa gtcgcagcag tggactcatc agtaccccga      420
acagctgagc ttgctgggat tactacactc gacgacccac tcggacatat gcctgaaaga      480
ttcgacgctt tcatttgcta ttgcccctct gacata                               516
```

```
<210> SEQ ID NO 57
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57
```

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

```
<210> SEQ ID NO 58
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
aagaaagttg caaagaaacc cacaaataaa gccccacacc ctaaacagga accccaagaa      60
atcaatttcc cagatgatct ccctggatct aatactgccg ccccggtcca agaaaccctg     120
catggttgcc agcctgtcac ccaagaggac ggaaaagaat cacggattag cgtacaagag     180
agacaa                                                               186
```

```
<210> SEQ ID NO 59
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 59

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtcgagtctg gcggtggatc cgga                                          24

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Glu Ser Gly Gly Gly Ser Gly
1               5

<210> SEQ ID NO 62
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ggcgttcaag tagaaacaat cagcccagga gacggaagga ctttccccaa acgaggccaa      60
acatgcgtag ttcattatac tgggatgctc gaagatggaa aaaagtagta tagtagtaga    120
gaccgaaaca aaccatttaa atttatgttg ggaaaacaag aagtaataag gggctgggaa    180
gaaggtgtag cacaaatgtc tgttggccag cgcgcaaaac tcacaatttc tcctgattat    240
gcttacggag ctaccggcca ccccggcatc atacccctc atgccacact ggtgtttgac     300
gtcgaattgc tcaaactgga a                                              321

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
65                   70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 gtcgag                                                                      6

<210> SEQ ID NO 65
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Glu
1

<210> SEQ ID NO 66
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ggagtgcagg tggagacgat tagtcctggg gatgggagaa cctttccaaa gcgcggtcag          60
acctgtgttg tccactacac cggtatgctg gaggacggga agaaggtgga ctcttcacgc         120
gatcgcaata agcctttcaa gttcatgctc ggcaagcagg aggtgatccg ggggtgggag         180
gagggcgtgg ctcagatgtc ggtcgggcaa cgagcgaagc ttaccatctc acccgactac         240
gcgtatgggg caacggggca tccgggaatt atccctcccc acgctacgct cgtattcgat         300
gtggagctct tgaagcttga g                                                   321

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tctggcggtg gatccggagt cgac                                             24

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Ser Gly Gly Gly Ser Gly Val Asp
1               5
```

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgcgcaaagc gt                                                          12

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Arg Ala Lys Arg
1
```

<210> SEQ ID NO 72
<211> LENGTH: 42
<212> TYPE: DNA

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic oligonucleotide

<400> SEQUENCE: 72
ggaaaaccta tacctaatcc attgctgggc ttagactcaa ca        42

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gly Lys Pro Ile Pro Asn Pro Leu Leu Gly Leu Asp Ser Thr
1               5                   10

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
ggcagcggaa gc        12

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gly Ser Gly Ser
1

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
gcaacgaatt tttccctgct gaaacaggca ggggacgtag aggaaaatcc tggtcct        57

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ala Thr Asn Phe Ser Leu Leu Lys Gln Ala Gly Asp Val Glu Glu Asn
1               5                   10                  15

Pro Gly Pro

<210> SEQ ID NO 78
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 acgcgt                                                                    6

<210> SEQ ID NO 79
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Arg
1

<210> SEQ ID NO 80
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
atgccccctc ctagactgct gttttcctg ctctttctca ccccaatgga agttagacct          60
gaggaaccac tggtcgttaa agtggaagaa ggtgataatg ctgtcctcca atgccttaaa       120
gggaccagcg acggaccaac gcagcaactg acttggagcc gggagtcccc tctcaagccg       180
tttctcaagc tgtcacttgg cctgccaggt cttggtattc acatgcgccc ccttgccatt       240
tggctcttca tattcaatgt gtctcaacaa atgggtggat tctacctttg ccagcccggc       300 ccccttctg agaaagcttg gcagcctgga tggaccgtca atgttgaagg ctccggtgag        360
ctgtttagat ggaatgtgag cgaccttggc ggactcggtt gcggactgaa aaataggagc       420
tctgaaggac cctcttctcc ctccggtaag ttgatgtcac ctaagctgta cgtgtgggcc       480
aaggaccgcc ccgaaatctg ggagggcgag cctccatgcc tgccgcctcg cgattcactg       540
aaccagtctc tgtcccagga tctcactatg gcgcccggat ctactctttg gctgtcttgc       600
ggcgttcccc cagatagcgt gtcaagagga cctctgagct ggacccacgt acaccctaag       660
ggccctaaga gcttgttgag cctggaactg aaggacgaca gacccgcacg cgatatgtgg       720
gtaatggaga ccggccttct gctccctcgc gctaccgcac aggatgcagg gaaatactac       780
tgtcatagag ggaatctgac tatgagcttt catctcgaaa ttacagcacg gcccgttctt       840
tggcattggc tcctccggac tggaggctgg aaggtgtctg ccgtaacact cgcttacttg       900 atttttttgcc tgtgtagcct ggttgggatc ctgcatcttc agcgagccct tgtattgcgc       960
cgaaaaagaa aacgaatgac tgaccctaca cgacgattct ga                         1002

<210> SEQ ID NO 81
<211> LENGTH: 333
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
atggggagta gcaagagcaa gcctaaggac cccagccagc gc                         42

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Met Gly Ser Ser Lys Ser Lys Pro Lys Asp Pro Ser Gln Arg
1               5                   10

<210> SEQ ID NO 84
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84 ctcgac                                                                  6

<210> SEQ ID NO 85
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Leu Asp
1

<210> SEQ ID NO 86
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86
atggctgcag gaggtcccgg cgcggggtct gcggccccgg tctcctccac atcctccctt        60
cccctggctg ctctcaacat gcgagtgcgg cgccgcctgt ctctgttctt gaacgtgcgg       120
acacaggtgg cggccgactg gaccgcgctg gcggaggaga tggactttga gtacttggag       180
atccggcaac tggagacaca gcggacccc actggcaggc tgctggacgc ctggcaggga        240
cgccctggcg cctctgtagg ccgactgctc gatctgctta ccaagctggg ccgcgacgac       300
gtgctgctgg agctgggacc cagcattgag gaggattgcc aaaagtatat cttgaagcag       360
cagcaggagg aggctgagaa gcctttacag gtggccgctg tagacagcag tgtcccacgg       420
acagcagagc tggcgggcat caccacactt gatgaccccc tggggcatat gcctgagcgt       480
ttcgatgcct tcatctgcta ttgccccagc gacatc                                 516

<210> SEQ ID NO 87
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 88
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88 gtcgag                                                                  6

<210> SEQ ID NO 89
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Glu
1

<210> SEQ ID NO 90
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
aaaaaggtgg ccaagaagcc aaccaataag gccccccacc ccaagcagga gccccaggag      60
atcaattttc ccgacgatct tcctggctcc aacactgctg ctccagtgca ggagacttta     120
catggatgcc aaccggtcac ccaggaggat ggcaaagaga gtcgcatctc agtgcaggag     180
agacag                                                                          186

<210> SEQ ID NO 91
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 92
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92 ccgcgg                                                                          6

<210> SEQ ID NO 93
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Pro Arg
1

<210> SEQ ID NO 94
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaaggccgag ggagcctgct gacatgtggc gatgtggagg aaaacccagg acca               54

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Gly Arg Gly Ser Leu Leu Thr Cys Gly Asp Val Glu Glu Asn Pro
1               5                   10                  15

Gly Pro

<210> SEQ ID NO 96
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

```
atggagtttg gactttcttg gttgttttttg gtggcaattc tgaagggtgt ccagtgtagc    60
agg                                                                   63
```

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met Glu Phe Gly Leu Ser Trp Leu Phe Leu Val Ala Ile Leu Lys Gly
1               5                   10                  15

Val Gln Cys Ser Arg
            20

<210> SEQ ID NO 98
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat acactcagg agtcccatca     180 aggttcagtg gcagtgggtc tggaacagat tattctctca ccattagcaa cctggagcaa    240
gaagatattg ccacttactt ttgccaacag ggtaatacgc ttccgtacac gttcggaggg    300
gggactaagt tggaaataac a                                              321
```

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggcggaggaa gcggaggtgg gggc                                              24

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Ser Gly Gly Gly Gly
1               5

<210> SEQ ID NO 102
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatggggta gtgaaaccac atactataat   180
tcagctctca atccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggtcaaggaa cctcagtcac cgtctcctca   360

<210> SEQ ID NO 103
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu

```
            35                  40                  45
Gly Val Ile Trp Gly Ser Glu Thr Thr Tyr Tyr Asn Ser Ala Leu Lys
         50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 104
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104 ggatcc                                                                  6

<210> SEQ ID NO 105
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser
 1

<210> SEQ ID NO 106
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gaacttccta ctcaggggac tttctcaaac gttagcacaa acgtaagt                   48

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Leu Pro Thr Gln Gly Thr Phe Ser Asn Val Ser Thr Asn Val Ser
 1               5                  10                  15

<210> SEQ ID NO 108
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 108
cccgccccaa gaccccccac acctgcgccg accattgctt ctcaacccct gagtttgaga        60
cccgaggcct gccggccagc tgccggcggg gccgtgcata caagaggact cgatttcgct       120
tgcgac                                                                  126

<210> SEQ ID NO 109
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 110
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
atctatatct gggcacctct cgctggcacc tgtggagtcc ttctgctcag cctggttatt        60
actctgtact gtaatcaccg gaatcgccgc cgcgtttgta agtgtcccag g                111

<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35

<210> SEQ ID NO 112
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112 gtcgac                                                                    6

<210> SEQ ID NO 113

```
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Asp
1

<210> SEQ ID NO 114
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
agagtgaagt tcagcaggag cgcagacgcc cccgcgtacc agcagggcca gaaccagctc       60
tataacgagc tcaatctagg acgaagagag gagtacgatg tttggacaa gagacgtggc      120 cgggaccctg agatggggg aaagccgaga aggaagaacc ctcaggaagg cctgtacaat      180
gaactgcaga aagataagat ggcggaggcc tacagtgaga ttgggatgaa aggcgagcgc      240 cggagggggca aggggcacga tggcctttac cagggtctca gtacagccac caaggacacc      300
tacgacgccc ttcacatgca ggccctgccc cctcgc                                336

<210> SEQ ID NO 115
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 116
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atgctggagg gagtgcaggt ggagactatt agccccggag atggcagaac attccccaaa       60
```

```
agaggacaga cttgcgtcgt gcattatact ggaatgctgg aagacggcaa gaaggtggac      120
agcagccggg accgaaacaa gcccttcaag ttcatgctgg ggaagcagga agtgatccgg      180
ggctgggagg aaggagtcgc acagatgtca gtgggacaga gggccaaact gactattagc      240
ccagactacg cttatggagc aaccggccac cccgggatca ttccccctca tgctacactg      300
gtcttcgatg tggagctgct gaagctggaa                                       330
```

```
<210> SEQ ID NO 117
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117
```

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
                20                  25                  30

Leu Glu Asp Gly Lys Lys Val Asp Ser Ser Arg Asp Arg Asn Lys Pro
            35                  40                  45

Phe Lys Phe Met Leu Gly Lys Gln Glu Val Ile Arg Gly Trp Glu Glu
        50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu
            100                 105                 110

```
<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
agcggaggag gatccgga                                                    18

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

Ser Gly Gly Gly Ser Gly
1               5

```
<210> SEQ ID NO 120
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 120

```
gtggacgggt tggagatgt gggagccctg aatccctgc ggggcaatgc cgatctggct      60
tacatcctgt ctatggagcc ttgcggccac tgtctgatca ttaacaatgt gaacttctgc    120
agagagagcg ggctgcggac cagaacagga tccaatattg actgtgaaaa gctgcggaga    180
aggttctcta gtctgcactt tatggtcgag gtgaaaggcg atctgaccgc taagaaaatg    240
gtgctggccc tgctgaact ggctcggcag gaccatgggg cactggattg ctgcgtggtc     300
gtgatcctga gtcacggctg ccaggcttca catctgcagt ccctggggc agtctatgga    360
actgacggct gtccagtcag cgtggagaag atcgtgaaca tcttcaacgg cacctcttgc    420
ccaagtctgg gcgggaagcc caaactgttc tttattcagg cctgtggagg cgagcagaaa    480
gatcacggct cgaagtggc tagcacctcc cccgaggacg aatcacctgg aagcaaccct     540
gagccagatg caaccccctt ccaggaaggc ctgaggacat tgaccagct ggatgccatc     600
tcaagcctgc ccacaccttc tgacattttc gtctcttaca gtactttccc tggatttgtg    660
agctggcgcg atccaaagtc aggcagctgg tacgtgaga cactgacga tatctttgag     720
cagtgggccc attctgaaga cctgcagagt ctgctgctgc gagtggccaa tgctgtctct    780
gtgaagggga tctacaaaca gatgccagga tgcttcaact ttctgagaaa gaaactgttc    840
tttaagacct ccgcatctag ggcc                                           864
```

<210> SEQ ID NO 121
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Val Asp Gly Phe Gly Asp Val Gly Ala Leu Glu Ser Leu Arg Gly Asn
1               5                   10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
        35                  40                  45

Thr Gly Ser Asn Ile Asp Cys Glu Lys Leu Arg Arg Arg Phe Ser Ser
    50                  55                  60

Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
        115                 120                 125

Glu Lys Ile Val Asn Ile Phe Asn Gly Thr Ser Cys Pro Ser Leu Gly
    130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175

Gly Ser Asn Pro Glu Pro Asp Ala Thr Pro Phe Gln Glu Gly Leu Arg
            180                 185                 190
```

```
Thr Phe Asp Gln Leu Asp Ala Ile Ser Ser Leu Pro Thr Pro Ser Asp
            195                 200                 205

Ile Phe Val Ser Tyr Ser Thr Phe Pro Gly Phe Val Ser Trp Arg Asp
        210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Arg Val Ala
            245                 250                 255

Asn Ala Val Ser Val Lys Gly Ile Tyr Lys Gln Met Pro Gly Cys Phe
                260                 265                 270

Asn Phe Leu Arg Lys Lys Leu Phe Phe Lys Thr Ser Ala Ser Arg Ala
            275                 280                 285

<210> SEQ ID NO 122
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122 ccgcgg                                                                6

<210> SEQ ID NO 123
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Pro Arg
1

<210> SEQ ID NO 124
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gaaggccgag ggagcctgct gacatgtggc gatgtggagg aaaacccagg acca         54

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Gly Arg Gly Ser Leu Leu Thr Cys Gly Asp Val Glu Glu Asn Pro
1               5                   10                  15

Gly Pro

<210> SEQ ID NO 126
<211> LENGTH: 6
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 126 ccatgg                                                                    6

<210> SEQ ID NO 127
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Trp
1

<210> SEQ ID NO 128
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
atggagtttg gactttcttg gttgtttttg gtggcaattc tgaagggtgt ccagtgtagc       60
agg                                                                     63

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Met Glu Phe Gly Leu Ser Trp Leu Phe Leu Val Ala Ile Leu Lys Gly
1               5                   10                  15

Val Gln Cys Ser Arg
            20

<210> SEQ ID NO 130
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gacatccaga tgacacagac tacatcctcc ctgtctgcct ctctgggaga cagagtcacc       60
atcagttgca gggcaagtca ggacattagt aaatatttaa attggtatca gcagaaacca      120
gatggaactg ttaaactcct gatctaccat acatcaagat tacactcagg agtcccatca      180
aggttcagtg gcagtgggtc tggaacagat tattctctca ccattagcaa cctggagcaa      240
gaagatattg ccacttactt ttgccaacag ggtaatacgc ttccgtacac gttcggaggg      300
gggactaagt tggaaataac a                                                321

<210> SEQ ID NO 131
```

<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 131

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 132
ggcggaggaa gcggaggtgg gggc                                          24

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 133

Gly Gly Gly Ser Gly Gly Gly Gly
1               5

<210> SEQ ID NO 134
<211> LENGTH: 360
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 134
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatggggta gtgaaaccac atactataat   180
tcagctctca aatccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggtcaaggaa cctcagtcac cgtctcctca   360

<210> SEQ ID NO 135
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 136
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136 ggatcc                                                                          6

<210> SEQ ID NO 137
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Ser
1

<210> SEQ ID NO 138
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaacttccta ctcaggggac tttctcaaac gttagcacaa acgtaagt                            48

<210> SEQ ID NO 139
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Glu Leu Pro Thr Gln Gly Thr Phe Ser Asn Val Ser Thr Asn Val Ser
1               5                   10                  15

<210> SEQ ID NO 140
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
cccgccccaa gacccccac acctgcgccg accattgctt ctcaacccct gagtttgaga      60
cccgaggcct gccggccagc tgccggcggg gccgtgcata caagaggact cgatttcgct    120
tgcgac                                                              126

<210> SEQ ID NO 141
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
                20                  25                  30

His Thr Arg Gly Leu Asp Phe Ala Cys Asp
            35                  40

<210> SEQ ID NO 142
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
atctatatct gggcacctct cgctggcacc tgtggagtcc ttctgctcag cctggttatt      60
actctgtact gtaatcaccg gaatcgccgc cgcgtttgta agtgtcccag g              111

<210> SEQ ID NO 143
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
                20                  25                  30
```

Cys Lys Cys Pro Arg
         35

<210> SEQ ID NO 144
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144 gtcgac                                                                  6

<210> SEQ ID NO 145
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Val Asp
1

<210> SEQ ID NO 146
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
atggccgctg ggggcccagg cgccggatca gctgctcccg tatcttctac ttcttctttg      60
ccgctggctg ctctgaacat gcgcgtgaga agacgcctct ccctgttcct taacgttcgc     120
acacaagtcg ctgccgattg gaccgccctt gccgaagaaa tggactttga atacctggaa     180
attagacaac ttgaaacaca ggccgacccc actggcagac tcctggacgc atggcaggga     240
agacctggtg caagcgttgg acggctcctg gatctcctga caaaactggg acgcgacgac     300
gtactgcttg aactcggacc tagcattgaa gaagactgcc aaaaatatat cctgaaacaa     360
caacaagaag aagccgaaaa acctctccaa gtcgcagcag tggactcatc agtaccccga     420
acagctgagc ttgctgggat tactacactc gacgacccac tcggacatat gcctgaaaga     480
ttcgacgctt tcatttgcta ttgcccctct gacata                              516

<210> SEQ ID NO 147
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

```
Ala Leu Ala Glu Glu Met Asp Phe Glu Tyr Leu Glu Ile Arg Gln Leu
            50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Asp Leu Leu Thr Lys Leu
                    85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 148
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
aagaaagttg caaagaaacc cacaaataaa gccccacacc ctaaacagga accccaagaa     60
atcaatttcc cagatgatct ccctggatct aatactgccg ccccggtcca agaaaccctg    120
catggttgcc agcctgtcac ccaagaggac ggaaaagaat cacggattag cgtacaagag    180
agacaa                                                               186

<210> SEQ ID NO 149
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Lys Lys Val Ala Lys Lys Pro Thr Asn Lys Ala Pro His Pro Lys Gln
 1               5                  10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
            35                  40                  45

Glu Asp Gly Lys Glu Ser Arg Ile Ser Val Gln Glu Arg Gln
        50                  55                  60

<210> SEQ ID NO 150
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
agagtgaagt tcagcaggag cgcagacgcc cccgcgtacc agcagggcca gaaccagctc    60
```

```
tataacgagc tcaatctagg acgaagagag gagtacgatg ttttggacaa gagacgtggc      120
cgggaccctg agatggggg aaagccgaga aggaagaacc ctcaggaagg cctgtacaat      180
gaactgcaga agataagat ggcggaggcc tacagtgaga ttgggatgaa aggcgagcgc      240 cggagggca aggggcacga tggcctttac cagggtctca gtacagccac caaggacacc      300
tacgacgccc ttcacatgca ggccctgccc cctcgc                               336
```

<210> SEQ ID NO 151
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 152
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
ggatttggtg atgtcggtgc tcttgagagt ttgaggggaa atgcagattt ggcttacatc       60
ctgagcatgg agccctgtgg ccactgcctc attatcaaca atgtgaactt ctgccgtgag      120
tccgggctcc gcacccgcac tggctccaac atcgactgtg agaagttgcg gcgtcgcttc      180
tcctcgctgc atttcatggt ggaggtgaag ggcgacctga ctgccaagaa aatggtgctg      240
gctttgctgg agctggcgca gcaggaccac ggtgctctgg actgctgcgt ggtggtcatt      300
ctctctcacg gctgtcaggc cagccaccct gcagttccag gggctgtcta cggcacagat      360
ggatgccctg tgtcggtcga aagattgtg aacatcttca atgggaccag ctgccccagc      420
ctgggaggga gcccaagct ctttttcatc caggcctgtg gtgggagca gaaagaccat      480 gggtttgagg tggcctccac ttcccctgaa gacgagtccc ctgcagtaa ccccgagcca      540 gatgccaccc cgttccagga aggtttgagg accttcgacc agctggacgc catatctagt      600
ttgcccacac ccagtgacat ctttgtgtcc tactctactt tcccaggttt tgtttcctgg      660
agggacccca gagtggctc ctggtacgtt gagccctgg acgacatctt tgagcagtgg      720
gctcactctg aagacctgca gtccctcctg cttagggtcg ctaatgctgt ttcggtgaaa      780
```

```
gggatttata aacagatgcc tggttgcttt aatttcctcc ggaaaaaact tttctttaaa      840
acatca                                                                846
```

<210> SEQ ID NO 153
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 154
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 154

```
gacatccaat tgacacaatc acacaaattt ctctcaactt ctgtaggaga cagagtgagc    60
ataacctgca aagcatccca ggacgtgtac aatgctgtgg cttggtacca acagaagcct   120
ggacaatccc caaaattgct gatttattct gcctctagta ggtacactgg ggtaccttct   180
cggtttacgg gctctgggtc cggaccagat ttcacgttca caatcagttc cgttcaagct   240
gaagacctcg ctgtttattt ttgccagcag cacttccgaa cccctttttac ttttggctca   300 ggcactaagt tggaaatcaa ggctttg                                       327
```

<210> SEQ ID NO 155
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Asp Ile Gln Leu Thr Gln Ser His Lys Phe Leu Ser Thr Ser Val Gly
1               5                   10                  15

Asp Arg Val Ser Ile Thr Cys Lys Ala Ser Gln Asp Val Tyr Asn Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Ser Arg Phe Thr Gly
    50                  55                  60

Ser Gly Ser Gly Pro Asp Phe Thr Phe Thr Ile Ser Ser Val Gln Ala
65                  70                  75                  80

Glu Asp Leu Ala Val Tyr Phe Cys Gln Gln His Phe Arg Thr Pro Phe
                85                  90                  95

Thr Phe Gly Ser Gly Thr Lys Leu Glu Ile Lys Ala Leu
            100                 105
```

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156

```
ggcggaggaa gcggaggtgg gggc                                          24
```

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Gly Gly Gly Ser Gly Gly Gly Gly
1               5
```

<210> SEQ ID NO 158
<211> LENGTH: 357
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 158

```
gaagtccaat tgcaacagtc aggccccgaa ttgaaaaagc ccggcgaaac agtgaagata    60
tcttgtaaag cctccggtta ccctttttacg aactatggaa tgaactgggt caaacaagcc   120
cctggacagg gattgaagtg gatgggatgg atcaatacat caacaggcga gtctaccttc   180
gcagatgatt tcaaaggtcg ctttgacttc tcactggaga ccagtgcaaa taccgcctac   240
cttcagatta caatcttaa aagcgaggat atggcaacct acttttgcgc aagatgggaa   300
gtttatcacg gtacgtgcc atactgggga caaggaacga cagtgacagt tagtagc      357
```

<210> SEQ ID NO 159
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Met Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser
        115
```

<210> SEQ ID NO 160
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160

```
ggatcc                                                              6
```

<210> SEQ ID NO 161
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Ser
1

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gaacttccta ctcaggggac tttctcaaac gttagcacaa acgtaagt                     48

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Leu Pro Thr Gln Gly Thr Phe Ser Asn Val Ser Thr Asn Val Ser
1               5                   10                  15

<210> SEQ ID NO 164
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
cccgccccaa gaccccccac acctgcgccg accattgctt ctcaacccct gagtttgaga        60
cccgaggcct gccggccagc tgccggcggg gccgtgcata caagaggact cgatttcgct       120
tgcgac                                                                  126

<210> SEQ ID NO 165
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 166
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
atctatatct gggcacctct cgctggcacc tgtggagtcc ttctgctcag cctggttatt        60
actctgtact gtaatcaccg gaatcgccgc cgcgtttgta agtgtcccag g                111

<210> SEQ ID NO 167
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35

<210> SEQ ID NO 168
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168 ctcgag                                                              6

<210> SEQ ID NO 169
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Glu
1

<210> SEQ ID NO 170
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
atggccgctg ggggcccagg cgccggatca gctgctcccg tatcttctac ttcttctttg    60
ccgctggctg ctctgaacat gcgcgtgaga agacgcctct ccctgttcct taacgttcgc   120
acacaagtcg ctgccgattg gaccgccctt gccgaagaaa tggactttga atacctggaa   180
attagacaac ttgaaacaca ggccgacccc actggcagac tcctggacgc atggcaggga   240
agacctggtg caagcgttgg acggctcctg gatctcctga caaaactggg acgcgacgac   300
gtactgcttg aactcggacc tagcattgaa gaagactgcc aaaaatatat cctgaaacaa   360
caacaagaag aagccgaaaa acctctccaa gtcgcagcag tggactcatc agtaccccga   420
acagctgagc ttgctgggat tactacactc gacgacccac tcggacatat gcctgaaaga   480
ttcgacgctt tcatttgcta ttgcccctct gacata                             516

<210> SEQ ID NO 171
<211> LENGTH: 172

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Ala Glu Lys Pro
        115                 120                 125

Leu Gln Val Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 172
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
aagaaagttg caaagaaacc cacaaataaa gccccacacc ctaaacagga accccaagaa      60
atcaatttcc cagatgatct ccctggatct aatactgccg ccccggtcca agaaaccctg     120
catggttgcc agcctgtcac ccaagaggac ggaaaagaat cacggattag cgtacaagag     180
agacaa                                                                186

<210> SEQ ID NO 173
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45
```

```
Glu Asp Gly Lys Glu Ser Arg Ile Ser Val Gln Glu Arg Gln
         50                  55                  60
```

<210> SEQ ID NO 174
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcggccgcag tcgag                                                       15

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Ala Ala Ala Val Glu
1               5
```

<210> SEQ ID NO 176
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
agagtgaagt tcagcaggag cgcagacgcc cccgcgtacc agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240 cggagggca aggggcacga tggcctttac cagggtctca gtacagccac caaggacacc      300
tacgacgccc ttcacatgca ggccctgccc cctcgc                                336

<210> SEQ ID NO 177
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 178
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280

<210> SEQ ID NO 179
<211> LENGTH: 846
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 179

```
ggatttggtg atgtcggtgc tcttgagagt ttgaggggaa atgcagattt ggcttacatc      60
ctgagcatgg agccctgtgg ccactgcctc attatcaaca atgtgaactt ctgccgtgag     120
tccgggctcc gcacccgcac tggctccaac atcgactgtg agaagttgcg gcgtcgcttc     180
tcctcgctgc atttcatggt ggaggtgaag ggcgacctga ctgccaagaa aatggtgctg     240
gctttgctgg agctggcgcg gcaggaccac ggtgctctgg actgctgcgt ggtggtcatt     300
ctctctcacg gctgtcaggc cagccacctg cagttcccag gggctgtcta cggcacagat     360
ggatgccctg tgtcggtcga aagattgtg aacatcttca atgggaccag ctgccccagc      420
ctgggaggga agcccaagct cttttttcatc caggcctgtg gtggggagca gaaagaccat     480
gggtttgagg tggcctccac ttcccctgaa gacgagtccc ctggcagtaa ccccgagcca     540
gatgccaccc cgttccagga aggtttgagg accttcgacc agctggccgc catatctagt     600
ttgcccacac ccagtgacat ctttgtgtcc tactctactt tcccaggttt tgtttcctgg     660
agggacccca agagtggctc ctggtacgtt gagaccctgg acgacatctt tgagcagtgg     720
gctcactctg aagacctgca gtccctcctg cttagggtcg ctaatgctgt ttcggtgaaa     780
gggatttata acagatgcc tggttgcttt aatttcctcc ggaaaaaact tttctttaaa      840
acatca                                                                846
```

<210> SEQ ID NO 180
<211> LENGTH: 282
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
```

```
                180             185             190
Asp Gln Leu Ala Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
        210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
            275                 280

<210> SEQ ID NO 181
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
ggatttggtg atgtcggtgc tcttgagagt ttgaggggaa atgcagattt ggcttacatc      60
ctgagcatgg agccctgtgg ccactgcctc attatcaaca atgtgaactt ctgccgtgag     120
tccgggctcc gcacccgcac tggctccaac atcgactgtg agaagttgcg gcgtcgcttc     180
tcctcgctgc atttcatggt ggaggtgaag ggcgacctga ctgccaagaa aatggtgctg     240
gctttgctgg agctggcgcg gcaggaccac ggtgctctgg actgctgcgt ggtggtcatt     300
ctctctcacg gctgtcaggc cagccacctg cagttcccag gggctgtcta cggcacagat     360
ggatgccctg tgtcggtcga aagattgtg aacatcttca atgggaccag ctgccccagc     420
ctgggaggga agcccaagct ctttttcatc caggcctgtg gtggggagca gaaagaccat     480
gggtttgagg tggcctccac ttcccctgaa gacgagtccc ctggcagtaa ccccgagcca     540
gatgccaccc cgttccagga aggtttgagg accttcgacc agctggacgc catatctagt     600
ttgcccacac ccagtgacat ctttgtgtcc tactctactt tcccaggttt tgtttcctgg     660
agggacccca agagtggctc ctggtacgtt gagaccctgg acgacatctt tgagcagtgg     720
gctcactctg aagacctgca gtccctcctg cttagggtcg ctaatgctgt ttcggtgaaa     780
gggatttata aacagatgcc tggttgcttt cagttcctcc ggaaaaaact tttctttaaa     840
acatca                                                                 846

<210> SEQ ID NO 182
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
```

```
               35                  40                  45
Ser Asn Ile Asp Cys Glu Lys Leu Arg Arg Arg Phe Ser Ser Leu His
 50                  55                  60

Phe Met Val Glu Val Lys Gly Asp Leu Thr Ala Lys Lys Met Val Leu
 65                  70                  75                  80

Ala Leu Leu Glu Leu Ala Arg Gln Asp His Gly Ala Leu Asp Cys Cys
                 85                  90                  95

Val Val Val Ile Leu Ser His Gly Cys Gln Ala Ser His Leu Gln Phe
                100                 105                 110

Pro Gly Ala Val Tyr Gly Thr Asp Gly Cys Pro Val Ser Val Glu Lys
                115                 120                 125

Ile Val Asn Ile Phe Asn Gly Thr Ser Cys Pro Ser Leu Gly Gly Lys
                130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
                180                 185                 190

Asp Gln Leu Asp Ala Ile Ser Ser Leu Pro Thr Pro Ser Asp Ile Phe
                195                 200                 205

Val Ser Tyr Ser Thr Phe Pro Gly Phe Val Ser Trp Arg Asp Pro Lys
                210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Gln Phe
                260                 265                 270

Leu Arg Lys Lys Leu Phe Phe Lys Thr Ser
                275                 280
```

<210> SEQ ID NO 183
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

```
ggatttggtg atgtcggtgc tcttgagagt ttgaggggaa atgcagattt ggcttacatc    60
ctgagcatgg agccctgtgg ccactgcctc attatcaaca atgtgaactt ctgccgtgag   120
tccgggctcc gcaccgcac tggctccaac atcgactgtg agaagttgcg gcgtcgcttc    180
tcctcgctgc atttcatggt ggaggtgaag ggcgacctga ctgccaagaa aatggtgctg   240
gctttgctgg agctggcgcg gcaggaccac ggtgctctgg actgctgcgt ggtggtcatt   300
ctctctcacg gctgtcaggc cagccacctg cagttcccag ggctgtcta cggcacagat    360 ggatgccctg tgtcggtcga gaagattgtg aacatcttca atgggaccag ctgccccagc   420
ctgggaggga agcccaagct cttttttcatc caggcctgtg gtgggagca gaaagaccat    480 gggtttgagg tggcctccac ttcccctgaa gacgagtccc ctggcagtaa ccccgagcca   540
gatgccaccc cgttccagga aggtttgagg accttcgacc agctggccgc catatctagt   600
ttgcccacac ccagtgacat ctttgtgtcc tactctactt tcccaggttt tgtttcctgg   660
```

```
agggacccca agagtggctc ctggtacgtt gagaccctgg acgacatctt tgagcagtgg      720
gctcactctg aagacctgca gtccctcctg cttagggtcg ctaatgctgt ttcggtgaaa      780
gggatttata acagatgcc tggttgcttt cagttcctcc ggaaaaaact tttctttaaa       840
acatca                                                                 846
```

<210> SEQ ID NO 184
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Ala Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Arg Val Ala Asn Ala
                245                 250                 255

Val Ser Val Lys Gly Ile Tyr Lys Gln Met Pro Gly Cys Phe Gln Phe
            260                 265                 270

Leu Arg Lys Lys Leu Phe Phe Lys Thr Ser
        275                 280
```

<210> SEQ ID NO 185
<211> LENGTH: 864
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 185
gtggacgggt tggagatgt gggagccctg gaatccctgc ggggcaatgc cgatctggct      60
tacatcctgt ctatggagcc ttgcggccac tgtctgatca ttaacaatgt gaacttctgc    120
agagagagcg ggctgcggac cagaacagga tccaatattg actgtgaaaa gctgcggaga    180
aggttctcta gtctgcactt tatggtcgag gtgaaaggcg atctgaccgc taagaaaatg    240
gtgctggccc tgctggaact ggctcggcag gaccatgggg cactggattg ctgcgtggtc    300
gtgatcctga gtcacggctg ccaggcttca catctgcagt tccctggggc agtctatgga    360
actgacggct gtccagtcag cgtggagaag atcgtgaaca tcttcaacgg cacctcttgc    420
ccaagtctgg gcgggaagcc caaactgttc tttattcagg cctgtggagg cgagcagaaa    480
gatcacggct cgaagtggc tagcacctcc cccgaggacg aatcacctgg aagcaaccct    540
gagccagatg caaccccctt ccaggaaggc ctgaggacat tgaccagct ggatgccatc    600 tcaagcctgc ccacaccttc tgacattttc gtctcttaca gtactttccc tggatttgtg    660
agctggcgcg atccaaagtc aggcagctgg tacgtggaga cactgaccga tatctttgag    720
cagtgggccc attctgaaga cctgcagagt ctgctgctgc gagtggccaa tgctgtctct    780
gtgaagggga tctacaaaca gatgccagga tgcttccagt ttctgagaaa gaaactgttc    840
tttaagacct ccgcatctag ggcc                                           864

<210> SEQ ID NO 186
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Val Asp Gly Phe Gly Asp Val Gly Ala Leu Glu Ser Leu Arg Gly Asn
1               5                   10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
        35                  40                  45

Thr Gly Ser Asn Ile Asp Cys Glu Lys Leu Arg Arg Arg Phe Ser Ser
    50                  55                  60

Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
        115                 120                 125

Glu Lys Ile Val Asn Ile Phe Asn Gly Thr Ser Cys Pro Ser Leu Gly
    130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175
```

Gly Ser Asn Pro Glu Pro Asp Ala Thr Pro Phe Gln Glu Gly Leu Arg
            180                 185                 190

Thr Phe Asp Gln Leu Asp Ala Ile Ser Ser Leu Pro Thr Pro Ser Asp
        195                 200                 205

Ile Phe Val Ser Tyr Ser Thr Phe Pro Gly Val Ser Trp Arg Asp
210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Arg Val Ala
                245                 250                 255

Asn Ala Val Ser Val Lys Gly Ile Tyr Lys Gln Met Pro Gly Cys Phe
            260                 265                 270

Gln Phe Leu Arg Lys Lys Leu Phe Phe Lys Thr Ser Ala Ser Arg Ala
        275                 280                 285

<210> SEQ ID NO 187
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gtcgacggat tggtgatgt cggtgctctt gagagtttga ggggaaatgc agatttggct      60
tacatcctga gcatggagcc ctgtggccac tgcctcatta tcaacaatgt gaacttctgc    120
cgtgagtccg ggctccgcac ccgcactggc tccaacatcg actgtgagaa gttgcggcgt    180
cgcttctcct cgctgcattt catggtggag gtgaagggcg acctgactgc caagaaaatg    240
gtgctggctt tgctggagct ggcgcggcag gaccacggtg ctctggactg ctgcgtggtg    300
gtcattctct ctcacggctg tcaggccagc cacctgcagt cccaggggc tgtctacggc    360 acagatggat gccctgtgtc ggtcgagaag attgtgaaca tcttcaatgg accagctgc    420 cccagcctgg agggaagcc caagctcttt ttcatccagg cctgtggtgg ggagcagaaa    480
gaccatgggt tgaggtggc ctccacttcc cctgaagacg agtcccctgg cagtaacccc    540
gagccagatg ccaccccgtt ccaggaaggt tgaggacct cgaccagct ggccgccata    600 tctagtttgc ccacacccag tgacatcttt gtgtcctact ctactttccc aggttttgtt    660
tcctggaggg accccaagag tggctcctgg tacgttgaga ccctggacga catctttgag    720
cagtgggctc actctgaaga cctgcagtcc ctcctgctta gggtcgctaa tgctgtttcg    780
gtgaaaggga tttataaaca gatgcctggt tgctttaatt tcctccggaa aaaacttttc    840
tttaaaacat cagctagcag agcc                                           864

<210> SEQ ID NO 188
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Val Asp Gly Phe Gly Asp Val Gly Ala Leu Glu Ser Leu Arg Gly Asn
1               5                   10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
            35                   40                  45

Thr Gly Ser Asn Ile Asp Cys Glu Lys Leu Arg Arg Arg Phe Ser Ser
    50                   55                  60

Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
            115                 120                 125

Glu Lys Ile Val Asn Ile Phe Asn Gly Thr Ser Cys Pro Ser Leu Gly
        130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175

Gly Ser Asn Pro Glu Pro Asp Ala Thr Pro Phe Gln Glu Gly Leu Arg
            180                 185                 190

Thr Phe Asp Gln Leu Glu Ala Ile Ser Ser Leu Pro Thr Pro Ser Asp
        195                 200                 205

Ile Phe Val Ser Tyr Ser Thr Phe Pro Gly Phe Val Ser Trp Arg Asp
    210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Leu Arg Val Ala
                245                 250                 255

Asn Ala Val Ser Val Lys Gly Ile Tyr Lys Gln Met Pro Gly Cys Phe
            260                 265                 270

Asn Phe Leu Arg Lys Lys Leu Phe Phe Lys Thr Ser Ala Ser Arg Ala
        275                 280                 285

<210> SEQ ID NO 189
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
atggagtttg gactttcttg gttgttttg gtggcaattc tgaagggtgt ccagtgtagc    60
agg                                                                63

<210> SEQ ID NO 190
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Met Glu Phe Gly Leu Ser Trp Leu Phe Leu Val Ala Ile Leu Lys Gly
1               5                   10                  15

Val Gln Cys Ser Arg

<210> SEQ ID NO 191
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
gacatccagc tgacacaaag tcccagtagc ctgtcagcca gtgtcggcga tagggtgaca      60
attacatgct ccgcaagtag tagcgtcaga ttcatacact ggtaccagca gaagcctggg     120
aaggccccaa agaggcttat ctacgatacc agtaaactcg cctctggagt tcctagccgg     180
ttttctggat ctggcagcgg aactagctac accctcacaa tctccagtct gcaaccagag     240
gactttgcaa cctactactg ccagcaatgg agcagctccc ctttcacctt tgggcagggt     300
actaaggtgg agatcaag                                                   318

<210> SEQ ID NO 192
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys
            100                 105

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ggcggaggaa gcggaggtgg gggc                                             24

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Gly Gly Ser Gly Gly Gly Gly
1               5

<210> SEQ ID NO 195
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
gaggtgcagc ttgtagagag cgggggaggc ctcgtacagc cagggggctc tctgcgcctg      60
tcatgtgcag cttcaggatt caatataaag gactattaca ttcactgggt acggcaagct     120
cccggtaagg gcctggaatg gatcggttgg atcgaccctg aaaacggaga tacagaattt     180
gtgcccaagt tccagggaaa ggctaccatg tctgccgata cttctaagaa tacagcatac     240
cttcagatga attctctccg cgccgaggac acagccgtgt attattgtaa aacgggaggg     300
ttctggggtc aggtaccct tgtgactgtg tcttcc                                336

<210> SEQ ID NO 196
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Ile
        35                  40                  45

Gly Trp Ile Asp Pro Glu Asn Gly Asp Thr Glu Phe Val Pro Lys Phe
    50                  55                  60

Gln Gly Lys Ala Thr Met Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

<210> SEQ ID NO 197
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggggatcccg cc                                                          12

<210> SEQ ID NO 198
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 198

Gly Asp Pro Ala
1

<210> SEQ ID NO 199
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gagcccaaat ctcctgacaa aactcacaca tgccca                                36

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Glu Pro Lys Ser Pro Asp Lys Thr His Thr Cys Pro
1               5                   10

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
ccgtgcccag cacctgaact cctggggggga ccgtcagtct tcctcttccc cccaaaaccc       60
aaagacaccc tcatgatctc ccggacccct gaggtcacat gcgtggtggt ggacgtgagc      120
cacgaagacc ctgaggtcaa gttcaactgg tatgtggacg gcgtggaggt gcataatgca      180
aagacaaagc cgcgggagga gcagtacaac agcacgtacc gtgtggtcag cgtcctcacc      240
gtcctgcacc aggactggct gaatggcaag gagtacaagt gcaaggtctc caacaaagcc      300
ctcccagccc ccatcgagaa aaccatctcc aaagccaaa                            339

<210> SEQ ID NO 202
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys

<210> SEQ ID NO 203
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
gggcagcccc gagaaccaca ggtgtacacc ctgcccccat cccgggatga gctgaccaag     60
aaccaggtca gcctgacctg cctggtcaaa ggcttctatc ccagcgacat cgccgtggag    120
tgggagagca atgggcaacc ggagaacaac tacaagacca cgcctcccgt gctggactcc    180
gacggctcct tcttcctcta cagcaagctc accgtggaca agagcaggtg gcagcagggg    240
aacgtcttct catgctccgt gatgcatgag gctctgcaca accactacac gcagaagagc    300
ctctccctgt ctccgggtaa a                                              321

<210> SEQ ID NO 204
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 205
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
aaagatccca aa 12

<210> SEQ ID NO 206
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Asp Pro Lys
1

<210> SEQ ID NO 207
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ttttgggtgc tggtggtggt tggtggagtc ctggcttgct atagcttgct agtaacagtg    60
gcctttatta tt    72

<210> SEQ ID NO 208
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Phe Trp Val Leu Val Val Val Gly Gly Val Leu Ala Cys Tyr Ser Leu
1               5                   10                  15

Leu Val Thr Val Ala Phe Ile Ile
            20

<210> SEQ ID NO 209
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209 gccggc    6

<210> SEQ ID NO 210
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Gly
1

<210> SEQ ID NO 211
<211> LENGTH: 336
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 211

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga agataagat ggcggaggcc tacagtgaga ttgggatgaa aggcgagcgc      240
cggagggggca aggggcacga tggcctttac cagggtctca gtacagccac caaggacacc   300
tacgacgccc ttcacatgca ggccctgccc cctcgc                              336
```

<210> SEQ ID NO 212
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

```
Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

<210> SEQ ID NO 213
<211> LENGTH: 513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213

```
gccgctgggg gcccaggcgc cggatcagct gctcccgtat cttctacttc ttctttgccg      60
ctggctgctc tgaacatgcg cgtgagaaga cgcctctccc tgttccttaa cgttcgcaca    120
caagtcgctg ccgattggac cgcccttgcc gaagaaatgg actttgaata cctgaaaatt   180
agacaacttg aaacacaggc cgaccccact ggcagactcc tggacgcatg cagggaaga    240
cctggtgcaa gcgttggacg gctcctggat ctcctgacaa aactgggacg cgacgacgta   300
ctgcttgaac tcggacctag cattgaagaa gactgccaaa aatatatcct gaaacaacaa    360
caagaagaag ccgaaaaacc tctccaagtc gcagcagtgg actcatcagt accccgaaca   420
gctgagcttg ctgggattac tacactcgac gaccactcg acatatgcc tgaaagattc      480
gacgctttca tttgctattg ccccctctgac ata                               513
```

<210> SEQ ID NO 214
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Ala Ala Gly Gly Pro Gly Ala Gly Ser Ala Ala Pro Val Ser Ser Thr
1               5                   10                  15

Ser Ser Leu Pro Leu Ala Ala Leu Asn Met Arg Val Arg Arg Arg Leu
            20                  25                  30

Ser Leu Phe Leu Asn Val Arg Thr Gln Val Ala Ala Asp Trp Thr Ala
        35                  40                  45

Leu Ala Glu Glu Met Asp Phe Glu Tyr Leu Glu Ile Arg Gln Leu Glu
    50                  55                  60

Thr Gln Ala Asp Pro Thr Gly Arg Leu Leu Asp Ala Trp Gln Gly Arg
65                  70                  75                  80

Pro Gly Ala Ser Val Gly Arg Leu Leu Asp Leu Leu Thr Lys Leu Gly
                85                  90                  95

Arg Asp Asp Val Leu Leu Glu Leu Gly Pro Ser Ile Glu Glu Asp Cys
            100                 105                 110

Gln Lys Tyr Ile Leu Lys Gln Gln Gln Glu Glu Ala Glu Lys Pro Leu
        115                 120                 125

Gln Val Ala Ala Val Asp Ser Ser Val Pro Arg Thr Ala Glu Leu Ala
    130                 135                 140

Gly Ile Thr Thr Leu Asp Asp Pro Leu Gly His Met Pro Glu Arg Phe
145                 150                 155                 160

Asp Ala Phe Ile Cys Tyr Cys Pro Ser Asp Ile
                165                 170

<210> SEQ ID NO 215
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
aagaaagttg caaagaaacc cacaaataaa gccccacacc ctaaacagga accccaagaa      60
atcaatttcc cagatgatct ccctggatct aatactgccg ccccggtcca agaaaccctg     120
catggttgcc agcctgtcac ccaagaggac ggaaaagaat cacggattag cgtacaagag     180
agacaatag                                                             189

<210> SEQ ID NO 216
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr

```
            20                  25                  30
Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 217
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
atggagtttg actttcttg gttgttttg gtggcaattc tgaagggtgt ccagtgtagc     60
agg                                                                 63

<210> SEQ ID NO 218
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Met Glu Phe Gly Leu Ser Trp Leu Phe Leu Val Ala Ile Leu Lys Gly
1               5                   10                  15

Val Gln Cys Ser Arg
            20

<210> SEQ ID NO 219
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag gtaatacgc ttccgtacac gttcggaggg    300
gggactaagt tggaaataac a                                              321

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ggcggaggaa gcggaggtgg gggc                                               24

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Gly Ser Gly Gly Gly Gly
1               5

<210> SEQ ID NO 223
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gaggtgaaac tgcaggagtc aggacctggc ctggtggcgc cctcacagag cctgtccgtc        60
acatgcactg tctcaggggt ctcattaccc gactatggtg taagctggat tcgccagcct       120
ccacgaaagg gtctggagtg gctgggagta atatggggta gtgaaaccac atactataat       180
tcagctctca aatccagact gaccatcatc aaggacaact ccaagagcca agtttttctta      240 aaaatgaaca gtctgcaaac tgatgacaca gccatttact actgtgccaa acattattac       300
tacggtggta gctatgctat ggactactgg ggtcaaggaa cctcagtcac cgtctcctca       360

<210> SEQ ID NO 224
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Lys Leu Gln Glu Ser Gly Pro Gly Leu Val Ala Pro Ser Gln
1               5                   10                  15

```
Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 225
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggggatcccg cc                                                            12

<210> SEQ ID NO 226
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Asp Pro Ala
1

<210> SEQ ID NO 227
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gagcccaaat ctcctgacaa aactcacaca tgccca                                  36

<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Glu Pro Lys Ser Pro Asp Lys Thr His Thr Cys Pro
1               5                   10

<210> SEQ ID NO 229
<211> LENGTH: 339
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
ccgtgcccag cacctgaact cctgggggga ccgtcagtct tcctcttccc cccaaaaccc       60
aaagacaccc tcatgatctc ccggacccct gaggtcacat gcgtggtggt ggacgtgagc      120
cacgaagacc ctgaggtcaa gttcaactgg tatgtggacg gcgtggaggt gcataatgca      180
aagacaaagc cgcgggagga gcagtacaac agcacgtacc gtgtggtcag cgtcctcacc      240
gtcctgcacc aggactggct gaatggcaag gagtacaagt gcaaggtctc caacaaagcc      300
ctcccagccc ccatcgagaa aaccatctcc aaagccaaa                             339

<210> SEQ ID NO 230
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Pro Cys Pro Ala Pro Glu Leu Leu Gly Gly Pro Ser Val Phe Leu Phe
1               5                  10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 231
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
gggcagcccc gagaaccaca ggtgtacacc ctgcccccat cccgggatga gctgaccaag       60
aaccaggtca gcctgacctg cctggtcaaa ggcttctatc ccagcgacat cgccgtggag      120
tgggagagca atgggcaacc ggagaacaac tacaagacca cgcctcccgt gctggactcc      180
gacggctcct tcttcctcta cagcaagctc accgtggaca agagcaggtg gcagcagggg      240
aacgtcttct catgctccgt gatgcatgag gctctgcaca accactacac gcagaagagc      300
ctctccctgt ctccgggtaa a                                                321

<210> SEQ ID NO 232
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 233
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
aaagatccca aa                                                            12

<210> SEQ ID NO 234
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Asp Pro Lys
1

<210> SEQ ID NO 235
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttttgggtgc tggtggtggt tggtggagtc ctggcttgct atagcttgct agtaacagtg        60
gcctttatta tt                                                            72

<210> SEQ ID NO 236
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Phe Trp Val Leu Val Val Gly Gly Val Leu Ala Cys Tyr Ser Leu
1               5                   10                  15

Leu Val Thr Val Ala Phe Ile Ile
            20

<210> SEQ ID NO 237
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237 ctcgag                                                                6

<210> SEQ ID NO 238
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Glu
1

<210> SEQ ID NO 239
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
atggccgctg ggggcccagg cgccggatca gctgctcccg tatcttctac ttcttctttg      60
ccgctggctg ctctgaacat gcgcgtgaga agacgcctct ccctgttcct taacgttcgc     120
acacaagtcg ctgccgattg gaccgccctt gccgaagaaa tggactttga atacctggaa     180
attagacaac ttgaaacaca ggccgacccc actggcagac tcctggacgc atggcaggga     240
agacctggtg caagcgttgg acggctcctg gatctcctga caaaactggg acgcgacgac     300
gtactgcttg aactcggacc tagcattgaa gaagactgcc aaaaatatat cctgaaacaa     360
caacaagaag aagccgaaaa acctctccaa gtcgcagcag tggactcatc agtaccccga     420
acagctgagc ttgctgggat tactacactc gacgacccac tcggacatat gcctgaaaga     480
ttcgacgctt tcatttgcta ttgcccctct gacata                               516

<210> SEQ ID NO 240
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
 50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Asp Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 241
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
aagaaagttg caaagaaacc cacaaataaa gccccacacc ctaaacagga accccaagaa      60
atcaatttcc cagatgatct ccctggatct aatactgccg ccccggtcca agaaaccctg     120
catggttgcc agcctgtcac ccaagaggac ggaaaagaat cacggattag cgtacaagag     180
agacaa                                                                186

<210> SEQ ID NO 242
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Lys Lys Val Ala Lys Lys Pro Thr Asn Lys Ala Pro His Pro Lys Gln
 1               5                  10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
 50                  55                  60

<210> SEQ ID NO 243
<211> LENGTH: 15
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 243
gcggccgcag tcgag                                                         15

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Ala Ala Val Glu
1               5

<210> SEQ ID NO 245
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatggggggg aaagccgaga aggaagaacc ctcaggaagg cctgtacaat       180
gaactgcaga agataagat ggcggaggcc tacagtgaga ttgggatgaa aggcgagcgc        240
cggaggggca aggggcacga tggcctttac cagggtctca gtacagccac caaggacacc       300
tacgacgccc ttcacatgca ggccctgccc cctcgctaa                              339

<210> SEQ ID NO 246
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 247
<211> LENGTH: 42

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
atggggagta gcaagagcaa gcctaaggac cccagccagc gc                         42

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Met Gly Ser Ser Lys Ser Lys Pro Lys Asp Pro Ser Gln Arg
1               5                   10

<210> SEQ ID NO 249
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249 ctcgac                                                                  6

<210> SEQ ID NO 250
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Asp
1

<210> SEQ ID NO 251
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
atggctgcag gaggtcccgg cgcggggtct gcggccccgg tctcctccac atcctccctt       60
cccctggctg ctctcaacat gcgagtgcgg cgccgcctgt ctctgttctt gaacgtgcgg      120
acacaggtgg cggccgactg gaccgcgctg gcggaggaga tggactttga gtacttggag      180
atccggcaac tggagacaca agcggacccc actggcaggc tgctggacgc ctggcaggga      240
cgccctggcg cctctgtagg ccgactgctc gatctgctta ccaagctggg ccgcgacgac      300
gtgctgctgg agctgggacc cagcattgag gaggattgcc aaaagtatat cttgaagcag      360
cagcaggagg aggctgagaa gcctttacag gtggccgctg tagacagcag tgtcccacgg      420
acagcagagc tggcgggcat caccacactt gatgaccccc tggggcatat gcctgagcgt      480
ttcgatgcct tcatctgcta ttgccccagc gacatc                                516
```

<210> SEQ ID NO 252
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 253
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253 gtcgag                                                             6

<210> SEQ ID NO 254
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val Glu
1

<210> SEQ ID NO 255
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255
aaaaaggtgg ccaagaagcc aaccaataag gcccccacc ccaagcagga gccccaggag    60
atcaattttc ccgacgatct tcctggctcc aacactgctg ctccagtgca ggagacttta   120
catggatgcc aaccggtcac ccaggaggat ggcaaagaga gtcgcatctc agtgcaggag   180
agacag                                                             186

<210> SEQ ID NO 256
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 257
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257 ccgcgg                                                               6

<210> SEQ ID NO 258
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Pro Arg
1

<210> SEQ ID NO 259
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gaaggccgag ggagcctgct gacatgtggc gatgtggagg aaaacccagg acca          54

<210> SEQ ID NO 260
<211> LENGTH: 18
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 260

Glu Gly Arg Gly Ser Leu Leu Thr Cys Gly Asp Val Glu Glu Asn Pro
1               5                   10                  15

Gly Pro

<210> SEQ ID NO 261
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
atggagtttg actttcttg gttgttttg gtggcaattc tgaagggtgt ccagtgtagc    60
agg                                                                63

<210> SEQ ID NO 262
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Met Glu Phe Gly Leu Ser Trp Leu Phe Leu Val Ala Ile Leu Lys Gly
1               5                   10                  15

Val Gln Cys Ser Arg
            20

<210> SEQ ID NO 263
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggactaagt tggaaataac a                                              321

<210> SEQ ID NO 264
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asp Ile Gln Met Thr Gln Thr Thr Ser Ser Leu Ser Ala Ser Leu Gly

```
                1               5                  10                 15
Asp Arg Val Thr Ile Ser Cys Arg Ala Ser Gln Asp Ile Ser Lys Tyr
                    20                 25                 30

Leu Asn Trp Tyr Gln Gln Lys Pro Asp Gly Thr Val Lys Leu Leu Ile
            35                 40                     45

Tyr His Thr Ser Arg Leu His Ser Gly Val Pro Ser Arg Phe Ser Gly
        50                 55                     60

Ser Gly Ser Gly Thr Asp Tyr Ser Leu Thr Ile Ser Asn Leu Glu Gln
65                  70                     75                 80

Glu Asp Ile Ala Thr Tyr Phe Cys Gln Gln Gly Asn Thr Leu Pro Tyr
                    85                 90                     95

Thr Phe Gly Gly Gly Thr Lys Leu Glu Ile Thr
                100                105
```

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggcggaggaa gcggaggtgg gggc                                          24

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Gly Gly Gly Ser Gly Gly Gly Gly
1               5
```

<210> SEQ ID NO 267
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267
gaggtgaaac tgcaggagtc aggacctggc ctggtggcgc cctcacagag cctgtccgtc      60
acatgcactg tctcaggggt ctcattaccc gactatggtg taagctggat tcgccagcct     120
ccacgaaagg gtctggagtg gctgggagta atatgggta gtgaaaccac atactataat     180
tcagctctca aatccagact gaccatcatc aaggacaact ccaagagcca agttttctta     240
aaaatgaaca gtctgcaaac tgatgacaca gccatttact actgtgccaa acattattac     300
tacggtggta gctatgctat ggactactgg ggtcaaggaa cctcagtcac cgtctcctca     360

<210> SEQ ID NO 268
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 269
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269 ggatcc                                                                      6

<210> SEQ ID NO 270
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Ser
1

<210> SEQ ID NO 271
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gaacttccta ctcaggggac tttctcaaac gttagcacaa acgtaagt                        48

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Leu Pro Thr Gln Gly Thr Phe Ser Asn Val Ser Thr Asn Val Ser
1               5                   10                  15

<210> SEQ ID NO 273
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
cccgccccaa gacccccac acctgcgccg accattgctt ctcaacccct gagtttgaga      60
cccgaggcct gccggccagc tgccggcggg gccgtgcata caagaggact cgatttcgct     120
tgcgac                                                                126

<210> SEQ ID NO 274
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 275
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275
atctatatct gggcacctct cgctggcacc tgtggagtcc ttctgctcag cctggttatt      60
actctgtact gtaatcaccg gaatcgccgc cgcgtttgta agtgtcccag g              111

<210> SEQ ID NO 276
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35

<210> SEQ ID NO 277
<211> LENGTH: 6
<212> TYPE: DNA
<213> ORGANISM: Artificial Sequence
<220> FEATURE:

<223> OTHER INFORMATION: Description of Artificial Sequence: Synthetic
    oligonucleotide

<400> SEQUENCE: 277 gtcgac                                                                  6

<210> SEQ ID NO 278
<211> LENGTH: 2
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 278

Val Asp
1

<210> SEQ ID NO 279
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 279
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatgggggg aaagccgaga aggaagaacc ctcaggaagg cctgtacaat       180
gaactgcaga agataagat ggcggaggcc tacagtgaga ttgggatgaa aggcgagcgc        240
cggaggggca aggggcacga tggcctttac cagggtctca gtacagccac caaggacacc       300
tacgacgccc ttcacatgca ggccctgccc cctcgc                                  336

<210> SEQ ID NO 280
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 280

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 281
<211> LENGTH: 888

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
atggctgcag gaggtcccgg cgcggggtct gcggccccgg tctcctccac atcctccctt    60
cccctggctg ctctcaacat gcgagtgcgg cgccgcctgt ctctgttctt gaacgtgcgg   120
acacaggtgg cggccgactg gaccgcgctg gcggaggaga tggactttga gtacttggag   180
atccggcaac tggagacaca agcggacccc actggcaggc tgctggacgc ctggcaggga   240
cgccctggcg cctctgtagg ccgactgctc gagctgctta ccaagctggg ccgcgacgac   300
gtgctgctgg agctgggacc cagcattgag gaggattgcc aaaagtatat cttgaagcag   360
cagcaggagg aggctgagaa gcctttacag gtggccgctg tagacagcag tgtcccacgg   420
acagcagagc tggcgggcat caccacactt gatgaccccc tggggcatat gcctgagcgt   480
ttcgatgcct tcatctgcta ttgccccagc gacatccagt ttgtgcagga gatgatccgg   540
caactggaac agacaaacta tcgactgaag ttgtgtgtgt ctgaccgcga tgtcctgcct   600
ggcacctgtg tctggtctat tgctagtgag ctcatcgaaa agaggtgccg ccggatggtg   660
gtggttgtct ctgatgatta cctgcagagc aaggaatgtg acttccagac caaatttgca   720
ctcagcctct ctccaggtgc ccatcagaag cgactgatcc ccatcaagta caaggcaatg   780
aagaaagagt tccccagcat cctgaggttc atcactgtct gcgactacac caaccccctgc   840 accaaatctt ggttctggac tcgccttgcc aaggccttgt ccctgccc                 888

<210> SEQ ID NO 282
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282
```

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

```
Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
        195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
        290                 295

<210> SEQ ID NO 283
<211> LENGTH: 16
<212> TYPE: PRT
<213> ORGANISM: Homo sapiens

<400> SEQUENCE: 283

Met Gly Ser Asn Lys Ser Lys Pro Lys Asp Ala Ser Gln Arg Arg Arg
1               5                   10                  15

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 284

Met Gly Cys Xaa Cys
1               5

<210> SEQ ID NO 285
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ser Gly Gly Gly Ser
1               5

<210> SEQ ID NO 286
<211> LENGTH: 7
<212> TYPE: PRT
<213> ORGANISM: Homo sapiens

<400> SEQUENCE: 286

Thr Asp Pro Thr Arg Arg Phe
```

```
1               5

<210> SEQ ID NO 287
<211> LENGTH: 8
<212> TYPE: PRT
<213> ORGANISM: Human herpesvirus 4

<400> SEQUENCE: 287

Arg Ala Lys Phe Lys Gln Leu Leu
1               5

<210> SEQ ID NO 288
<211> LENGTH: 9
<212> TYPE: PRT
<213> ORGANISM: Human herpesvirus 5

<400> SEQUENCE: 288

Asn Leu Val Pro Met Val Ala Thr Val
1               5

<210> SEQ ID NO 289
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ser Gly Gly Gly
1

<210> SEQ ID NO 290
<211> LENGTH: 5
<212> TYPE: PRT
<213> ORGANISM: Homo sapiens

<400> SEQUENCE: 290

Gly Cys Phe Asn Phe
1               5

<210> SEQ ID NO 291
<211> LENGTH: 5
<212> TYPE: PRT
<213> ORGANISM: Homo sapiens

<400> SEQUENCE: 291

Ile Ser Ala Gln Thr
1               5

<210> SEQ ID NO 292
<211> LENGTH: 4
<212> TYPE: PRT
<213> ORGANISM: Homo sapiens

<400> SEQUENCE: 292

Ala Thr Pro Phe
1

<210> SEQ ID NO 293
<211> LENGTH: 4
<212> TYPE: PRT
<213> ORGANISM: Homo sapiens

<400> SEQUENCE: 293
```

Ala Val Pro Ile
1

<210> SEQ ID NO 294
<211> LENGTH: 5
<212> TYPE: PRT
<213> ORGANISM: Homo sapiens

<400> SEQUENCE: 294

Ala Ala Ala Ala Ala
1               5

<210> SEQ ID NO 295
<211> LENGTH: 5
<212> TYPE: PRT
<213> ORGANISM: Homo sapiens

<400> SEQUENCE: 295

Tyr Cys Ser Thr Leu
1               5

<210> SEQ ID NO 296
<211> LENGTH: 5
<212> TYPE: PRT
<213> ORGANISM: Homo sapiens

<400> SEQUENCE: 296

Cys Ile Val Ser Met
1               5

<210> SEQ ID NO 297
<211> LENGTH: 5
<212> TYPE: PRT
<213> ORGANISM: Homo sapiens

<400> SEQUENCE: 297

Gln Pro Thr Phe Thr
1               5

<210> SEQ ID NO 298
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 298
atgggagtgc aggtggagac tattagcccc ggagatggca gaacattccc caaaagagga        60
cagacttgcg tcgtgcatta tactggaatg ctggaagacg gcaagaaggt ggacagcagc       120
cgggaccgaa acaagcccct caagttcatg ctggggaagc aggaagtgat ccggggctgg       180
gaggaaggag tcgcacagat gtcagtggga cagagggcca aactgactat tagcccagac       240
tacgcttatg gagcaaccgg ccaccccggg atcattcccc ctcatgctac actggtcttc       300
gatgtggagc tgctgaagct ggaa                                              324

<210> SEQ ID NO 299
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 300
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
agcggaggag gatccgga                                                18

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ser Gly Gly Gly Ser Gly
1               5

<210> SEQ ID NO 302
<211> LENGTH: 864
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302
gtggacgggt tggagatgt gggagccctg gaatccctgc ggggcaatgc cgatctggct      60
tacatcctgt ctatggagcc ttgcggccac tgtctgatca ttaacaatgt gaacttctgc    120
agagagagcg ggctgcggac cagaacagga tccaatattg actgtgaaaa gctgcgagaa    180
aggttctcta gtctgcactt tatggtcgag gtgaaaggcg atctgaccgc taagaaaatg    240
gtgctggccc tgctggaact ggctcggcag gaccatgggg cactggattg ctgcgtggtc    300
gtgatcctga gtcacggctg ccaggcttca catctgcagt ccctggggc agtctatgga    360 actgacggct gtccagtcag cgtggagaag atcgtgaaca tcttcaacgg cacctcttgc    420
ccaagtctgg gcgggaagcc caaactgttc tttattcagg cctgtggagg cgagcagaaa    480
gatcacggct tcgaagtggc tagcacctcc cccgaggacg aatcacctgg aagcaaccct    540

```
gagccagatg caaccccctt ccaggaaggc ctgaggacat ttgaccagct ggatgccatc    600
tcaagcctgc ccacaccttc tgacattttc gtctcttaca gtactttccc tggatttgtg    660
agctggcgcg atccaaagtc aggcagctgg tacgtggaga cactggacga tatctttgag    720
cagtgggccc attctgaaga cctgcagagt ctgctgctgc gagtggccaa tgctgtctct    780
gtgaagggga tctacaaaca gatgccagga tgcttcaact ttctgagaaa gaaactgttc    840
tttaagacct ccgcatctag ggcc                                            864
```

<210> SEQ ID NO 303
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

```
Val Asp Gly Phe Gly Asp Val Gly Ala Leu Glu Ser Leu Arg Gly Asn
 1               5                  10                  15

Ala Asp Leu Ala Tyr Ile Leu Ser Met Glu Pro Cys Gly His Cys Leu
            20                  25                  30

Ile Ile Asn Asn Val Asn Phe Cys Arg Glu Ser Gly Leu Arg Thr Arg
        35                  40                  45

Thr Gly Ser Asn Ile Asp Cys Glu Lys Leu Arg Arg Arg Phe Ser Ser
    50                  55                  60

Leu His Phe Met Val Glu Val Lys Gly Asp Leu Thr Ala Lys Lys Met
65                  70                  75                  80

Val Leu Ala Leu Leu Glu Leu Ala Arg Gln Asp His Gly Ala Leu Asp
                85                  90                  95

Cys Cys Val Val Val Ile Leu Ser His Gly Cys Gln Ala Ser His Leu
            100                 105                 110

Gln Phe Pro Gly Ala Val Tyr Gly Thr Asp Gly Cys Pro Val Ser Val
        115                 120                 125

Glu Lys Ile Val Asn Ile Phe Asn Gly Thr Ser Cys Pro Ser Leu Gly
    130                 135                 140

Gly Lys Pro Lys Leu Phe Phe Ile Gln Ala Cys Gly Gly Glu Gln Lys
145                 150                 155                 160

Asp His Gly Phe Glu Val Ala Ser Thr Ser Pro Glu Asp Glu Ser Pro
                165                 170                 175

Gly Ser Asn Pro Glu Pro Asp Ala Thr Pro Phe Gln Glu Gly Leu Arg
            180                 185                 190

Thr Phe Asp Gln Leu Asp Ala Ile Ser Ser Leu Pro Thr Pro Ser Asp
        195                 200                 205

Ile Phe Val Ser Tyr Ser Thr Phe Pro Gly Phe Val Ser Trp Arg Asp
    210                 215                 220

Pro Lys Ser Gly Ser Trp Tyr Val Glu Thr Leu Asp Asp Ile Phe Glu
225                 230                 235                 240

Gln Trp Ala His Ser Glu Asp Leu Gln Ser Leu Leu Leu Arg Val Ala
                245                 250                 255

Asn Ala Val Ser Val Lys Gly Ile Tyr Lys Gln Met Pro Gly Cys Phe
            260                 265                 270

Asn Phe Leu Arg Lys Lys Leu Phe Phe Lys Thr Ser Ala Ser Arg Ala
        275                 280                 285
```

<210> SEQ ID NO 304

```
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304 ccgcgg                                                                      6

<210> SEQ ID NO 305
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Pro Arg
1

<210> SEQ ID NO 306
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gaaggccgag ggagcctgct gacatgtggc gatgtggagg aaaacccagg acca              54

<210> SEQ ID NO 307
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Glu Gly Arg Gly Ser Leu Leu Thr Cys Gly Asp Val Glu Glu Asn Pro
1               5                   10                  15

Gly Pro

<210> SEQ ID NO 308
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308 ccatgg                                                                      6

<210> SEQ ID NO 309
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Pro Trp
```

<210> SEQ ID NO 310
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310

```
atggagtttg gactttcttg gttgttttg gtggcaattc tgaagggtgt ccagtgtagc    60
agg                                                                 63
```

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

```
Met Glu Phe Gly Leu Ser Trp Leu Phe Leu Val Ala Ile Leu Lys Gly
  1               5                  10                  15

Val Gln Cys Ser Arg
                 20
```

<210> SEQ ID NO 312
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 312

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggactaagt tggaaataac a                                             321
```

<210> SEQ ID NO 313
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 313

```
Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Lys Tyr
             20                  25                  30

Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
     50                  55                  60
```

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggcggaggaa gcggaggtgg gggc                                            24

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Gly Gly Ser Gly Gly Gly Gly
1               5

<210> SEQ ID NO 316
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
gaggtgaaac tgcaggagtc aggacctggc ctggtggcgc cctcacagag cctgtccgtc     60
acatgcactg tctcaggggt ctcattaccc gactatggtg taagctggat tcgccagcct    120
ccacgaaagg gtctggagtg gctgggagta atatggggta gtgaaaccac atactataat    180
tcagctctca aatccagact gaccatcatc aaggacaact ccaagagcca gttttctta     240 aaaatgaaca gtctgcaaac tgatgacaca gccatttact actgtgccaa acattattac    300
tacggtggta gctatgctat ggactactgg ggtcaaggaa cctcagtcac cgtctcctca    360

<210> SEQ ID NO 317
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 318
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318 ggatcc                                                                6

<210> SEQ ID NO 319
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Ser
1

<210> SEQ ID NO 320
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gaacttccta ctcaggggac tttctcaaac gttagcacaa acgtaagt                  48

<210> SEQ ID NO 321
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Glu Leu Pro Thr Gln Gly Thr Phe Ser Asn Val Ser Thr Asn Val Ser
1               5                   10                  15

<210> SEQ ID NO 322
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
cccgccccaa gacccccac acctgcgccg accattgctt ctcaacccct gagtttgaga        60
cccgaggcct gccggccagc tgccggcggg gccgtgcata caagaggact cgatttcgct      120
tgcgac                                                                 126

<210> SEQ ID NO 323
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 324
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 324
atctatatct gggcacctct cgctggcacc tgtggagtcc ttctgctcag cctggttatt        60
actctgtact gtaatcaccg gaatcgccgc cgcgtttgta agtgtcccag g                111

<210> SEQ ID NO 325
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35

<210> SEQ ID NO 326
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326 gtcgac                                                                   6

<210> SEQ ID NO 327
<211> LENGTH: 2

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Val Asp
1

<210> SEQ ID NO 328
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 328
agagtgaagt tcagcaggag cgcagacgcc cccgcgtacc agcagggcca gaaccagctc      60
tataacgagc tcaatctagg acgaagagag gagtacgatg tttggacaa gagacgtggc     120 cgggaccctg agatggggggg aaagccgaga aggaagaacc ctcaggaagg cctgtacaat     180
gaactgcaga aagataagat ggcggaggcc tacagtgaga ttgggatgaa aggcgagcgc     240 cggagggggca aggggcacga tggccttttac cagggtctca gtacagccac caaggacacc     300
tacgacgccc ttcacatgca agctcttcca cctcgt                              336

<210> SEQ ID NO 329
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 330
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gcaacgaatt tttccctgct gaaacaggca ggggacgtag aggaaaatcc tggtcct        57

<210> SEQ ID NO 331
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Thr Asn Phe Ser Leu Leu Lys Gln Ala Gly Asp Val Glu Glu Asn
1               5                   10                  15

Pro Gly Pro

<210> SEQ ID NO 332
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
atggggagta gcaagagcaa gcctaaggac cccagccagc gc                         42

<210> SEQ ID NO 333
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Met Gly Ser Ser Lys Ser Lys Pro Lys Asp Pro Ser Gln Arg
1               5                   10

<210> SEQ ID NO 334
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334 ctcgac                                                                  6

<210> SEQ ID NO 335
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Leu Asp
1

<210> SEQ ID NO 336
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336

```
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca agcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatc                              516
```

<210> SEQ ID NO 337
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

```
Met Ala Ala Gly Gly Pro Gly Ala Gly Ser Ala Ala Pro Val Ser Ser
1               5                   10                  15
Thr Ser Ser Leu Pro Leu Ala Ala Leu Asn Met Arg Val Arg Arg Arg
            20                  25                  30
Leu Ser Leu Phe Leu Asn Val Arg Thr Gln Val Ala Ala Asp Trp Thr
        35                  40                  45
Ala Leu Ala Glu Glu Met Asp Phe Glu Tyr Leu Glu Ile Arg Gln Leu
    50                  55                  60
Glu Thr Gln Ala Asp Pro Thr Gly Arg Leu Leu Asp Ala Trp Gln Gly
65                  70                  75                  80
Arg Pro Gly Ala Ser Val Gly Arg Leu Leu Asp Leu Leu Thr Lys Leu
                85                  90                  95
Gly Arg Asp Asp Val Leu Leu Glu Leu Gly Pro Ser Ile Glu Glu Asp
            100                 105                 110
Cys Gln Lys Tyr Ile Leu Lys Gln Gln Gln Glu Glu Ala Glu Lys Pro
        115                 120                 125
Leu Gln Val Ala Ala Val Asp Ser Ser Val Pro Arg Thr Ala Glu Leu
    130                 135                 140
Ala Gly Ile Thr Thr Leu Asp Asp Pro Leu Gly His Met Pro Glu Arg
145                 150                 155                 160
Phe Asp Ala Phe Ile Cys Tyr Cys Pro Ser Asp Ile
                165                 170
```

<210> SEQ ID NO 338
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338

```
gtcgag                                                                 6
```

<210> SEQ ID NO 339

```
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Val Glu
1

<210> SEQ ID NO 340
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340
aaaaaggtgg ccaagaagcc aaccaataag gccccccacc ccaagcagga gccccaggag     60
atcaattttc ccgacgatct tcctggctcc aacactgctg ctccagtgca ggagacttta    120
catggatgcc aaccggtcac ccaggaggat ggcaaagaga gtcgcatctc agtgcaggag    180
agacag                                                               186

<210> SEQ ID NO 341
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Lys Lys Val Ala Lys Lys Pro Thr Asn Lys Ala Pro His Pro Lys Gln
1               5                  10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 342
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Met Leu Glu Met Leu Glu
1               5

<210> SEQ ID NO 343
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
```

```
atggagtttg gactttcttg gttgttttg gtggcaattc tgaagggtgt ccagtgtagc      60
agg                                                                    63
```

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

```
Met Glu Phe Gly Leu Ser Trp Leu Phe Leu Val Ala Ile Leu Lys Gly
1               5                   10                  15

Val Gln Cys Ser Arg
            20
```